US012644137B2

(12) United States Patent
Chakraborty et al.

(10) Patent No.: US 12,644,137 B2
(45) Date of Patent: Jun. 2, 2026

(54) MATERIALS AND METHODS FOR TREATMENT OF HEMOGLOBINOPATHIES

(71) Applicant: Vertex Pharmaceuticals Incorporated, Boston, MA (US)

(72) Inventors: Tirtha Chakraborty, Cambridge, MA (US); Bibhu Prasad Mishra, Cambridge, MA (US); Chad Albert Cowan, Cambridge, MA (US); Ante Sven Lundberg, Cambridge, MA (US); Samarth Kulkarni, Cambridge, MA (US); Todd Douglass Borland, Cambridge, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 785 days.

(21) Appl. No.: 16/758,990

(22) PCT Filed: Oct. 26, 2018

(86) PCT No.: PCT/IB2018/001338
§ 371 (c)(1),
(2) Date: Apr. 24, 2020

(87) PCT Pub. No.: WO2019/081982
PCT Pub. Date: May 2, 2019

(65) Prior Publication Data
US 2021/0180091 A1 Jun. 17, 2021

Related U.S. Application Data

(60) Provisional application No. 62/577,434, filed on Oct. 26, 2017, provisional application No. 62/583,146, filed on Nov. 8, 2017.

(51) Int. Cl.
| | |
|---|---|
| *C12N 5/078* | (2010.01) |
| *A61K 9/51* | (2006.01) |
| *A61K 31/395* | (2006.01) |
| *A61K 31/70* | (2006.01) |
| *A61K 35/28* | (2015.01) |
| *A61K 38/19* | (2006.01) |
| *A61K 38/46* | (2006.01) |
| *C12N 5/074* | (2010.01) |
| *C12N 15/11* | (2006.01) |
| *C12N 15/113* | (2010.01) |
| *C12N 15/90* | (2006.01) |
| *A61K 35/12* | (2015.01) |

(52) U.S. Cl.
CPC .......... *C12N 15/907* (2013.01); *A61K 9/5123* (2013.01); *A61K 31/395* (2013.01); *A61K 31/70* (2013.01); *A61K 35/28* (2013.01); *A61K 38/193* (2013.01); *A61K 38/465* (2013.01); *C12N 5/0696* (2013.01); *C12N 15/11* (2013.01); *A61K 2035/124* (2013.01); *C12N 2310/20* (2017.05); *C12N 2506/1353*

(2013.01); *C12N 2506/27* (2013.01); *C12N 2510/00* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 9,738,693 | B2 | 8/2017 | Telford et al. |
| 9,840,538 | B2 | 12/2017 | Telford et al. |
| 10,738,305 | B2 | 8/2020 | Porteus |
| 11,268,077 | B2 | 3/2022 | Chakraborty et al. |
| 11,566,236 | B2 | 1/2023 | Chakraborty et al. |
| 2014/0093913 | A1 | 4/2014 | Cost et al. |
| 2015/0044772 | A1 | 2/2015 | Zhao |
| 2015/0132269 | A1 | 5/2015 | Orkin et al. |
| 2015/0166969 | A1 | 6/2015 | Takeuchi et al. |
| 2015/0168547 | A1 | 6/2015 | Lee et al. |
| 2015/0183025 | A1 | 7/2015 | Aoki |
| 2015/0307867 | A1 | 10/2015 | Orkin et al. |
| 2016/0029604 | A1 | 2/2016 | Fahrenkrug et al. |
| 2016/0168594 | A1 | 6/2016 | Zhang et al. |
| 2016/0289675 | A1 | 10/2016 | Ryan et al. |
| 2017/0191123 | A1 | 7/2017 | Kim et al. |
| 2018/0016589 | A1 | 1/2018 | Gao et al. |

(Continued)

FOREIGN PATENT DOCUMENTS

| | | |
|---|---|---|
| CN | 104284669 A | 1/2015 |
| CN | 104955943 A | 9/2015 |

(Continued)

OTHER PUBLICATIONS

Huang et al, In vivo delivery of CRISPR-Cas9 genome editing components for therapeutic applications, Biomaterials, 2022, pp. 1-20.*

(Continued)

*Primary Examiner* — Maria Marvich

(74) *Attorney, Agent, or Firm* — McNeill PLLC

(57) ABSTRACT

Provided are materials and methods for treating patients with hemoglobinopathies, either ex vivo or in vivo. Also provided are materials and methods for deleting and/or mutating a portion of a human beta globin locus on chromosome 11 and one or more of: a BCL11 A gene on chromosome 2, and a DNA sequence that encodes a transcriptional control region of the BCL11 A gene on chromosome 2, in a human cell by genome editing and thereby increasing the production of fetal hemoglobin (HbF) in the genome-edited human cells.

18 Claims, 79 Drawing Sheets

Specification includes a Sequence Listing.

(56) References Cited

U.S. PATENT DOCUMENTS

| | | | |
|---|---|---|---|
| 2018/0021413 A1 | 1/2018 | Porteus | |
| 2018/0030438 A1 | 2/2018 | Porteus et al. | |
| 2018/0094033 A1 | 4/2018 | Telford et al. | |
| 2018/0112213 A1 | 4/2018 | Welstead et al. | |
| 2018/0119138 A1 | 5/2018 | Bauer et al. | |
| 2018/0119140 A1 | 5/2018 | Porteus et al. | |
| 2018/0179521 A1 | 6/2018 | Rahdar et al. | |
| 2018/0200387 A1 | 7/2018 | Porteus | |
| 2018/0273609 A1 | 9/2018 | Porteus | |
| 2019/0201553 A1 | 7/2019 | Cowan et al. | |
| 2019/0256829 A1 | 8/2019 | Chakraborty et al. | |
| 2019/0284542 A1 | 9/2019 | Chakraborty et al. | |
| 2020/0157515 A1* | 5/2020 | Gori | A61K 38/465 |
| 2020/0330609 A1* | 10/2020 | Cowan | A61K 31/395 |
| 2020/0384033 A1 | 12/2020 | Morawa et al. | |
| 2021/0009998 A1 | 1/2021 | Porteus | |
| 2021/0317450 A9 | 10/2021 | Chakraborty et al. | |
| 2022/0211874 A1 | 7/2022 | Cowan et al. | |
| 2022/0259578 A1 | 8/2022 | Chakraborty et al. | |

FOREIGN PATENT DOCUMENTS

| | | | | |
|---|---|---|---|---|
| JP | 2000201672 A | 7/2000 | | |
| JP | 2019-500043 A | 1/2019 | | |
| JP | 2019-513407 A | 5/2019 | | |
| WO | WO 2013/126794 A1 | 8/2013 | | |
| WO | WO 2013/169398 A2 | 11/2013 | | |
| WO | WO 2013/176772 A1 | 11/2013 | | |
| WO | WO 2014/036219 A2 | 3/2014 | | |
| WO | WO 2015/183026 A1 | 5/2014 | | |
| WO | WO 2014/085593 A1 | 6/2014 | | |
| WO | WO 2014/093712 A1 | 6/2014 | | |
| WO | WO 2014/186585 A2 | 11/2014 | | |
| WO | WO 2014/197748 A2 | 12/2014 | | |
| WO | WO 2014/204723 A1 | 12/2014 | | |
| WO | WO 2015/006498 A2 | 1/2015 | | |
| WO | WO 2015/006747 A2 | 1/2015 | | |
| WO | WO 2015/026885 A1 | 2/2015 | | |
| WO | WO 2015/073683 A2 | 5/2015 | | |
| WO | WO 2015/113063 A1 | 7/2015 | | |
| WO | WO 2015/148860 A1 | 10/2015 | | |
| WO | WO 2015/148863 A2 | 10/2015 | | |
| WO | WO 2015/168547 A2 | 11/2015 | | |
| WO | WO 2015/183025 A1 | 12/2015 | | |
| WO | WO 2016/135557 A2 | 9/2016 | | |
| WO | WO 2016/135558 A2 | 9/2016 | | |
| WO | WO 2016/135559 A2 | 9/2016 | | |
| WO | WO 2016/164356 A1 | 10/2016 | | |
| WO | WO 2016/182917 A1 | 11/2016 | | |
| WO | WO 2016/183298 A2 | 11/2016 | | |
| WO | WO 2017/077394 A2 | 5/2017 | | |
| WO | WO2017115268 A1* | 7/2017 | C12N 15/113 | |
| WO | WO 2017/160890 A1 | 9/2017 | | |
| WO | WO 2017/182881 A2 | 10/2017 | | |
| WO | WO 2017/191503 A1 | 11/2017 | | |
| WO | WO 2018/081470 A1 | 5/2018 | | |
| WO | WO 2018/218135 A1 | 11/2018 | | |
| WO | WO 2019/081982 A1 | 5/2019 | | |
| WO | 110832075 * | 2/2020 | | |

OTHER PUBLICATIONS

Li et al, Application of induced pluripotent stem cell transplants: Autologous or allogeneic? Life Sciences vol. 212, Nov. 1, 2018, pp. 145-149.*
Ortuno et al, The Challenge of Bringing iPSCs to the Patient, International Journal of Molecular Sciences, 2019, pp. 1-16.*
Huang et a., iPSC-based Gene Therapy: Applications And Challenges, cell &gene, 2024, pp. 1-4.*
Ye et al, Genome editing using CRISPR-Cas9 to create the HPFH genotype in HSPCs: An approach for treating sickle cell disease and B-thalassemia, PNAS< 2016, pp. 10661-10665.*

[No Author Listed], Addgene, lentiGuide-Puro, plasmid #52963. Retrieved Sep. 4, 2020 from https://www.addgene.org/52963/. 22 pages.
Boulad et al., Safe mobilization of CD34+ cells in adults with ?-thalassemia and validation of effective globin gene transfer for clinical investigation. Blood. Mar. 6, 2014;123(10):1483-86.
Cong et al., Multiplex genome engineering using CRISPR/Cas systems. Sci. Feb. 15, 2013;339:819-23.
Costa et al., Genome Editing Using Engineered Nucleases and Their Use in Genomic Screening. Assay Guidance Manual. Nov. 20, 2017:1-24.
Hendel et al., Chemically modified guide RNAs enhance CRISPR-Cas genome editing in human primary cells. Nat Biotechnol. Sep. 1, 2015;33(9):985-9. Epub Jun. 29, 2015. Author manuscript provided, available in PMC Sep. 1, 2016:14 pages. doi: 10.1038/nbt. 3290.
Koonin et al., Diversity, classification and evolution of CRISPR-Cas systems. Curr Opin Microbiol. Jun. 2017;37:67-78. Author manuscript, available Jun. 9, 2018: 20 pages. Epub Jun. 9, 2017. doi: 10.1016/j.mib.2017.05.008.
International Search Report and Written Opinion mailed Apr. 15, 2019 for International Application No. PCT/IB2018/001338.
International Preliminary Report on Patentability mailed May 7, 2020 for International Application No. PCT/IB2018/001338.
[No Author Listed] Endonuclease. Wikipedia. Accessed Aug. 9, 2019. 6 pages.
[No Author Listed] Geneseq Submission; GSN, Database Accession No. GS_NUC_ALERT:WO2016161380.324727. Oct. 6, 2016. 1 page.
[No Author Listed], CRISPR Therapeutics and Vertex Announce New Clinical Data for Investigational Gene-Editing Therapy CTX001™ in Severe Hemoglobinopathies at the 25th Annual European Hematology Association (EHA) Congress. Vertex. Retrieved from: <https://news.vrtx.com/press-release/crispr-therapeutics-and-vertex-announce-new-clinical-data-investigational-gene>. Accessed on Jun. 25, 2020. 11 pages.
Bauer et al., An Erythroid Enhancer of BCL11A Subject to Genetuc Variation Determines Fetal Hemoglobin Level. Science. Oct. 11, 2013;342(6155):253-257.
Bauer et al., Crispr-Cas9 Saturating Mutagenesis Reveals an Achilles Heel in the BCL11A Erythroid Enhancer for Fetal Hemoglobin Induction (by Genome Editing). Blood. Dec. 2015;126(23): 638 pages.
Bauer et al., Fine-Mapping and Genome Editing Reveal An Essential Erythroid Enhancer At The HbF-Associated BCL11A Locus. Blood. Nov. 15, 2013;122(21):437, 1 page.
Bauer et al., Hemoglobin switching's surprise: the versatile transcription factor BCL11A is a master repressor of fetal hemoglobin. Curr Opin Genet Dev. Aug. 2015;33:62-70.
Blobel et al., An international effort to cure a global health problem: A report on the 19th Hemoglobin Switching Conference. Exp Hematol. Oct. 2015;43(10):1-30.
Brinkman et al., Easy quantification of template-directed CRISPR/Cas9 editing. Nucleic Acids Res. Jun. 1, 2018;46(10):e58. Doi: 10.1093/nar/gky164.
Brinkman et al., Easy quantitative assessment of genome editing by sequence trace decomposition. Nucleic Acids Res. Dec. 16, 2014;42(22):e168. Doi: 10.1093/nar/gku936. Epub Oct. 9, 2014.
Camaschella et al., A New Hereditary Persistence of Fetal Hemoglobin Deletion Has the Breakpoint Within the 3' β-Globin Gene Enhancer.Blood. 1990;75(4):1000-1005.
Canver et al., BCL11A enhancer dissection by Cas9-mediated in situ saturating mutagenesis. Nature. Nov. 12, 2015;527(7577):192-7.
Canver et al., Customizing the genome as therapy for the beta-hemoglobinopathies. Blood. Apr. 6, 2016;127(21):2536-45.
Chandrakasan et al., Gene Therapy for Hemoglobinopathies: The State of the Field and the Future. Hematol Oncol Clin North Am. Apr. 2014;28(2):1-23.
Cottle et al., Controlled delivery of beta-globin-targeting TALENs and CRISPR/Cas9 into mammalian cells for genome editing using microinjection. Sci Rep. Nov. 12, 2015;5:16031,13pages.

(56) References Cited

OTHER PUBLICATIONS

Cradick et al., CRISPR/Cas9 systems targeting β-globin and CCR5 genes have substantial off-target activity.Nucleic Acids Research. 2013;41(20):9584-9592.

De Montalembert, Management of Sickle Cell Disease. BMJ. Sep. 8, 2008;337:a1397. doi: 10.1136/bmj.a1397.

Deltcheva et al., CRISPR RNA maturation by trans-encoded small RNA and host factor Rnase III. Nature. Mar. 31, 2011;471(7340):602-7. Doi: 10.1038/nature09886.

Dever et al., CRISPR/Cas9 beta-globin gene targeting in human haematopoietic stem cells. Nature. Nov. 17, 2016;539(7629):384-389.

Dipersio et al., Plerixafor and G-CSF versus placebo and G-CSF to mobilixe hematopoietic stem cells for autologous stem cell transplantation in patients with multiple myeloma. Blood. Jun. 4, 2009;113(23):5720-6.

Ferrari et al., Gene Therapy Approaches to Hemoglobinopathies. Hematology-Oncology Clinics of North America. Sep. 9, 2019;31(5):835-852.

Flomenberg et al., The use of AMD3100 plus G-CSF for autologous hematopoietic progenitor cell mobilization is superior to G-CSF alone. Blood. Sep. 1, 2005;106(5):1867-74. Epub May 12, 2005.

Fonfara et al., Phylogeny of Cas9 determines functional exchange-ability of dual-RNA and Cas9 among orthologous type II CRISPR-Cas systems. Nucleic Acids Res. Feb. 2014;42(4):2577-90. Doi: 10.1093/nar/gkt1074. Epub Nov. 22, 2013.

Haridy, More early data revealed from landmark CRISPR gene editing human trial. New Atlas.Jun. 16, 2020. Retrieved from: <https://newatlas.com/medical/early-data-ctx001-crispr-gene-editing-human-trial/>. 6 pages.

Hendel et al., Chemically modified guide RNAs enhance CRISPR-Cas genome editing in human primary cells. Nat Biotechnol. Sep. 2015;33(9):985-89. Author manuscript provided. Available in PMC Sep. 1, 2016, 14 pages. doi: 10.1038/nbt.3290.

Henthorn et al., (A gamma delta beta)0-Thalassaemia in Blacks is due to a deletion of 34 kbp of DNA.British Journal of Haematology. 1985;59(2):343-356.

Howden et al., CRISPR gene editing causes hundreds of unintended, off-target mutations. Cosmos. 2017. 3 pages.

Huang et al., Abstract:Production of Gene-Corrected Adult Beta Globin Protein in Human Erythrocytes Differentiated from Patient iPSCs After Genome Editing of the Sickle Point Mutation. Stem Cells.2015;33(5):3.

Huang et al., Production of Gene-Corrected Adult Beta Globin Protein in Human Erythrocytes Differentiated from Patient iPSCs After Genome Editing of the Sickle Point Mutation. Stem Cells. May 2015;33(5):1470-9. doi: 10.1002/stem.1969.

Jinek et al., A programmable dual-RNA-guided DNA endonuclease in adaptive bacterial immunity. Science. Aug. 17, 2012;337(6096):816-21. Doi: 10.1126/science.1225829. Epub Jun. 28, 2012.

Joly et al., Identification and molecular characterization of four new large deletions in the β-globin gene cluster.Blood Cells, Molecules, and Diseases.2009;43:53-57.

Kuchler, Crispr puts first human in-body gene editing to test. Financial Times. Jan. 7, 2020. 6 pages.

Le Page, Three people with inherited diseases successfully treated with CRISPR. NewScientist. Jun. 12, 2020. Retrieved from: <https://www.newscientist.com/article/2246020-three-people-with-inherited-diseases-successfully-treated-with-crispr/>. 6 pages.

Li et al., Efficient CRISPR-Cas9 mediated gene disruption in primary erythroid progenitor cells. Haematologica. Jun. 2016;101(6):e216-9.

Li et al., Genome Editing in Erythroid Progenitor Cells Mediated By Crispr/Cas9. Blood. Dec. 2014; 124(21): 1345 pages.

Lin et al., Enhanced homology-directed human genome engineering by controlled timing of CRISPR/Cas9 delivery. eLIFE. Dec. 15, 2014;3:e04766, 13pages. doi: 10.7554/eLife.04766.

Maeder et al., Genome-editing Technologies for Geneand Cell Therapy. Mol Ther. Mar. 2016;24(3):430-446.

Mansilla-Soto et al., Cell and Gene Therapy for the Beta-Thalassemias: Advances and Prospects. Hum Gene Ther. Apr. 2016;27(4):295-304. doi: 10.1089/hum.2016.037.

Maresca et al., Obligate ligation-gated recombination (ObLiGaRe): custom-designed nuclease-mediated targeted integration through nonhomologous end joining. Genome Res. Mar. 2013;23(3):539-46. Doi: 10.1101/gr.145441.112. Epub Nov. 14, 2012.

Moreno-Mateos et al., CRISPRscan: designing highly efficient sgRNAs for CRISPR-Cas9 targeting in vivo. Nat Methods. Oct. 2015;12(10):982-8. doi: 10.1038/nmeth.3543. Epub Aug. 31, 2015.

Mullin, CRISPR eliminated symptoms of genetic disease in 2 patients. One Zero. Nov. 20, 2019. 5 pages.

Orkin et al., Recent advances in globin research using genome-wide association studies and gene editing. Ann N Y Acad Sci. Mar. 2016;1368(1):1-11.

Parsons, Vertex reveals promising data from first CRISPR-treated patients. PMLive. Nov. 20, 2020. Retrieved from: <http://www.pmlive.com/pharma_news/vertex_reveals_promising_data_from_first_crispr-treated_patients_1317564>. 2 pages.

Roosjen et al., Transcriptional regulators Myb and BCL11A interplay with DNA methyltransferase 1 in developmental silencing of embryonic and fetal β-like globin genes. FASEB J. Apr. 2014;28(4):1610-20. Epub Dec. 26, 2013.

Saglio et al., Italian Type of Deletional Hereditary Persistence of Fetal Hemoglobin.Blood.1986;686(3):646-651.

Sanjana et al., Improved vectors and genome-wide libraries for CRISPR screening. Nat Methods. Aug. 2014;11(8):783-4. doi: 10.1038/nmeth.3047.

Sanjana et al., Supplementary Materials: Improved vectors and genome-wide libraries for CRISPR screening. Nat Methods. Aug. 2014;11(8):22 pages. doi: 10.1038/nmeth.3047.

Sebastiano et al., In Situ Genetic Correction of the Sickle Cell Anemia Mutation in Human Induced Pluripotent Stem Cells Using Engineered Zinc Finger Nucleases.Stem Cells.2011;29:1717-1726.

Sheth et al., Sickle cell disease: time for a closer look at treatment options? BJH. Aug. 2013;162(4):455-64.

Song et al., Improved hematopoietic differentiation efficiency of gene-corrected beta-thalassemia induced pluripotent stem cells by CRISPR/Cas9 system. Stem Cells Dev. May 1, 2015;24(9):1053-65. doi: 10.1089/scd.2014.0347. Epub Feb. 5, 2015.

Stein et al., Compilation of Press Releases. Vertex, CRISPR Therapeutics. Nov. 19, 2019. 40 pages.

Stein, A Year In, 1st Patient To Get Gene Editing For Sickle Cell Disease Is Thriving. NPR. Jun. 23, 2020. Retrieved from: <https://www.npr.org/sections/health-shots/2020/06/23/877543610/a-year-in-1st-patient-to-get-gene-editing-for-sickle-cell-disease-is-thriving>. 26 pages.

Suzuki et al., Fetal globin gene repressors as drug targets for molecular therapies to treat the β-globinopathies. Mol Cell Biol. Oct. 1, 2014;34(19):3560-9. Epub Jul. 14, 2014.

Townes et al., Modified IPS Cells for Hemoglobinopathies. Blood. Dec. 2015;126(23):SCI-17.

Traxler et al., Genome Editing Recreates Hereditary Persistence of Fetal Hemoglobin in Primary Human Erythroblasts. Blood. Dec. 3, 2015;126(23):4 pages.

Urnov et al., Genome editing with engineered zinc finger nucleases. Nat Rev Genet. Sep. 2010;11:636-46. doi: 10.1038/nrg2842.

Wartiovaara et al., CRISPR-Cas9 gene editing of CD34+cells to increase fetal hemoglobin (HbF) production. Collaborative Congress of the European-Society-of-Gene-and-Cell-Therapy. Oct. 2015;26.

Xie et al., Seamless gene correction of [beta]-thalassemia mutation in patient-specific iPSCs using CRISPR/Cas9 and piggyBac. Genome Res. Aug. 5, 2014;24(9):1526-1533.

Xu et al., Both TALENs and CRISPR/Cas9 directly target the HBB IVS2-654 (C>T) mutation in [beta]-thalassemia-derived iPSCs. Scientific Reports. Jul. 9, 2015;5(12065):1-12.

Ye et al., Genome editing using CRISPR-Cas9 to create the HPFH genotype in HSPCs: An approach for treating sickle cell disease and β-thalassemia. Proc Natl Acad Sci U S A. Sep. 20, 2016;113(38):10661-5. doi: 10.1073/pnas.1612075113. Epub Sep. 6, 2016.

Zhu, Overview of guide RNA design tools for CRISPR-Cas9 genome editing technology. Front Biol. Aug. 2015;10(4):289-296. doi: 10.1007/s11515-015-1366-y.

(56)     References Cited

OTHER PUBLICATIONS

Zipkin, CRISPR's "magnificent moment" in the clinic. Nat Biotechnol. Dec. 6, 2019. 4 pages.

[No Author Listed] Endonuclease. Wikipedia. Accessed Jun. 3, 2021. 6 pages.

[No Author Listed]. Synth-a-Freeze, Product Manual. GIBCO. 2010;1-2.

Sun et al., Seamless correction of the sickle cell disease mutation of the HBB gene in human induced pluripotent stem cells using TALENs. Biotechnol Bioeng. May 2014;111(5):1048-53. doi: 10.1002/bit.25018. Epub Aug. 26, 2013.

Thein et al., Control of fetal hemoglobin: new insights emerging from genomics and clinical implications. Hum Mol Genet. Oct. 15, 2009:18(R2):R216-23. doi: 10.1093/hmg/ddp401.

Tuan et al., Different 3' end points of deletions causing delta beta-thalassemia and hereditary persistence of fetal hemoglobin: implications for the control of gamma-globin gene expression in man. Proc Natl Acad Sci U S A. Nov. 1983;80(22):6937-41. doi: 10.1073/pnas.80.22.6937.

Zhang et al., Optimization of genome editing through CRISPR-Cas9 engineering. Bioengineered. Apr. 2016;7(3):166-74. doi: 10.1080/21655979.2016.1189039.

[No Author Listed], Addgene, lentiCas9-Blast, plasmid #52962. Retrieved Apr. 2, 2023 from https://www.addgene.org/52963/. 2 pages.

Brendel et al., Lineage-specific BCL11A knockdown circumvents toxicities and reverses sickle phenotype. J Clin Invest. Oct. 3, 2016;126(10):3868-3878. doi: 10.1172/JCI87885. Epub Sep. 6, 2016.

Frangoul et al., CRISPR-Cas9 gene editing for sickle cell disease and β-thalassemia. New England Journal of Medicine. Jan. 21, 2021;384(3):252-60.

Hsu et al., Development and applications of CRISPR-Cas9 for genome engineering. Cell. Jun. 5, 2014;157(6):1262-78.

Kim et al., Highly efficient RNA-guided genome editing in human cells via delivery of purified Cas9 ribonucleoproteins. Genome research. Jun. 1, 2014;24(6):1012-9.

Leake et al., Gene therapy cures patient with sickle cell disease. Article Image. The Sunday Times. Dec. 1, 2019. Accessed Jun. 2020. 1 page.

Staahl et al., Efficient genome editing in the mouse brain by local delivery of engineered Cas9 ribonucleoprotein complexes. Nat Biotechnol. May 2017;35(5):431-434. doi: 10.1038/nbt.3806. Epub Feb. 13, 2017.

Svalgaard et al., Low-molecular-weight carbohydrate Pentaisomaltose may replace dimethyl sulfoxide as a safer cryoprotectant for cryopreservation of peripheral blood stem cells. Transfusion. May 2016;56(5):1088-95. doi: 10.1111/trf.13543. Epub Mar. 15, 2016.

Yannaki et al., Hematopoietic stem cell mobilization for gene therapy: superior mobilization by the combination of granulocyte-colony stimulating factor plus plerixafor in patients with β-thalassemia major. Human gene therapy. Oct. 1, 2013;24(10):852-60.

* cited by examiner

FIG. 5B ggggcccccttcactatctcaatgcaaataggccgaacgaccgggctaaactcccctgggttgg   SEQ ID NO: 228,309

BCL11A_58+ Region Indel Freq in K562

BCL11A_58+ Region Indel Freq in K562

FIG. 10B

| | gRNA Combination | | | | |
|---|---|---|---|---|---|
| sample | left gRNA | position | right gRNA | position | deletion size |
| 1 | BCL11A_74F | 1340bp | BCL11A_19 | 1490bp | 150bp |
| 2 | BCL11A_74F | 1340bp | BCL11A_24 | 1580bp | 240bp |
| 3 | BCL11A_74F | 1340bp | BCL11A_51 | 1510bp | 170bp |
| 4 | BCL11A_74F | 1340bp | BCL11A_26 | 2470bp | 1130bp |
| 5 | BCL11A_74F | 1340bp | BCL11A_83 | 2430bp | 1090bp |
| 6 | BCL11A_74F | 1340bp | BCL11A_86 | 2360bp | 1010bp |
| 7 | BCL11A_74F | 1340bp | BCL11A_45 | 2350bp | 1020bp |
| 8 | BCL11A_74F | 1340bp | BCL11A_90 | 2220bp | 880bp |
| 9 | BCL11A_74F | 1340bp | BCL11A_74R | 2170bp | 830bp |
| 10 | BCL11A_74F | 1340bp | BCL11A_57 | 2100bp | 760bp |
| 11 | BCL11A_62 | 1400bp | NA | 1400bp | NA |
| 12 | BCL11A_74 | 1340bp | NA | 1340bp | NA |
| 13 | BCL11A_19 | 1490bp | NA | 1490bp | NA |
| 14 | BCL11A_24 | 1580bp | NA | 1580bp | NA |
| 15 | BCL11A_51 | 1510bp | NA | 1510bp | NA |
| 16 | BCL11A_26 | 2470bp | NA | 2470bp | NA |
| 17 | BCL11A_83 | 2430bp | NA | 2430bp | NA |
| 18 | BCL11A_86 | 2360bp | NA | 2360bp | NA |
| 19 | BCL11A_45 | 2350bp | NA | 2350bp | NA |
| 20 | BCL11A_90 | 2220bp | NA | 2220bp | NA |
| 21 | BCL11A_74 | 2170bp | NA | 2170bp | NA |
| 22 | BCL11A_57 | 2100bp | NA | 2100bp | NA |
| 23 | CL01 | controls | NA | controls | NA |
| 24 | CL08 | controls | NA | controls | NA |
| 25 | CL01 | controls | CL08 | controls | 7200bp |
| 26 | IL2RG | controls | NA | controls | NA |
| 27 | hEMX1 | controls | NA | controls | NA |

FIG. 11A

| COSMID gRNA NAME | CTX gRNA name | gRNA Seq (20nt) without PAM | gRNA |
|---|---|---|---|
| BCL11A_26 | R1 | AATACATCCTTGAGCTACAC | R1 |
| BCL11A_83 | R2 | GTGATGCTGACAGGCCACAT | R2 |
| BCL11A_30 | R3 | CATGGGAGAGTGGGAAGACG | R3 |
| BCL11A_85 | R4 | ATGGGAGAGTGGGAAGACGT | R4 |
| BCL11A_60 | R5 | AGAGTGGGAAGACGTGGGCT | R5 |
| BCL11A_50 | R6 | TCTGTGCATGGCCTCTAAAC | R6 |
| BCL11A_86 | R7 | CTGTGCATGGCCTCTAAACT | R7 |
| BCL11A_45 | R8 | TCTAAACTGGGCAGTGACCA | R8 |
| BCL11A_49 | R9 | ACTGGGCAGTGACCATGGCC | R9 |
| BCL11A_84 | R10 | TTGCCCCTCTGTAAACAAGG | R10 |
| BCL11A_92 | R11 | TTTTGCCAAGATGGGAGTAT | R11 |
| BCL11A_90 | R12 | TTTGCCAAGATGGGAGTATG | R12 |
| BCL11A_74 | R13 | AGTGAGATGAGATATCAAAG | R13 |
| BCL11A_42 | R14 | CCATCTCCCTAATCTCCAAT | R14 |
| BCL11A_31 | R15 | AATTGGCAAAGCCAGACTTG | R15 |
| BCL11A_57 | R16 | AGACTTGGGGCAATACAGAC | R16 |
| BCL11A_54 | R17 | TGAACTAAAATGCTGCCTCC | R17 |
| BCL11A_52 | R18 | CCTTTCCCCAATTCCTAGTT | R18 |
| BCL11A_20 | R19 | AAGGAAAGAATATGACGTC | R19 |
| BCL11A_65 | R20 | AGGAAAGAATATGACGTCA | R20 |
| BCL11A_1 | R21 | GAAAAGAATATGACGTCAGG | R21 |
| BCL11A_16 | R22 | AAGAATATGACGTCAGGGGG | R22 |
| BCL11A_41 | R23 | TCAGGGGGAGGCAAGTCAGT | R23 |
| BCL11A_38 | R24 | ACAGATCCTAACACAGTAGC | R24 |
| BCL11A_10 | R25 | CACAGTAGCTGGTACCTGAT | R25 |
| BCL11A_61 | R26 | TGATAGGTGCCTATATGTGA | R26 |
| BCL11A_70 | R27 | AGGTGCCTATATGTGATGGA | R27 |
| BCL11A_76 | R28 | GGTGCCTATATGTGATGGAT | R28 |
| BCL11A_21 | R29 | GAGGAGGGGAGAGTGCAGAC | R29 |
| BCL11A_66 | R30 | AGGAGGGGAGAGTGCAGACA | R30 |
| BCL11A_93 | R31 | TTTTGGGAGTCCACACGGCA | R31 |
| BCL11A_34 | R32 | CCAAGAGAGCCTTCCGAAAG | R32 |
| BCL11A_51 | R33 | CCTTCCGAAAGAGGCCCCCC | R33 |
| BCL11A_89 | R34 | CTTCCGAAAGAGGCCCCCCT | R34 |
| BCL11A_48 | R35 | CCTGGGCAAACGGCCACCGA | R35 |
| BCL11A_14 | R36 | CACGCCCCCACCCTAATCAG | R36 |
| BCL11A_81 | R37 | ATCAGAGGCCAAACCCTTCC | R37 |
| BCL11A_87 | R38 | CTTCAAAGTTGTATTGACCC | R38 |
| BCL11A_62 | R39 | GGCCTATGTTATTACCTGTA | R39 |
| BCL11A_13 | R40 | TACCTGTATGGACTTTGCAC | R40 |
| BCL11A_64 | R41 | TGCTCTTACTTATGCACACC | R41 |
| BCL11A_78 | R42 | CTAGCTGCCTTCCTTATCAC | R42 |
| BCL11A_27 | R43 | TATCACAGGAATAGCACCCA | R43 |
| BCL11A_3 | R44 | GAACCCCCTATAAACTAGTC | R44 |
| BCL11A_15 | R45 | AACTAGTCTGGTTTGCCCAT | R45 |

FIG. 11B

| | | | | |
|---|---|---|---|---|
| BCL11A_46 | R46 | ACTAGTCTGGTTTGCCCATG | | R46 |
| BCL11A_82 | R47 | GTCAGGCTGTTTTCCAGGGT | | R47 |
| BCL11A_81 | F1 | ATGGTCACTGCCCAGTTTAG | | F1 |
| BCL11A_51 | F2 | GGGCAACCCAGGTCCAGAGT | | F2 |
| BCL11A_60 | F3 | TGTTTACAGAGGGGCAACCC | | F3 |
| BCL11A_7 | F4 | TACAACCTCCTTGTTTACAG | | F4 |
| BCL11A_84 | F5 | TTTATAAGACATTAGGGTAT | | F5 |
| BCL11A_49 | F6 | GGCTTTGCCAATTGGAGATT | | F6 |
| BCL11A_58 | F7 | AGTCTGTATTGCCCCAAGTC | | F7 |
| BCL11A_56 | F8 | AGGTGTAACTAATAAATACC | | F8 |
| BCL11A_39 | F9 | TCTGACCCAAACTAGGAATT | | F9 |
| BCL11A_72 | F10 | TTCTGACCCAAACTAGGAAT | | F10 |
| BCL11A_92 | F11 | CTTTTCTTCTGACCCAAACT | | F11 |
| BCL11A_65 | F12 | ATCACATATAGGCACCTATC | | F12 |
| BCL11A_11 | F13 | GACTCCCAAAATTGTAAAGG | | F13 |
| BCL11A_78 | F14 | GTGGACTCCCAAAATTGTAA | | F14 |
| BCL11A_24 | F15 | AATTTGTATGCCATGCCGTG | | F15 |
| BCL11A_34 | F16 | TCGGAAGGCTCTCTTGGTGA | | F16 |
| BCL11A_37 | F17 | CCTCTTTCGGAAGGCTCTCT | | F17 |
| BCL11A_30 | F18 | CCAGGGGGGCCTCTTTCGGA | | F18 |
| BCL11A_55 | F19 | CGGTGGCCGTTTGCCCAGGG | | F19 |
| BCL11A_35 | F20 | TCGGTGGCCGTTTGCCCAGG | | F20 |
| BCL11A_68 | F21 | ATCGGTGGCCGTTTGCCCAG | | F21 |
| BCL11A_19 | F22 | CATCGGTGGCCGTTTGCCCA | | F22 |
| BCL11A_31 | F23 | CCATCGGTGGCCGTTTGCCC | | F23 |
| BCL11A_79 | F24 | CTGGCAGACCTCTCCATCGG | | F24 |
| BCL11A_43 | F25 | GGACTGGCAGACCTCTCCAT | | F25 |
| BCL11A_91 | F26 | GTTTGGCCTCTGATTAGGGT | | F26 |
| BCL11A_61 | F27 | GGTTTGGCCTCTGATTAGGG | | F27 |
| BCL11A_14 | F28 | AAGGGTTTGGCCTCTGATTA | | F28 |
| BCL11A_62 | F29 | CTAACAGTTGCTTTTATCAC | Spy101 | F29 |
| BCL11A_74 | F30 | CTCTTAGACATAACACACCA | | F30 |
| BCL11A_36 | F31 | ACTCTTAGACATAACACACC | | F31 |
| BCL11A_67 | F32 | GTCCATACAGGTAATAACAT | | F32 |
| BCL11A_66 | F33 | TTCCAGTGCAAAGTCCATAC | | F33 |
| BCL11A_38 | F34 | GCTGAAAAGCGATACAGGGC | | F34 |
| BCL11A_21 | F35 | GATGGCTGAAAAGCGATACA | | F35 |
| BCL11A_45 | F36 | AGATGGCTGAAAAGCGATAC | | F36 |
| BCL11A_12 | F37 | AAGGCAGCTAGACAGGACTT | | F37 |
| BCL11A_5 | F38 | GAAGGCAGCTAGACAGGACT | | F38 |
| BCL11A_17 | F39 | GATAAGGAAGGCAGCTAGAC | | F39 |
| BCL11A_53 | F40 | TGGGTGCTATTCCTGTGATA | | F40 |
| BCL11A_75 | F41 | CTGAGGTACTGATGGACCTT | | F41 |
| BCL11A_40 | F42 | TCTGAGGTACTGATGGACCT | | F42 |
| BCL11A_64 | F43 | TTATGGGGGTTCTACTCTG | | F43 |
| BCL11A_4 | F44 | AAACCAGACTAGTTTATGG | | F44 |
| BCL11A_1 | F45 | CAAACCAGACTAGTTTATAG | | F45 |

FIG. 11C

| BCL11A_46 | F46 | GGCAAACCAGACTAGTTTAT | F46 |
| BCL11A_28 | F47 | ACAGCCTGACTGTGCCCCAT | F47 |
| IL2RG | ctrl | TGGTAATGATGGCTTCAACA | IL2RG |
| hEMX1 | ctrl | GAGTCCGAGCAGAAGAAGAA | hEMX1 |

FIG. 12

Donor LKP06B:
144hrs Thaw to Differentiation

Donor LKP06B:
144hrs Thaw to Differentiation

| RXN | Guides | Electroporated (ug) |
|---|---|---|
| 1 | SPY101 then SD2 | 1.5/1.5 |
| 2 | SD2 then SPY101 | 1.5/1.5 |
| 3 | SPY101 and SD2 | 1.5&1.5 |
| 4 | SPY101 | 3 |
| 5 | SD2 | 3 |
| 6 | EX2-2_EX2-3 | 1.5/1.5 |
| 7 | Mock | |
| 8 | Untreated | |

- Reaction 1
- Reaction 2
- Reaction 3
- Reaction 4
- Reaction 5
- Reaction 6
- Reaction 7
- Reaction 8

Fred Hutch Donor 304:
168hrs Thaw to Differentiation

Donor LKP06B:
144hrs Thaw to Differentiation

| | Guides | Electroporated (ug) |
|---|---|---|
| 1 | SPY101 then SD2 | 1.5/1.5 |
| 2 | SD2 then SPY101 | 1.5/1.5 |
| 3 | SPY101 and SD2 | 1.5&1.5 |
| 4 | SPY101 alone | 3 |
| 5 | SD2 alone | 3 |

Donor LKP06B:
144hrs Thaw to Differentiation

Donor LKP06B:
144hrs Thaw to Differentiation

| Reaction | Guides | Electroporated |
|---|---|---|
| 1 | SPY101 then SD2 | 1.5/1.5 |
| 2 | SD2 then SPY101 | 1.5/1.5 |
| 3 | SPY101 and SD2 | 1.5&1.5 |
| 4 | SPY101 | 3 |
| 5 | SD2 | 3 |
| 6 | EX2-2_EX2-3 | 1.5/1.5 |
| 7 | Mock | |
| 8 | Untreated | |

FIG. 16
Donor LKP06B:
144hrs Thaw to Differentiation

| Reaction | Guides | Electroporated |
|---|---|---|
| 1 | SPY101 then SD2 | 1.5/1.5 |
| 2 | SD2 then SPY101 | 1.5/1.5 |
| 3 | SPY101 and SD2 | 1.5&1.5 |
| 4 | SPY101 | 3 |
| 5 | SD2 | 3 |
| 6 | EX2-2_EX2-3 | 1.5/1.5 |
| 7 | Mock | |
| 8 | Untreated | |

Donor LKP06B:
*144hrs Thaw to Differentiation*

Fred Hutch Donor 304:
*168hrs Thaw to Differentiation*

| Reaction | Guides | Electroporated |
|---|---|---|
| 1 | SPY101 then SD2 | 1.5/1.5 |
| 2 | SD2 then SPY101 | 1.5/1.5 |
| 3 | SPY101 and SD2 | 1.5&1.5 |
| 4 | SPY101 | 3 |
| 5 | SD2 | 3 |
| 6 | EX2-2_EX2-3 | 1.5/1.5 |
| 7 | Mock | |
| 8 | Untreated | |

Donor LKP06B:
144hrs Thaw to Differentiation

Fred Hutch Donor 304:
168hrs Thaw to Differentiation

| Reaction | Guides | Electroporated |
|---|---|---|
| 1 | SPY101 then SD2 | 1.5/1.5 |
| 2 | SD2 then SPY101 | 1.5/1.5 |
| 3 | SPY101 and SD2 | 1.5&1.5 |
| 4 | SPY101 | 3 |
| 5 | SD2 | 3 |
| 6 | EX2-2_EX2-3 | 1.5/1.5 |
| 7 | Mock | |
| 8 | Untreated | |

Donor LKP06B:
*144hrs Thaw to Differentiation*

Fred Hutch Donor 304:
*168hrs Thaw to Differentiation*

| Reaction | Guides | Electroporated |
|---|---|---|
| 1 | SPY101 then SD2 | 1.5/1.5 |
| 2 | SD2 then SPY101 | 1.5/1.5 |
| 3 | SPY101 and SD2 | 1.5&1.5 |
| 4 | SPY101 | 3 |
| 5 | SD2 | 3 |
| 6 | EX2-2_EX2-3 | 1.5/1.5 |
| 7 | Mock | |
| 8 | Untreated | |

FIG. 20

Donor LKP06B:
144hrs Thaw to Differentiation

% HbF Expression
HbF/(HbF+HbA)

Reaction

| Reaction | Guides | Electroporated |
|---|---|---|
| 1 | SPY101 then SD2 | 1.5/1.5 |
| 2 | SD2 then SPY101 | 1.5/1.5 |
| 3 | SPY101 and SD2 | 1.5&1.5 |
| 4 | SPY101 | 3 |
| 5 | SD2 | 3 |
| 6 | EX2-2_EX2-3 | 1.5/1.5 |
| 7 | Mock | |
| 8 | Untreated | |

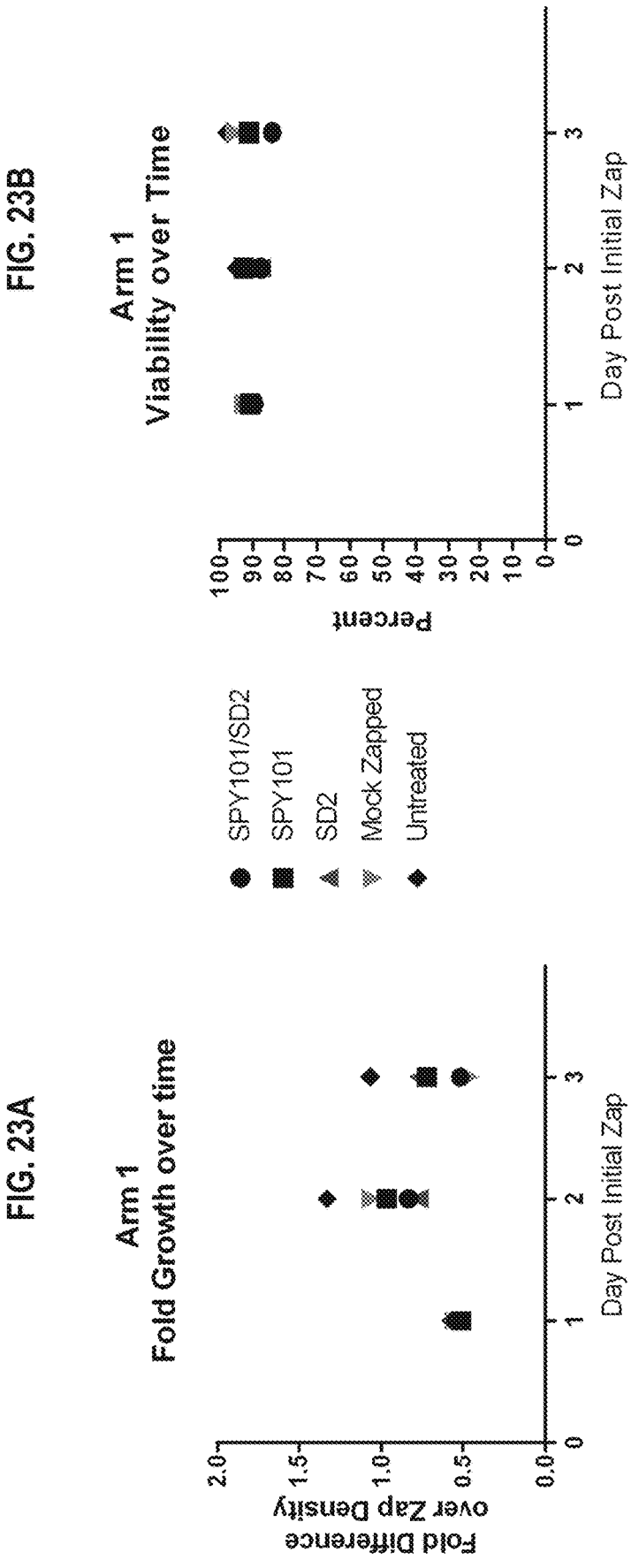

Arm 2
Viability over Time

SPY101/SD2
SPY101
SD2
Mock Zapped
Untreated

Arm 2
Fold Growth over time

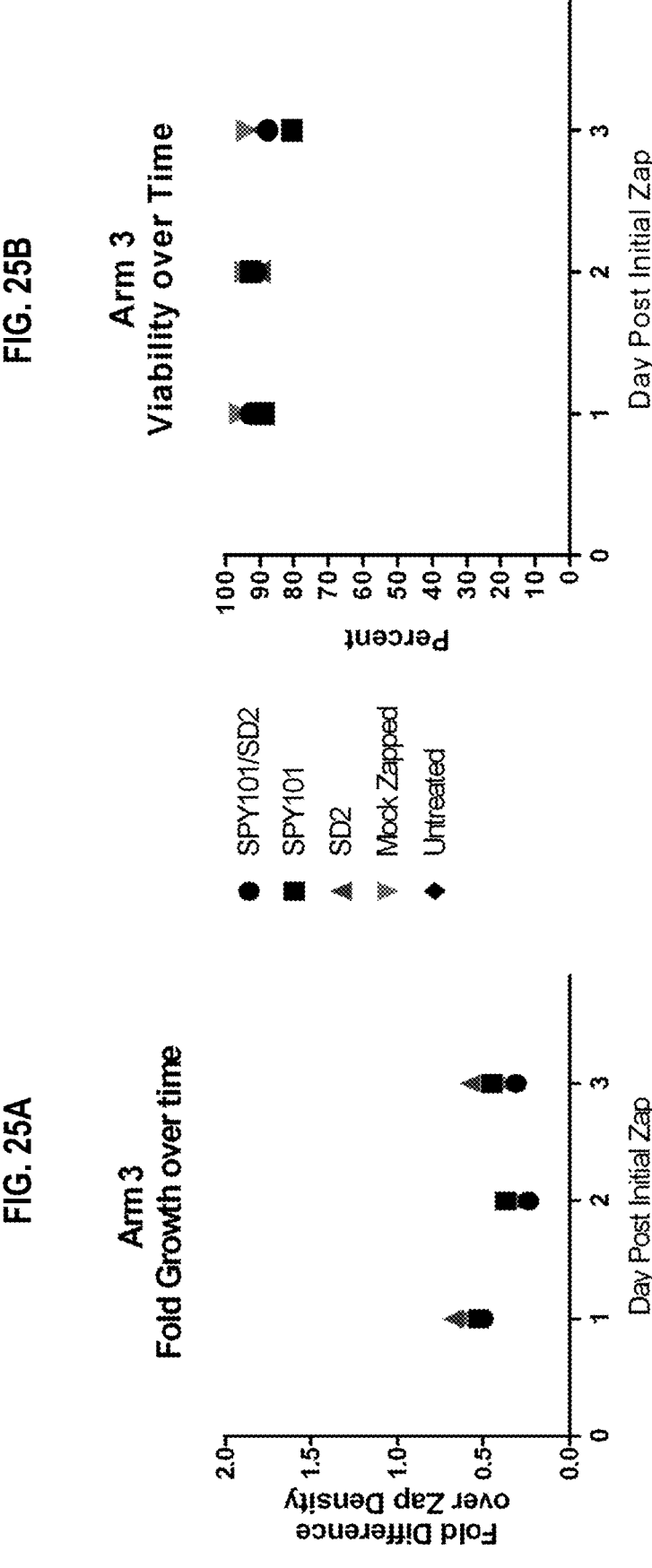

Donor LKP06B:
*96hrs Thaw to Differentiation*

Donor LKP06B:
*96hrs Thaw to Differentiation*

⁎ Arm 1/Reaction 1
⁎ Arm 2/Reaction 1
⁎ Arm 3/Reaction 1
⁑ Arm 1/Reaction 2
⁑ Arm 1/Reaction 3
⁑ Arm1/Reaction 4
⁑ Arm 1/Reaction 5

| Reaction | Guides | Electroporated (ug) |
|---|---|---|
| 1 | SPY101 then SD2 | 1.5/1.5 |
| 2 | SPY101 | 3 |
| 3 | SD2 | 3 |
| 4 | Mock | |
| 5 | Untreated | |

FIG. 27

Donor LKP06B:
96hrs Thaw to Differentiation

| Reaction | Guides | Electroporated (ug) |
|---|---|---|
| 1 | SPY101 then SD2 | 1.5/1.5 |
| 2 | SPY101 | 3 |
| 3 | SD2 | 3 |
| 4 | Mock | |
| 5 | Untreated | |

FIG. 28B (cont.)

Arm 2

Arm 2

| Reaction | Guides | Electroporated (ug) |
|---|---|---|
| 1 | SPY101 then SD2 | 1.5/1.5 |
| 2 | SPY101 | 3 |
| 3 | SD2 | 3 |
| 4 | Mock | |
| 5 | Untreated | |

Donor LKP06B:
96hrs Thaw to Differentiation

FIG. 33B

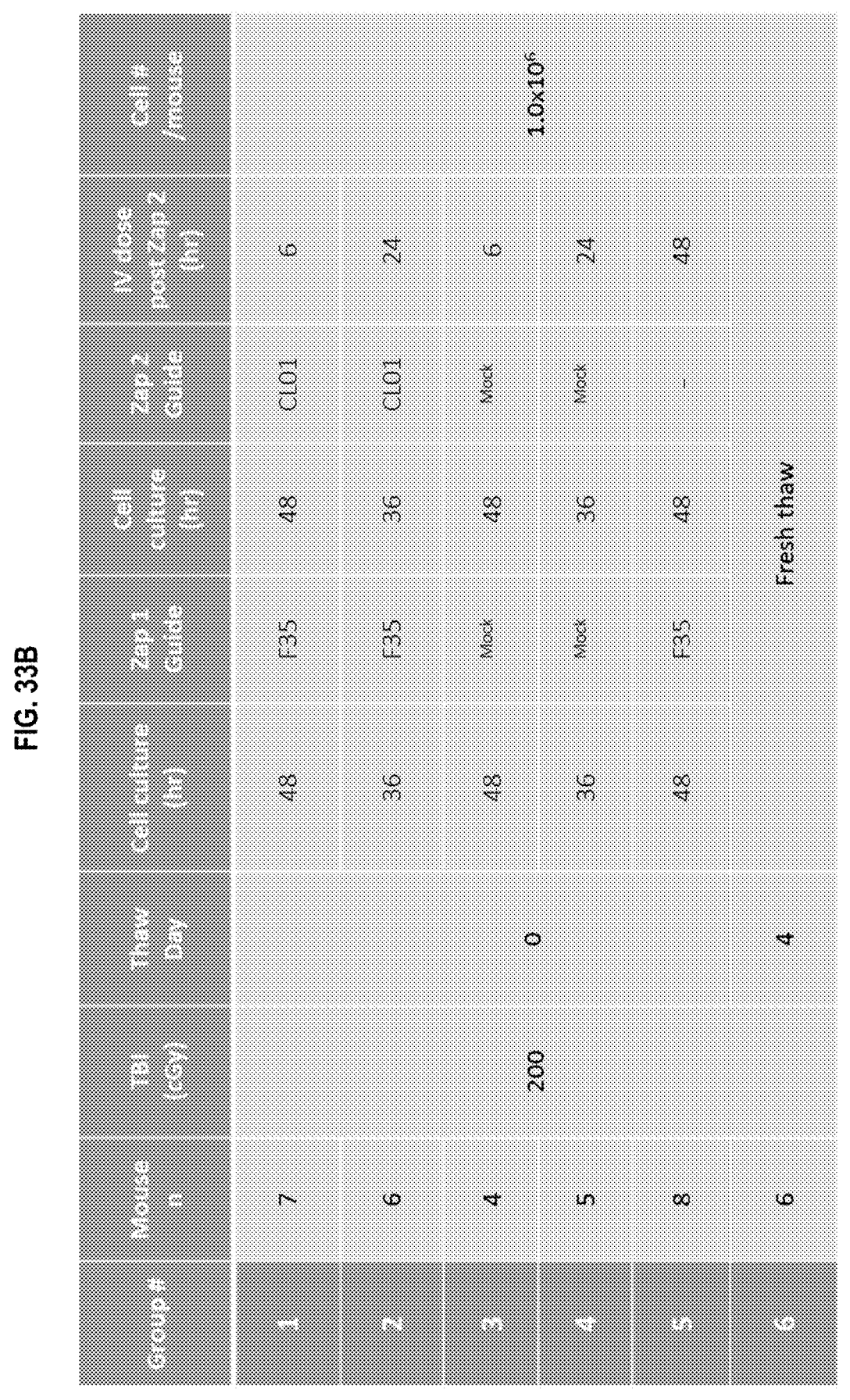

| Group# | Mouse ID | TBI TBD (cGy) | TBI calculation Day | Cell calculation (h) | Zap1 Guide | Cell culture (h) | Zap2 Guide | M-dose Day 2/Zap2 (h) | Cells /mouse |
|---|---|---|---|---|---|---|---|---|---|
| 1 | 7 | | | 48 | F35 | 48 | CI01 | 6 | |
| 2 | 6 | | | 36 | F35 | 36 | CI01 | 24 | |
| 3 | 4 | 200 | 0 | 48 | Mock | 48 | Mock | 6 | $1.0 \times 10^6$ |
| 4 | 5 | | | 36 | Mock | 36 | Mock | 24 | |
| 5 | 8 | | | 48 | F35 | 48 | – | 48 | |
| 6 | 6 | | 4 | | Fresh thaw | | | | |

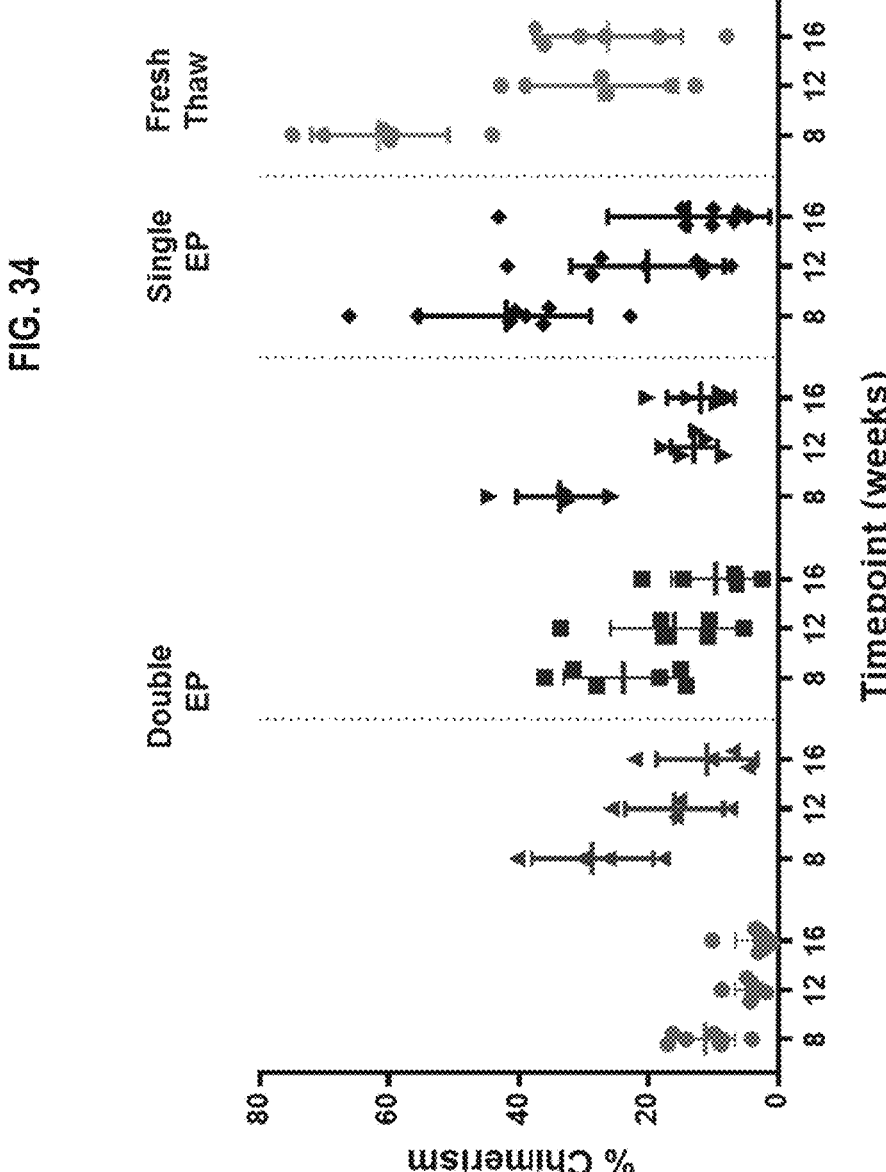
FIG. 34

FIG. 36
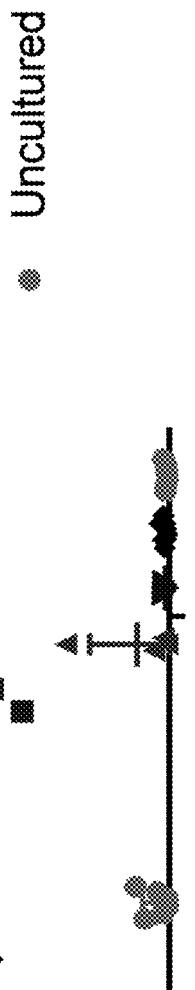
● 48/48/6 with Guides
■ 36/36/24 with Guides
▲ 48/48/6 Mock EP
▼ 36/36/24 Mock EP
◆ 48/48 Single EP with Guide
● Uncultured CD34 cells
Editing Persistance in Bone Marrow at Week 16
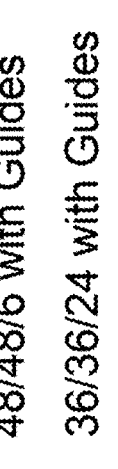
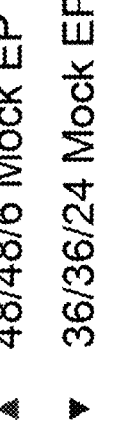
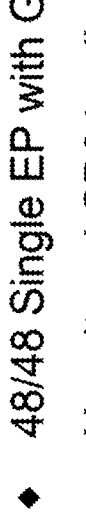

FIG. 37

Timeline: Thaw D-5, D-3.5, D-2, D0 (1st gDNA harvest), Phase I, D3, D5, D7 (2nd gDNA harvest), Phase II, D10, D12, D14 (Differentiation/Enucleation FACS), Phase III, D18, RNA/HPLC

| Reaction | Electroporation #1 Day 3.5 | Electroporation #2 Day 2 |
| --- | --- | --- |
| 1 | SPY101 (1.5ug) | HPFH5_1 And HPFH5_D (0.75ug each) |
| 2 | 1450 (1.5ug) | HPFH5_1 And HPFH5_D (0.75ug each) |
| 3 | SPY101 (1.5ug) | Kenya (K5 And K17) (1ug&2ug) |
| 4 | 1450 (1.5ug) | Kenya (K5 And K17) (1ug&2ug) |
| 5 | HFPH5_T7 And HPFH5_D (0.75ug each) | HFPH5_1 And HPFH5_T5 (0.75ug each) |
| 6 | SPY101 (3ug) | - |
| 7 | 1450 (3ug) | - |
| 8 | HFPH5_T7 And HPFH5_D (0.75ug each) | - |
| 9 | HPFH5_1 And HPFH5_T5 (0.75ug each) | - |
| 10 | HFPH5_T7, HPFH5_D, HPFH5_1 And HPFH5_T5 (0.75ug each) | - |
| 11 | Kenya (K5 And K17) (1ug&2ug) | - |
| 12 | Exon 2-2/2-3 | - |
| 13 | Mock EP | Mock EP |
| 14 | Untreated | |

FIG. 38

| Guide Combinations | Electroporation #1 | Electroporation #2 | Average Fold Growth during Diff Relative to Mock EP | Chr2 Editing Analysis (Done 4 Days Post 2nd Zap) | Chr11 Deletion Analysis (Done 4 Days Post 2nd Zap) | %HbF/(HbF+HbA) |
|---|---|---|---|---|---|---|
| SPY Alone | SPY101 | - | 0.90±0.01 | 88±0 | - | 38±7 |
| SPY Then HPFH5_1&D | SPY101 | HPFH5_1 HPFH5_D | 0.83±0.02 | 88±0 | 46±6 | 64±2 |
| SPY Then Kenya | SPY101 | K05 K17 | 0.77±0.02 | 90±2 | 28±3 | 53±3 |
| 1450 Alone | 1450 | - | 0.93±0.05 | 93±0 | - | 40±5 |
| 1450 Then HPFH5_1&D | 1450 | HPFH5_1 HPFH5_D | 0.82±0.02 | 91±3 | 41±8 | 62±5 |
| 1450 Then Kenya | 1450 | K05 K17 | 0.80±0.04 | 92±1 | 30±3 | 59±2 |
| HPFH5_T7&D | HPFH5_T7 HPFH5_D | - | 0.96±0.01 | - | 39±4 | 37±8 |
| HPFH5_1&T5 | HPFH5_1 HPFH5_T5 | - | 0.96±0.08 | - | 39±5 | 40±3 |
| HPFH5_T7&D Then HPFH5_1&T5 | HPFH5_T7 HPFH5_D | HPFH5_1 HPFH5_T5 | 0.88±0.01 | - | 61±1 | 53±5 |
| HPFH5_T7,D,1 &T5 | HPFH5_T7,D,1 &T5 | - | 0.99±0.03 | - | 33±1 | 32±8 |
| Kenya (K17&K05) | K05 K17 | - | 0.94±0.03 | - | 30±3 | 24±11 |
| Exon 2-2/2-3 | Exon 2-2/2-3 | - | 0.65±0.01 | - | 63±2 | 42±9 |
| Mock EP | Cas9 alone | Cas9 alone | 1 | - | - | 11±3 |

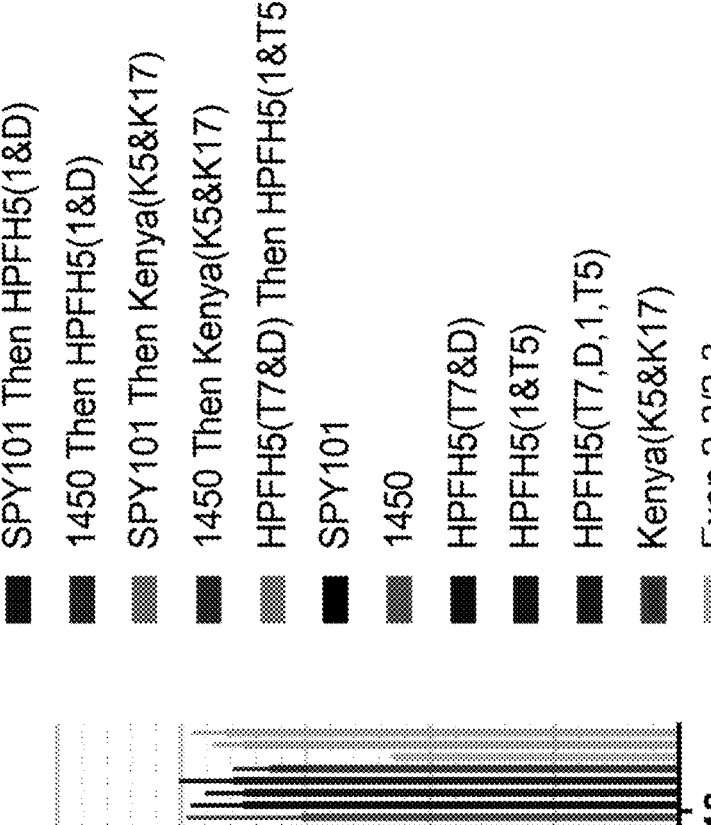
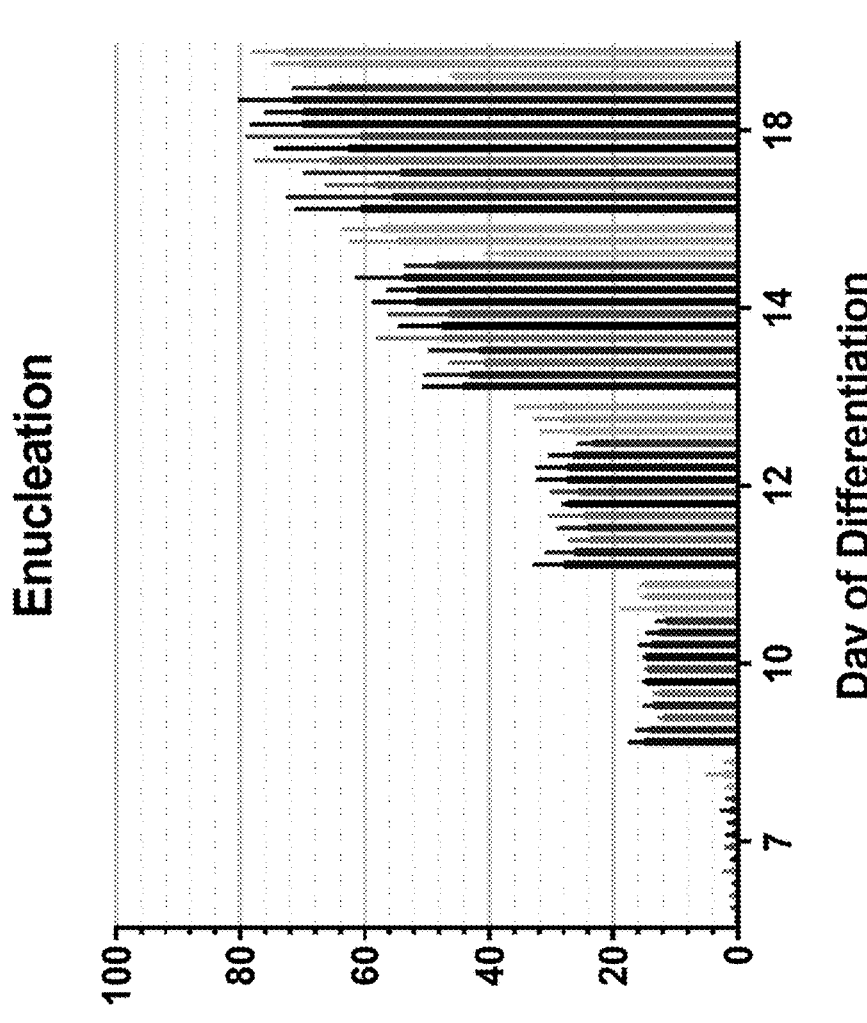
FIG. 41

FIG. 42B

γ/(γ+β) globin
mRNA Expression

HbF via HPLC
Day 18 of In-vitro Differentiation

| EP#1: 1.5ug 1450 | EP#2: 0.75ug HPFH5(s) | Chr2 Editing | Chr1 Deletion |
|---|---|---|---|
| 0.375ug Cas9 | 1.5ug Cas9 | 88% | 44% |
|  | 0.75ug Cas9 | 87% | 47% |
|  | 0.375ug Cas9 | 88% | 36% |
|  | Mock EP | 89% |  |
| 0.1875ug Cas9 | 1.5ug Cas9 | 69% | 44% |
|  | 0.75ug Cas9 | 69% | 43% |
|  | 0.375ug Cas9 | 70% | 29% |
|  | Mock EP | 71% |  |
| Mock EP | 1.5ug Cas9 |  | 35% |
|  | 0.75ug Cas9 |  | 44% |
|  | 0.375ug Cas9 |  | 36% |
|  | Mock EP |  |  |

| EP#1: 1.5ug 1450 | EP#2: 0.75ug HPFH5(s) | Chr2 Editing | Chr1 Deletion |
|---|---|---|---|
| 3ug Cas9 | 1.5ug Cas9 | 88% | 46% |
|  | 0.75ug Cas9 | 89% | 46% |
|  | 0.375ug Cas9 | 89% | 41% |
|  | Mock EP | 89% |  |
| 1.5ug Cas9 | 1.5ug Cas9 | 94% | 44% |
|  | 0.75ug Cas9 | 92% | 43% |
|  | 0.375ug Cas9 | 94% | 32% |
|  | Mock EP | 93% |  |
| 0.75ug Cas9 | 1.5ug Cas9 | 91% | 43% |
|  | 0.75ug Cas9 | 91% | 40% |
|  | 0.375ug Cas9 | 90% | 29% |
|  | Mock EP | 91% |  |

FIG. 45

| EP#1: 1.5ug 1450 | EP#2: 0.75ug HPFH5(s) | V/α mRNA Ratio | V/(γ+β) mRNA Ratio |
|---|---|---|---|
| 3ug Cas9 | 1.5ug Cas9 | 1.36 | 0.87 |
| | 0.75ug Cas9 | 1.40 | 0.87 |
| | 0.375ug Cas9 | 1.43 | 0.83 |
| | Mock EP | 1.04 | 0.66 |
| 1.5ug Cas9 | 1.5ug Cas9 | 1.58 | 0.88 |
| | 0.75ug Cas9 | 1.41 | 0.85 |
| | 0.375ug Cas9 | 1.34 | 0.80 |
| | Mock EP | 1.10 | 0.66 |
| 0.75ug Cas9 | 1.5ug Cas9 | 1.36 | 0.83 |
| | 0.75ug Cas9 | 1.44 | 0.84 |
| | 0.375ug Cas9 | 1.30 | 0.78 |
| | Mock EP | 1.04 | 0.66 |

| EP#1: 1.5ug 1450 | EP#2: 0.75ug HPFH5(s) | V/α mRNA Ratio | V/(γ+β) mRNA Ratio |
|---|---|---|---|
| 0.375ug Cas9 | 1.5ug Cas9 | 0.52 | 0.87 |
| | 0.75ug Cas9 | 0.50 | 0.87 |
| | 0.375ug Cas9 | 0.47 | 0.84 |
| | Mock EP | 0.34 | 0.66 |
| 0.1875ug Cas9 | 1.5ug Cas9 | 0.41 | 0.81 |
| | 0.75ug Cas9 | 0.40 | 0.81 |
| | 0.375ug Cas9 | 0.34 | 0.72 |
| | Mock EP | 0.28 | 0.57 |
| Mock EP | 1.5ug Cas9 | 0.20 | 0.56 |
| | 0.75ug Cas9 | 0.25 | 0.67 |
| | 0.375ug Cas9 | 0.21 | 0.60 |
| | Mock EP | 0.22 | 0.67 |

FIG. 46

| EP#1: 1.5ug 1450 | EP#2: 0.75ug HPFH5(s) | %HbF/(HbF+ HbA) |
|---|---|---|
| 0.375ug Cas9 | 1.5ug Cas9 | 75% |
| | 0.75ug Cas9 | 74% |
| | 0.375ug Cas9 | 67% |
| | Mock EP | 43% |
| 0.1875ug Cas9 | 1.5ug Cas9 | 66% |
| | 0.75ug Cas9 | 70% |
| | 0.375ug Cas9 | 60% |
| | Mock EP | 38% |
| Mock EP | 1.5ug Cas9 | 45% |
| | 0.75ug Cas9 | 55% |
| | 0.375ug Cas9 | 43% |
| | Mock EP | 53% |

| EP#1: 1.5ug 1450 | EP#2: 0.75ug HPFH5(s) | %HbF/(HbF+ HbA) |
|---|---|---|
| 3ug Cas9 | 1.5ug Cas9 | 81% |
| | 0.75ug Cas9 | 79% |
| | 0.375ug Cas9 | 71% |
| | Mock EP | 48% |
| 1.5ug Cas9 | 1.5ug Cas9 | 76% |
| | 0.75ug Cas9 | 77% |
| | 0.375ug Cas9 | 69% |
| | Mock EP | 50% |
| 0.75ug Cas9 | 1.5ug Cas9 | 74% |
| | 0.75ug Cas9 | 75% |
| | 0.375ug Cas9 | 66% |
| | Mock EP | 45% |

FIG. 47

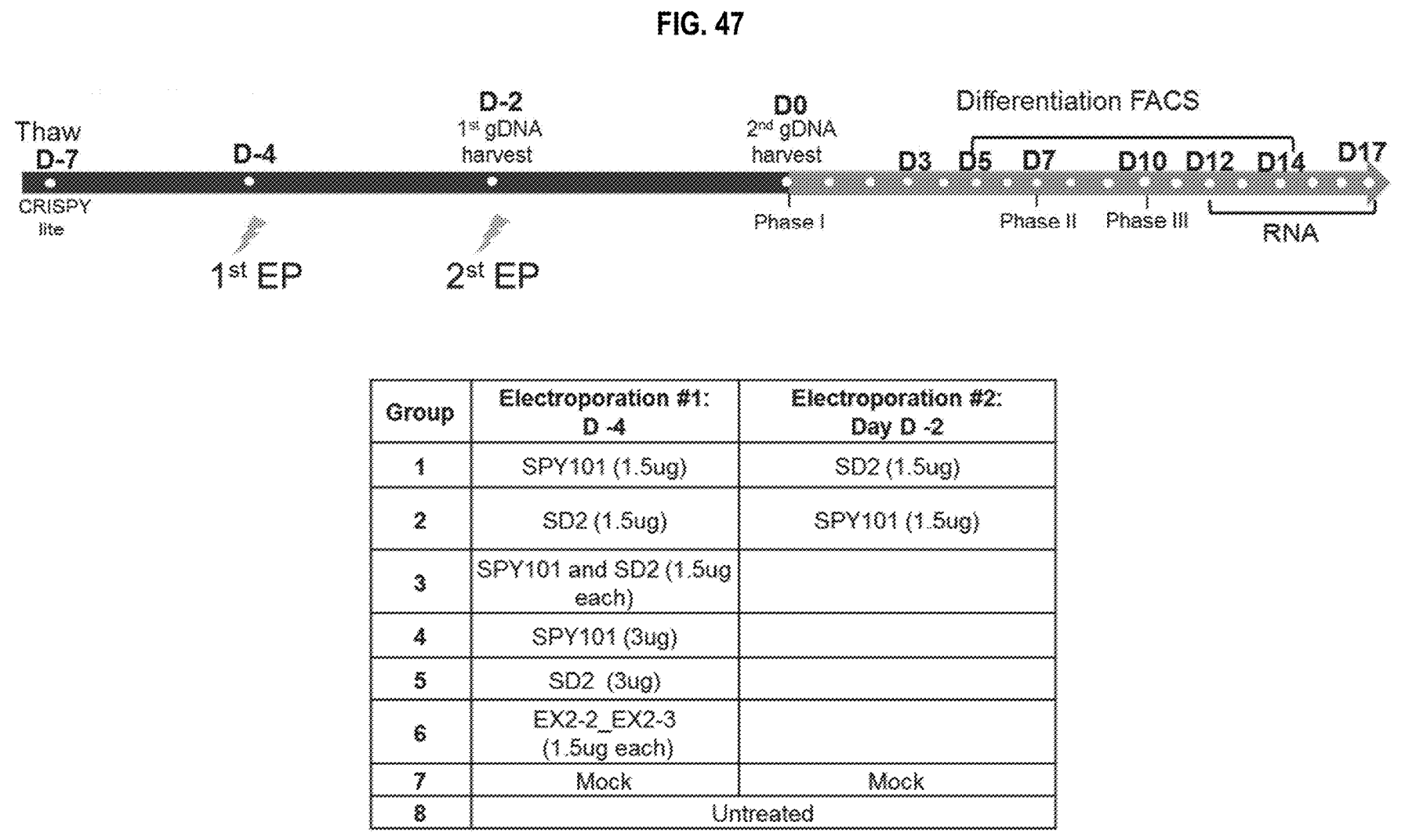

| Group | Electroporation #1: D -4 | Electroporation #2: Day D -2 |
|---|---|---|
| 1 | SPY101 (1.5ug) | SD2 (1.5ug) |
| 2 | SD2 (1.5ug) | SPY101 (1.5ug) |
| 3 | SPY101 and SD2 (1.5ug each) | |
| 4 | SPY101 (3ug) | |
| 5 | SD2 (3ug) | |
| 6 | EX2.2_EX2-3 (1.5ug each) | |
| 7 | Mock | Mock |
| 8 | Untreated | |

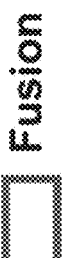
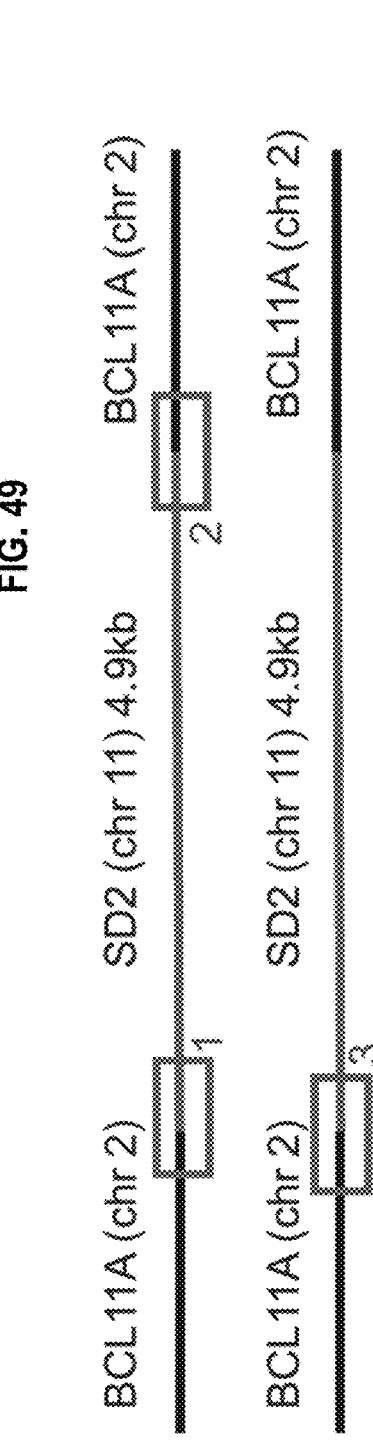
FIG. 49

FIG. 50
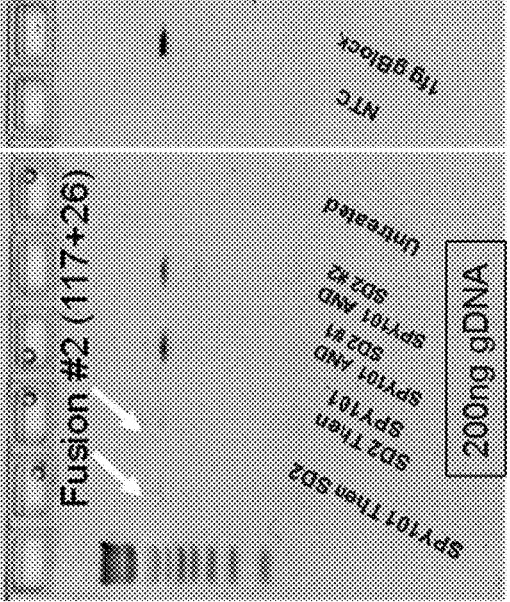
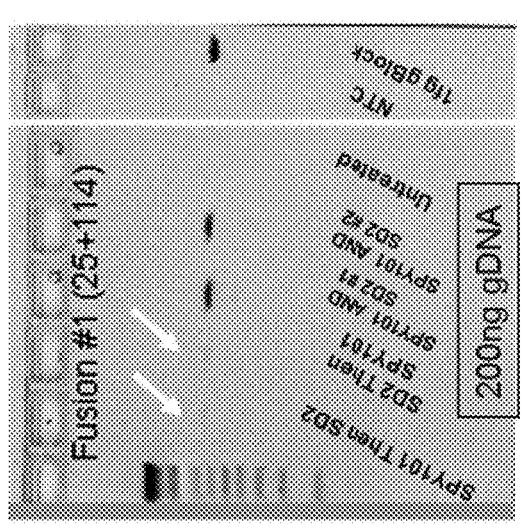

FIG. 51

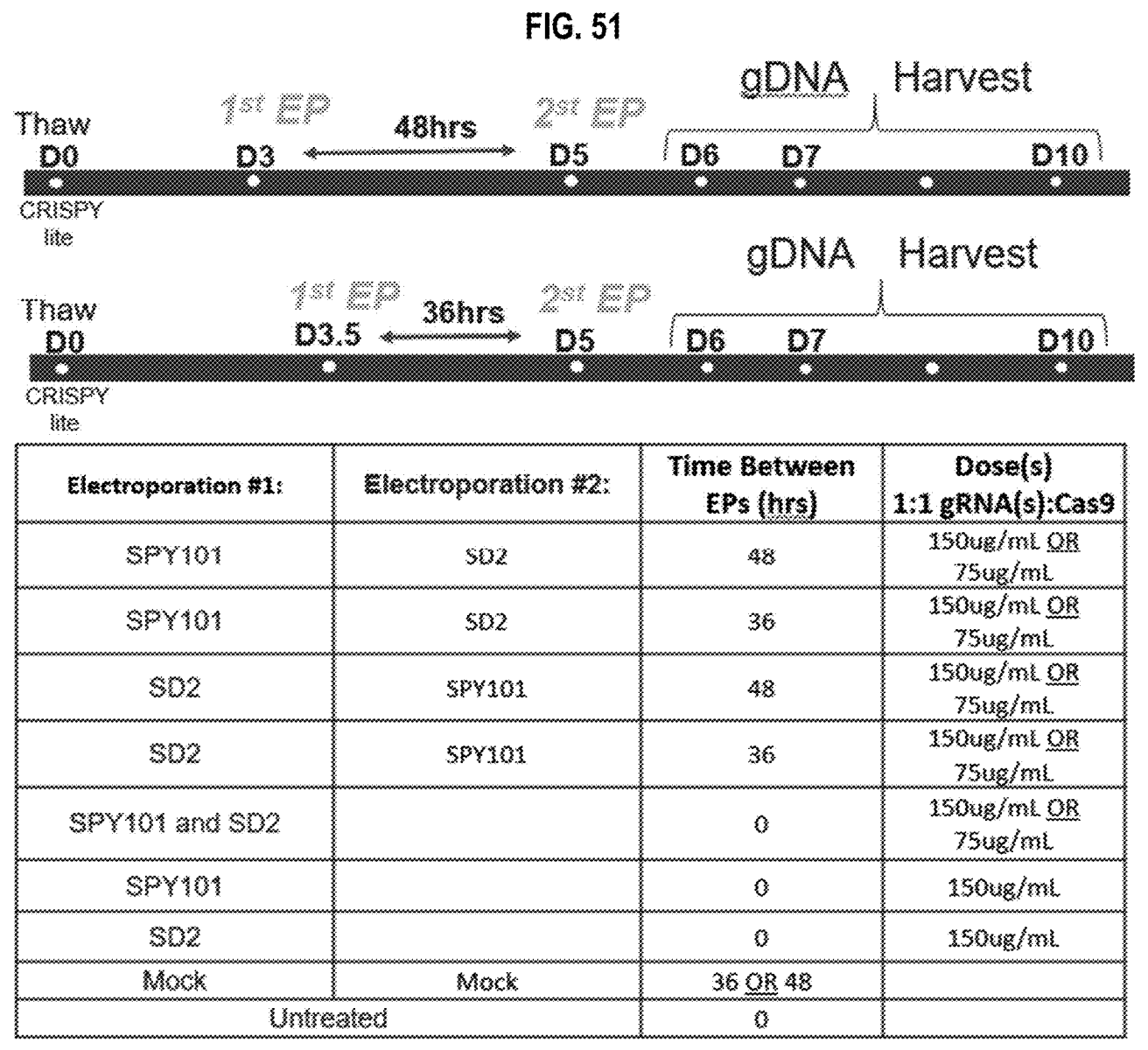

| Electroporation #1: | Electroporation #2: | Time Between EPs (hrs) | Dose(s) 1:1 gRNA(s):Cas9 |
|---|---|---|---|
| SPY101 | SD2 | 48 | 150ug/mL OR 75ug/mL |
| SPY101 | SD2 | 36 | 150ug/mL OR 75ug/mL |
| SD2 | SPY101 | 48 | 150ug/mL OR 75ug/mL |
| SD2 | SPY101 | 36 | 150ug/mL OR 75ug/mL |
| SPY101 and SD2 | | 0 | 150ug/mL OR 75ug/mL |
| SPY101 | | 0 | 150ug/mL |
| SD2 | | 0 | 150ug/mL |
| Mock | Mock | 36 OR 48 | |
| Untreated | | 0 | |

| Group | Electroporation #1 | Electroporation #2 |
|---|---|---|
| 1 | SPY101 | SD2 |
| 2 | SD2 | SPY101 |
| 3 | SPY101 and SD2 | |
| 4 | SPY101 | |
| 5 | SD2 | |
| 7 | Mock | Mock |
| 8 | Untreated | |

FIG. 55

| Guide(s) | Time Between EPs | Translocation A:E Primer Set #1 | | Translocation A:E Primer Set #2 | | Translocation A:F Primer Set #3 | | Translocation A:F Primer Set #4 | |
|---|---|---|---|---|---|---|---|---|---|
| | | Translocation Events | Reference Events | Translocation Events | Reference Events | Translocation Events | Reference Events | Translocation Events | Reference Events |
| SPY101 Then SD2 | 48hrs | 5 | 7040 | 0 | 6626 | 0 | 5997 | 1 | 6717 |
| SD2 Then SPY101 | 48hrs | 1 | 5383 | 0 | 5490 | 0 | 4865 | 0 | 5311 |
| SPY101 Then SD2 | 36hrs | 2 | 3813 | 1 | 3589 | 1 | 3520 | 1 | 3767 |
| SD2 Then SPY101 | 36hrs | 6 | 5456 | 0 | 4708 | 3 | 4336 | 3 | 4270 |
| SPY101 | 0hrs | 1 | 5141 | 0 | 4433 | 1 | 4555 | 0 | 4846 |
| SD2 | 0hrs | 1 | 3990 | 0 | 4150 | 0 | 3684 | 1 | 4277 |
| Mock EP | 0hrs | 1 | 5650 | 0 | 4609 | 7 | 5366 | 0 | 4981 |
| SPY101 And SD2 | 0hrs | 28 | 5885 | 23 | 5921 | 32 | 5153 | 21 | 6070 |

FIG. 56A

| RXN | Guides |
|---|---|
| 1 | SPY101 then SD2 |
| 2 | SD2 then SPY101 |
| 3 | SPY101 and SD2 |
| 4 | SPY101 and SD2 |
| 5 | SPY101 |
| 6 | SD2 |
| 7 | SPY101 |
| 8 | SD2 |
| 9 | EX2-2 |
| 10 | EX2-3 |
| 11 | EX2-2_EX2-3 |
| 12 | Mock |
| 13 | Untreated |

| % indel | Rxn 1 | Rxn 2 | Rxn 3 | Rxn 4 | Rxn 5 | Rxn 6 | Rxn 7 | Rxn 8 |
|---|---|---|---|---|---|---|---|---|
| SPY101 editing | 86.4 | 49.8 | 77.3 | 48.6 | 79.5 | 1 | 69.1 | 1.2 |
| SD2 editing | 65.9 | 91.9 | 70.7 | 46.4 | 0.7 | 90.4 | - | 58.3 |

| | Rxn 1 | Rxn 2 | Rxn 3 | Rxn 4 | Rxn 5 | Rxn 6 | Rxn 7 | Rxn 8 |
|---|---|---|---|---|---|---|---|---|
| | | | | | % indel | | | |
| SPY101 editing | 86.4 | 49.8 | 77.3 | 48.6 | 79.5 | 1 | 69.1 | 1.2 |
| SD2 editing | 65.9 | 91.9 | 70.7 | 46.4 | 0.7 | 90.4 | - | 58.3 |

| RXN | Guides |
|---|---|
| 1 | SPY101 then SD2 |
| 2 | SD2 then SPY101 |
| 3 | SPY101 and SD2 |
| 4 | SPY101 and SD2 |
| 5 | SPY101 |
| 6 | SD2 |
| 7 | SPY101 |
| 8 | SD2 |
| 9 | EX2-2 |
| 10 | EX2-3 |
| 11 | EX2-2_EX2-3 |
| 12 | Mock |
| 13 | Untreated |

| RXN | Guides |
|---|---|
| 1 | SPY101 then SD2 |
| 2 | SD2 then SPY101 |
| 3 | SPY101 and SD2 |
| 4 | SPY101 and SD2 |
| 5 | SPY101 |
| 6 | SD2 |
| 7 | SPY101 |
| 8 | SD2 |
| 9 | EX2-2 |
| 10 | EX2-3 |
| 11 | EX2-2_EX2-3 |
| 12 | Mock |
| 13 | Untreated |

| % indel | Rxn 1 | Rxn 2 | Rxn 3 | Rxn 4 | Rxn 5 | Rxn 6 | Rxn 7 | Rxn 8 |
|---|---|---|---|---|---|---|---|---|
| SPY101 editing | 86.4 | 49.8 | 77.3 | 48.6 | 79.5 | 1 | 69.1 | 1.2 |
| SD2 editing | 65.9 | 91.9 | 70.7 | 46.4 | 0.7 | 90.4 | - | 58.3 |

MATERIALS AND METHODS FOR TREATMENT OF HEMOGLOBINOPATHIES

CROSS-REFERENCE TO RELATED APPLICATIONS

This Application is a national stage filing under 35 U.S.C. § 371 of international application number PCT/IB2018/001338, filed Oct. 26, 2018, and claims the benefit of priority under 35 U.S.C. § 119 (e) of U.S. provisional application No. 62/577,434, filed on Oct. 26, 2017 and U.S. provisional application No. 62/583,146, filed on Nov. 8, 2017; the contents of each of which are incorporated by reference herein in their entirety.

FIELD

The present application provides materials and methods for treating patients with hemoglobinopathies, both ex vivo and in vivo. In addition, the present application provides materials and methods for deleting and/or mutating a portion of a human beta globin locus on chromosome 11 and one or more of: a BCL11A gene on chromosome 2, and a DNA sequence that encodes a transcriptional control region of the BCL11A gene on chromosome 2, in a human cell by genome editing and thereby increasing the production of fetal hemoglobin (HbF) in the genome-edited human cells.

INCORPORATION BY REFERENCE OF SEQUENCE LISTING

This application contains a Sequence Listing which has been filed electronically in ASCII format and is hereby incorporated by reference in its entirety. Said ASCII copy, created on Jul. 25, 2023, is named C154270030US03-SUBSEQ-MSB.txt and is 706,400 bytes in size.

BACKGROUND

Hemoglobinopathies encompass a number of anemias that are associated with changes in the genetically determined structure or expression of hemoglobin. These include changes to the molecular structure of the hemoglobin chain, such as occur with sickle cell anemia, as well as changes in which synthesis of one or more chains is reduced or absent, such as occur in various thalassemias.

A potential treatment for patients diagnosed with hemoglobinopathies includes genome engineering. Genome engineering refers to the strategies and techniques for the targeted, specific modification of the genetic information of living organisms. Genome engineering is a very active field of research because of the wide range of possible applications, particularly in the areas of human health. Early genome engineering technologies developed to insert a transgene into a living cell were often limited by the random nature of the insertion of the new sequence into the genome. Random insertions into the genome can result in disrupting normal regulation of neighboring genes leading to severe unwanted effects. Furthermore, random integration technologies offer little reproducibility, as there is no guarantee that the sequence would be inserted at the same place in two different cells.

Recent genome engineering strategies, such as Zinc finger nucleases (ZFNs), Transcription Activator-Like Effector Nucleases (TALENs), Homing endonucleases (HEs) and MegaTALs, enable a specific area of the DNA to be modified, thereby increasing the precision of the correction or insertion compared to early technologies. These newer platforms offer a much larger degree of reproducibility, but still have their limitations.

Despite efforts from researchers and medical professionals worldwide who have been trying to address hemoglobinopathies, such as β-thalassemia and sickle cell disease, and despite the promise of gene therapy approaches, there still remains a critical need for developing safe and effective treatments for hemoglobinopathies.

SUMMARY

The present disclosure presents an approach to address the genetic basis of hemoglobinopathies. By using genome engineering tools to create permanent changes to the genome that can delete and/or mutate the human beta globin locus on chromosome 11 and BCL11A gene on chromosome 2, or a DNA sequence that encodes a transcriptional control region of the BCL11A gene on chromosome 2, with as few as a single treatment, the resulting therapy may ameliorate the effects of hemoglobinopathies.

Provided herein are cellular, ex vivo and in vivo methods to create permanent changes to the genome by deleting or mutating the human beta globin locus on chromosome 11 and BCL11A gene on chromosome 2, or a DNA sequence that encodes a transcriptional control region of the BCL11A gene on chromosome 2, which can be used to treat hemoglobinopathies. Also provided herein are components, kits, and compositions for performing such methods. Also provided are cells produced by such methods.

Provided herein is a method of increasing fetal hemoglobin (HbF) in a human cell by genome editing, the method comprises the step of introducing into the human cell one or more deoxyribonucleic acid (DNA) endonuclease to effect two or more single-strand break (SSB) or double-strand break (DSB). A first SSB or DSB can be within or near a human beta globin locus on chromosome 11. A second SSB or DSB can be within or near one or more of: a BCL11A gene on chromosome 2, and a DNA sequence that encodes a transcriptional control region of the BCL11A gene on chromosome 2. The first SSB or DSB can result in one or more of: a permanent deletion or inversion within or near the human beta globin locus on chromosome 11, and a mutation within or near the human beta globin locus on chromosome 11. The second SSB or DSB can result in one or more of: a permanent deletion or inversion within or near the BCL11A gene on chromosome 2, a mutation within or near the BCL11A gene on chromosome 2, a permanent deletion or inversion within or near the DNA sequence that encodes a transcriptional control region of the BCL11A gene on chromosome 2, and a mutation within or near the DNA sequence that encodes a transcriptional control region of the BCL11A gene on chromosome 2. The two or more permanent deletion, inversion, or mutation can result in an increased expression of γ-globin and an increase of HbF in the human cell.

The permanent deletion within or near the human beta globin locus on chromosome 11 can be a hereditary persistence of fetal hemoglobin (HPFH) deletion. The HPFH deletion can be selected from the group consisting of: a HPFH-4 deletion, a HPFH-5 deletion, a HPFH-Kenya deletion, a HPFH-Black deletion, a large Corfu deletion, a small Corfu deletion, a small deletion, and combinations thereof. The HPFH deletion can be a 7.2 Kb deletion. The HPFH deletion can be a 3.5 Kb deletion. The HPFH deletion can be a 12.9 Kb deletion. The HPFH deletion can be a 22 Kb deletion. The HPFH deletion can be a 13 bp deletion.

The HPFH deletion can be located downstream of a HBG1 gene and can result in a repositioning of a BCL11A enhancing region closer to the HBG1 gene. The HPFH deletion can be located downstream of a HBG2 gene and can result in a repositioning of a BCL11A enhancing region closer to the HBG2 gene. The HPFH deletion can be located downstream of a HBG1 gene and HBG2 gene and can result in a repositioning of a BCL11A enhancing region closer to the HBG1 gene and HBG2 gene. The HPFH deletion can include all or a portion of a β-globin gene. The HPFH deletion can include all or a portion of a 8-globin gene and all or a portion of a β-globin gene. The permanent deletion within or near the human beta globin locus on chromosome 11 can be in a region of the human beta globin locus comprising a HBG1 gene and a HBG2 gene.

The permanent deletion within or near the human beta globin locus on chromosome 11 can be a 13-base pair deletion located upstream of the HBG1 gene. The permanent deletion within or near the human beta globin locus on chromosome 11 can be a 4.9 Kb deletion located upstream of the HBG1 gene. The permanent deletion within or near the human beta globin locus on chromosome 11 can be a 13-base pair deletion located upstream of the HGB1 gene and a 4.9 Kb deletion located upstream of the HBG1 gene. The 4.9 Kb deletion can include the HBG2 gene. The DNA sequence that encodes a transcriptional control region of the BCL11A gene can be located within a second intron of the BCL11A gene on chromosome 2. The DNA sequence that encodes a transcriptional control region of the BCL11A gene can be located within a +58 DNA hypersensitive site (DHS) of the BCL11A gene on chromosome 2.

The one or more DNA endonuclease can be selected from the group consisting of a zinc finger nuclease, TAL effector nuclease, meganuclease, MegaTAL, Tev-m TALEN, Mega-Tev, homing endonuclease, FokI, StsI, Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, a homolog thereof, a recombination of the naturally occurring molecule thereof, a codon-optimized thereof, modified versions thereof, and combinations thereof.

One or more guide ribonucleic acid (gRNA) can be introduced into the human cell. The one or more gRNA can be one or more single-molecule guide RNA (sgRNA).

The one or more gRNA can be a concatenated gRNA comprising a first gRNA and a second gRNA. The first gRNA and second gRNA can be attached via a linker. The linker can be a chemical linker or one or more nucleotides. The first gRNA can comprise a spacer sequence that is complementary to a segment of the human beta globin locus on chromosome 11, the BCL11A gene on chromosome 2, or the DNA sequence that encodes a transcriptional control region of the BCL11A gene on chromosome 2. The second gRNA can comprise a spacer sequence that is complementary to a segment of the human beta globin locus on chromosome 11, the BCL11A gene on chromosome 2, or the DNA sequence that encodes a transcriptional control region of the BCL11A gene on chromosome 2.

The one or more gRNA can be a concatenated gRNA comprising a first gRNA, a second gRNA, and a third gRNA. The first gRNA and second gRNA are attached via a first linker and the second gRNA and third gRNA are attached via a second linker. The first linker and second linker can be chemical linkers or one or more nucleotides. The first gRNA can comprise a spacer sequence that is complementary to a segment of the human beta globin locus on chromosome 11, the BCL11A gene on chromosome 2, or the DNA sequence that encodes a transcriptional control region of the BCL11A gene on chromosome 2. The second gRNA can comprise a spacer sequence that is complementary to a segment of the human beta globin locus on chromosome 11, the BCL11A gene on chromosome 2, or the DNA sequence that encodes a transcriptional control region of the BCL11A gene on chromosome 2. The third gRNA can comprise a spacer sequence that is complementary to a segment of a human beta globin locus on chromosome 11, the BCL11A gene on chromosome 2, or the DNA sequence that encodes a transcriptional control region of the BCL11A gene on chromosome 2.

The increase of fetal hemoglobin (HbF) in the genome-edited human cells can be compared to HbF levels in wild-type human cells.

Also provided herein is an ex vivo method for treating a patient (e.g., a human) with a hemoglobinopathy, the method comprises: creating a patient specific induced pluripotent stem cell (iPSC); editing within or near a human beta globin locus on chromosome 11 and one or more of: a BCL11A gene on chromosome 2 and a DNA sequence that encodes a transcriptional control region of the BCL11A gene on chromosome 2 of the iPSC; differentiating the genome-edited iPSC into a hematopoietic progenitor cell; and implanting the hematopoietic progenitor cell into the patient.

The step of creating a patient specific iPSC can comprise: isolating a somatic cell from the patient; and introducing a set of pluripotency-associated genes into the somatic cell to induce the somatic cell to become a pluripotent stem cell. The somatic cell can be a fibroblast. The set of pluripotency-associated genes can be one or more of the genes selected from the group consisting of OCT4, SOX2, KLF4, Lin28, NANOG and cMYC.

The step of editing within or near a human beta globin locus on chromosome 11, and within or near one or more of: a BCL11A gene on chromosome 2, and a DNA sequence that encodes a transcriptional control region of the BCL11A gene on chromosome 2 can comprise: introducing into the iPSC one or more DNA endonuclease to effect two or more SSB or DSB, a first SSB or DSB within or near a human beta globin locus on chromosome 11, and a second SSB or DSB within or near one or more of: a BCL11A gene on chromosome 2, and a DNA sequence that encodes a transcriptional control region of the BCL11A gene on chromosome 2. The first SSB or DSB can result in one or more of: a permanent deletion or inversion within or near the human beta globin locus on chromosome 11, and a mutation within or near the human beta globin locus on chromosome 11. The second SSB or DSB can result in one or more of: a permanent deletion or inversion within or near the BCL11A gene on chromosome 2, a mutation within or near the BCL11A gene on chromosome 2, a permanent deletion or inversion within or near the DNA sequence that encodes a transcriptional control region of the BCL11A gene on chromosome 2, and a mutation within or near the DNA sequence that encodes a transcriptional control region of the BCL11A gene on chromosome 2. The two permanent deletion, inversion, or mutation can result in an increased expression of γ-globin and an increase of HbF in the iPSC.

The step of differentiating the genome-edited iPSC into a hematopoietic progenitor cell can comprise: treatment with a combination of small molecules, delivery of master transcription factors, delivery of mRNA encoding master transcription factors, and delivery of mRNA encoding transcription factors.

The step of implanting the hematopoietic progenitor cell into the patient can comprise implanting the hematopoietic progenitor cell by transplantation, local injection, systemic infusion, and combinations thereof.

Also provided herein is an ex vivo method for treating a patient (e.g., a human) with a hemoglobinopathy, the method comprising the steps of: isolating a mesenchymal stem cell from the patient; editing within or near a human beta globin locus on chromosome 11 and one or more of: a BCL11A gene on chromosome 2, and a DNA sequence that encodes a transcriptional control region of the BCL11A gene on chromosome 2 of the mesenchymal stem cell; differentiating the genome-edited mesenchymal stem cell into a hematopoietic progenitor cell; and implanting the hematopoietic progenitor cell into the patient.

The mesenchymal stem cell can be isolated from the patient's bone marrow by performing a biopsy of the patient's bone marrow or the mesenchymal stem cell can be isolated from peripheral blood. The step of isolating a mesenchymal stem cell from the patient can comprise aspiration of bone marrow and isolation of mesenchymal cells by density gradient centrifugation.

The step of editing within or near a human beta globin locus on chromosome 11, and within or near one or more of: a BCL11A gene on chromosome 2, and a DNA sequence that encodes a transcriptional control region of the BCL11A gene on chromosome 2 can comprise: introducing into the mesenchymal stem cell one or more DNA endonuclease to effect two or more SSB or DSB, a first SSB or DSB within or near a human beta globin locus on chromosome 11, and a second SSB or DSB within or near one or more of: a BCL11A gene on chromosome 2 and a DNA sequence that encodes a transcriptional control region of the BCL11A gene on chromosome 2. The first SSB or DSB can result in one or more of: a permanent deletion or inversion within or near the human beta globin locus on chromosome 11, and a mutation within or near the human beta globin locus on chromosome 11. The second SSB or DSB can result in one or more of: a permanent deletion or inversion within or near the BCL11A gene on chromosome 2, a mutation within or near the BCL11A gene on chromosome 2, a permanent deletion or inversion within or near the DNA sequence that encodes a transcriptional control region of the BCL11A gene on chromosome 2, and a mutation within or near the DNA sequence that encodes a transcriptional control region of the BCL11A gene on chromosome 2. The two or more permanent deletion, inversion, or mutation can result in an increased expression of γ-globin and an increase of fetal hemoglobin (HbF) in the mesenchymal stem cell.

The step of differentiating the genome-edited mesenchymal stem cell into a hematopoietic progenitor cell can comprise one or more of the following: treatment with a combination of small molecules, delivery of master transcription factors, delivery of mRNA encoding master transcription factors, and delivery of mRNA encoding transcription factors.

The step of implanting the hematopoietic progenitor cell into the patient can comprise implanting the hematopoietic progenitor cell into the patient by transplantation, local injection, systemic infusion, or combinations thereof.

Also provided herein is an ex vivo method for treating a patient (e.g., a human) with a hemoglobinopathy, the method comprising the steps of: isolating a hematopoietic progenitor cell from the patient; editing within or near a human beta globin locus on chromosome 11 and one or more of: a BCL11A gene on chromosome 2 and a DNA sequence that encodes a transcriptional control region of the BCL11A gene on chromosome 2 of the hematopoietic progenitor cell; and implanting the genome-edited hematopoietic progenitor cell into the patient.

The method can further comprise treating the patient with granulocyte colony stimulating factor (GCSF) prior to the step of isolating a hematopoietic progenitor cell from the patient. The step of treating the patient with GCSF can be performed in combination with Plerixaflor.

The step of isolating a hematopoietic progenitor cell from the patient can comprise isolating CD34+ cells.

The step of editing within or near a human beta globin locus on chromosome 11, and within or near one or more of: a BCL11A gene on chromosome 2, and a DNA sequence that encodes a transcriptional control region of the BCL11A gene on chromosome 2 can comprise: introducing into the hematopoietic progenitor cell one or more DNA endonuclease to effect two or more SSB or DSB, a first SSB or DSB within or near a human beta globin locus on chromosome 11, and a second SSB or DSB within or near one or more of: a BCL11A gene on chromosome 2 and a DNA sequence that encodes a transcriptional control region of the BCL11A gene on chromosome 2. The first SSB or DSB can result in one or more of: a permanent deletion within or near the human beta globin locus on chromosome 11, and a mutation within or near the human beta globin locus on chromosome 11. The second SSB or DSB can result in one or more of: a permanent deletion within or near the BCL11A gene on chromosome 2, a mutation within or near the BCL11A gene on chromosome 2, a permanent deletion within or near the DNA sequence that encodes a transcriptional control region of the BCL11A gene on chromosome 2, and a mutation within or near the DNA sequence that encodes a transcriptional control region of the BCL11A gene on chromosome 2. The two or more permanent deletion, inversion, or mutation can result in an increased expression of γ-globin and a increase of fetal hemoglobin (HbF) in the hematopoietic progenitor cell.

The step of implanting the genome-edited hematopoietic progenitor cell into the patient can comprise implanting the genome-edited hematopoietic progenitor cell into the patient by transplantation, local injection, systemic infusion, or combinations thereof.

The hemoglobinopathy can be selected from a group consisting of sickle cell anemia and thalassemia. The hemoglobinopathy can be selected from the group consisting of sickle cell disease, sickle cell trait, hemoglobin C disease, hemoglobin C trait, hemoglobin S/C disease, hemoglobin D disease, hemoglobin E disease, a thalassemia, a condition associated with hemoglobin with increased oxygen affinity, a condition associated with hemoglobin with decreased oxygen affinity, unstable hemoglobin disease, methemoglobinemia, and combinations thereof.

Also provided herein is an in vivo method for treating a patient (e.g., a human) with a hemoglobinopathy, the method comprising the steps of: editing within or near a human beta globin locus on chromosome 11 and within or near one or more of: a BCL11A gene on chromosome 2, and a DNA sequence that encodes a transcriptional control region of the BCL11A gene on chromosome 2 in a cell of the patient. The cell can a bone marrow cell, a hematopoietic progenitor cell, or a CD34+ cell.

The step of editing within or near a human beta globin locus on chromosome 11, and within or near one or more of: a BCL11A gene on chromosome 2, and a DNA sequence that encodes a transcriptional control region of the BCL11A gene on chromosome 2 can comprise: introducing into the cell one or more DNA endonuclease to effect two or more SSB or DSB, a first SSB or DSB within or near a human beta globin locus on chromosome 11, and a second SSB or DSB within or near one or more of: a BCL11A gene on chromosome 2, and a DNA sequence that encodes a transcriptional control region of the BCL11A gene on chromosome 2. The first SSB or DSB can result in one or more of: a permanent deletion or inversion within or near the human beta globin locus on chromosome 11, and a mutation within or near the human beta globin locus on chromosome 11. The second SSB or DSB can result in one or more of: a permanent deletion or inversion within or near the BCL11A gene on chromosome 2, a mutation within or near the BCL11A gene on chromosome 2, a permanent deletion or inversion within or near the DNA sequence that encodes a transcriptional control region of the BCL11A gene on chromosome 2, and a mutation within or near the DNA sequence that encodes a transcriptional control region of the BCL11A gene on chromosome 2. The two or more permanent deletion, inversion, or mutation result in an increased expression of Y-globin and a increase of fetal hemoglobin (HbF) in the cell.

The one or more DNA endonuclease is selected from the group consisting of a zinc finger nuclease, TAL effector nuclease, meganuclease, MegaTAL, Tev-m TALEN, Mega-Tev, homing endonuclease, FokI, StsI, Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Cse1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, a homolog thereof, a recombination of the naturally occurring molecule thereof, a codon-optimized thereof, modified versions thereof, and combinations thereof.

The method can comprise introducing into the cell one or more polynucleotide encoding the one or more DNA endonuclease. The method can comprise introducing into the cell one or more RNA encoding the one or more DNA endonuclease. The one or more polynucleotide or one or more RNA can be one or more modified polynucleotide or one or more modified RNA. The DNA endonuclease can be a protein or polypeptide.

The method can further comprise introducing into the cell one or more gRNA. The one or more gRNA can be sgRNA. The one or more gRNA or one or more sgRNA can be one or more modified gRNA, one or more modified sgRNA, or combinations thereof. The one or more DNA endonuclease can be pre-complexed with one or more gRNA, one or more sgRNA, or combinations thereof.

The method can further comprise: introducing into the cell one or more gRNA or one or more concatenated gRNA, and wherein the one or more DNA endonuclease is one or more Cas9 endonuclease that effect or create two or more pair of SSBs or DSBs, a first pair of SSB or DSB within or near a human beta globin locus on chromosome 11, and a second pair of SSB or DSB within or near one or more of: a BCL11A gene on chromosome 2 and a DNA sequence that encodes a transcriptional control region of the BCL11A gene on chromosome 2. The first pair of SSB or DSB can be a SSB or DSB at a 5' locus within or near the human beta globin locus on chromosome 11; and a SSB or DSB at a 3' locus within or near of the human beta globin locus on chromosome 11. The second pair of SSB or DSB can be a SSB or DSB at the 5' locus within or near the BCL11A gene on chromosome 2, or the DNA sequence that encodes a transcriptional control region of the BCL11A gene on chromosome 2; and a SSB or DSB at the 3' locus within or near the BCL11A gene on chromosome 2, or the DNA sequence that encodes a transcriptional control region of the BCL11A gene on chromosome 2. The SSB or DSB at the 5' locus and the SSB or DSB at the 3' locus can result in two or more permanent deletion of the chromosomal DNA between the 5' locus and the 3' locus within or near the human beta globin locus on chromosome 11, the BCL11A gene on chromosome 2, or the DNA sequence that encodes a transcriptional control region of the BCL11A gene on chromosome 2.

The SSB or DSB at the 5' locus within or near the human beta globin locus on chromosome 11 can be proximal to a 5' boundary of a HPFH deletion. The SSB or DSB at the 5' locus within or near the human beta globin locus on chromosome 11 can be proximal to a 5' boundary of a HPFH deletion selected from the group consisting of: a HPFH-4 deletion, a HPFH-5 deletion, a HPFH-Kenya deletion, a HPFH-Black deletion, a large Corfu deletion, a small deletion, and the small Corfu deletion.

The SSB or DSB at the 3'locus within or near the human beta globin locus on chromosome 11 can be proximal to a 3' boundary of a HPFH deletion.

The SSB or DSB at the 3' locus within or near the human beta globin locus on chromosome 11 can be proximal to a 3' boundary of a HPFH deletion selected from the group consisting of: a HPFH-4 deletion, a HPFH-5 deletion, a HPFH-Kenya deletion, a HPFH-Black deletion, the large Corfu deletion, and a small Corfu deletion.

The SSB or DSB at the 5' locus within or near the human beta globin locus on chromosome 11 can be proximal to a 5' boundary of a HPFH deletion and the SSB or DSB at the 3' locus within or near the human beta globin locus on chromosome 11 can be proximal to a 3' boundary of the HPFH deletion.

The SSB or DSB at the 5' locus within or near the human beta globin locus on chromosome 11 is proximal to a 5' boundary of a HPFH deletion and the SSB or DSB at the 3' locus within or near the human beta globin locus on chromosome 11 can be proximal to a 3' boundary of the HPFH deletion, wherein the HPFH deletion can be selected from the group consisting of: a HPFH-4 deletion, a HPFH-5 deletion, a HPFH-Kenya deletion, a HPFH-Black deletion, a large Corfu deletion, and a small Corfu deletion.

A 3' boundary of the deletion can be proximal to Chr11:5224779 and a 5' boundary of the deletion can be proximal to Chr11:5237723.

A 3' boundary of the deletion can be proximal to Chr11:5234665 and a 5' boundary of the deletion can be proximal to Chr11:5238138.

A 3' boundary of the deletion can be proximal to Chr11:5233055 and a 5' boundary of the deletion can be proximal to Chr11:5240389.

A 3' boundary of the deletion can be proximal to Chr11:5226631 and a 5' boundary of the deletion can be proximal to Chr11:5249422.

A 3' boundary of the deletion can be proximal to Chr11:5196709 and a 5' boundary of the deletion can be proximal to Chr11:5239223.

A 3' boundary of the deletion can be proximal to Chr11:5225700 and a 5' boundary of the deletion can be proximal to Chr11:5236750.

The deletion can include all or a portion of the 8-globin upstream region. The deletion can include all or a portion of the β-globin gene.

The permanent deletion of the chromosomal DNA between the 5' locus and the 3' locus can be in a region of the human beta globin locus comprising a HBG1 gene and a HBG2 gene. The permanent deletion of the chromosomal DNA between the 5' locus and the 3' locus can be a 13-base pair deletion located upstream of the HBG1 gene. The permanent deletion of the chromosomal DNA between the 5' locus and the 3' locus can be a 4.9 Kb deletion located upstream of the HBG1 gene. The permanent deletion of the chromosomal DNA between the 5' locus and the 3' locus can be a 13-base pair deletion located upstream of the HBG1 gene and a 4.9 Kb deletion located upstream of the HBG1 gene.

The permanent deletion of the chromosomal DNA between the 5' locus and the 3' locus can be located within a second intron of the BCL11A gene on chromosome 2. The permanent deletion of the chromosomal DNA between the 5' locus and the 3' locus can be located within a +58 DNA DHS of the BCL11A gene on chromosome 2.

The one or more DNA endonuclease can be selected from the group consisting of a zinc finger nuclease, TAL effector nuclease, meganuclease, MegaTAL, Tev-m TALEN, Mega-Tev, homing endonuclease, FokI, StsI, Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, a homolog thereof, a recombination of the naturally occurring molecule thereof, a codon-optimized thereof, modified versions thereof, and combinations thereof.

The one or more gRNA or the one or more concatenated gRNA can comprise a spacer sequence that is complementary to either the 5' locus of the human beta globin locus on chromosome 11, 5' locus of the BCL11A gene on chromosome 2, 5' locus of the DNA sequence that encodes a transcriptional control region of the BCL11A gene on chromosome 2, 3' locus of the human beta globin locus on chromosome 11, 3' locus of the BCL11A gene on chromosome 2, or the 3' locus of the DNA sequence that encodes a transcriptional control region of the BCL11A gene on chromosome 2.

The one or more gRNA or the one or more concatenated gRNA can be one or more sgRNA or one or more concatenated sgRNA. The one or more gRNA or one or more concatenated gRNA can comprise one or more modified gRNA. The one or more sgRNA or one or more concatenated sgRNA can comprise one or more modified sgRNA. The one or more DNA endonuclease can be pre-complexed with one or more gRNA, one or more sgRNA, one or more concatenated gRNA, or one or more concatenated sgRNA.

The Cas9 mRNA, and gRNA or concatenated gRNA, can be either each formulated into separate lipid nanoparticles or all co-formulated into a lipid nanoparticle. The Cas9 mRNA can be formulated into a lipid nanoparticle, and the gRNA or concatenated gRNA can be delivered to the cell by an adeno-associated virus (AAV) vector. The Cas9 mRNA can be formulated into a lipid nanoparticle and the gRNA or concatenated gRNA can be delivered to the cell by electroporation.

The increase of HbF in the genome-edited human cells can be compared to HbF levels in wild-type human cells.

The hemoglobinopathy can be selected from a group consisting of sickle cell anemia and thalassemia. The hemoglobinopathy can be selected from the group consisting of sickle cell disease, sickle cell trait, hemoglobin C disease, hemoglobin C trait, hemoglobin S/C disease, hemoglobin D disease, hemoglobin E disease, a thalassemia, a condition associated with hemoglobin with increased oxygen affinity, a condition associated with hemoglobin with decreased oxygen affinity, unstable hemoglobin disease, methemoglobinemia, and combinations thereof.

Also provided herein is one or more gRNA for editing within or near a human beta globin locus on chromosome 11 and within or near one or more of: a BCL11A gene on chromosome 2, and a DNA sequence that encodes a transcriptional control region of the BCL11A gene on chromosome 2, in a cell from a patient with a hemoglobinopathy. The one or more gRNA can comprise a spacer sequence selected from a Sequence Listing disclosed herein. The one or more gRNA can be one or more sgRNA. The one or more gRNA or one or more sgRNA can be one or more modified gRNA or one or more modified sgRNA.

Also provided herein is a concatenated gRNA for editing within or near a human beta globin locus on chromosome 11 and within or near one or more of: a BCL11A gene on chromosome 2 and a DNA sequence that encodes a transcriptional control region of the BCL11A gene on chromosome 2, in a cell from a patient with a hemoglobinopathy. The concatenated gRNA can comprise one or more gRNA and the one or more gRNA comprise a spacer sequence selected from a Sequence Listing disclosed herein. The one or more gRNA of the concatenated gRNA can be one or more single-molecule guide RNA (sgRNA). The one or more gRNA or one or more sgRNA of the concatenated gRNA is one or more modified gRNA or one or more modified sgRNA.

The hemoglobinopathy can be selected from a group consisting of sickle cell anemia and thalassemia.

Also provided herein is a method of increasing fetal hemoglobin (HbF) in a human cell by genome editing. The method comprises: introducing a first guide RNA into the human cell using a first electroporation wherein the first guide RNA targets a human beta globin locus on chromosome 11; introducing a second guide RNA into the human cell using a second electroporation wherein the second guide RNA targets one or more of: a BCL11A gene on chromosome 2, and a DNA sequence that encodes a transcriptional control region of the BCL11A gene on chromosome 2; wherein two or more permanent deletion, inversion, or mutation result in an increased expression of γ-globin and an increase of fetal hemoglobin (HbF) in the human cell.

Also provided herein is a method of increasing fetal hemoglobin (HbF) in a human cell by genome editing. The method comprises: introducing a first guide RNA into the human cell using a first electroporation wherein the first guide RNA targets one or more of: a BCL11A gene on chromosome 2, and a DNA sequence that encodes a transcriptional control region of the BCL11A gene on chromosome 2; introducing a second guide RNA into the human cell using a second electroporation wherein the second guide RNA targets a human beta globin locus on chromosome 11; wherein two or more permanent deletion, inversion, or mutation result in an increased expression of γ-globin and an increase of fetal hemoglobin (HbF) in the human cell.

Also provided herein is a method of increasing fetal hemoglobin (HbF) in a human cell by genome editing. The method comprises: introducing a first guide RNA into the human cell using a first electroporation wherein the first guide RNA targets a human beta globin locus on chromosome 11; introducing a second guide RNA into the human cell using a second electroporation wherein the second guide RNA targets the human beta globin locus on chromosome 11; wherein two or more permanent deletion, inversion, or mutation result in an increased expression of Y-globin and an increase of fetal hemoglobin (HbF) in the human cell.

Also provided herein is a method of increasing fetal hemoglobin (HbF) in a human cell by genome editing. The method comprises: introducing a first guide RNA into the human cell using a first electroporation wherein the first guide RNA targets one or more of: a BCL11A gene on chromosome 2, and a DNA sequence that encodes a transcriptional control region of the BCL11A gene on chromosome 2; introducing a second guide RNA into the human cell using a second electroporation wherein the second guide RNA targets one or more of: a BCL11A gene on chromosome 2, and a DNA sequence that encodes a transcriptional control region of the BCL11A gene on chromosome 2; wherein two or more permanent deletion, inversion, or mutation result in an increased expression of γ-globin and an increase of fetal hemoglobin (HbF) in the human cell.

Also provided herein is a method of increasing fetal hemoglobin (HbF) in a human cell by genome editing. The method comprises: introducing a first guide RNA into the human cell using a first electroporation wherein the first guide RNA targets a human beta globin locus on chromosome 11; introducing one or more deoxyribonucleic acid (DNA) endonuclease into the human cell to effect one or more single-strand break (SSB) or double-strand break (DSB), a first SSB or DSB within or near the human beta globin locus on chromosome 11, wherein the first SSB or DSB results in one or more of: a permanent deletion or inversion within or near the human beta globin locus on chromosome 11, and a mutation within or near the human beta globin locus on chromosome 11; introducing a second guide RNA into the human cell using a second electroporation wherein the second guide RNA targets one or more of: a BCL11A gene on chromosome 2, and a DNA sequence that encodes a transcriptional control region of the BCL11A gene on chromosome 2; introducing one or more DNA endonuclease into the human cell to effect one or more SSB or DSB, a second SSB or DSB within or near one or more of: the BCL11A gene on chromosome 2, and the DNA sequence that encodes a transcriptional control region of the BCL11A gene on chromosome 2, wherein the second SSB or DSB results in one or more of: a permanent deletion or inversion within or near the BCL11A gene on chromosome 2, a mutation within or near the BCL11A gene on chromosome 2, a permanent deletion or inversion within or near the DNA sequence that encodes a transcriptional control region of the BCL11A gene on chromosome 2, and a mutation within or near the DNA sequence that encodes a transcriptional control region of the BCL11A gene on chromosome 2; wherein the two or more permanent deletion, inversion, or mutation results in an increased expression of γ-globin and an increase of fetal hemoglobin (HbF) in the human cell.

Also provided herein is a method of increasing fetal hemoglobin (HbF) in a human cell by genome editing. The method comprises: introducing a first guide RNA into the human cell using a first electroporation wherein the first guide RNA targets one or more of: a BCL11A gene on chromosome 2, and a DNA sequence that encodes a transcriptional control region of the BCL11A gene on chromosome 2; introducing into the human cell one or more deoxyribonucleic acid (DNA) endonuclease to effect one or more single-strand break (SSB) or double-strand break (DSB), a first SSB or DSB within or near one or more of: the BCL11A gene on chromosome 2, and the DNA sequence that encodes a transcriptional control region of the BCL11A gene on chromosome 2, wherein the first SSB or DSB results in one or more of: a permanent deletion or inversion within or near the BCL11A gene on chromosome 2, a mutation within or near the BCL11A gene on chromosome 2, a permanent deletion or inversion within or near the DNA sequence that encodes a transcriptional control region of the BCL11A gene on chromosome 2, and a mutation within or near the DNA sequence that encodes a transcriptional control region of the BCL11A gene on chromosome 2; introducing a second guide RNA into the human cell using a second electroporation wherein the second guide RNA targets a human beta globin locus on chromosome 11; introducing into the human cell one or more DNA endonuclease to effect one or more SSB or DSB, a second SSB or DSB within or near the human beta globin locus on chromosome 11, wherein the second SSB or DSB results in one or more of: a permanent deletion or inversion within or near the human beta globin locus on chromosome 11, and a mutation within or near the human beta globin locus on chromosome 11; wherein the two or more permanent deletion, inversion, or mutation results in an increased expression of γ-globin and an increase of fetal hemoglobin (HbF) in the human cell.

Also provided herein is a method of increasing fetal hemoglobin (HbF) in a human cell by genome editing. The method comprises: introducing a first guide RNA into the human cell using a first electroporation wherein the first guide RNA targets a human beta globin locus on chromosome 11; introducing one or more deoxyribonucleic acid (DNA) endonuclease into the human cell to effect one or more single-strand break (SSB) or double-strand break (DSB), a first SSB or DSB within or near the human beta globin locus on chromosome 11, wherein the first SSB or DSB results in one or more of: a permanent deletion or inversion within or near the human beta globin locus on chromosome 11, and a mutation within or near the human beta globin locus on chromosome 11; introducing a second guide RNA into the human cell using a second electroporation wherein the second guide RNA targets the human beta globin locus on chromosome 11; introducing one or more DNA endonuclease into the human cell to effect one or more SSB or DSB, a second SSB or DSB within or near the human beta globin locus on chromosome 11, wherein the second SSB or DSB results in one or more of: a permanent deletion or inversion within or near the human beta globin locus on chromosome 11, and a mutation within or near the human beta globin locus on chromosome 11; wherein the two or more permanent deletion, inversion, or mutation results in an increased expression of γ-globin and an increase of fetal hemoglobin (HbF) in the human cell.

Also provided herein is a method of increasing fetal hemoglobin (HbF) in a human cell by genome editing. The method comprises: introducing a first guide RNA into the human cell using a first electroporation wherein the first guide RNA targets one or more of: a BCL11A gene on chromosome 2, and a DNA sequence that encodes a transcriptional control region of the BCL11A gene on chromosome 2; introducing into the human cell one or more deoxyribonucleic acid (DNA) endonuclease to effect one or more single-strand break (SSB) or double-strand break (DSB), a first SSB or DSB within or near one or more of: a BCL11A gene on chromosome 2, and a DNA sequence that encodes a transcriptional control region of the BCL11A gene on chromosome 2, wherein the first SSB or DSB results in one or more of: a permanent deletion or inversion within or near the BCL11A gene on chromosome 2, a mutation within or near the BCL11A gene on chromosome 2, a permanent deletion or inversion within or near the DNA sequence that encodes a transcriptional control region of the BCL11A gene on chromosome 2, and a mutation within or near the DNA sequence that encodes a transcriptional control region of the BCL11A gene on chromosome 2; introducing a second guide RNA into the human cell using a second electroporation wherein the second guide RNA targets one or more of: a BCL11A gene on chromosome 2, and a DNA sequence that encodes a transcriptional control region of the BCL11A gene on chromosome 2; introducing into the human cell one or more DNA endonuclease to effect one or more SSB or DSB, a second SSB or DSB within or near one or more of: a BCL11A gene on chromosome 2, and a DNA sequence that encodes a transcriptional control region of the BCL11A gene on chromosome 2, wherein the second SSB or DSB results in one or more of: a permanent deletion or inversion within or near the BCL11A gene on chromosome 2, a mutation within or near the BCL11A gene on chromosome 2, a permanent deletion or inversion within or near the DNA sequence that encodes a transcriptional control region of the BCL11A gene on chromosome 2, and a mutation within or near the DNA sequence that encodes a transcriptional control region of the BCL11A gene on chromosome 2; wherein the two or more permanent deletion, inversion, or mutation results in an increased expression of γ-globin and an increase of fetal hemoglobin (HbF) in the human cell.

Also provided herein are edited cells (e.g., isolated edited cells, such as isolated edited human cells) obtained by or obtainable by any method provided herein.

It is understood that the inventions described in this specification are not limited to the examples summarized in this Summary. Various other aspects are described and exemplified herein.

BRIEF DESCRIPTION OF THE DRAWINGS

Various aspects of materials and methods for treatment of hemoglobinopathies disclosed and described in this specification can be better understood by reference to the accompanying figures, in which:

FIG. 1A shows a restriction map of the HPFH5 deletion variant (lower part) compared with wild type β-globin locus (upper part), as defined by Camaschella et al, *Haematologica*, 75 (Suppl 5): 26-30 (1990);

FIG. 1B shows a schematic of the human β-globin locus with hollow boxes highlighting illustrative HPFH5-like 5' and 3' target sites for CRISPR. The 12.9 kb deletion starts 3 kb 5' to the 8 gene and ends 1.7 kb 3' to the end of the β gene (690 bp downstream from the β polyA signal), as described by Camaschella et al., supra;

FIGS. 5A-5B show the location of the HPFH-SD 13 bp deletion;

FIG. 5A shows a sequence alignment of wild type and 13 bp deletion variant of human γ-globin locus (SEQ ID NOs: 228,305-228,308) from top to bottom;

FIG. 5B shows a sequence alignment of HBG1 and HBG2 genes showing the conserved target region (dotted box), along with the potential ~5 kb deletion arising from cleavage at the target site in both genes (lower panel);

FIG. 6A shows a schematic showing location of the HPFH-4 deletion (SEQ ID NO: 228,309);

FIG. 6B shows a schematic showing location of the HPFH Black deletion;

FIG. 6C shows a genomic sequence in the region of the $^{G}$γ-175 (T to C) mutation;

FIG. 7A is a plasmid (CTx-1) comprising a codon optimized gene for *S. pyogenes* Cas9 endonuclease. The CTx-1 plasmid also comprises a gRNA scaffold sequence, which includes a 20 bp spacer sequence from the sequences listed in the Sequence Listing;

FIG. 7B is a plasmid (CTx-2) comprising a different codon optimized gene for *S. pyogenes* Cas9 endonuclease. The CTx-2 plasmid also comprises a gRNA scaffold sequence, which includes a 20 bp spacer sequence from the sequences listed in the Sequence Listing;

FIG. 7C is a plasmid (CTx-3) comprising yet another different codon optimized gene for *S. pyogenes* Cas9 endonuclease. The CTx-3 plasmid also comprises a gRNA scaffold sequence, which includes a 20 bp spacer sequence from the sequences listed in the Sequence Listing;

FIG. 8A is a depiction of the type II CRISPR/Cas system including gRNA;

FIG. 8B is a depiction of the type II CRISPR/Cas system including sgRNA;

FIGS. 10A-10B show a depiction of gRNA combinations that can be used to delete a portion of the +58 DNA hypersensitive site (DHS) of the BCL11A gene and a table showing various gRNA combinations that can be used to delete a portion of the +58 DHS of the BCL11A gene;

FIG. 10A is a depiction of gRNA combinations that can be used to delete a portion of the +58 DHS of the BCL11A gene (SEQ ID NOs: 228,310-228,331 shown from top to bottom);

FIG. 10B is a table showing various gRNA combinations that can be used to delete a portion of the +58 DHS of the BCL11A gene and the deletion size resulting from each gRNA combination;

FIGS. 11A-11C refer to the +58 DHS gRNAs that are included in FIG. 9. FIG. 11A shows SEQ ID NOs: 228,332-228,376 from top to bottom. FIG. 11B shows SEQ ID NOs: 228,377-228,423 from top to bottom. FIG. 11C shows SEQ ID NOs: 228,424-228,427 from top to bottom;

FIG. 12 shows an experimental design that includes successive electroporations using dual guide RNAs;

FIG. 13A shows the viability of human mPB CD34+ cells from Donor LKP06B successively electroporated with dual guide RNA compared to human mPB CD34+ cells from Donor LKP06B electroporated with a single guide RNA;

FIG. 13B shows the growth kinetics of human mPB CD34+ cells from Donor LKP06B successively electroporated with dual guide RNA compared to human mPB CD34+ cells from Donor LKP06B electroporated with a single guide RNA;

FIG. 14A shows the rate of DNA editing (% indels) at the BCL11a locus and HBG2 locus in human mPB CD34+ cells from Fred Hutch Donor 304 successively electroporated with dual guide RNAs compared to human mPB CD34+ cells from Fred Hutch Donor 304 electroporated with a single guide RNA;

FIG. 14B shows the rate of DNA editing (% indels) at the BCL11a locus and HBG2 locus in human mPB CD34+ cells from Donor LKP06B successively electroporated with dual guide RNAs compared to human mPB CD34+ cells from Donor LKP06B electroporated with a single guide RNA;

FIG. 15A shows the differentiation of human mPB CD34+ cells from Donor LKP06B successively electroporated with dual guide RNAs compared to human mPB CD34+ cells from Donor LKP06B electroporated with a single guide RNA. Differentiation was determined by measuring the percentage of Band3 and Alpha4;

FIG. 15B shows the differentiation of human mPB CD34+ cells from Donor LKP06B successively electroporated with dual guide RNAs compared to human mPB CD34+ cells from Donor LKP06B electroporated with a single guide RNA. Differentiation was determined by measuring the percentage of GYPA, and CD71;

FIG. 16 shows the enucleation of human mPB CD34+ cells from Donor LKP06B successively electroporated with dual guide RNAs compared to human mPB CD34+ cells from Donor LKP06B electroporated with a single guide RNA;

FIG. 17A shows the γ/α globin mRNA ratio in human mPB CD34+ cells from Fred Hutch Donor 304 successively electroporated with dual guide RNAs compared to human mPB CD34+ cells from Fred Hutch Donor 304 electroporated with a single guide RNA;

FIG. 17B shows the γ/α globin mRNA ratio in human mPB CD34+ cells from Donor LKP06B successively electroporated with dual guide RNAs compared to human mPB CD34+ cells from Donor LKP06B electroporated with a single guide RNA;

FIG. 18A shows the globin mRNA ratio in human mPB CD34+ cells from Fred Hutch Donor 304 successively electroporated with dual guide RNAs compared to human mPB CD34+ cells from Fred Hutch Donor 304 electroporated with a single guide RNA;

FIG. 18B shows the globin mRNA ratio in human mPB CD34+ cells from Donor LKP06B successively electroporated with dual guide RNAs compared to human mPB CD34+ cells from Donor LKP06B electroporated with a single guide RNA;

FIG. 19A shows the γ/18S globin mRNA ratio in human mPB CD34+ cells from Fred Hutch Donor 304 successively electroporated with dual guide RNAs compared to human mPB CD34+ cells from Fred Hutch Donor 304 electroporated with a single guide RNA;

FIG. 19B shows the γ/18S globin mRNA ratio in human mPB CD34+ cells from Donor LKP06B successively electroporated with dual guide RNAs compared to human mPB CD34+ cells from Donor LKP06B electroporated with a single guide RNA;

FIG. 20 shows the percentage of HbF expression in human mPB CD34+ cells from Donor LKP06B successively electroporated with dual guide RNAs compared to human mPB CD34+ cells from Donor LKP06B electroporated with a single guide RNA;

FIG. 21A shows HbF expression in untreated human mPB CD34+ cells;

FIG. 21B shows HbF expression in human mPB CD34+ cells electroporated with SPY101;

FIG. 21C shows HbF expression in human mPB CD34+ cells electroporated with SD2;

FIG. 21D shows HbF expression in human mPB CD34+ cells successively electroporated with SPY101 and then SD2;

FIG. 21E shows HbF expression in human mPB CD34+ cells electroporated with two guide RNAs (Exon 2-2 and Exon 2-3) at the same time;

FIGS. 23A-23B show the growth kinetics and viability of human mPB CD34+ cells successively electroporated with dual guide RNAs under Arm 1 conditions compared to human mPB CD34+ cells electroporated with a single guide RNA under Arm 1 conditions;

FIG. 23A shows the growth kinetics of human mPB CD34+ cells successively electroporated with dual guide RNAs under Arm 1 conditions compared to human mPB CD34+ cells electroporated with a single guide RNA under Arm 1 conditions;

FIG. 23B shows the viability of human mPB CD34+ cells successively electroporated with dual guide RNAs under Arm 1 conditions compared to human mPB CD34+ cells electroporated with a single guide RNA under Arm 1 conditions;

FIG. 24A shows the growth kinetics of human mPB CD34+ cells successively electroporated with dual guide RNAs under Arm 2 conditions compared to human mPB CD34+ cells electroporated with a single guide RNA under Arm 2 conditions;

FIG. 24B shows the viability of human mPB CD34+ cells successively electroporated with dual guide RNAs under Arm 2 conditions compared to human mPB CD34+ cells electroporated with a single guide RNA under Arm 2 conditions;

FIGS. 25A-25B show the growth kinetics and viability of human mPB CD34+ cells successively electroporated with dual guide RNAs under Arm 3 conditions compared to human mPB CD34+ cells electroporated with a single guide RNA under Arm 3 conditions.

FIG. 25A shows the growth kinetics of human mPB CD34+ cells successively electroporated with dual guide RNAs under Arm 3 conditions compared to human mPB CD34+ cells electroporated with a single guide RNA under Arm 3 conditions;

FIG. 25B shows the viability of human mPB CD34+ cells successively electroporated with dual guide RNAs under Arm 3 conditions compared to single guide RNA electroporated human mPB CD34+ cells electroporated with a single guide RNA under Arm 3 conditions;

FIG. 26A shows the viability of human mPB CD34+ cells successively electroporated with dual guide RNAs under Arm conditions 1-3 compared to human mPB CD34+ cells electroporated with a single guide RNA under Arm conditions 1-3;

FIG. 26B shows the growth kinetics of human mPB CD34+ cells successively electroporated with dual guide RNAs under Arm conditions 1-3 compared to human mPB CD34+ cells electroporated with a single guide RNA under Arm conditions 1-3;

FIG. 27 shows the rate of DNA editing (% indels) at the BCL11a locus and HBG2 locus in human mPB CD34+ cells from Donor LKP06B successively electroporated with dual guide RNAs under Arm conditions 1-3 compared to human mPB CD34+ cells from Donor LKP06B electroporated with a single guide RNA under Arm conditions 1-3;

FIG. 28A shows the differentiation of human mPB CD34+ cells successively electroporated with dual guide RNAs under Arm conditions 1-3 compared to human mPB CD34+ cells electroporated with a single guide RNA under Arm conditions 1-3. Differentiation was determined by measuring the percentage of GYPA, and CD71;

FIG. 28B shows the differentiation of human mPB CD34+ cells successively electroporated with dual guide RNAs under Arm conditions 1-3 compared to human mPB CD34+ cells electroporated with a single guide RNA under Arm conditions 1-3. Differentiation was determined by measuring the percentage of Band3 and Alpha4;

Figure 31:
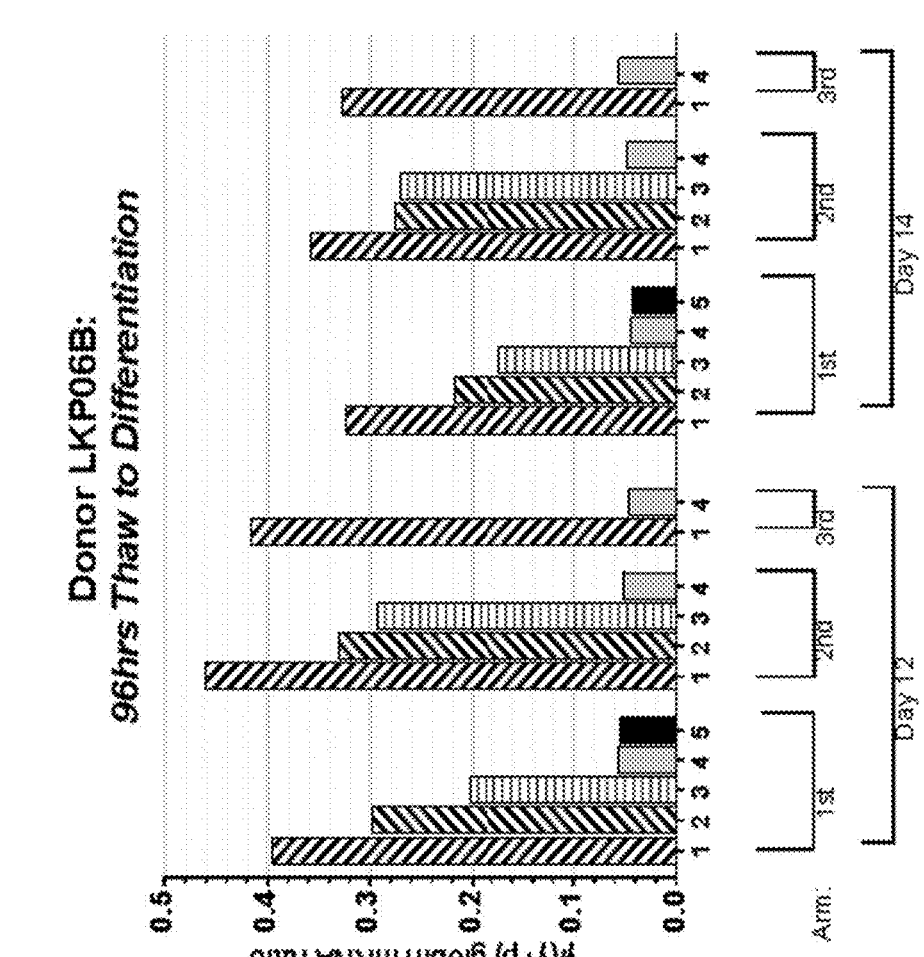
Figure 32:
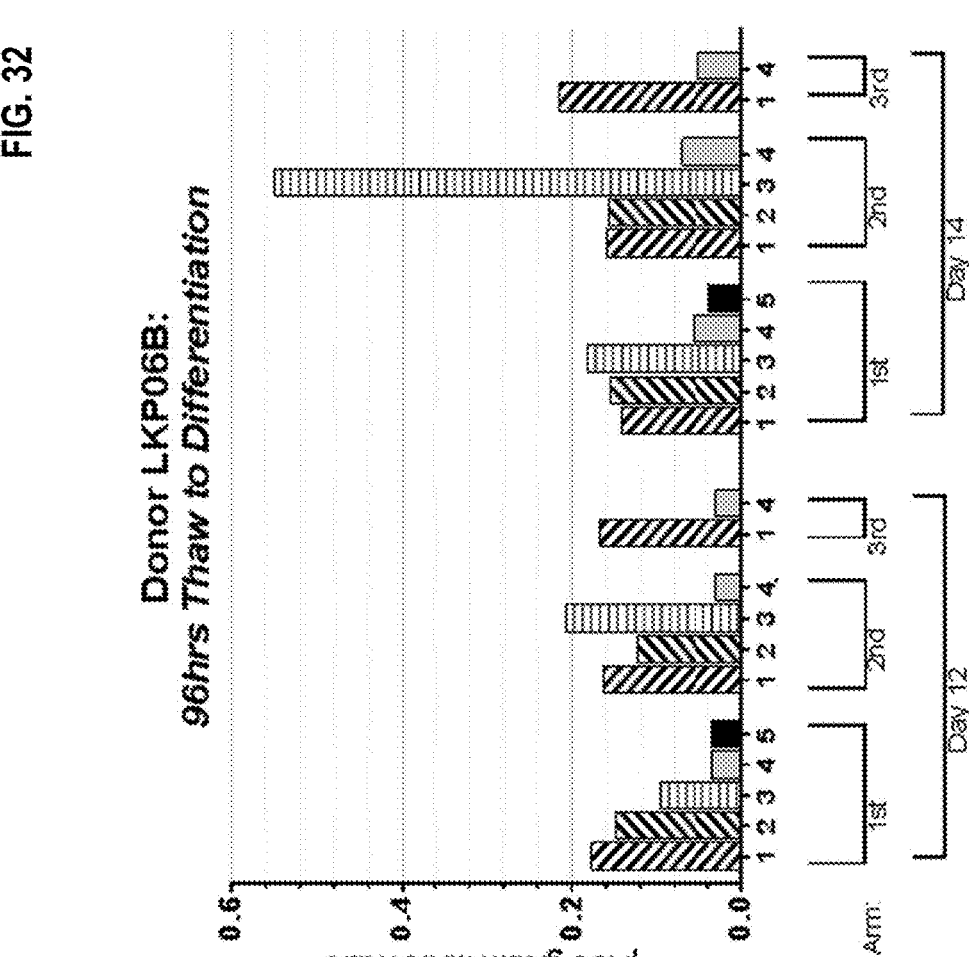
Figure 33A:
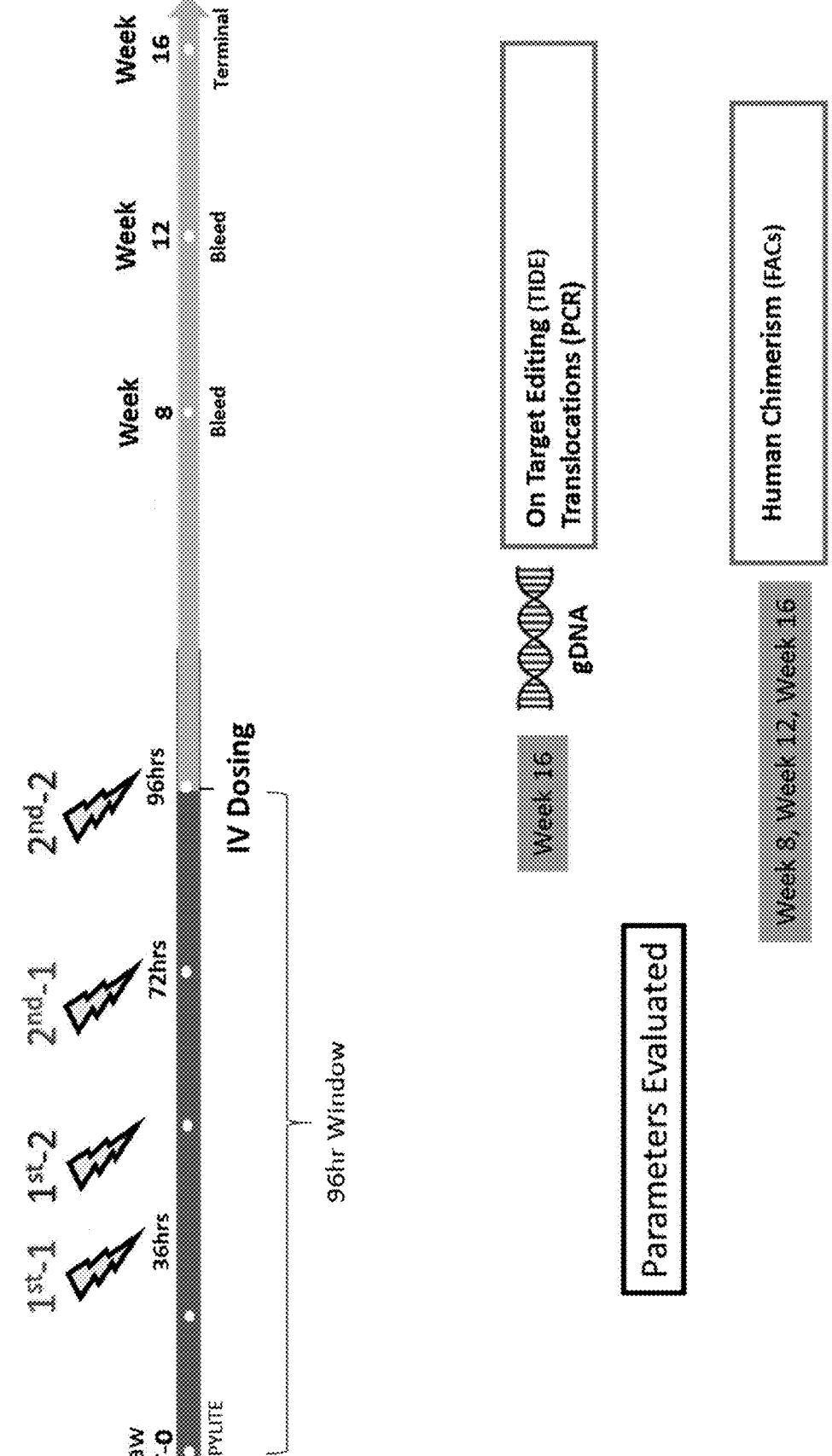
Figure 35:
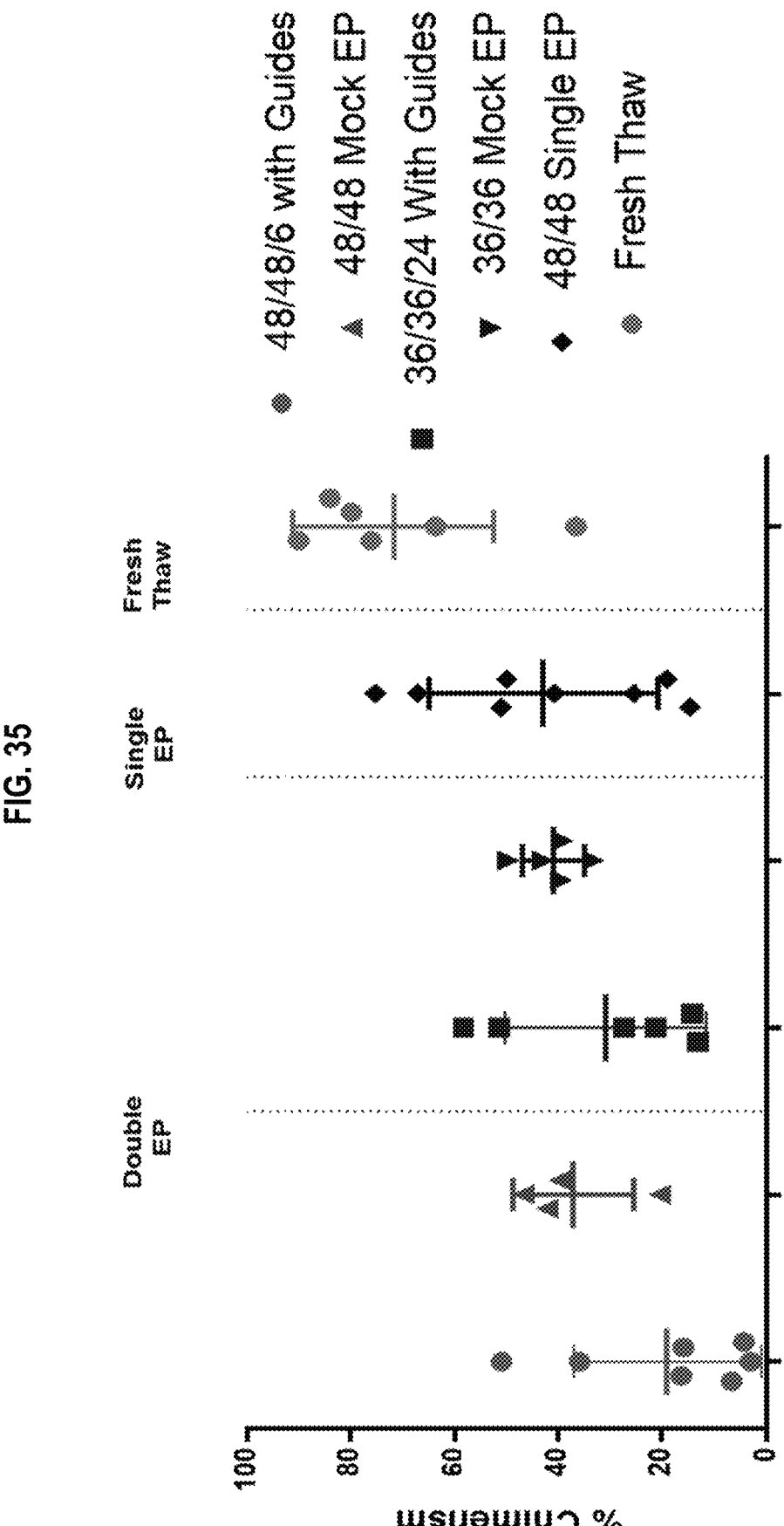
Figure 39:
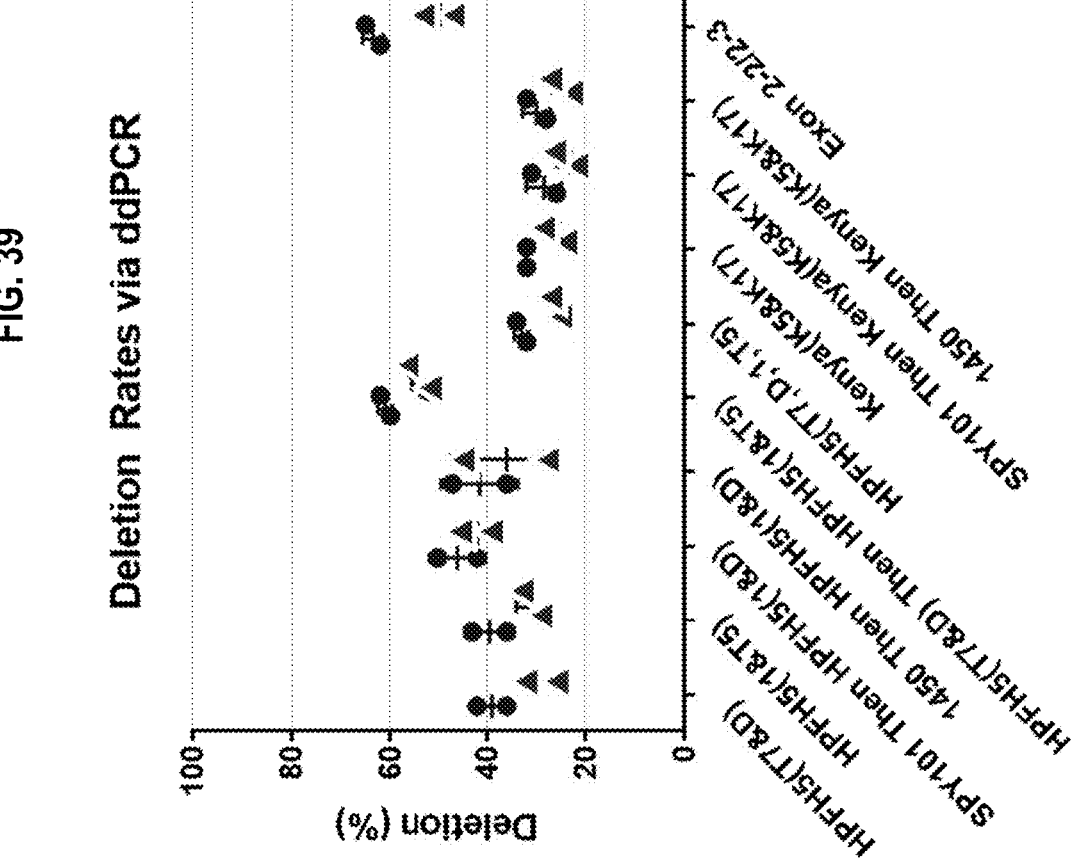
Figure 40:
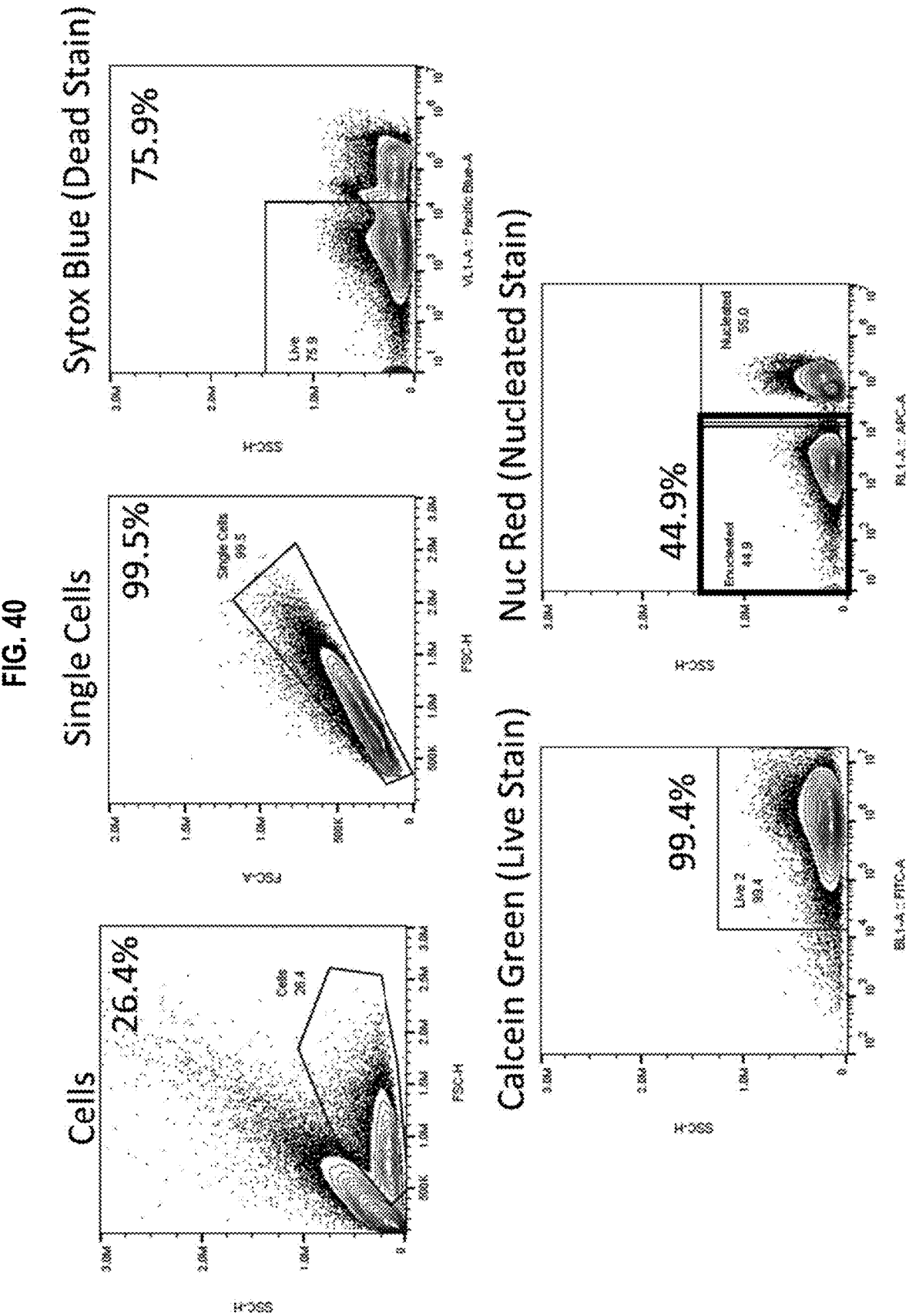

FIG. 31 shows the globin mRNA ratio in human mPB CD34+ cells from Donor LKP06B successively electroporated with dual guide RNAs under Arm conditions 1-3 compared to human mPB CD34+ cells from Donor LKP06B electroporated with a single guide RNA under Arm conditions 1-3;

FIG. 32 shows the γ/18S globin mRNA ratio in human mPB CD34+ cells from Donor LKP06B successively electroporated with dual guide RNAs under Arm conditions 1-3 compared to human mPB CD34+ cells from Donor LKP06B electroporated with a single guide RNA under Arm conditions 1-3;

FIGS. 33A-33B show an experimental design that includes successive electroporations using dual guide RNAs in a NSG mouse model system;

FIG. 33A shows the gene editing and transplantation schedules;

FIG. 33B shows a table of different experimental groups;

FIG. 34 shows human chimerism in peripheral blood samples of mice over a period of 16 weeks after gene editing and transplantation. Mice transplanted with cells edited using a successive electroporation method (e.g., 48/48/6 group with guides, e.g., first electroporation at hour 48, second electroporation at hour 96, transplantation at hour 102) show a reduction in % chimerism relative to the Mock EP group;

FIG. 35 shows human chimerism in bone marrow samples of mice at 16 weeks after gene editing and transplantation. Mice transplanted with cells edited using a successive electroporation method (e.g., 48/48/6 group with guides, e.g., first electroporation at hour 48, second electroporation at hour 96, transplantation at hour 102) show a reduction in % chimerism relative to the Mock EP group;

FIG. 36 shows genomic DNA analysis of bone marrow 16 weeks post transplant. Mice in the 48/48/6 group with guides, e.g., first electroporation at hour 48, second electroporation at hour 96, transplantation at hour 102, show high % indels;

FIG. 37 shows an experimental design that utilizes successive electroporations using dual guide RNAs to edit Chr2 and Chr11 in human mPB CD34+ cells from Donor LP06a and Donor LKP12;

FIG. 38 shows a table of experimental conditions that utilized successive electroporations using dual guide RNAs to edit Chr2 and Chr11 in human mPB CD34+ cells from Donor LP06a and Donor LKP12. Successive electroporation conditions provided increased HbF expression relative to single electroporation conditions;

FIG. 39 shows deletion rates (%) in experimental conditions that utilized successive electroporations using dual guide RNAs to edit Chr2 and Chr11 in human mPB CD34+ cells from Donor LP06a and Donor LKP12;

FIG. 40 shows an enucleation gating strategy of human mPB CD34+ cells from Donor LP06a and Donor LKP12 that had been successively electroporated with dual guide RNAs;

FIG. 41 shows enucleation over time for human mPB CD34+ cells from Donor LP06a and Donor LKP12 that had been edited using successive electroporations using dual guide RNAs to edit Chr2 and Chr11. The bars for each day of differentiation show, from left to right, SPY101 then HPFH5 (1&D), 1450 then HPFH5 (1&D), SPY101 then Kenya (K5&K17), 1450 then Kenya (K5&K17), HPFH5 (T7&D) then HPFH5 (1&T5), SPY101, 1450, HPFH5

Figure 42A:
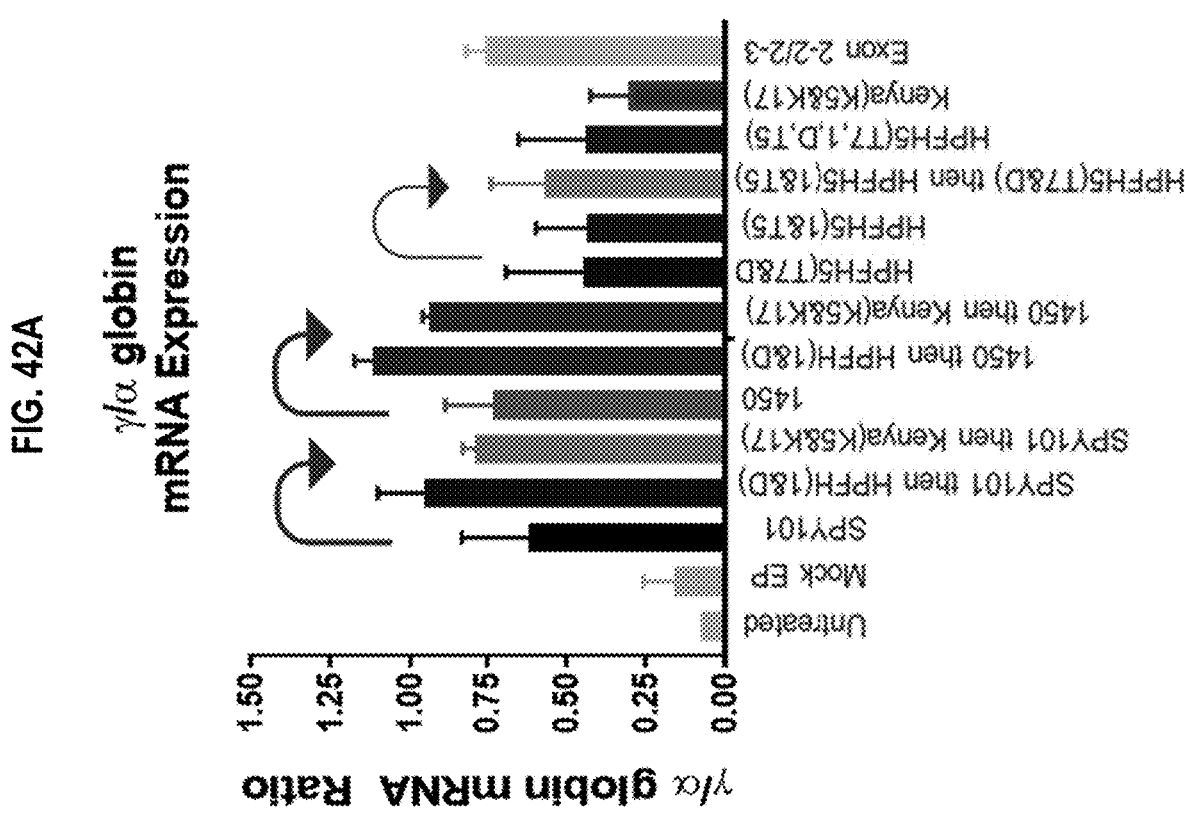
Figure 42C:
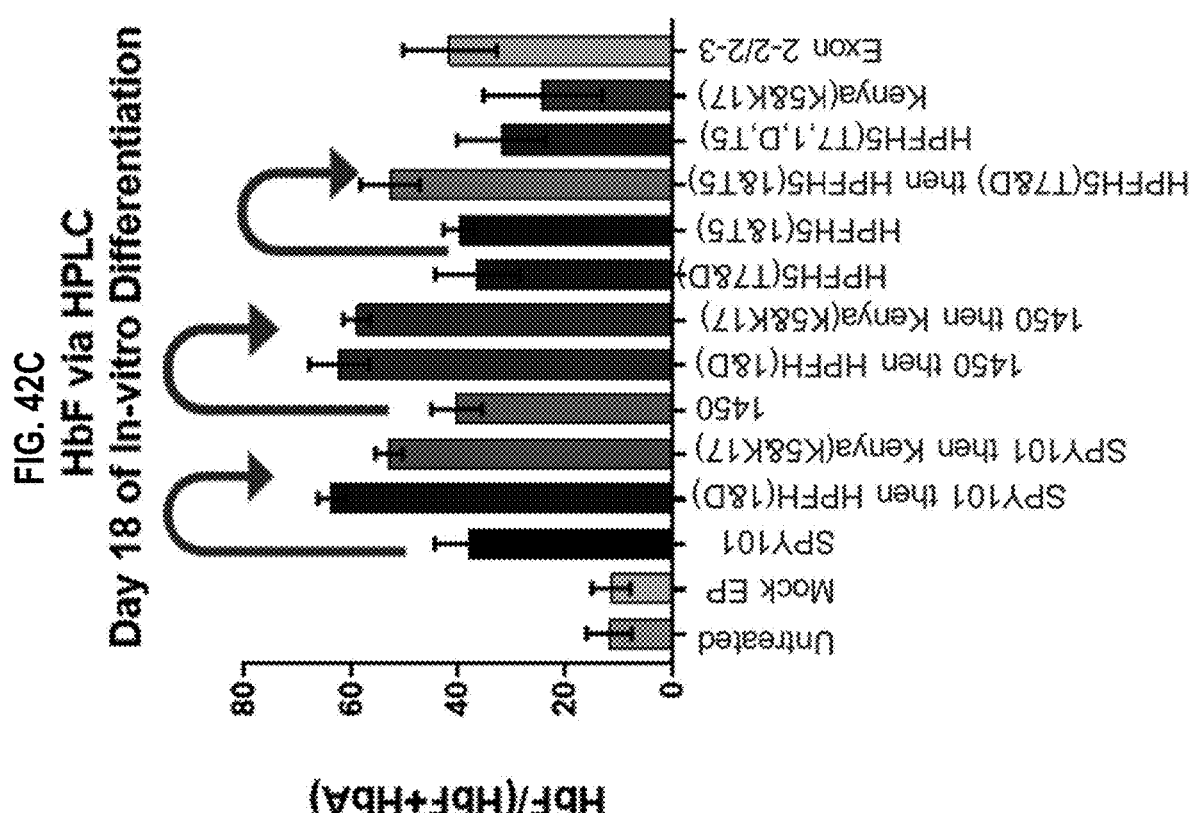
Figure 48:
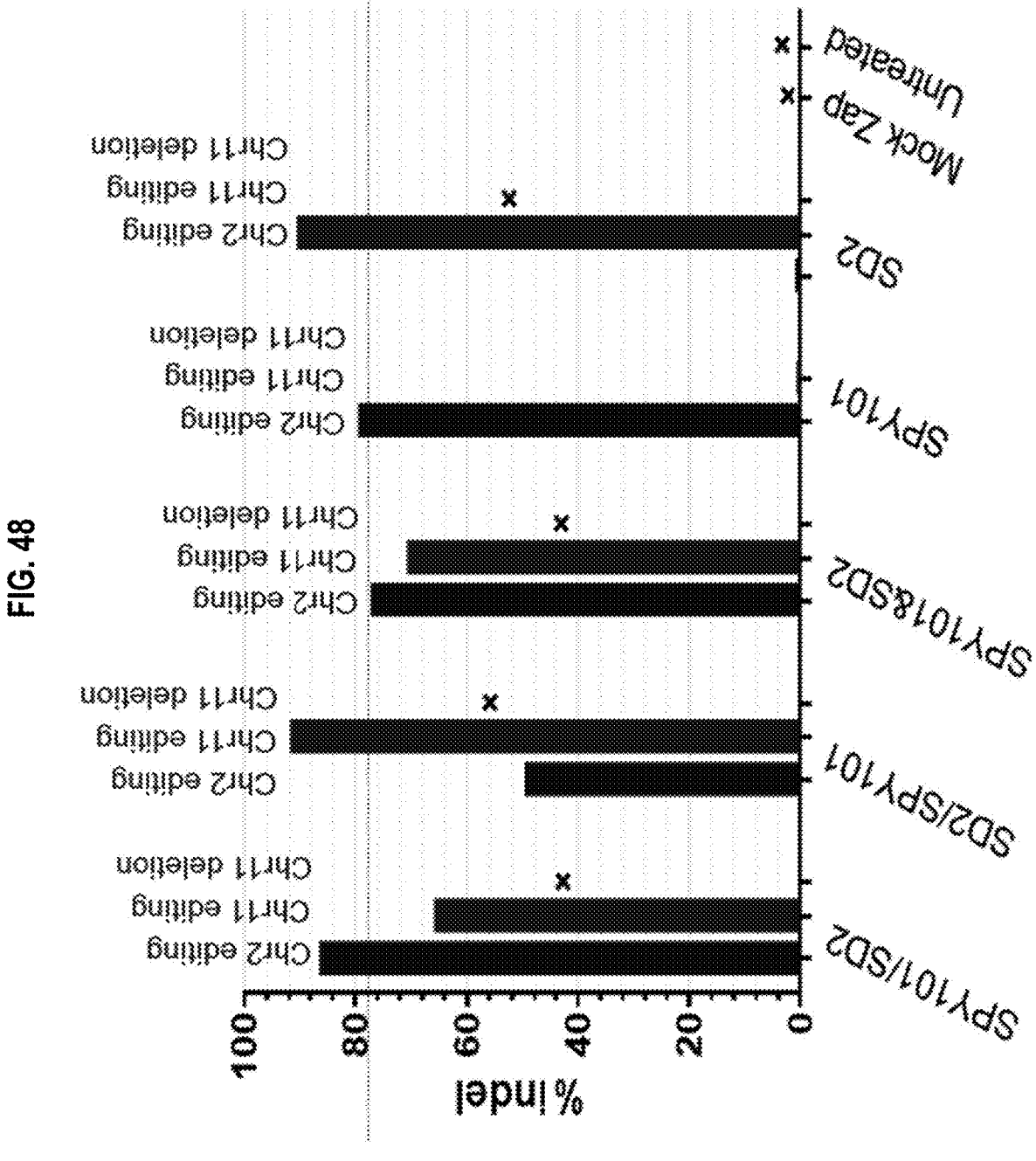
Figure 52:
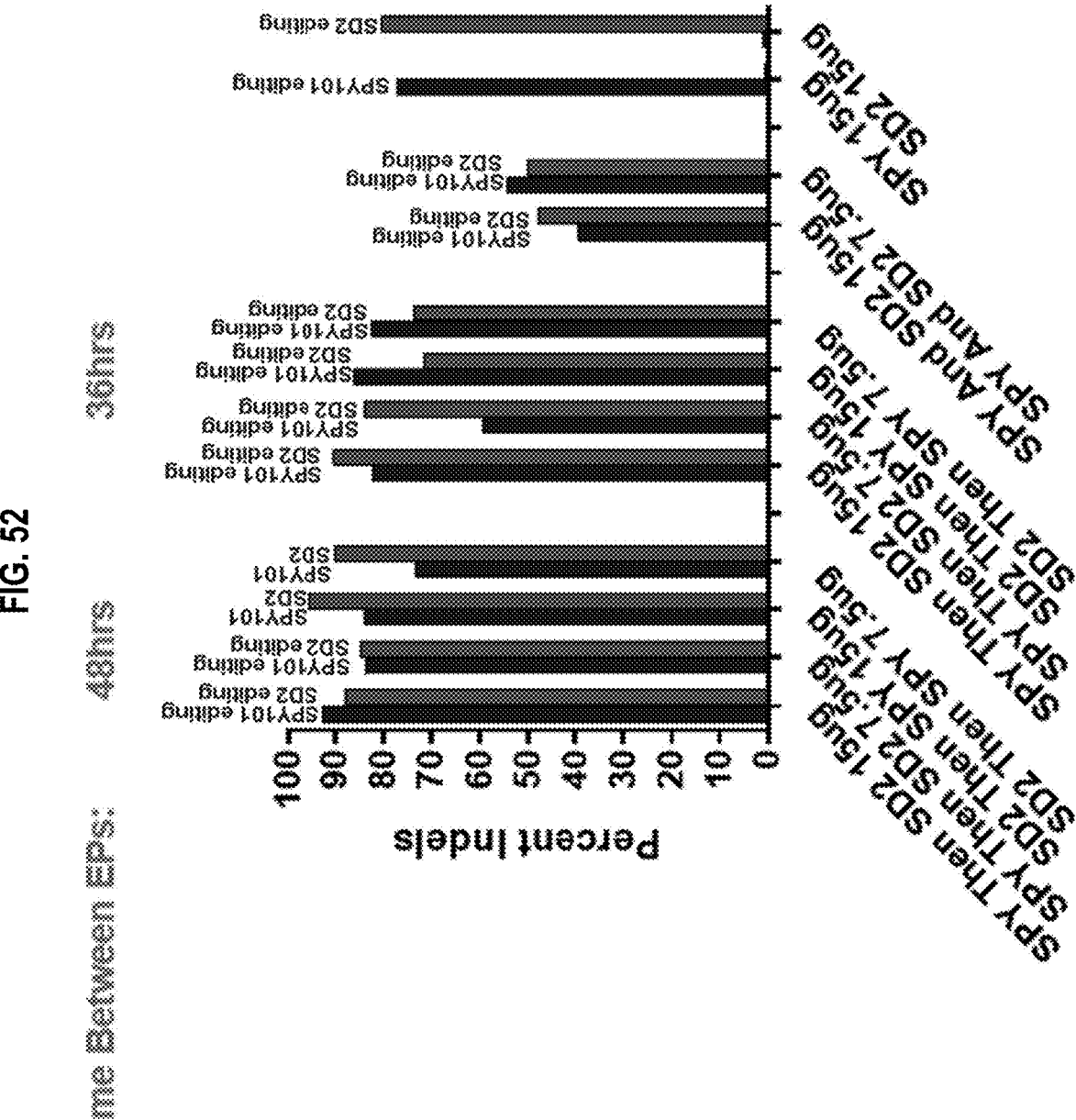
Figure 53A:
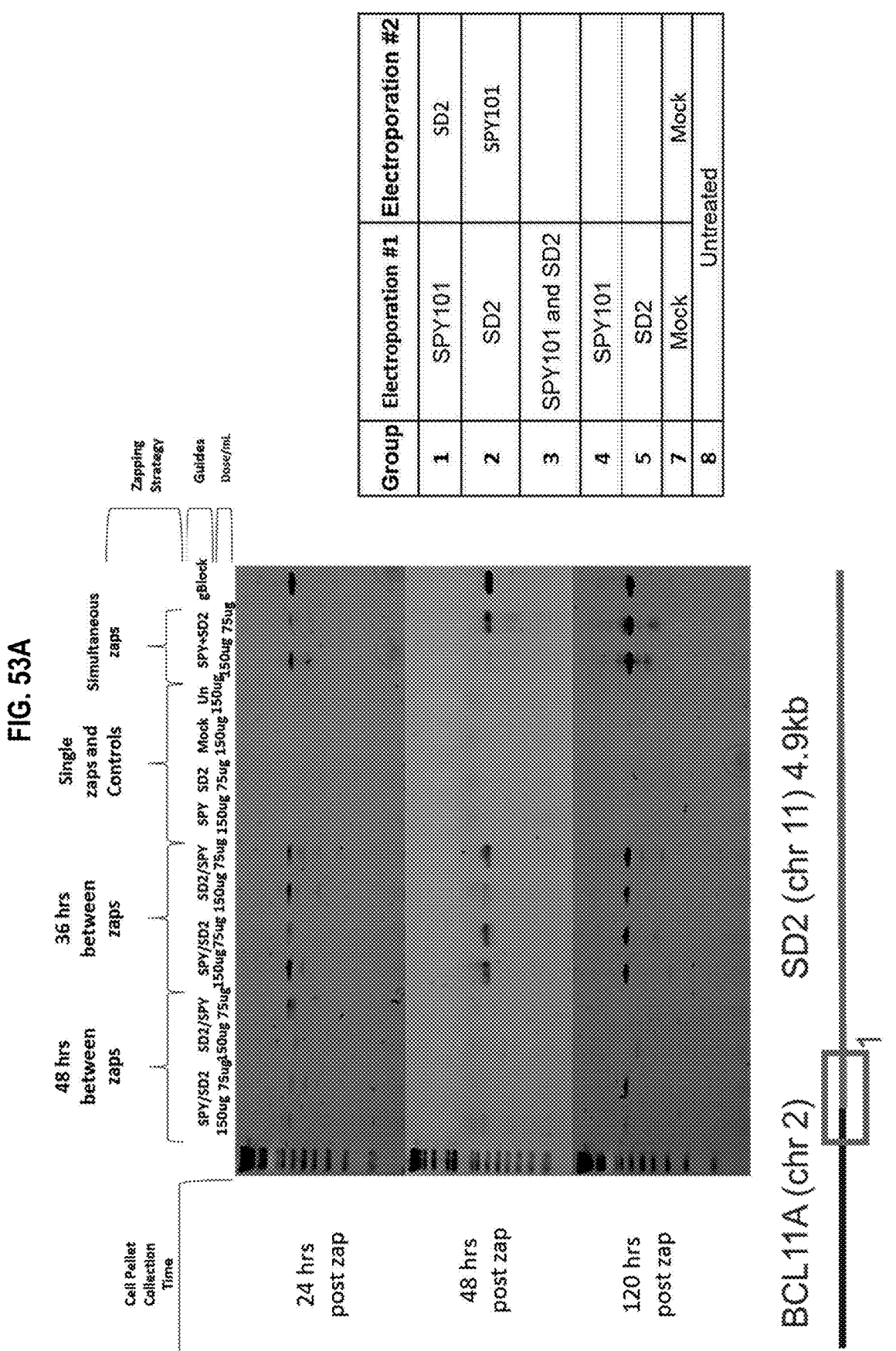
Figure 53B:
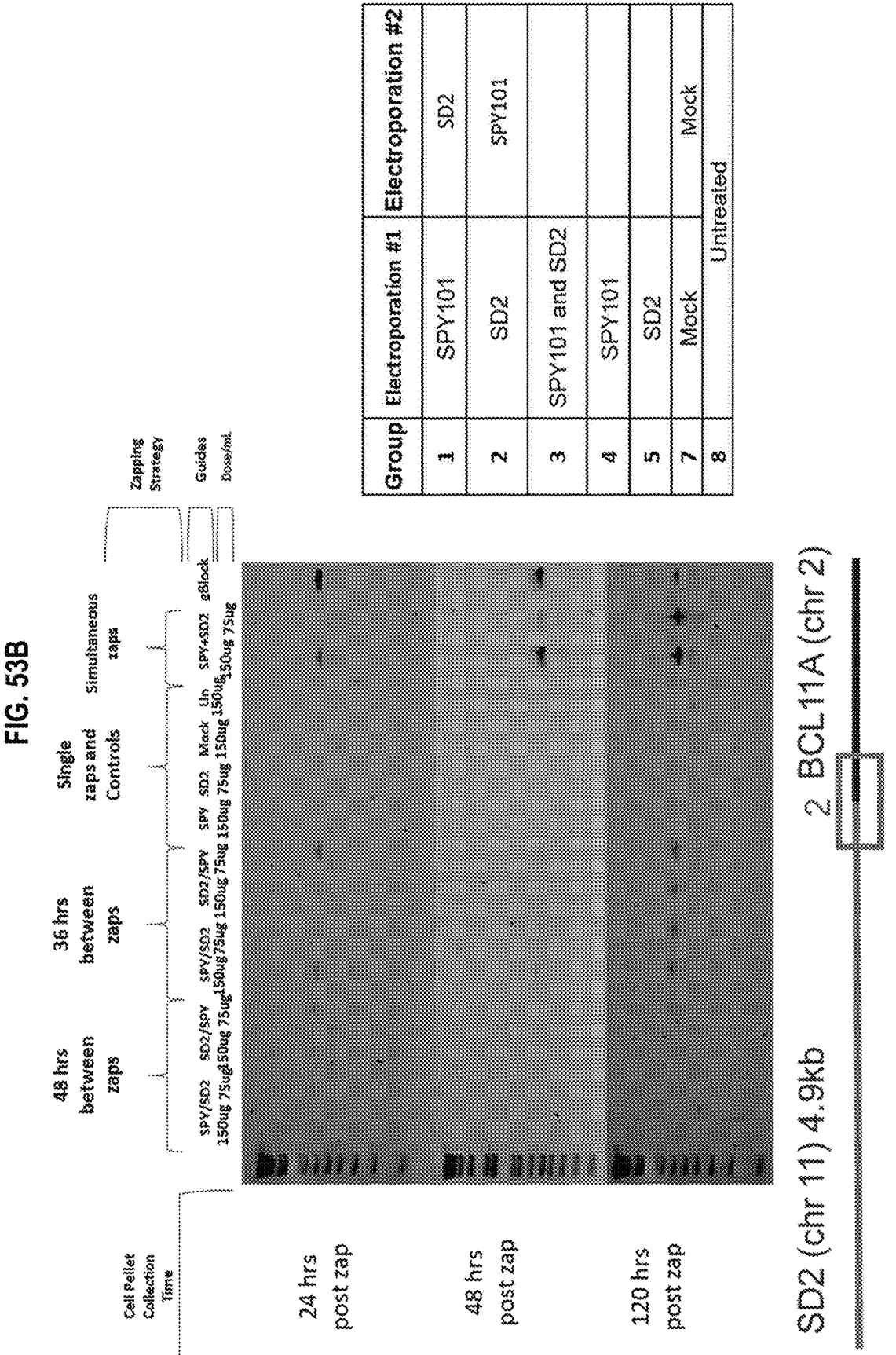
Figure 53C:
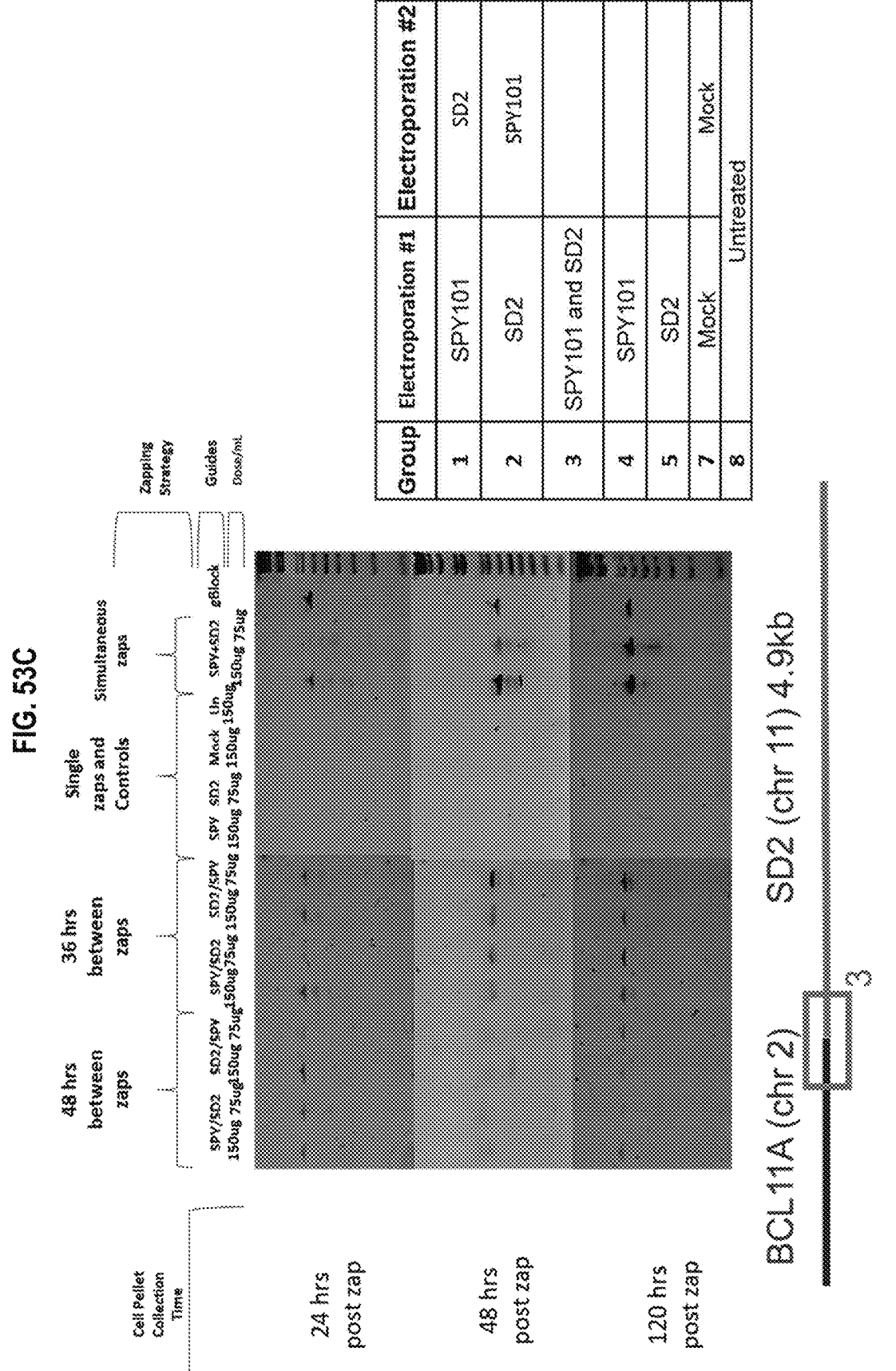
Figure 54:
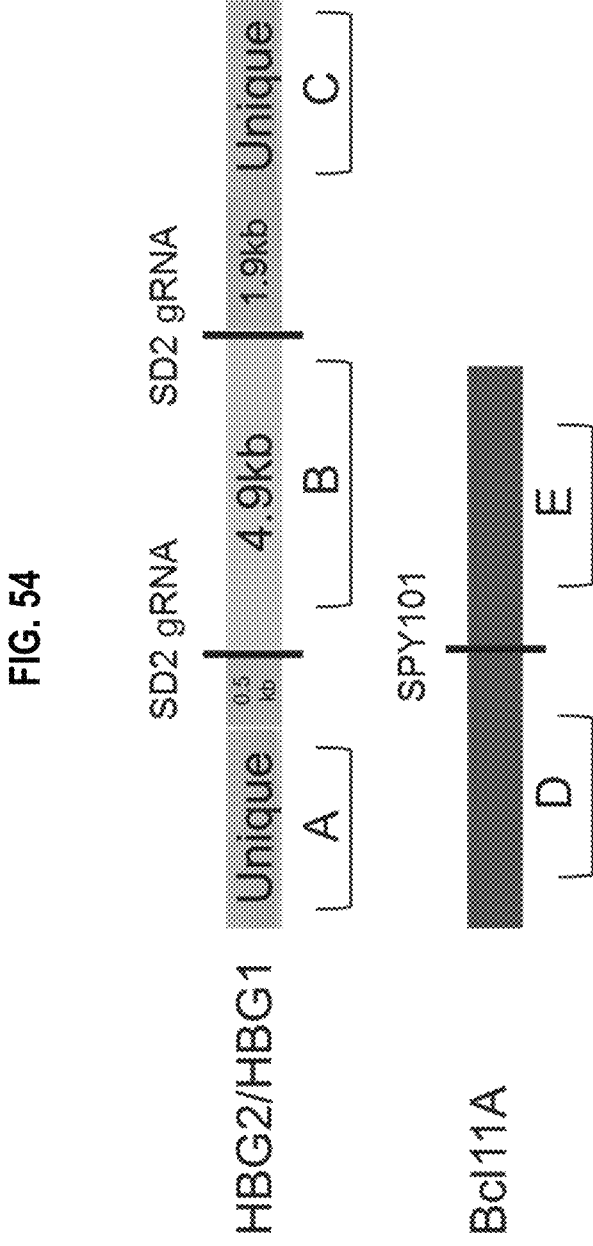
Figure 56B:
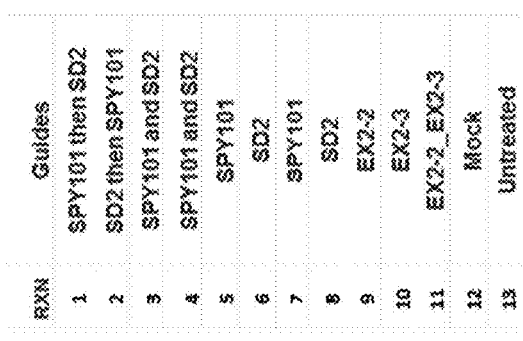
Figure 56C:
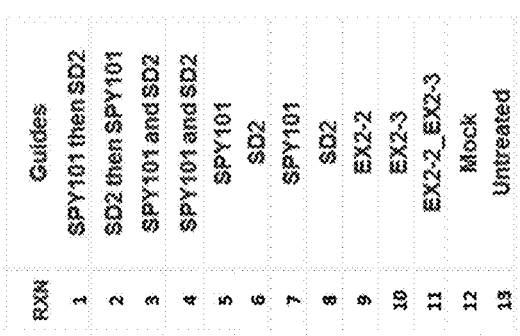

(T7&D), HPFH5 (1&T5), HPFH5 (T7,D,1,T5), Kenya (K5&K17), Exon2-2/2-3, Mock EP, and Untreated CD34 cells. There was minimal difference between cells that had been singly or doubly electroporated;

Figure 42B:
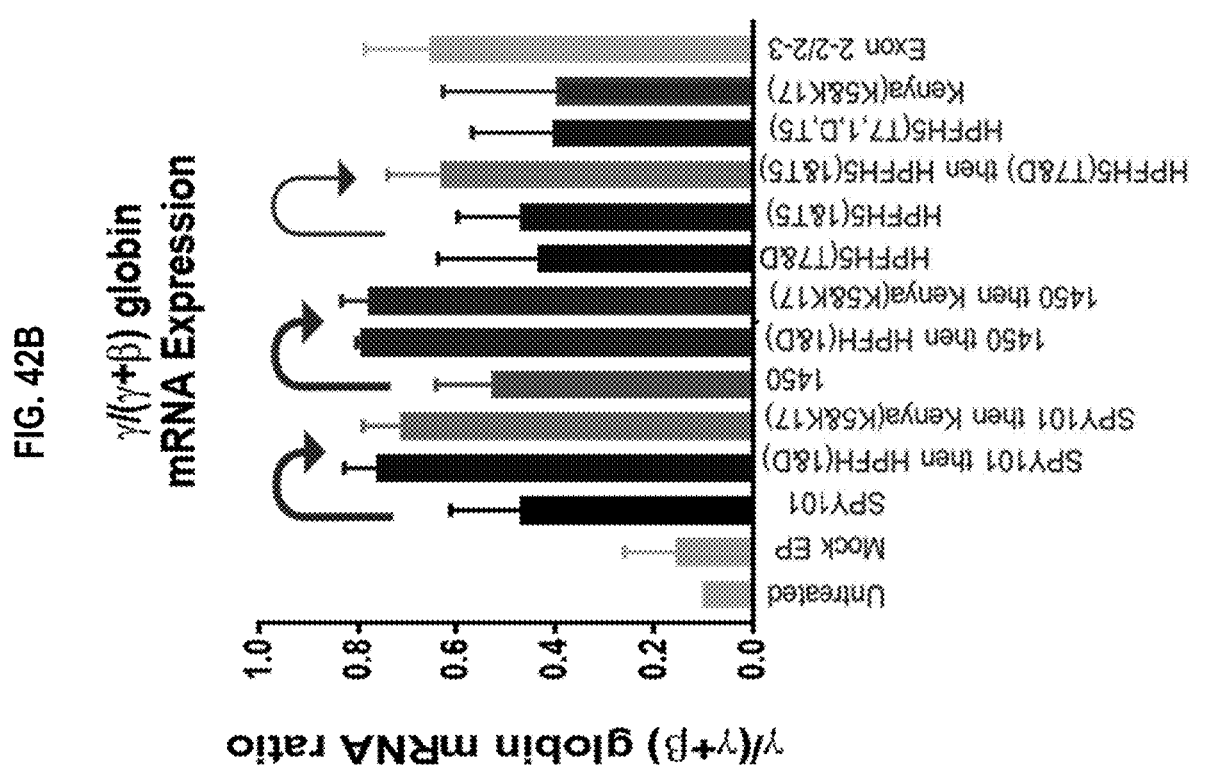

FIGS. 42A-42C show levels of globin expression in human mPB CD34+ cells from Donor LP06a and Donor LKP12 that had been edited using successive electroporations using dual guide RNAs to edit Chr2 and Chr11;

FIG. 42A shows mRNA transcript ratios for (γ globin)/(α globin);

FIG. 42B shows mRNA transcript ratios for (γ globin)/(γ globin+β globin);

FIG. 42C shows protein levels of HbF relative to (HbF+ HbA). Cells that had undergone double electroporated had a higher relative amount of HbF that cells that had undergone single electroporation;

Figure 43:
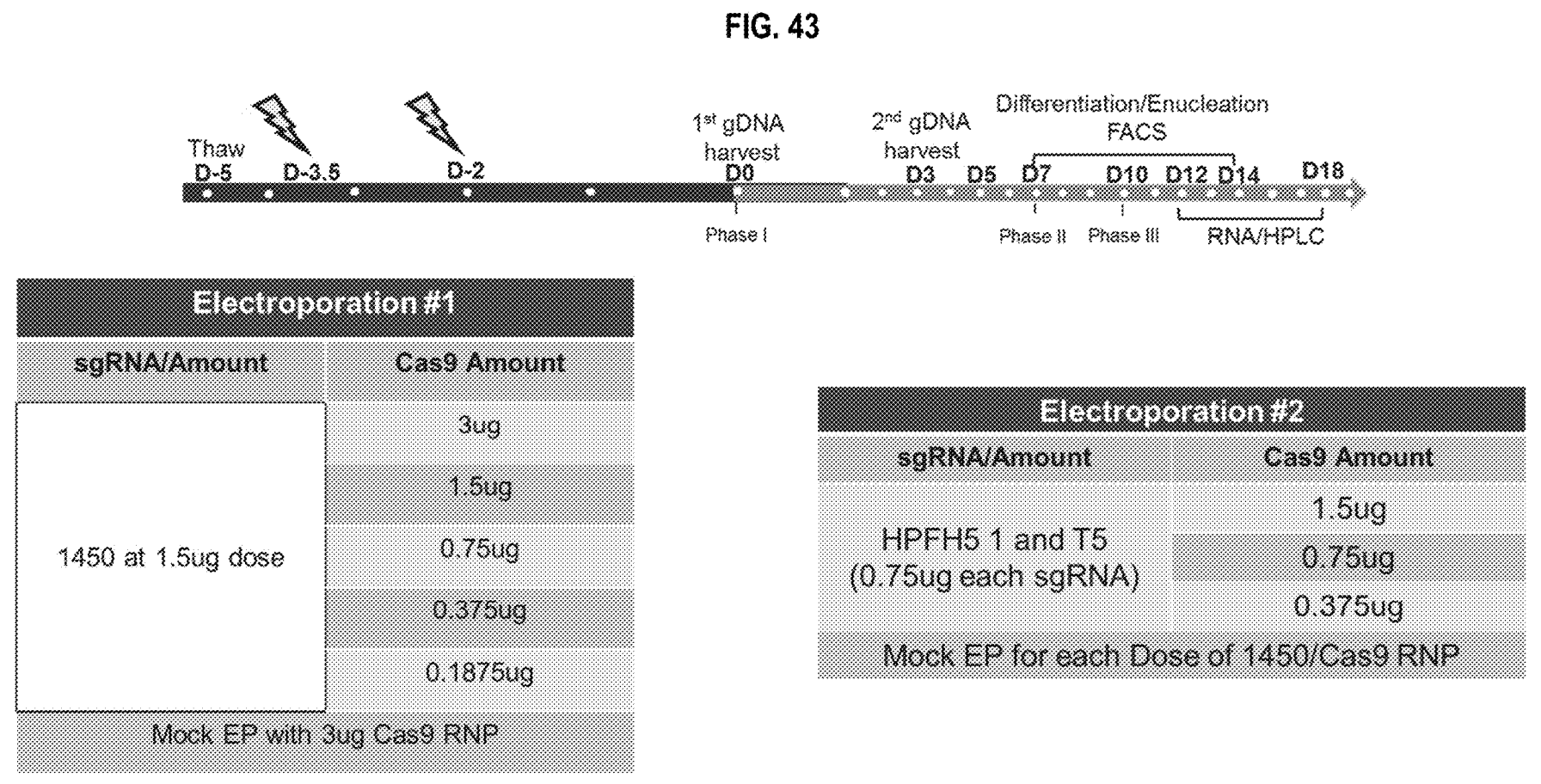

FIG. 43 shows an experimental design that utilizes varying amounts of Cas9 endonuclease during successive electroporations using dual guide RNAs to edit Chr2 and Chr11 in human mPB CD34+ cells;

FIG. 44 show percent gene editing at Chr2 and Chr11 in human mPB CD34+ cells after successive electroporations utilizing 1450 gRNA and HPFH5 gRNA. The amount of Cas9 endonuclease during the first electroporation was varied. Levels of gene editing were consistent for experiments using 0.375-3 µg Cas9;

FIG. 45 show mRNA transcript ratios for (γ globin)/(α globin) and (γ globin)/(γ globin+β globin) in human mPB CD34+ cells after successive electroporations utilizing 1450 gRNA and HPFH5 gRNA in human mPB CD34+ cells. The amount of Cas9 endonuclease during the first electroporation was varied. Levels of mRNA transcripts were consistent for experiments using 0.75-3 µg Cas9;

FIG. 46 show HbF percentages in human mPB CD34+ cells after successive electroporations utilizing 1450 gRNA and HPFH5 gRNA. The amount of Cas9 endonuclease during the first electroporation was varied. Levels of % HbF were consistent for experiments using 0.375-3 µg Cas9;

FIG. 47 shows an experimental design to compare single electroporation with one guide RNA, single electroporation with two guide RNAs, and successive electroporations with two guide RNAs to edit Chr2 and Chr11 in human mPB CD34+ cells;

FIG. 48 shows percent indels in human mPB CD34+ cells from Fred Hutch Donor 304 following gene editing. Cells that were successively electroporated with two guide RNAs (SPY101/SD2; SD2/SPY101) had comparable levels of percent indels relative to control experiments;

FIG. 49 shows three potential translocations, including points of fusion, that may occur when targeting Chr2 and Chr11 in cells with gRNAs specific for BCL11A and the site of SD2 targeting. Note that Fusion 3 represents a SD2-induced inversion;

FIG. 50 show nucleic acid agarose gels demonstrating that translocation events (fusions) that may occur when targeting Chr2 and Chr11 in cells are minimized when performing successive electroporation with two gRNAs (SPY101 then SD2; SD2 then SPY101) compared to simultaneous electroporation with two gRNAs (SPY101 AND SD2);

FIG. 51 shows an experimental design to compare single electroporation with one guide RNA, single electroporation with two guide RNAs, and successive electroporations with two guide RNAs to edit Chr2 and Chr11 in human mPB CD34+ cells;

FIG. 52 shows percent indels in human mPB CD34+ cells from Fred Hutch Donor 304 following gene editing. Cells that were successively electroporated with two guide RNAs (SPY101 Then SD2; SD2 Then SPY101) with a 48 hour period between electroporations had higher levels of percent indels than cells successively electroporated with a 36 hour period between electroporations;

FIGS. 53A-53C show nucleic acid agarose gels demonstrating that translocation events (fusions) that may occur when targeting Chr2 and Chr11 in cells are minimized when performing successive electroporation with two gRNAs (SPY101 then SD2; SD2 then SPY101) with a 48 hour period between electroporations compared a 36 hour period between electroporations;

FIG. 53A shows data corresponding to a translocation fusion 1 event;

FIG. 53B shows data corresponding to a translocation fusion 2 event;

FIG. 53A shows data corresponding to a translocation fusion 3 event (SD2-induced inversion);

FIG. 54 shows a ddPCR assay for determination of chromosomal translocations following gene editing with SD2 and SPY101 gRNAs;

FIG. 55 shows a table of ddPCR data demonstrating that single electroporation with two gRNAs (SPY101 And SD2) leads to increased translocation events compared to successive electroporation with two gRNAs (e.g., SPY101 Then SD2);

FIGS. 56A-56C show effects of single electroporation with one guide RNA, single electroporation with two guide RNAs, and successive electroporations with two guide RNAs to edit Chr2 and Chr11 in human mPB CD34+ cells;

FIG. 56A shows mRNA transcript ratios for (γ globin)/ (18S globin);

FIG. 56B shows mRNA transcript ratios for (γ globin)/(α globin);

FIG. 56C shows mRNA transcript ratios for (γ globin)/(γ globin+β globin).

BRIEF DESCRIPTION OF THE SEQUENCE LISTING

SEQ ID NOs: 1-56,961 is a list of gRNA 20 bp spacer sequences, associated PAM, chromosomal and gene location of the target sequence, cut site, and strand for targeting the human beta globin locus with a *S. pyogenes* Cas9 endonuclease.

SEQ ID NOs: 56,962-64,104 is a list of gRNA 20 bp spacer sequences, associated PAM, chromosomal and gene location of the target sequence, cut site, and strand for targeting the human beta globin locus with a *S. aureus* Cas9 endonuclease.

SEQ ID NOs: 64,105-66,258 is a list of gRNA 24 bp spacer sequences, associated PAM, chromosomal and gene location of the target, cut site, and strand for targeting the human beta globin locus with a *N. meningitides* Cas9 endonuclease.

SEQ ID NOs: 66,259-69, 152 is a list of gRNA 24 bp spacer sequences, associated PAM, chromosomal and gene location of the target, cut site, and strand for targeting the human beta globin locus with a *S. thermophilus* Cas9 endonuclease.

SEQ ID NOs: 69,153-70,300 is a list of gRNA 24 bp spacer sequences, associated PAM, chromosomal and gene location of the target, cut site, and strand for targeting the human beta globin locus with a *T. denticola* Cas9 endonuclease.

SEQ ID NOs: 70,301-156,352 is a list of gRNA 22 bp spacer sequences, associated PAM, chromosomal and gene location of the target, two cut sites, and strand for targeting the human beta globin locus with an *Acidominococcus*, a Lachnospiraceae, and a *Franciscella novicida* Cpf1 endonuclease.

SEQ ID NOs: 156,353-185,834 is a list of gRNA 20 bp spacer sequences, associated PAM, chromosomal and gene location of the target sequence, cut site, and strand for targeting within or near a BCL11A gene or a DNA sequence that encodes a regulatory element of the BCL11A gene with a *S. pyogenes* Cas9 endonuclease.

SEQ ID NOs: 185,835-188,739 is a list of gRNA 20 bp spacer sequences, associated PAM, chromosomal and gene location of the target sequence, cut site, and strand for targeting within or near a BCL11A gene or a DNA sequence that encodes a regulatory element of the BCL11A gene with a *S. aureus* Cas9 endonuclease.

SEQ ID NOs: 188,740-189,772 is a list of gRNA 24 bp spacer sequences, associated PAM, chromosomal and gene location of the target, cut site, and strand for targeting within or near a BCL11A gene or a DNA sequence that encodes a regulatory element of the BCL11A gene with a *S. thermophilus* Cas9 endonuclease.

SEQ ID NOs: 189,773-190,203 is a list of gRNA 24 bp spacer sequences, associated PAM, chromosomal and gene location of the target, cut site, and strand for targeting within or near a BCL11A gene or a DNA sequence that encodes a regulatory element of the BCL11A gene with a *T. denticola* Cas9 endonuclease.

SEQ ID NOs: 190,204-193,083 is a list of gRNA 24 bp spacer sequences, associated PAM, chromosomal and gene location of the target, cut site, and strand for targeting within or near a BCL11A gene or a DNA sequence that encodes a regulatory element of the BCL11A gene with a *N. meningitides* Cas9 endonuclease.

SEQ ID NOs: 193,084-228,299 is a list of gRNA 22 bp spacer sequences, associated PAM, chromosomal and gene location of the target, two cut sites, and strand for targeting within or near a BCL11A gene or a DNA sequence that encodes a regulatory element of the BCL11A gene with an *Acidominococcus*, a Lachnospiraceae, and a *Franciscella novicida* Cpf1 endonuclease.

SEQ ID NO: 228,300 shows a known family of homing endonuclease, as classified by its structure.

SEQ ID NO: 228,301 is a sample guide RNA (gRNA) for a *S. pyogenes* Cas9 endonuclease.

SEQ ID NOs: 228,302-228,304 show sample sgRNA sequences.

DETAILED DESCRIPTION

Hemoglobinopathies

As used herein, the term "hemoglobinopathy" means any defect in the structure, function or expression of any hemoglobin of an individual, and includes defects in the primary, secondary, tertiary or quaternary structure of hemoglobin caused by any mutation, such as deletion mutations or substitution mutations in the coding regions of the β-globin gene, or mutations in, or deletions of, the promoters or enhancers of such genes that cause a reduction in the amount of hemoglobin produced as compared to a normal or standard condition. The term "hemoglobinopathy" further includes any decrease in the amount or effectiveness of hemoglobin, whether normal or abnormal, caused by external factors such as disease, chemotherapy, toxins, poisons, or the like. β-hemoglobinopathies contemplated herein include, but are not limited to, sickle cell disease (SCD, also referred to a sickle cell anemia or SCA), sickle cell trait, hemoglobin C disease, hemoglobin C trait, hemoglobin S/C disease, hemoglobin D disease, hemoglobin E disease, thalassemias, hemoglobins with increased oxygen affinity, hemoglobins with decreased oxygen affinity, unstable hemoglobin disease and methemoglobinemia.

Disorders specifically associated with the β-globin protein are referred to generally as β-hemoglobinopathies. For example, β-thalassemias result from a partial or complete defect in the expression of the β-globin gene, leading to deficient or absent hemoglobin A (HbA). HbA is the most common human hemoglobin tetramer and consists of two α-chains and two β-chains ($\alpha_2\beta_2$). β-thalassemias are due to mutations in the adult β-globin gene (HBB) on chromosome 11, and are inherited in an autosomal, recessive fashion. β-thalassemia or β-thal is classified into two clinically-significant types (which are a focus of symptom management, medical treatments and the present application) that are distinguished by the severity of symptoms: β-thalassemia major (or $\beta^0$, in which mutations block production of β-globin chains, resulting in a severe condition that is also known as "Cooley's anemia") and β-thalassemia intermedia (or $\beta^+$, an intermediate condition in which mutations reduce but do not block production of β-globin chains). In contrast, β-thalassemia minor or β-thalassemia trait refers to the heterozygous situation in which only one of the β-globin alleles contains a mutation, so that β-globin chains can be produced via expression from the other (i.e. unmutated) chromosome 11 allele. While such individuals are carriers of a β-thalassemia mutant allele that they may pass on to their children, individuals with β-thalassemia minor are generally either asymptomatic or nearly asymptomatic themselves as a result of β-globin production from the unaffected allele.

The signs and symptoms of thalassemia major generally appear within the first 2 years of life, when children with the disease can develop life-threatening anemia. Children with thalassemia major often fail to gain sufficient weight or grow at the expected rate (failure to thrive) and may develop jaundice. Affected individuals may also have an enlarged spleen, liver, and heart, and their bones may be misshapen. Many people with thalassemia major have such severe symptoms that they need frequent blood transfusions to replenish their red blood cell supply, which is referred to as transfusion-dependent thalassemia. While transfusions have been a critical life-saver for many patients, they are expensive and are frequently associated with significant side effects. Among others, over time the administration of iron-containing hemoglobin from chronic blood transfusions tends to lead to a buildup of iron in the body, which can result in liver, heart, and endocrine problems.

Thalassemia intermedia is milder than thalassemia major. The signs and symptoms of thalassemia intermedia appear in early childhood or later in life. Although symptoms are less severe, affected individuals still have mild to moderate anemia and may also suffer from slow growth and bone abnormalities.

Sickle cell disease (SCD) is a group of disorders that affects millions of people worldwide. It is most common among people who live in or whose ancestors come from Africa; Mediterranean countries such as Greece, Turkey, and Italy; the Arabian Peninsula; India; Spanish-speaking regions in Central and South America, and parts of the Caribbean. However, SCD is also the most common inherited blood disorder in the United States. SCD includes sickle cell anemia, as well as sickle hemoglobin C disease (HbSC), sickle beta-plus-thalassemia (HbS/$\beta^+$) and sickle beta-zero-thalassemia (HbS/$\beta^0$).

Sickle cell anemia (SCA), which is the most prevalent form of SCD, is among the most common severe monogenic disorders worldwide, with approximately 250,000 children born with SCD every year. The incidence of SCA is greatest in West and Central Africa, where 1-2% of babies are born with the disease, and as many as 25% of people are heterozygous carriers. The SCA point mutation is believed to have been spread through selective advantage because heterozygosity provides modest protection against death from childhood malaria. In India, where malaria is also prevalent, it is estimated that there are more than 2.5 million heterozygous carriers of SCA and approximately 150,000 homozygotes with the disease.

Despite the relative absence of malaria in North America and Europe, the fact that each has large populations with genetic origins in affected areas has meant that both regions have substantial populations of heterozygous SCA carriers, and therefore affected homozygous individuals. For example, the U.S. Centers for Disease Control (CDC) estimates that there are approximately 90,000 to 100,000 Americans with SCA; and incidence is also high in countries of Western Europe, particularly those with large immigrant populations, with an estimated 10,000 in France and 12,000 to 15,000 in the United Kingdom for example. Associated costs to healthcare systems are likewise substantial. In a five-year U.S. study conducted from 1989 through 1993, the CDC estimated that SCD resulted in more than 75,000 hospitalizations annually, and cost approximately $0.5 billion. System wide costs would be expected to be substantially greater now given the steady rise in healthcare costs over the intervening two decades.

All forms of SCD are caused by mutations in the β-globin structural gene (HBB). Sickle cell anemia (SCA) is an autosomal recessive disease caused by a single missense mutation in the sixth codon of the β-globin gene (HBB; A→T) resulting in the substitution of glutamic acid by valine (Glu→Val). The mutant protein, when incorporated into hemoglobin (Hb), results in unstable hemoglobin HbS (which is $\alpha_2\beta_2^{\,S}$) in contrast to normal adult hemoglobin or HbA (which is $\alpha_2\beta_2^{\,A}$). Upon de-oxygenation, HbS polymerizes to form HbSS through hydrophobic interactions between $\beta^S$-6 valine of one tetramer and β-85 phenylalanine and β-88 leucine of an adjacent tetramer in the erythron, which leads to rigidity and vaso-occlusion [Atweh, *Semin. Hematol.* 38 (4): 367-73 (2001)].

When HbS is the predominant form of hemoglobin, as in individuals with SCA, their red blood cells (RBCs) tend to be distorted into a sickle or crescent shape. The sickle-shaped RBCs die prematurely, which can lead to anemia. In addition, the sickle-shaped cells are less flexible than normal RBCs and tend to get stuck in small blood vessels causing vaso-occlusive events. Such vaso-occlusive events are associated with tissue ischemia leading to acute and chronic pain as well as organ damage that can affect any organ in the body, including the bones, lungs, liver, kidneys, brain, eyes, and joints. The spleen is particularly subject to infarction and the majority of individuals with SCD are functionally asplenic in early childhood, increasing their risk for certain types of bacterial infections. Occlusions of small vessels can also cause acute episodic febrile illness called "crises," which are associated with severe pain and multiple organ dysfunction. Over the course of decades there is progressive organ disease and premature death.

Children with SCD may be diagnosed by newborn screening but otherwise do not present until later, when levels of fetal hemoglobin (HbF) decline and levels of HbS increase as a result of the hemoglobin allelic "switch" from fetal hemoglobin (encoded by HBG1 (A-gamma, also written $^A\gamma$) and HBG2 (G-gamma, also written $^G\gamma$)) to the adult β form encoded by HBB). The switch from HbF to the adult form of β-globin (i.e. HbA in unaffected children or HbS in those with SCA) typically begins a few months prior to birth and is complete by about the age of 6 months. The clinical effects of SCD are not manifested until HbF levels become significantly low relative to HbS, which typically occurs two to three months after birth. SCD often first presents as dactylitis or "hand-foot syndrome," a condition associated with pain in the hands and/or feet that may be accompanied by swelling. In addition, the spleen can become engorged with blood cells resulting in a condition known as "splenic sequestration." Hemolysis associated with SCD can result in anemia, jaundice, cholelithiasis, as well as delayed growth. Individuals with the highest rates of SCD hemolysis also tend to experience pulmonary artery hypertension, priapism, and leg ulcers.

Sickle cell anemia (homozygous HbSS) accounts for 60%-70% of sickle cell disease in the United States. The other forms of sickle cell disease result from coinheritance of HbS with other abnormal globin β chain variants, the most common forms being sickle-hemoglobin C disease (HbSC) and two types of sickle β-thalassemia (HbSβ+-thalassemia and HbSβ°-thalassemia). The β-thalassemias are divided into β°-thalassemia, in which reduced levels of normal β-globin chains are produced, and β°-thalassemia, in which there is no β-globin chain synthesis. Other globin β chain variants such as D-Punjab, O-Arab, and E also result in sickle cell disease when coinherited with HbS.

Although improvements in the management of SCD have reduced mortality in affected children followed up since neonatal screening, the mainstay of treatment for the majority of individuals with SCD remains supportive. Current treatments aim at relieving symptoms and treating complications such as: pain from vaso-occlusive crisis, infection, anemia, stroke, priapism, pulmonary hypertension or chronic organ damage. Preventative therapies include infection prophylaxis with regular penicillin, vaccination against *Streptococcus pneumoniae* and *Haemophilus influenzae*, as well as regular transfusions in children with abnormal transcranial Doppler ultrasonography to prevent strokes and iron chelation for transfusional iron overload. Stroke is also considered an indication for bone marrow transplantation in children and adolescents, who have siblings with identical human leukocyte antigen (HLA). Effective treatment of acute pain is one of the most common problems raised by the management of SCA. Thus, at the present time, definitive therapies that substantially alter the natural history of the disease (such as regular transfusion or exchange transfusion, long-term hydroxycarbamide and HSC transplants) are limited.

Fetal Hemoglobin (HbF)

Fetal hemoglobin (HbF) is a tetramer of two adult α-globin polypeptides and two fetal β-like γ-globin polypeptides. The γ-globin genes (HBG1 and HBG2) are normally expressed in the fetal liver, spleen and bone marrow. A tetramer of two γ-chains together with two α-chains constitute HbF. During gestation, the duplicated γ-globin genes constitute the predominant genes transcribed from the β-globin locus. Following birth, γ-globin becomes progressively replaced by adult β-globin, a process referred to as the "fetal switch." This developmental switch from production of predominantly HbF (α2γ2) to production of adult hemoglobin or HbA (α2β2) begins at about 28 to 34 weeks of gestation and continues shortly after birth at which point HbA becomes predominant. The switch results primarily from decreased transcription of the γ-globin genes and increased transcription of β-globin genes. On average, the blood of a normal adult contains only about 2% of total hemoglobin in the form of HbF, though residual HbF levels have a variance of over 20 fold in healthy adults (Atweh, Semin. Hematol. 38 (4): 367-73 (2001)). The two types of γ-chains differ at residue 136 where glycine is found in the G-γ-product (HBG2) and alanine is found in the A-γ-product (HBG1). The HBG1 hemoglobin gene ($^A$γ or A-gamma [*Homo sapiens* (human)] Gene ID: 3047), was updated on 16 Apr. 2014 (www dot ncbi dot nlm dot nih dot gov/gene/3047).

Many of the forms of hemoglobinopathies are a result of the failure to produce normal β-globin protein in sufficient amounts or failure to produce normal β-globin protein entirely. Increased expression of γ-globin (i.e., HbF) will ameliorate β-globin disease severity.

The potential for addressing β-hemoglobinopathies by increasing levels of fetal hemoglobin ($\alpha_2\gamma_2$; HbF) is supported by observations of the mild phenotype of individuals who have co-inherited homozygous β-thalassemia and hereditary persistence of fetal hemoglobin (HPFH), as well as by those patients with homozygous β-thalassemia who synthesize no adult hemoglobin, but in whom a reduced requirement for transfusions is observed in the presence of increased concentrations of HbF. Additional support comes from the observation that certain populations of adult patients with β chain abnormalities have higher than normal levels of HbF, and have been observed to have a milder clinical course of disease than patients with normal adult levels of HbF. For example, a group of Saudi Arabian sickle-cell anemia patients who express 20-30% HbF (as a percent of total hemoglobin) have only mild clinical manifestations of the disease [Pembrey et al., *Br. J. Haematol.* 40:415-429 (1978)]. β-hemoglobinopathies, such as sickle cell anemia and the β-thalassemias, can therefore be ameliorated by increased HbF production.

B-Cell Lymphoma 11A (BCL11A)

B-cell E lymphoma 11A (BCL11A) is a gene located on Chromosome 2 and ranges from 60,451,167-60,553,567 bp (GRCh38). BCL11A is a zinc finger transcription factor that represses HbF and downregulates HbF expression starting at about 6 weeks after birth. The BCL11A gene contains 4 exons, spanning 102.4 kb of genomic DNA. BCL11A also is under transcription regulation, including a binding domain in intron 2 for the master transcription factor GATA-1. GATA-1 binding enhances BCL11A expression which, in turn, represses HbF expression. Intron 2 contains multiple DNase hypersensitive sites (DHS), including sites referred to as +55, +58, and +62 based on the distance in kilobases from the transcriptional start site. Various editing strategies are discussed below to delete, modulate, or inactivate the transcriptional control sequences of BCL11A. Naturally occurring SNPs within this region have been associated with decreased BCL11A expression and increased fetal Hb levels (Orkin et al. 2013 GWAS study). These SNPs are organized around 3 DNA Hypersensitivity sites, +55DHS, +58DHS and +62DHS. Of the 3 regions, the +58 DHS region, appears to be the key region associated with increased fetal Hb levels and also harbors a GATA1 transcriptional control region.

Human β-Globin Locus

Figures 1A, 1B:
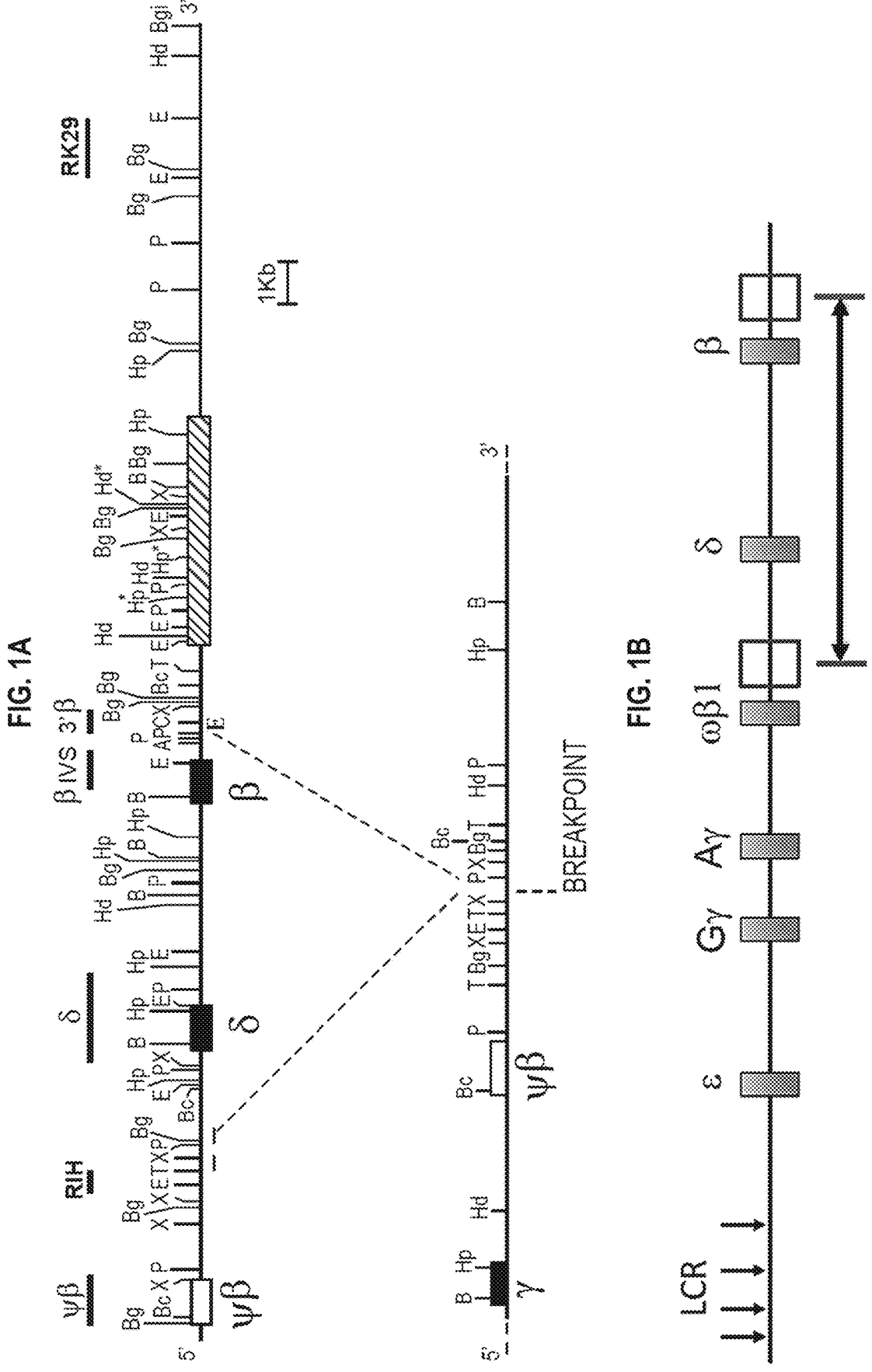
FIGS. 1A-1B show the genomic location of CRISPR target sites for the HPFH5 deletion.
Figure 2:
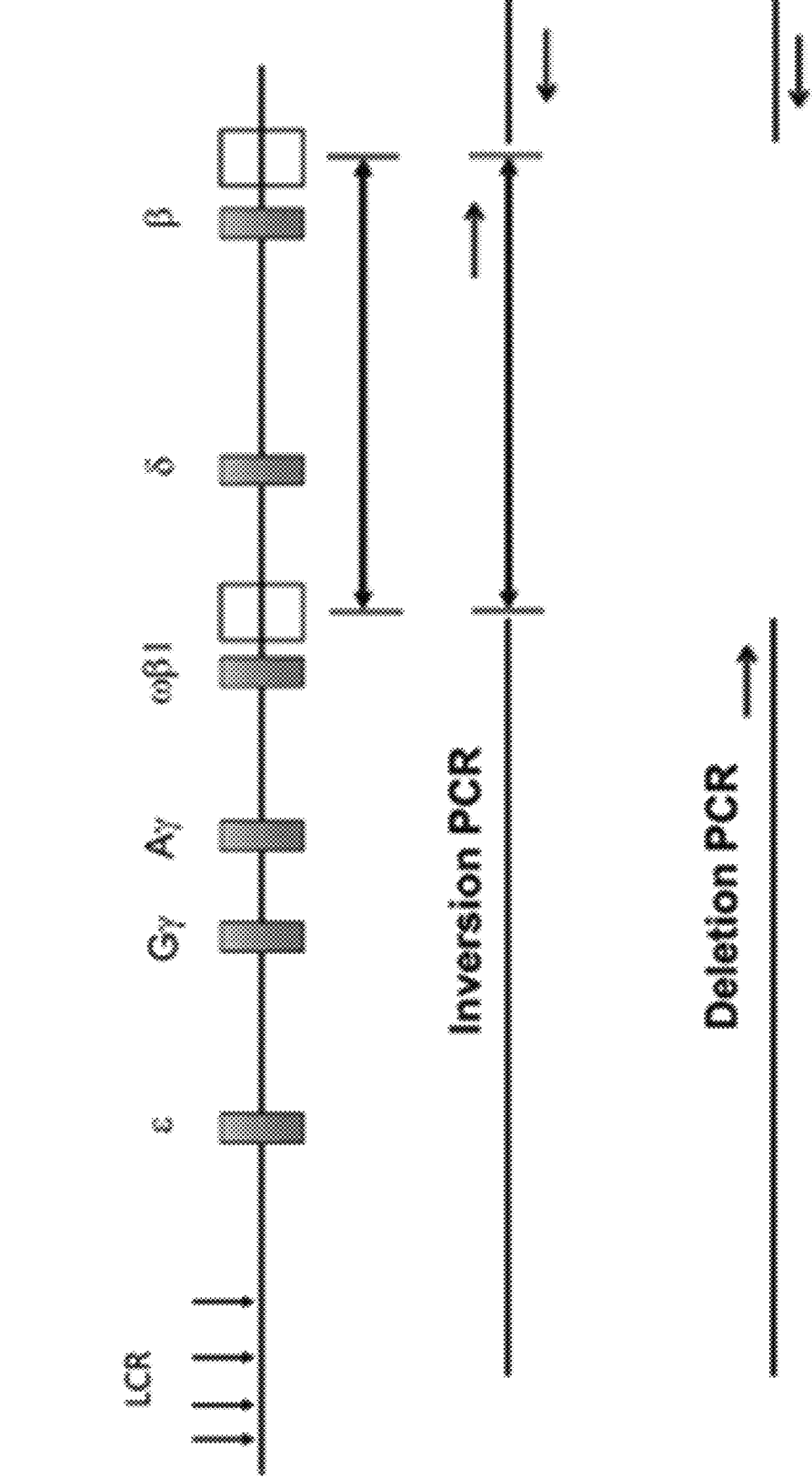
FIG. 2 is a schematic of PCR primer locations for detection of inversions and deletions of the 13 kb fragment.

The human β-globin locus is composed of five β-like genes and one pseudo-β gene located on a short region of chromosome 11 (approximately 45 kb), responsible for the creation of the β chains of hemoglobin. Expression of all of these genes is controlled by single locus control region (LCR), and the genes are differentially expressed throughout development. The order of the LCR and genes in the β-globin cluster, as illustrated in FIG. 1B, is as follows: 5'-[LCR]-ε (epsilon, HBE1)-Gγ (G-gamma, HBG1)-Aγ (A-gamma, HBG2)-[ψβ (psi-beta pseudogene)]-δ (delta, HBD)-β (beta, HBB)-3'.

The arrangement of the five β-like genes reflects the temporal differentiation of their expression during development, with the early-embryonic stage version HbE (encoded by the epsilon gene) being located closest to the LCR, followed by the fetal version HbF (encoded by the γ genes), the delta version, which begins shortly prior to birth and is expressed at low levels in adults as HbA-2 (constituting approximately 3% of adult hemoglobin in normal adults), and finally the beta gene, which encodes the predominant adult version HbA-1 (constituting the remaining 97% of HbA in normal adults).

Expression of the β-like genes is regulated in embryonic erythropoiesis by many transcription factors, including KLF1, which is associated with the upregulation of HbA in adult definitive erythrocytes, and KLF2, which is associated with the expression of embryonic hemoglobin. BCL11A is activated by KLF1 and is likewise known to be involved in the switch from fetal to adult hemoglobin. Down-regulation of BCL11A expression or disruption of its activity or binding to transcriptional regulatory sites has been a focus of long-terms efforts from various groups to increase levels of HbF. See, e.g., U.S. Pat. No. 8,383,604, US2014085593, US20140093913, and references cited therein.

Certain naturally-occurring genetic mutations within the human β-globin locus are associated with de-repression of γ-globin gene expression and the clinical manifestation of HPFH. Such mutations range from single base substitutions associated with various forms of non-deletional HFPF, to deletions spanning tens of kb in the case of some forms of deletional HPFH. A variety of naturally-occurring HPFHs were described in *A Syllabus of Thalassemia Mutations* (1997) by Titus H. J. Huisman, Marianne F. H. Carver, and Erol Baysal, published by The Sickle Cell Anemia Foundation in Augusta, GA, USA, and references cited therein, including both deletional and non-deletional types.

A number of different forms of deletional HPFH have been reported based on studies from individuals and families found to have deletions in a region referred to herein as the "δβ-globin region" which extends from the psi-beta pseudo-gene through delta, beta and the region downstream of beta that is deleted in the larger HPFH alleles such as HPFH-1, as described in the art.

In some cases of HPFH, nearly all of the hemoglobin produced is HbF. However, in most cases, HbF ranges from approximately 15-30% of total hemoglobin depending on the type of HPFH as well as variation among individuals.

Deletions Disrupting or Eliminating the β-Globin Gene and Advantages of Such Deletions in Treating SCD In certain aspects as described and illustrated herein, in addition to increasing expression of the γ-globin gene product HbF, expression of the β-globin gene product is substantially reduced or eliminated by disruption or elimination of the β-globin gene in connection with the genome editing procedure. This occurs when the genome editing uses DNA endonuclease to effect a pair of DSBs, the first at a 5' DSB locus and the second at a 3' DSB locus within the 08-globin region of human chromosome 11, causing a deletion of the chromosomal DNA between the 5' DSB locus and the 3' DSB locus that results in increased expression of γ-globin, the deletion also removes all or a portion of the β-globin gene (HBB) causing a concomitant decrease in expression of or elimination of the β-globin gene product, thereby resulting in a combination of (i) increasing the level of HbF in the cell, and (ii) reducing or eliminating expression of the β-globin gene product from at least one HBB allele on chromosome 11.

The combined effects of increased HbF and reduced or eliminated β-globin gene expression has particular additional advantages in the context of ameliorating hemoglobinopathies such as SCD in which the product of the variant β-globin allele (i.e. HbS) is harmful to cells expressing it, causing premature cell death (as well as other negative effects associated with HbS). Thus, not only do sickled RBCs cause multiple problems for patients, as discussed above and in the art, but sickled RBCs have a substantially reduced life span relative to normal RBCs. The presence of HbS and sickled RBCs also leads to numerous other negative effects as described herein and in the art.

In the case of aspects in which the β-globin gene is effectively disrupted or eliminated as described herein, even "knocking down" (reducing) or "knocking out" (eliminating) only one of the β-globin alleles expressing HbS, e.g., by successfully editing only one of the two copies of the gene in homozygous SCD patients (who have two defective β-globin alleles, one on each copy of chromosome 11) can have a very substantial benefit. In particular, increasing levels of HbF to the range of about 20% is considered to substantially eliminate sickling. However, as a relatively continuous or incremental factor (often referred to as a "quantitative trait") over a significant range, even lower levels HbF can have significant beneficial effects as described herein and in the art. In these aspects, therefore, even though the SCD patient has two defective β-globin alleles, the combination of increasing HbF (which is itself helpful for reducing the effects of SCD) along with reducing HbS (which is itself a driver of many of the deleterious effects in a quantitative manner), by genome editing using the method described and illustrated for these aspects can bring about a combination of effects that together ameliorate one of more symptoms of the disease.

In some cases, the genome editing procedure can effectively alter both copies of an allele. Such bi-allelic editing can in some cases be screened for or selected for, but even if not selected for it can naturally occur, albeit at lower frequency as compared to mono-allelic or single allele hits, since the same target site generally exists on each member of the pairs of chromosomes.

For technical reasons as noted above, however, aspects as described and illustrated herein in which only one of the β-globin alleles is disrupted or eliminated—in addition to increasing levels of HbF—would be expected to have significant positive effects in ameliorating one or more symptoms or conditions associated with SCD.

The ability to generate these significant "cis-type" (on the same allele) effects using the types of genome editing reflected in such aspects can be more advantageous than approaches depending on "trans-type" effects such as those involving knock out or knock down or a trans-acting factor such as a repressor. In particular, as noted above, the genome editing in aspects in which the β-globin gene is effectively disrupted or eliminated can substantially ameliorate effects of HbS by successfully editing on one of the two alleles. In the case of trans-acting repressors, such as a repressor of γ-globin gene expression, knocking down or knocking out one copy of the repressor gene may not be sufficient since expression of the repressor from the other copy of the gene can still reduce γ-globin gene expression limiting the levels of HbF that might be achieved.

Effects of Increased HbF in the Context of β-Thalassemia

As noted above, β-thalassemias result from a partial or complete defect in the expression of the β-globin gene, leading to deficient or absent hemoglobin A (HbA). Since there is no production of HbS, RBCs in β-thal patients do not exhibit the sickling and associated problems associated with SCD. However, a different sort of RBC 'toxicity' and premature cell death occurs as a result of the lack of HbA in the context of β-thal. In particular, the excess of unpaired alpha globin (α-globin) chains in β thalassemia interact with the red cell (RBC) membrane, causing oxidative damage to membrane skeletal components, and potentially other components. This interaction results in a rigid, mechanically unstable membrane that causes increased apoptosis (i.e. programmed cell death) and shortened RBC survival, marked by ineffective erythropoiesis and anemia.

Increasing the levels of HbF in RBCs of such patients can significantly ameliorate one or more symptoms of β-thalassemia because the beta-chains produced by increasing γ-globin gene expression can pair with the previously unpaired alpha-chains to produce HbF, which not only results in a functioning hemoglobin tetramer but concomitantly reduces the levels of unpaired α-globin chains that are a contributing cause of the β-thalassemia condition because of premature RBC cell death.

Positive Selective Advantages of Certain Genome-Edited Cells

In connection with the foregoing advantages provided in certain aspects of the invention, in particular the advantages in terms of RBC survival for sickle cell RBCs that can be mediated by genome editing that not only increases levels of HbF but reduces levels of HbS, and the advantages in terms of RBC survival for β-thal RBCs that not only increases levels of HbF but reduces levels of unpaired alpha-chains, cells that are modified by such genome editing techniques as described and illustrated herein, in some embodiments, will have selective advantages relative to the population of diseased RBCs into which they can be introduced, e.g., by gene editing a patients' own HSC's or erythroid progenitor cells ex vivo and then reintroducing such cells to the patient, where reintroduced cells must generally successfully persist or "engraft" in order for beneficial effects to be sufficient and sustained.

As a result of the foregoing selective advantages, the introduction of even modest numbers of suitable stem cells edited as described herein, in some embodiments, would be expected over time to result in improved cells representing a significantly higher fraction of the overall population of RBCs than they were initially following introduction into a patient. By way of illustration, with successfully gene edited stem cells representing as few as several percent of corresponding cells initially (i.e., compared to the population of resident cells that carry the unedited hemoglobinopathy-associated alleles), the gene edited cells could, in some embodiments, come to represent a majority of cells as a result of selective survival advantages conveyed upon them through use of gene editing techniques as described further herein. The eventual numbers reflecting such positively selected engraftment will vary depending generally on both the degree to which the resident diseased cells exhibit reduced lifespan in a given patient, and the relative survival advantage exhibited by the gene edited cells. However, as noted above, the diseased cells associated with SCD and β-thalassemia have significantly reduced lifespans (due to the presence of HbS and unpaired alpha-chains respectively), and certain aspects not only increase levels of HbF but reduce the levels of HbS (associated with SCD) or reduce the levels of unpaired alpha-chains (associated with β-thalassemia), and therefore the relative survival benefits and with them increased engraftment, are expected to be significant.

Corfu and Corfu-Like Deletions

Although the Corfu chromosomal allele first discovered in a Greek child results in a δβ-thalassemia, it shares some important characteristics with various deletional forms of HPFH, in particular increased levels of HbF, and therefore the deletion associated with Corfu is included with deletional HPFH forms as described herein.

However, Corfu is different from forms of deletional HPFH in terms of HbF levels and β-globin expression. Extremely high levels of HbF are associated with Corfu, approaching 100% of total hemoglobin in the case of the first child identified—and this was particularly surprising because Corfu heterozygotes (the child's parents in the first case) were found to have only normal very low levels of HbF (1-2% of total hemoglobin)—a situation that's been referred to by hematologists as the "Corfu Paradox."

A putative explanation is that the Corfu chromosomal allele was found to contain a splice site mutation in IVS—I position 5 ("IVS—I-5") of the β-globin gene and lower levels of the β-globin gene transcript. It has been reported that the high levels of HbF observed are contributed to post-transcriptionally by enhanced mRNA maturation and/or stabilization of the γ-globin transcript, which is apparently associated with the reduced levels of β-globin mRNA; see, e.g., Chakalova, L. et al., *Blood* 105:2154-2160 (2005).

Since the Corfu chromosomal allele contains both the large deletion and the IVS-1-5 mutation, and reduced levels of β-globin mRNA associated with the latter are believed to independently contribute to the unusually high levels of HbF produced, the IVS-1-5 "Corfu-related β-globin mutation" could be used alone or in combination with other gene edited alterations as described herein in order to increase HbF levels for use in ameliorating hemoglobinopathies.

Target Sequence Selection

For the amelioration of hemoglobinopathies via gene editing, as described herein, it is desirable but not necessary to achieve levels of HbF at the high end of those observed in naturally-occurring cases in order to bring about relative improvements in the disease. In particular, while it had originally been assumed that relatively high levels of HbF were essential for ameliorative effects to be observed, especially with respect to certain complications, studies have shown that even small incremental increases of HbF can have beneficial effects on mortality. See, e.g., Powars et al., *Blood* 63 (4): 921-926 (1984); Platt et al., *N Engl J Med* 330 (23): 1639-1644 (1994); and Akinsheye et al., *Blood* 118: 19-27 (2011).

One reason for the beneficial effects of even low levels of HbF in the context of sickle cell disease, is that even small incremental increases in HbF have been shown to have some beneficial effects, and levels of less than 9% of HbF (relative to total hemoglobin, Hb) appear to be associated with significantly decreased mortality; see, e.g., Platt et al., supra.

Higher levels of HbF are associated with additional clinical benefits and further decreases in morbidity and mortality, as observed in the case of SCD co-inherited with certain naturally-occurring HPFH alleles and/or Corfu thalassemia alleles, in which HbF levels in the 20-30% range have been associated with very substantial to nearly complete normalization of the SCD phenotype.

Genetic modifications within the δβ-globin region that are contemplated for increasing HbF expression to ameliorate a hemoglobinopathy as described herein result in at least about 5%, at least about 9%, at least about 14%, at least about 20%, at least about 25%, or above 30% HbF (relative to total Hb in a subject).

As described and illustrated further herein, exemplary genetic modifications within the δβ-globin region that are contemplated for increasing HbF expression to such levels include, but are not limited to, the following deletions, as well as variations thereof in which the size of the deletion is reduced (e.g., by shifting the 5' boundary of the deletion specified below further toward the 3' boundary of the deletion specified below or shifting the 3' boundary of the deletion further toward the 5' boundary) or increased (by shifting either boundary in the opposite direction). Deletions made by other combinations of two of the following deletion boundaries that increase HbF expression are also specifically contemplated by the disclosure.

A. Deletions in chromosome 11 within the region Chr11:5224779-5237723 based on the GRCh38/hg38 version of the human genome assembly, wherein the 3' boundary of the deletion is proximal (as defined below) to Chr11:5224779 and the 5' boundary of the deletion is proximal to Chr11:5237723;

B. Deletions in chromosome 11 within region Chr11:5234665-5238138 based on the GRCh38/hg38 version of the human genome assembly, wherein the 3' boundary of the deletion is proximal to Chr11:5234665 and the 5' boundary of the deletion is proximal to Chr11:5238138;

C. Deletions in chromosome 11 within region Chr11:5233055-5240389 based on the GRCh38/hg38 version of the human genome assembly, wherein the 3' boundary of the deletion is proximal to Chr11:5233055 and the 5' boundary of the deletion is proximal to Chr11:5240389;

D. Deletions in chromosome 11 within region Chr11:5226631-5249422 based on the GRCh38/hg38 version of the human genome assembly, wherein the 3' boundary of the deletion is proximal to Chr11:5226631 and the 5' boundary of the deletion is proximal to Chr11:5249422;

E. Deletions in chromosome 11 within region Chr11:5249959-5249971 based on the GRCh38/hg38 version of the human genome assembly wherein the 3' boundary of the deletion is at or adjacent to (as defined below) Chr11:5249959 and the 5' boundary of the deletion is at or adjacent to Chr11:5249971;

F. Deletions in chromosome 11 within region Chr11:5196709-5239223 based on the GRCh38/hg38 version of the human genome assembly, wherein the 3' boundary of the deletion is proximal to Chr11:5196709 and the 5' boundary of the deletion is proximal to Chr11:5239223;

G. Deletions in chromosome 11 within region Chr11:5225700-5236750 based on the GRCh38/hg38 version of the human genome assembly, wherein the 3' boundary of the deletion is proximal to Chr11:5225700 and the 5' boundary of the deletion is proximal to Chr11:5236750;

H. Deletions in chromosome 11 within region Chr11:5234655-5238138 based on the GRCh38/hg38 version of the human genome assembly, wherein the 3' boundary of the deletion is proximal to Chr11:5234655 and the 5' boundary of the deletion is proximal to Chr11:5238138;

I. Deletions in chromosome 11 within region Chr11:5255885-5259368 based on the GRCh37/hg19 version of the human genome assembly, wherein the 3' boundary of the deletion is proximal to Chr11:5255885 and the 5' boundary of the deletion is proximal to Chr11: 5259368.

In another aspect, provided herein are methods of increasing the level of HbF in a human cell by genome editing using DNA endonuclease to effect a double-strand break (DSB) positioned at one or more loci within the human β-globin region of human chromosome 11, wherein at least one SSB or DSB is positioned within the γ-globin regulatory region of human chromosome 11, which is located within a region less than 2 kb, less than 1 kb, less than 0.5 kb, or less than 0.25 kb upstream of the start of one of the γ-globin genes (HBG1 or HBG2), causing deletions or insertions of chromosomal DNA at the one or more loci that results in increased expression of γ-globin, thereby increasing the level of HbF in the cell. In another type of method exemplifying this aspect, at least one SSB or DSB is positioned within the δβ-globin region of human chromosome 11.

Illustrative modifications in chromosome 11 in the γ-globin regulatory region include the creation of single base substitutions such as −175 (T to C), −202 (C to G), and −114 (C to T) in the $^G\gamma$ gene; and −196 (C to T), −175 (T to C), −117 (G to A) in the $^A\gamma$ gene.

Illustrative modifications within the δβ-globin region include deletions and insertions within or proximal to the HPFH deletion loci referred to above, and deletions within the δ-globin regulatory region of human chromosome 11 which is located within the region of less than 3 kb, less than 2 kb, less than 1 kb, less than 0.5 kb upstream of the start of the δ-globin gene (HBD), and deletions within the β-globin regulatory region of human chromosome 11, which is located within the region of less than 3 kb, less than 2 kb, and less than 1 kb, or less than 0.5 kb upstream of the start of the β-globin gene (HBB).

Given the relatively wide variations in deletions that are associated with various forms of HPFH, coupled with the fact that even low levels of HbF can provide significant levels of amelioration of hemoglobinopathy (as noted above), and the understanding from a variety of studies that there appear to be multiple loci and types of controls that can contribute to repression of HbF, it will be appreciated that numerous variations of the deletions referenced above (including without limitation larger as well as smaller deletions), would be expected to result in levels of HbF that are within the contemplated ranges, as noted above.

Such variants include deletions that are larger in the 5' and/or 3' direction than naturally-occurring HPFH deletions, or smaller in either direction. Accordingly, by "proximal" with respect to HPFH-like deletions, it is intended that the DSB locus associated with a desired deletion boundary (also referred to herein as an endpoint) can be within a region that is less than about 3 kb from the reference locus noted. In some aspects, the DSB locus is more proximal and within 2 kb, within 1 kb, within 0.5 kb, or within 0.1 kb. In the case of small deletions such as that identified in group E, the desired endpoint can be at or "adjacent to" the reference locus, by which it is intended that the endpoint can be within 100 bp, within 50 bp, within 25 bp, or less than about 10 bp to 5 bp from the reference locus.

A group of aspects can comprise deletions within the "δ-region" (which includes the downstream half of the intergenic sequence between the ωβ1 pseudogene and the δ gene HBD, and proximal sequences downstream sequences in the δ). The δ-proximal-region appears to include a number of elements associated with repression of γ-globin. The 7.2 kb "Large Corfu" δβ thalassemia deletion described and exemplified further herein falls within the δ-region, deleting approximately 1 kb of the δ gene and 6 kb upstream, and can be associated with a significant increase in levels of HbF. A 3.5 "Small Corfu" deletion, described further and illustrated herein, likewise has a deletion in the δ-region, and can be also associated with increased levels of HbF. The δ-region can be also deleted in all major forms of HPFH.

With respect to regions further downstream in the 3' direction, which would be associated with larger deletions as described herein, HPFH-1 through HPFH-5 all have the δ and β genes deleted. Besides regulatory elements in the δ-region that may contribute to active repression of γ-globin, activity of the δ and β promoters can also indirectly contribute to suppression via competition for transcriptional factors required for γ-globin expression.

Many HPFH types also have even larger deletions extending further downstream, and these additional downstream regions can also be incorporated into deletions as described and illustrated herein, since they are known to be associated with substantial increases of HbF, well above the ranges of HbF known to ameliorate hemoglobinopathies as noted above.

One advantage for patients with hemoglobinopathies of replicating or mimicking aspects of deletions that are found naturally in individuals with HPFH is that such deletions are already known to be both safe and associated with the amelioration of hemoglobinopathy. However, among deletional HPFH, it is also clear that smaller deletions such as HPFH-5 are effective for generating substantial increases in HbF. Other aspects comprising smaller deletions are expected to provide substantial increases, and as noted above, even modest levels of increase of HbF have beneficial effects. It is thus expected that many variations of the deletions described and illustrated herein will be effective for ameliorating hemoglobinopathies.

Preferentially, shifts in the location of the 5' boundary and/or the 3' boundary relative to particular reference loci are used to facilitate or enhance particular applications of gene editing, which depend in part on the endonuclease system selected for the editing, as further described and illustrated herein. In a first aspect of such target sequence selection, many endonuclease systems have rules or criteria that guide the initial selection of potential target sites for cleavage, such as the requirement of a PAM sequence motif in a particular position adjacent to the DNA cleavage sites in the case of CRISPR Type II endonucleases.

In another aspect of target sequence selection or optimization, the frequency of "off-target" activity for a particular combination of target sequence and gene editing endonuclease (i.e. the frequency of DSBs occurring at sites other than the selected target sequence) is assessed relative to the frequency of on-target activity. In some cases, cells that have been correctly edited at the desired locus may have a selective advantage relative to other cells. Illustrative but nonlimiting examples of a selective advantage include the acquisition of attributes such as enhanced rates of replication, persistence, resistance to certain conditions, enhanced rates of successful engraftment or persistence in vivo following introduction into a patient, and other attributes associated with the maintenance or increased numbers or viability of such cells. In other cases, cells that have been correctly edited at the desired locus may be positively selected for by one or more screening methods used to identify, sort or otherwise select for cells that have been correctly edited. Both selective advantage and directed selection methods may take advantage of the phenotype associated with the correction.

Whether or not any selective advantage is applicable or any directed selection is to be applied in a particular case, target sequence selection is can also be guided by consideration of off-target frequencies in order to enhance the effectiveness of the application and/or reduce the potential for undesired alterations at sites other than the desired target. As described further and illustrated herein and in the art, the occurrence of off-target activity is influenced by a number of factors including similarities and dissimilarities between the target site and various off target sites, as well as the particular endonuclease used. In many cases, bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein and others are known in the art.

Another aspect of target sequence selection relates to homologous recombination events. It is well known that sequences sharing regions of homology can serve as focal points for homologous recombination events that result in deletion of intervening sequences. Such recombination events occur during the normal course of replication of chromosomes and other DNA sequences, and also at other times when DNA sequences are being synthesized, such as in the case of repairs of double-strand breaks (DSBs) which occur on a regular basis during the normal cycle but may also be enhanced by the occurrence of various events (such as UV light and other inducers of DNA breakage) or the presence of certain agents (such as various chemical inducers). Many such inducers cause DSBs to occur indiscriminately in the genome, and DSBs are regularly being induced and repaired in normal cells. During repair, the original sequence may be reconstructed with complete fidelity, however, in some cases, small insertions or deletions (referred to as "indels") are introduced at the DSB site.

DSBs may also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems such as CRISPR in which homology directed repair (HDR) is used to insert a sequence of interest, provided through use of a "donor" polynucleotide, into a desired chromosomal location.

Regions of homology between particular sequences, which can be small regions of "microhomology" that may comprise as few as ten basepairs or less, can also be used to bring about desired deletions. For example, in the case of the so-called "small deletion" exemplified herein, a single DSB is introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process. In the case of this small deletion, which is in the upstream region of the γ-globin gene, the result of the deletion is to increase levels of HbF, apparently through disruption of a gene silencing sequence.

In some circumstances, however, selecting target sequences within regions of homology can also give rise to much larger deletions including gene fusions (when the deletions are in coding regions), which may or may not be desired given the particular circumstances. For example, as illustrated in FIG. 5B, the homologies that exist between the two closely-related γ-globin genes HBG1 and HBG2 can give rise to large deletions arising through homologous recombination between more distal sites of homology.

The examples provided herein further illustrate the selection of various target regions for the creation of DSBs designed to induce deletions that result in the increase of HbF levels in human cells, as well as the selection of specific target sequences within such regions that are designed to minimize off-target events relative to on-target events.

HBS1L-MYB on Chromosome 6

Genetic studies have identified common variants within the intergenic region (HBS1L-MYB) between GTP-binding elongation factor HBS1L and myeloblastosis oncogene MYB on chromosome 6.

Therapeutic Approach

In some aspects, the overall therapeutic approach is to introduce a permanent deletion, inversion, or mutation within or near two or more of: a human beta globin locus on chromosome 11; a BCL11A gene on chromosome 2 or a DNA sequence that encodes a transcriptional control region of the BCL11A gene on chromosome 2; and an intergenic region HBS1L-MYB on chromosome 6. For example, one therapeutic approach includes introducing a permanent deletion, inversion, or mutation within or near a human beta globin locus on chromosome 11; and a BCL11A gene on chromosome 2 or a DNA sequence that encodes a transcriptional control region of the BCL11A gene on chromosome 2. A second example therapeutic approach includes introducing a permanent deletion, inversion, or mutation within or near a human beta globin locus on chromosome 11; and an intergenic region HBS1L-MYB on chromosome 6. A third example therapeutic approach includes introducing a permanent deletion, inversion, or mutation within or near a BCL11A gene on chromosome 2 or a DNA sequence that encodes a transcriptional control region of the BCL11A gene on chromosome 2; and an intergenic region HBS1L-MYB on chromosome 6. A fourth example therapeutic approach includes introducing a permanent deletion, inversion, or mutation within or near a human beta globin locus on chromosome 11; a BCL11A gene on chromosome 2 or a DNA sequence that encodes a transcriptional control region of the BCL11A gene on chromosome 2; and an intergenic region HBS1L-MYB on chromosome 6. These therapeutic approaches can lead to an increase in expression of γ-globin and thereby increase production of HbF.

Additional Therapeutic Approach

In some embodiments, permanent deletions within or near the human beta globin locus on chromosome 11 can be used to reposition a BCL11A enhancing region (located within the human beta globin locus) closer to the HBG1 and/or HBG2 genes. For example, a HPFH deletion can be located downstream of a HBG1 gene and result in a repositioning of a BCL11A enhancing region closer to the HBG1 gene. A HPFH deletion can be located downstream of a HBG2 gene and result in a repositioning of a BCL11A enhancing region closer to the HBG2 gene. A HPFH deletion can be located downstream of a HBG1 gene and HBG2 gene and result in a repositioning of a BCL11A enhancing region closer to the HBG1 gene and HBG2 gene.

Genome Editing

Genome editing generally refers to the process of modifying the nucleotide sequence of a genome, preferably in a precise or pre-determined manner. Examples of methods of genome editing described herein include methods of using site-directed nucleases to cut DNA at precise target locations in the genome, thereby creating single-strand or double-strand DNA breaks at particular locations within the genome. Such breaks can be and regularly are repaired by natural, endogenous cellular processes such as homology-directed repair (HDR) and non-homologous end-joining (NHEJ), as recently reviewed in Cox et al., *Nature Medicine* 21 (2), 121-31 (2015). These two main DNA repair processes consist of a family of alternative pathways. NHEJ directly joins the DNA ends resulting from a double-strand break sometimes with the loss or addition of nucleotide sequence which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid such as a plasmid, a single-strand oligonucleotide, a double-stranded oligonucleotide, a duplex oligonucleotide or a virus, that has regions of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ, in which the genetic outcome is similar to NHEJ in that small deletions and insertions can occur at the cleavage site. MMEJ can make use of homologous sequences of a few basepairs flanking the DNA break site to drive a more favored DNA end joining repair outcome, and recent reports have further elucidated the molecular mechanism of this process; see, e.g., Cho and Greenberg, *Nature* 518, 174-76 (2015); Kent et al., *Nature Structural and Molecular Biology*, Adv. Online doi: 10.1038/nsmb.2961 (2015); Mateos-Gomez et al., *Nature* 518, 254-57 (2015); Ceccaldi et al., *Nature* 528, 258-62 (2015). In some instances it may be possible to predict likely repair outcomes based on analysis of potential microhomologies at the site of the DNA break.

Each of these genome editing mechanisms can be used to create desired genomic alterations. A step in the genome editing process can be to create one or two DNA breaks, the latter as double-strand breaks or as two single-stranded breaks, in the target locus as near the site of intended mutation. This can be achieved via the use of site-directed polypeptides, as described and illustrated herein.

Site-directed polypeptides, such as a DNA endonuclease, can introduce double-strand breaks or single-strand breaks in nucleic acids, e.g., genomic DNA. The double-strand break can stimulate a cell's endogenous DNA-repair pathways (e.g., homology-dependent repair or non-homologous end joining or alternative non-homologous end joining (A-NHEJ) or microhomology-mediated end joining). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template can comprise sequences that can be homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligonucleotide, single-strand oligonucleotide, double-stranded oligonucleotide, or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few basepairs flanking the cleavage site to drive a favored end-joining DNA repair outcome. In some instances it may be possible to predict likely repair outcomes based on analysis of potential microhomologies in the nuclease target regions.

Thus, in some cases, homologous recombination can be used to insert an exogenous polynucleotide sequence into the target nucleic acid cleavage site. An exogenous poly-nucleotide sequence is termed a donor polynucleotide (or donor or donor sequence or polynucleotide donor template) herein. The donor polynucleotide, a portion of the donor polynucleotide, a copy of the donor polynucleotide, or a portion of a copy of the donor polynucleotide can be inserted into the target nucleic acid cleavage site. The donor poly-nucleotide can be an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

Nucleases

Gene editing can be conducted using nucleases engineered to target specific sequences. To date there are four major types of nucleases: meganucleases and their derivatives, zinc finger nucleases (ZFNs), transcription activator like effector nucleases (TALENs), and CRISPR endonuclease (e.g., CRISPR-Cas9 nuclease) systems. The nuclease platforms vary in difficulty of design, targeting density and mode of action, particularly as the specificity of ZFNs and TALENs is through protein-DNA interactions, while RNA-DNA interactions primarily guide CRISPR endonucleases such as Cas9. Cas9 cleavage also requires an adjacent motif, the PAM, which differs between different CRISPR systems. Cas9 from *Streptococcus pyogenes* cleaves using a NGG PAM, CRISPR from *Neisseria meningitidis* can cleave at sites with PAMs including NNNNGATT, NNNNNGTTT and NNNNGCTT. A number of other Cas9 orthologs target protospacer adjacent to alternative PAMs.

In some embodiments, CRISPR endonucleases, such as Cas9, can be used in the methods of the present disclosure. However, the teachings described herein, such as therapeutic target sites, could be applied to other forms of endonucleases, such as ZFNs, TALENs, HEs, or MegaTALs, or using combinations of nucleases. However, in order to apply the teachings of the present disclosure to such endonucleases, one would need to, among other things, engineer proteins directed to the specific target sites.

Additional binding domains can be fused to the Cas9 or other CRISPR endonuclease protein to increase specificity. The target sites of these constructs would map to the identified gRNA specified site, but would require additional binding motifs, such as for a zinc finger domain. In the case of Mega-TAL, a meganuclease can be fused to a TALE DNA-binding domain. The meganuclease domain can increase specificity and provide the cleavage. Similarly, inactivated or dead Cas9 (dCas9) can be fused to a cleavage domain and require the sgRNA/Cas9 target site and adjacent binding site for the fused DNA-binding domain. This likely would require some protein engineering of the dCas9, in addition to the catalytic inactivation, to decrease binding without the additional binding site.

Zinc Finger Nucleases

Zinc finger nucleases (ZFNs) are modular proteins comprised of an engineered zinc finger DNA binding domain linked to the catalytic domain of the type II endonuclease FokI. Since FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN can comprise 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein can selectively recognize a 12 bp target sequence, where the target sequence is a composite of the triplet preferences contributed by each finger, although triplet preference can be influenced to varying degrees by neighboring fingers. An important aspect then of ZFNs is that they can be readily retargeted to almost any genomic address simply by modifying individual fingers, although considerable expertise is required to do this well. In most applications of ZFNs, proteins of 4-6 fingers can be used, recognizing 12-18 bp respectively. Hence, a pair of ZFNs will typically recognize a combined target sequence of 24-36 bp, not including the 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity and so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other and not with themselves. Forcing the obligate heterodimer prevents formation of the homodimer. This has greatly enhanced specificity of ZFNs, as well as, of any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., *Proc Natl Acad Sci USA* 96 (6): 2758-63 (1999); Dreier B et al., *J Mol Biol.* 303 (4): 489-502 (2000); Liu Q et al., *J Biol Chem.* 277 (6): 3850-6 (2002); Dreier et al., *J Biol Chem* 280 (42): 35588-97 (2005); and Dreier et al., *J Biol Chem.* 276 (31): 29466-78 (2001).

Transcription Activator-Like Effector Nucleases (TALENs)

TALENs represent another format of modular nucleases whereby, as with ZFNs, an engineered DNA binding domain is linked to the FokI nuclease domain, and a pair of TALENs operates in tandem to achieve targeted DNA cleavage. The major difference from ZFNs is the nature of the DNA binding domain and the associated target DNA sequence recognition properties. The TALEN DNA binding domain derives from TALE proteins, which were, originally described in the plant bacterial pathogen *Xanthomonas* sp. TALEs are comprised of tandem arrays of 33-35 amino acid repeats, with each repeat recognizing a single basepair in the target DNA sequence that is typically up to 20 bp in length, giving a total target sequence length of up to 40 bp. Nucleotide specificity of each repeat is determined by the repeat variable diresidue (RVD) which includes just two amino acids at positions 12 and 13. The bases guanine, adenine, cytosine and thymine are predominantly recognized by the four RVDs Asn-Asn, Asn-Ile, His-Asp and Asn-Gly, respectively. This constitutes a much simpler recognition code than for zinc fingers and thus represents an advantage over the latter for nuclease design. Nevertheless, as with ZFNs, the protein-DNA interactions of TALENs are not absolute in their specificity and TALENs have also benefitted from the use of the obligate heterodimer variants of the FokI domain to reduce off-target activity.

Additional variants of the FokI domain have been created that can be deactivated in their catalytic function. If one half of either a TALEN or a ZFN pair contains an inactive FokI domain then only single-strand DNA cleavage (nicking) will occur at the target site rather than a DSB. The outcome is comparable to the use of CRISPR/Cas9/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB which is prone to NHEJ-mediated mis-repair.

A variety of TALEN-based systems have been described in the art, and modifications thereof are regularly reported; see, e.g., Boch, *Science* 326 (5959): 1509-12 (2009); Mak et al., *Science* 335 (6069): 716-9 (2012); and Moscou et al., *Science* 326 (5959): 1501 (2009). The use of TALENs based on the "Golden Gate" platform, or cloning scheme, has been described by multiple groups; see, e.g., Cermak et al., *Nucleic Acids Res.* 39 (12): e82 (2011); Li et al., *Nucleic Acids Res.* 39 (14): 6315-25 (2011); Weber et al., *PLOS One.* 6 (2): e16765 (2011); Wang et al., *J Genet Genomics* 41 (6): 339-47, Epub 2014 May 17 (2014); and Cermak T et al., *Methods Mol Biol.* 1239:133-59 (2015).

Homing Endonucleases

Homing endonucleases (HE) are sequence-specific endonucleases that have long recognition sequences (14-44 base pairs) and cleave DNA with high specificity-often at sites unique in the genome. There are at least six known families of HEs as classified by their structure, including LAGLIDADG (SEQ ID NO 228,300), GIY-YIG, His-Cis box, H—N—H, PD-(D/E)×K, and Vsr-like that are derived from a broad range of hosts including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of the DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., *Glycobiology* 24 (8): 663-80 (2014); Belfort and Bonocora, *Methods Mol Biol.*

1123:1-26 (2014); Hafez and Hausner, *Genome* 55 (8): 553-69 (2012); and references cited therein.

MegaTAL/Tev-mTALEN/MegaTev

As further examples of hybrid nucleases, the MegaTAL platform and Tev-mTALEN platform use a fusion of the TALE DNA binding domains to catalytically active HEs, taking advantage of both the tunable DNA binding and specificity of the TALE as well as the cleavage sequence specificity of the HE; see, e.g., Boissel et al., *NAR* 42:2591-2601 (2014); Kleinstiver et al., *G3* 4:1155-65 (2014); and Boissel and Scharenberg, *Methods Mol. Biol.* 1239:171-96 (2015).

In a further variation, the MegaTev architecture is the fusion of a meganuclease (Mega) with the nuclease domain derived from the GIY-YIG homing endonuclease I-TevI (Tev). The two active sites are positioned ~30 bp apart on DNA substrate and generate two DSBs with non-compatible cohesive ends; see, e.g., Wolfs et al., *NAR* 42, 8816-29 (2014). It is anticipated that other combinations of existing nuclease-based approaches can evolve and be useful in achieving the targeted genome modifications described herein.

dCas9-FokI and Other Nucleases

Combining the structural and functional properties of the nuclease platforms described above can offer a further approach to genome editing that can potentially overcome some of the inherent deficiencies. As an example, the CRISPR genome editing system can use a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated particularly in the 5' half of the target sequence, effectively reducing the number of bases that drive specificity. One solution to this has been to completely deactivate the Cas9 or Cpf-1 catalytic function-retaining only the RNA-guided DNA binding function—and instead fusing a FokI domain to the deactivated Cas9; see, e.g., Tsai et al., *Nature Biotech* 32:569-76 (2014); and Guilinger et al., *Nature Biotech.* 32:577-82 (2014). Since FokI has to dimerize to become catalytically active, two guide RNAs are required to tether two Cas9-FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE as well as the cleavage sequence specificity of I-TevI, with the expectation that off-target cleavage can be further reduced.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats". When expressed, the repeats can form secondary structures (e.g., hairpins) and/or comprise unstructured single-stranded sequences. The repeats usually occur in clusters and frequently diverge between species. The repeats are regularly interspaced with unique intervening sequences referred to as "spacers", resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA comprises a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also comprises polynucleotide sequences encoding CRISPR Associated (Cas) genes. Cas genes encode endonucleases involved in the biogenesis and the interference stages of crRNA function in prokaryotes. Some Cas genes comprise homologous secondary and/or tertiary structures.

Type II CRISPR Systems crRNA biogenesis in a Type II CRISPR system in nature requires a trans-activating CRISPR RNA (tracrRNA). The tracrRNA can be modified by endogenous RNaseIII, and then hybridizes to a crRNA repeat in the pre-crRNA array. Endogenous RNaseIII can be recruited to cleave the pre-crRNA. Cleaved crRNAs can be subjected to exoribonuclease trimming to produce the mature crRNA form (e.g., 5' trimming). The tracrRNA can remain hybridized to the crRNA, and the tracrRNA and the crRNA associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid can activate Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek et al., *Science,* 337 (6096): 816-821 (2012) showed that the CRISPR/Cas9 system is useful for RNA-programmable genome editing, and international patent application publication number WO2013/176772 provides numerous examples and applications of the CRISPR/Cas endonuclease system for site-specific gene editing.

Type V CRISPR Systems

Type V CRISPR systems have several important differences from Type II systems. For example, Cpf1 is a single RNA-guided endonuclease that, in contrast to Type II systems, lacks tracrRNA. In fact, Cpf1-associated CRISPR arrays can be processed into mature crRNAs without the requirement of an additional trans-activating tracrRNA. The Type V CRISPR array can be processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems can start with 20-24 nucleotides of spacer sequence followed by about 22 nucleotides of direct repeat. Also, Cpf1 can utilize a T-rich protospacer-adjacent motif such that Cpf1-crRNA complexes efficiently cleave target DNA preceded by a short T-rich PAM, which is in contrast to the G-rich PAM following the target DNA for Type II systems. Thus, Type V systems cleave at a point that is distant from the PAM, while Type II systems cleave at a point that is adjacent to the PAM. In addition, in contrast to Type II systems, Cpf1 cleaves DNA via a staggered DNA double-stranded break with a 4 or 5 nucleotide 5' overhang. Type II systems cleave via a blunt double-stranded break. Similar to Type II systems, Cpf1 contains a predicted RuvC-like endonuclease domain, but lacks a second HNH endonuclease domain, which is in contrast to Type II systems.

Cas Genes/Polypeptides and Protospacer Adjacent Motifs

Exemplary CRISPR Cas polypeptides include the Cas9 polypeptides in FIG. 1 of Fonfara et al., *Nucleic Acids Research,* 42:2577-2590 (2014). The CRISPR/Cas gene naming system has undergone extensive rewriting since the Cas genes were discovered. FIG. 5 of Fonfara, supra, provides PAM sequences for the Cas9 polypeptides from various species.

Site-Directed Polypeptides

A site-directed polypeptide is a nuclease used in genome editing to cleave DNA. The site-directed nuclease or poly-peptide can be administered to a cell or a patient as either: one or more polypeptides, or one or more mRNAs encoding the polypeptide.

In the context of a CRISPR/Cas or CRISPR/Cpf1 system, the site-directed polypeptide can bind to a guide RNA that, in turn, specifies the site in the target DNA to which the polypeptide is directed. In the CRISPR/Cas or CRISPR/ Cpf1 systems disclosed herein, the site-directed polypeptide can be an endonuclease, such as a DNA endonuclease.

A site-directed polypeptide can comprise a plurality of nucleic acid-cleaving (i.e., nuclease) domains. Two or more nucleic acid-cleaving domains can be linked together via a linker. For example, the linker can comprise a flexible linker. Linkers can comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild-type Cas9 enzymes comprise two nuclease domains, a HNH nuclease domain and a RuvC domain. Herein, the "Cas9" refers to both naturally-occur-ring and recombinant Cas9s. Cas9 enzymes contemplated herein can comprise a HNH or HNH-like nuclease domain, and/or a RuvC or RuvC-like nuclease domain.

HNH or HNH-like domains comprise a McrA-like fold. HNH or HNH-like domains comprises two antiparallel β-strands and an α-helix. HNH or HNH-like domains com-prises a metal binding site (e.g., a divalent cation binding site). HNH or HNH-like domains can cleave one strand of a target nucleic acid (e.g., the complementary strand of the crRNA targeted strand).

RuvC or RuvC-like domains comprise an RNaseH or RNaseH-like fold. RuvC/RNaseH domains are involved in a diverse set of nucleic acid-based functions including acting on both RNA and DNA. The RNaseH domain comprises 5 β-strands surrounded by a plurality of α-helices. RuvC/ RNaseH or RuvC/RNaseH-like domains comprise a metal binding site (e.g., a divalent cation binding site). RuvC/ RNaseH or RuvC/RNaseH-like domains can cleave one strand of a target nucleic acid (e.g., the non-complementary strand of a double-stranded target DNA).

Site-directed polypeptides can introduce double-strand breaks or single-strand breaks in nucleic acids, (e.g., genomic DNA). The double-strand break can stimulate a cell's endogenous DNA-repair pathways (e.g., homology-dependent repair (HDR) or non-homologous end joining (NHEJ) or alternative non-homologous end joining (A-NHEJ) or microhomology-mediated end joining (MMEJ)). NHEJ can repair cleaved target nucleic acid without the need for a homologous template. This can sometimes result in small deletions or insertions (indels) in the target nucleic acid at the site of cleavage and can lead to disruption or alteration of gene expression. HDR can occur when a homologous repair template, or donor, is available. The homologous donor template can comprise sequences that are homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligo-nucleotide, single-strand oligonucleotide or viral nucleic acid. With exogenous donor templates, an additional nucleic acid sequence (such as a transgene) or modification (such as a single base or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few basepairs flanking the cleavage site to drive a favored end-joining DNA repair outcome. In some instances it can be possible to predict likely repair outcomes based on analysis of potential microhomologies in the nuclease target regions.

Thus, in some cases, homologous recombination can be used to insert an exogenous polynucleotide sequence into the target nucleic acid cleavage site. An exogenous poly-nucleotide sequence is termed a donor polynucleotide (or donor or donor sequence) herein. The donor polynucleotide, a portion of the donor polynucleotide, a copy of the donor polynucleotide, or a portion of a copy of the donor poly-nucleotide can be inserted into the target nucleic acid cleavage site. The donor polynucleotide can be an exog-enous polynucleotide sequence, i.e., a sequence that does not naturally occur at the target nucleic acid cleavage site.

The modifications of the target DNA due to NHEJ and/or HDR can lead to, for example, mutations, deletions, altera-tions, integrations, gene correction, gene replacement, gene tagging, transgene insertion, nucleotide deletion, gene dis-ruption, translocations and/or gene mutation. The processes of deleting genomic DNA and integrating non-native nucleic acid into genomic DNA are examples of genome editing.

The site-directed polypeptide can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100%, amino acid sequence identity to a wild-type exemplary site-directed polypeptide [e.g., Cas9 from *S. pyogenes,* US2014/0068797 Sequence ID No. 8 or Sapranauskas et al., *Nucleic Acids Res,* 39 (21): 9275-9282 (2011)], and various other site-directed polypep-tides.

The site-directed polypeptide can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100%, amino acid sequence identity to the nuclease domain of a wild-type exemplary site-directed polypeptide (e.g., Cas9 from *S. pyogenes,* supra).

The site-directed polypeptide can comprise at least 70, 75, 80, 85, 90, 95, 97, 99, or 100% identity to a wild-type site-directed polypeptide (e.g., Cas9 from *S. pyogenes*, supra) over 10 contiguous amino acids. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids. The site-directed polypeptide can comprise at least: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. The site-directed polypeptide can comprise at least: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide.

The site-directed polypeptide can comprise a modified form of a wild-type exemplary site-directed polypeptide. The modified form of the wild-type exemplary site-directed polypeptide can comprise a mutation that reduces the nucleic acid-cleaving activity of the site-directed polypeptide. The modified form of the wild-type exemplary site-directed polypeptide can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from *S. pyogenes*, supra). The modified form of the site-directed polypeptide can have no substantial nucleic acid-cleaving activity. When a site-directed polypeptide is a modified form that has no substantial nucleic acid-cleaving activity, it is referred to herein as "enzymatically inactive".

The modified form of the site-directed polypeptide can comprise a mutation such that it can induce a SSB on a target nucleic acid (e.g., by cutting only one of the sugar-phosphate backbones of a double-strand target nucleic acid). The mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from *S. pyogenes*, supra). The mutation can result in one or more of the plurality of nucleic acid-cleaving domains retaining the ability to cleave the complementary strand of the target nucleic acid, but reducing its ability to cleave the non-complementary strand of the target nucleic acid. The mutation can result in one or more of the plurality of nucleic acid-cleaving domains retaining the ability to cleave the non-complementary strand of the target nucleic acid, but reducing its ability to cleave the complementary strand of the target nucleic acid. For example, residues in the wild-type exemplary *S. pyogenes* Cas9 polypeptide, such as Asp10, His840, Asn854 and Asn856 are mutated to inactivate one or more of the plurality of nucleic acid-cleaving domains (e.g., nuclease domains). The residues to be mutated can correspond to residues Asp10, His840, Asn854 and Asn856 in the wild-type exemplary *S. pyogenes* Cas9 polypeptide (e.g., as determined by sequence and/or structural alignment). Non-limiting examples of mutations can include D10A, H840A, N854A or N856A. One skilled in the art will recognize that mutations other than alanine substitutions can be suitable.

A D10A mutation can be combined with one or more of H840A, N854A, or N856A mutations to produce a site-directed polypeptide substantially lacking DNA cleavage activity. A H840A mutation can be combined with one or more of D10A, N854A, or N856A mutations to produce a site-directed polypeptide substantially lacking DNA cleavage activity. A N854A mutation can be combined with one or more of H840A, D10A, or N856A mutations to produce a site-directed polypeptide substantially lacking DNA cleavage activity. A N856A mutation can be combined with one or more of H840A, N854A, or D10A mutations to produce a site-directed polypeptide substantially lacking DNA cleavage activity. Site-directed polypeptides that comprise one substantially inactive nuclease domain are referred to herein as "nickases".

Nickase variants of RNA-guided endonucleases, for example Cas9, can be used to increase the specificity of CRISPR-mediated genome editing. Wild type Cas9 is typically guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13nt of homology, and thereby resulting in elevated potential for binding and double-strand nucleic acid cleavage by the CRISPR/Cas9 complex elsewhere in the target genome—also known as off-target cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable the double-strand break to form. As described in the art, nickases can also be used to promote HDR versus NHEJ. HDR can be used to introduce selected changes into target sites in the genome through the use of specific donor sequences that effectively mediate the desired changes. Descriptions of various CRISPR-Cas systems for use in gene editing can be found, e.g., in WO2013/176772, and in Nature Biotechnology 32, 347-355 (2014), and references cited therein.

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagines, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation can convert the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

The site-directed polypeptide (e.g., variant, mutated, enzymatically inactive and/or conditionally enzymatically inactive site-directed polypeptide) can target nucleic acid. The site-directed polypeptide (e.g., variant, mutated, enzymatically inactive and/or conditionally enzymatically inactive endoribonuclease) can target DNA. The site-directed polypeptide (e.g., variant, mutated, enzymatically inactive and/or conditionally enzymatically inactive endoribonuclease) can target RNA.

The site-directed polypeptide can comprise one or more non-native sequences (e.g., the site-directed polypeptide is a fusion protein).

The site-directed polypeptide can comprise an amino acid sequence comprising at least 15% amino acid identity to a Cas9 from a bacterium (e.g., *S. pyogenes*), a nucleic acid binding domain, and two nucleic acid cleaving domains (i.e., a HNH domain and a RuvC domain).

The site-directed polypeptide can comprise an amino acid sequence comprising at least 15% amino acid identity to a Cas9 from a bacterium (e.g., *S. pyogenes*), and two nucleic acid cleaving domains (i.e., a HNH domain and a RuvC domain).

The site-directed polypeptide can comprise an amino acid sequence comprising at least 15% amino acid identity to a Cas9 from a bacterium (e.g., *S. pyogenes*), and two nucleic acid cleaving domains, wherein one or both of the nucleic acid cleaving domains comprise at least 50% amino acid identity to a nuclease domain from Cas9 from a bacterium (e.g., *S. pyogenes*).

The site-directed polypeptide can comprise an amino acid sequence comprising at least 15% amino acid identity to a Cas9 from a bacterium (e.g., *S. pyogenes*), two nucleic acid cleaving domains (i.e., a HNH domain and a RuvC domain), and non-native sequence (for example, a nuclear localization signal) or a linker linking the site-directed polypeptide to a non-native sequence.

The site-directed polypeptide can comprise an amino acid sequence comprising at least 15% amino acid identity to a Cas9 from a bacterium (e.g., *S. pyogenes*), two nucleic acid cleaving domains (i.e., a HNH domain and a RuvC domain), wherein the site-directed polypeptide comprises a mutation in one or both of the nucleic acid cleaving domains that reduces the cleaving activity of the nuclease domains by at least 50%.

The site-directed polypeptide can comprise an amino acid sequence comprising at least 15% amino acid identity to a Cas9 from a bacterium (e.g., *S. pyogenes*), and two nucleic acid cleaving domains (i.e., a HNH domain and a RuvC domain), wherein one of the nuclease domains can comprise a mutation of aspartic acid 10, and/or wherein one of the nuclease domains can comprise a mutation of histidine 840, and wherein the mutation reduces the cleaving activity of the nuclease domain(s) by at least 50%.

The one or more site-directed polypeptides, e.g. DNA endonucleases, can comprise two nickases that together effect one double-strand break at a specific locus in the genome, or four nickases that together effect or cause two double-strand breaks at specific loci in the genome. Alternatively, one site-directed polypeptide, e.g. DNA endonuclease, can effect or cause one double-strand break at a specific locus in the genome.

The site-directed polypeptide can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS.

Genome-Targeting Nucleic Acid

The present disclosure provides a genome-targeting nucleic acid that can direct the activities of an associated polypeptide (e.g., a site-directed polypeptide) to a specific target sequence within a target nucleic acid. The genome-targeting nucleic acid can be an RNA. A genome-targeting RNA is referred to as a "guide RNA" or "gRNA" herein. A guide RNA can comprise at least a spacer sequence that hybridizes to a target nucleic acid sequence of interest, and a CRISPR repeat sequence. In Type II systems, the gRNA also comprises a second RNA called the tracrRNA sequence. In the Type II guide RNA (gRNA), the CRISPR repeat sequence and tracrRNA sequence hybridize to each other to form a duplex. In the Type V guide RNA (gRNA), the crRNA forms a duplex. In both systems, the duplex can bind a site-directed polypeptide, such that the guide RNA and site-direct polypeptide form a complex. The genome-targeting nucleic acid can provide target specificity to the complex by virtue of its association with the site-directed polypeptide. The genome-targeting nucleic acid thus can direct the activity of the site-directed polypeptide.

Each genome-targeting nucleic acid (guide RNA or sgRNA) is designed to include a spacer sequence complementary to its genomic target sequence.

gRNA spacer sequences for targeting the human beta globin locus with a CRISPR/Cas9 endonuclease from *S. pyogenes* have been identified in SEQ ID NOs: 1-56,961 of the Sequence Listing.

gRNA spacer sequences for targeting the human beta globin locus with a CRISPR/Cas9 endonuclease from *S. aureus* have been identified in SEQ ID NOs: 56,962-64,104 of the Sequence Listing.

gRNA spacer sequences for targeting the human beta globin locus with a CRISPR/Cas9 endonuclease from *N. meningitides* have been identified in SEQ ID NOs: 64,105-66,258 of the Sequence Listing.

gRNA spacer sequences for targeting the human beta globin locus with a CRISPR/Cas9 endonuclease from *S. thermophilus* have been identified in SEQ ID NOs: 66,259-69,152 of the Sequence Listing.

gRNA spacer sequences for targeting the human beta globin locus with a CRISPR/Cas9 endonuclease from *T. denticola* have been identified in SEQ ID NOs: 69,153-70,300 of the Sequence Listing.

gRNA spacer sequences for targeting the human beta globin locus with a CRISPR/Cpf1 endonuclease from *Acidominococcus, Lachnospiracease*, and *Franciscell novicida* have been identified in SEQ ID NOs: 70,301-156,352 of the Sequence Listing.

The genome-targeting nucleic acid can be a double-molecule guide RNA. The genome-targeting nucleic acid can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) in a Type II system can comprise in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

A single-molecule guide RNA (sgRNA) in a Type V system can comprise, in the 5' to 3' direction, a minimum CRISPR repeat sequence and a spacer sequence.

The sgRNA can comprise a 20 nucleotide spacer sequence at the 5' end of the sgRNA sequence. The sgRNA can comprise a less than a 20 nucleotide spacer sequence at the 5' end of the sgRNA sequence. The sgRNA can comprise a more than 20 nucleotide spacer sequence at the 5' end of the sgRNA sequence. The sgRNA can comprise a variable length spacer sequence with 17-30 nucleotides at the 5' end of the sgRNA sequence (see Table 1).

The sgRNA can comprise no uracil at the 3'end of the sgRNA sequence, such as in SEQ ID NO: 228,303 of Table 1. The sgRNA can comprise one or more uracil at the 3'end of the sgRNA sequence, such as in SEQ ID NO: 228,304 in Table 1. For example, the sgRNA can comprise 1 uracil (U) at the 3' end of the sgRNA sequence. The sgRNA can comprise 2 uracil (UU) at the 3' end of the sgRNA sequence. The sgRNA can comprise 3 uracil (UUU) at the 3' end of the sgRNA sequence. The sgRNA can comprise 4 uracil (UUUU) at the 3' end of the sgRNA sequence. The sgRNA can comprise 5 uracil (UUUUU) at the 3' end of the sgRNA sequence. The sgRNA can comprise 6 uracil (UUUUUU) at the 3' end of the sgRNA sequence. The sgRNA can comprise 7 uracil (UUUUUUU) at the 3' end of the sgRNA sequence. The sgRNA can comprise 8 uracil (UUUUUUUU) at the 3' end of the sgRNA sequence.

The sgRNA can be unmodified or modified. For example, modified sgRNAs can comprise one or more 2'-O-methyl phosphorothioate nucleotides.

TABLE 1

| SEQ ID NO. | sgRNA sequence |
|---|---|
| 228, 302 | nnnnnnnnnnnnnnnnnnnnnguuuuagagcuagaaauagc aaguuaaaauaaggcuaguccguuaucaacuugaaaaag uggcaccgagucggugcuuuu |
| 228, 303 | nnnnnnnnnnnnnnnnnnnnnguuuuagagcuagaaauagc aaguuaaaauaaggcuaguccguuaucaacuugaaaaag uggcaccgagucggugc |
| 228, 304 | $n_{(17-30)}$guuuuagagcuagaaauagcaaguuaaaaua aggcuaguccguuaucaacuugaaaaaguggcaccgag ucggugcu$_{(1-8)}$ |

A gRNA may be a HPFH5 gRNA, e.g., HPFH5-1, HPFH5-D, HPFH5-T5, or HPFH5-T7, or a Kenya gRNA, e.g., Kenya-K5, Kenya-K17, a 1450 gRNA, a SPY101 gRNA, or a SD2 gRNA. A gRNA may be as described in Table 2.

TABLE 2

| Name | SEQ ID NO. | gRNA sequence |
|---|---|---|
| SD2 | 228, 428 | csususGUCAAGGCUAUUGGUCAGUUUUAG AGCUAGAAAUAGCAAGUUAAAAUAAGGCUA GUCCGUUAUCAACUUGAAAAAGUGGCACCG AGUCGGUGCusususU |
| SPY101 | 228, 429 | csusasACAGUUGCUUUUAUCACGUUUUAG AGCUAGAAAUAGCAAGUUAAAAUAAGGCUA GUCCGUUAUCAACUUGAAAAAGUGGCACCG AGUCGGUGCusususU |
| 1450 | 228, 430 | usgscsUUGGUCGGCACUGAUAGGGUUUUAG AGCUAGAAAUAGCAAGUUAAAAUAAGGCUA GUCCGUUAUCAACUUGAAAAAGUGGCACCG AGUCGGUGCusususU |
| HPFH5-1 | 228, 431 | asususUUUCUUAUUCAAUACCUGUUUUAG AGCUAGAAAUAGCAAGUUAAAAUAAGGCUA GUCCGUUAUCAACUUGAAAAAGUGGCACCG AGUCGGUGCusususU |
| HPFH5-D | 228, 432 | csusgsUUGGUUUCAGAGCAGGUGUUUUAG AGCUAGAAAUAGCAAGUUAAAAUAAGGCUA GUCCGUUAUCAACUUGAAAAAGUGGCACCG AGUCGGUGCusususU |
| HPFH5-T5 | 228, 433 | csuscsCCCCACUCACAGUGACCGUUUUAG AGCUAGAAAUAGCAAGUUAAAAUAAGGCUA GUCCGUUAUCAACUUGAAAAAGUGGCACCG AGUCGGUGCusususU |
| HPFH5-T7 | 228, 434 | asasusCUGCAGUGCUAGUCUCCGUUUUAG AGCUAGAAAUAGCAAGUUAAAAUAAGGCUA GUCCGUUAUCAACUUGAAAAAGUGGCACCG AGUCGGUGCusususU |
| Kenya-K17 | 228, 312 228, 435 | gsususAAGUUCAUGUCAUAGGAGUUUUAG AGCUAGAAAUAGCAAGUUAAAAUAAGGCUA GUCCGUUAUCAACUUGAAAAAGUGGCACCG AGUCGGUGCusususU |
| Kenya-K5 | 228, 436 | cscsasGUGACUAGUGCUUGAAGGUUUUAG AGCUAGAAAUAGCAAGUUAAAAUAAGGCUA GUCCGUUAUCAACUUGAAAAAGUGGCACCG AGUCGGUGCusususU | a, c, g, u: 2'-0-methyl residues
s: phosphorothioate
A, C, G, U: RNA residues

In some embodiments, two or more gRNAs are provided. In some embodiments, the two or more gRNAs are two or more gRNAs provided in Table 2. In some embodiments, the two or more gRNAs comprise at least one SPY101 gRNA in combination with at least one HPFH5 gRNA. In some embodiments, the two or more gRNAs comprise a SPY101 gRNA in combination with a HPFH5-1 gRNA. In some embodiments, the two or more gRNAs comprise a SPY101 gRNA in combination with a HPFH5-D gRNA. In some embodiments, the two or more gRNAs comprise SPY101 gRNA in combination with a HPFH5-T5 gRNA. In some embodiments, the two or more gRNAs comprise a SPY101 gRNA in combination with a HPFH5-T7 gRNA. In some embodiments, the two or more gRNAs comprise at least one SPY101 gRNA in combination with at least one Kenya gRNA. In some embodiments, the two or more gRNAs comprise a SPY101 gRNA in combination with a Kenya-K5 gRNA. In some embodiments, the two or more gRNAs comprise a SPY101 gRNA in combination with a Kenya-K17 gRNA. In some embodiments, the two or more gRNAs comprise a SPY101 gRNA in combination with HPFH5-1 and HPFH5-D gRNAs. In some embodiments, the two or more gRNAs comprise a SPY101 gRNA in combination with HPFH5-T7 and HPFH5-D gRNAs. In some embodiments, the two or more gRNAs comprise a SPY101 gRNA in combination with HPFH5-T5 and HPFH5-1 gRNAs. In some embodiments, the two or more gRNAs comprise a SPY101 gRNA in combination with Kenya-K5 and Kenya-K17 gRNAs. In some embodiments, the two or more gRNAs comprise a SPY101 gRNA in combination with a SD2 gRNA. In some embodiments, the two or more gRNAs comprise at least one 1450 gRNA in combination with at least one HPFH5 gRNA. In some embodiments, the two or more gRNAs comprise a 1450 gRNA in combination with a HPFH5-1 gRNA. In some embodiments, the two or more gRNAs comprise a 1450 gRNA in combination with a HPFH5-D gRNA. In some embodiments, the two or more gRNAs comprise a 1450 gRNA in combination with a HPFH5-T5 gRNA. In some embodiments, the two or more gRNAs comprise a 1450 gRNA in combination with a HPFH5-T7 gRNA. In some embodiments, the two or more gRNAs comprise at least one 1450 gRNA in combination with at least one Kenya gRNA. In some embodiments, the two or more gRNAs comprise a 1450 gRNA in combination with a Kenya-K5 gRNA. In some embodiments, the two or more gRNAs comprise a 1450 gRNA in combination with a Kenya-K17 gRNA. In some embodiments, the two or more gRNAs comprise a 1450 gRNA in combination with HPFH5-1 and HPFH5-D gRNAs. In some embodiments, the two or more gRNAs comprise a 1450 gRNA in combination with HPFH5-T7 and HPFH5-D gRNAs. In some embodiments, the two or more gRNAs comprise a 1450 gRNA in combination with HPFH5-T5 and HPFH5-1 gRNAs. In some embodiments, the two or more gRNAs comprise a 1450 gRNA in combination with Kenya-K5 and Kenya-K17 gRNAs. In some embodiments, the two or more gRNAs comprise a 1450 gRNA in combination with a SD2 gRNA. In some embodiments, the two or more gRNAs comprise at least one of a HPFH5-1, HPFH5-D, HPFH5-T5, HPFH5-T7, Kenya-K5, or Kenya-K1 gRNA in combination with at least one additional HPFH5-1, HPFH5-D, HPFH5-T5, HPFH5-T7, Kenya-K5, or Kenya-K1 gRNA. In some embodiments, the two or more gRNAs comprise a HPFH5-1 gRNA in combination with a HPFH5-1, HPFH5-D, HPFH5-T5, HPFH5-T7, Kenya-K5, or Kenya-K1 gRNA. In some embodiments, the two or more gRNAs comprise a HPFH5-D gRNA in combination with a HPFH5-1, HPFH5-D, HPFH5-T5, HPFH5-T7, Kenya-K5, or Kenya-K1 gRNA. In some embodiments, the two or more gRNAs comprise a HPFH5-T5 gRNA in combination with a HPFH5-1, HPFH5-D, HPFH5-T5, HPFH5-T7, Kenya-K5, or Kenya-K1 gRNA. In some embodiments, the two or more gRNAs comprise a HPFH5-T7 gRNA in combination with a HPFH5-1, HPFH5-D, HPFH5-T5, HPFH5-T7, Kenya-K5, or Kenya-K1 gRNA.

By way of illustration, guide RNAs used in the CRISPR/Cas/Cpf1 system, or other smaller RNAs can be readily synthesized by chemical means as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

Concatenated gRNAs

A concatenated gRNA comprising a first gRNA and second gRNA can be used to introduce a deletion, inversion, or mutation within or near a human beta globin locus on chromosome 11 and within or near one or more of: a BCL11A gene on chromosome 2, and a DNA sequence that harbors a transcriptional control region of the BCL11A gene on chromosome 2. The first gRNA can comprise a gRNA specific for the human beta globin locus, as described in Examples 1-6 and disclosed in the Sequence Listing. The second gRNA can comprise a gRNA specific for the BCL11A gene or a DNA sequence that encodes a transcriptional control region of the BCL11A gene, as described in Examples 14-19 or the Figures; and disclosed in the Sequence Listing.

A concatenated gRNA comprising a first gRNA, a second gRNA, and a third gRNA can be used to introduce a deletion, inversion, or mutation within or near a human beta globin locus on chromosome 11 and within or near one or more of: a BCL11A gene on chromosome 2, and a DNA sequence that encodes a transcriptional control region of the BCL11A gene on chromosome 2. The first gRNA can comprise a gRNA specific for the human beta globin locus, as described in Examples 1-6 and disclosed in the Sequence Listing. The second gRNA can comprise a gRNA specific for the human beta globin locus, as described in Examples 1-6 and disclosed in the Sequence Listing. The third gRNA can comprise a gRNA specific for the BCL11A gene or a DNA sequence that encodes a transcriptional control region of the BCL11A gene, as described in Examples 14-19 or the Figures; and disclosed in the Sequence Listing.

A concatenated gRNA comprising a first gRNA, a second gRNA, and a third gRNA can be used to introduce a deletion, inversion, or mutation within or near a human beta globin locus on chromosome 11 and within or near one or more of: a BCL11A gene on chromosome 2, and a DNA sequence that encodes a transcriptional control region of the BCL11A gene on chromosome 2. The first gRNA can comprise a gRNA specific for the human beta globin locus, as described in Examples 1-6 and disclosed in the Sequence Listing. The second gRNA can comprise a gRNA specific for the BCL11A gene or a DNA sequence that encodes a transcriptional control region of the BCL11A gene, as described in Examples 14-19 or the Figures; and disclosed in the Sequence Listing. The third gRNA can comprise a gRNA specific for the BCL11A gene or a DNA sequence that encodes a transcriptional control region of the BCL11A gene, as described in Examples 14-19 or the Figures; and disclosed in the Sequence Listing.

In some embodiments, a concatenated gRNA may comprise a HPFH5 gRNA, e.g., HPFH5-1, HPFH5-D, HPFH5-T5, or HPFH5-T7, a Kenya gRNA, e.g., Kenya-K5, Kenya-K17, a 1450 gRNA, a SPY101 gRNA, or a SD2 gRNA. In some embodiments, a concatenated gRNA may comprise a gRNA as described in Table 2. In some embodiments, a concatenated gRNA may comprise at least one SPY101 gRNA in combination with at least one HPFH5 gRNA. In some embodiments, a concatenated gRNA may comprise a SPY101 gRNA in combination with a HPFH5-1 gRNA. In some embodiments, a concatenated gRNA may comprise a SPY101 gRNA in combination with a HPFH5-D gRNA. In some embodiments, a concatenated gRNA may comprise a SPY101 gRNA in combination with a HPFH5-T5 gRNA. In some embodiments, a concatenated gRNA may comprise a SPY101 gRNA in combination with a HPFH5-T7 gRNA. In some embodiments, a concatenated gRNA may comprise at least one SPY101 gRNA in combination with at least one Kenya gRNA. In some embodiments, a concatenated gRNA may comprise a SPY101 gRNA in combination with a Kenya-K5 gRNA. In some embodiments, a concatenated gRNA may comprise a SPY101 gRNA in combination with a Kenya-K17 gRNA. In some embodiments, a concatenated gRNA may comprise a SPY101 gRNA in combination with HPFH5-1 and HPFH5-D gRNAs. In some embodiments, a concatenated gRNA may comprise a SPY101 gRNA in combination with HPFH5-T7 and HPFH5-D gRNAs. In some embodiments, a concatenated gRNA may comprise a SPY101 gRNA in combination with HPFH5-T5 and HPFH5-1 gRNAs. In some embodiments, a concatenated gRNA may comprise a SPY101 gRNA in combination with Kenya-K5 and Kenya-K17 gRNAs. In some embodiments, a concatenated gRNA may comprise a SPY101 gRNA in combination with a SD2 gRNA. In some embodiments, a concatenated gRNA may comprise at least one 1450 gRNA in combination with at least one HPFH5 gRNA. In some embodiments, a concatenated gRNA may comprise a 1450 gRNA in combination with a HPFH5-1 gRNA. In some embodiments, a concatenated gRNA may comprise a 1450 gRNA in combination with a HPFH5-D gRNA. In some embodiments, a concatenated gRNA may comprise a 1450 gRNA in combination with a HPFH5-T5 gRNA. In some embodiments, a concatenated gRNA may comprise a 1450 gRNA in combination with a HPFH5-T7 gRNA. In some embodiments, a concatenated gRNA may comprise at least one 1450 gRNA in combination with at least one Kenya gRNA. In some embodiments, a concatenated gRNA may comprise a 1450 gRNA in combination with a Kenya-K5 gRNA. In some embodiments, a concatenated gRNA may comprise a 1450 gRNA in combination with a Kenya-K17 gRNA. In some embodiments, a concatenated gRNA may comprise a 1450 gRNA in combination with HPFH5-1 and HPFH5-D gRNAs. In some embodiments, a concatenated gRNA may comprise a 1450 gRNA in combination with HPFH5-T7 and HPFH5-D gRNAs. In some embodiments, a concatenated gRNA may comprise a 1450 gRNA in combination with HPFH5-T5 and HPFH5-1 gRNAs. In some embodiments, a concatenated gRNA may comprise a 1450 gRNA in combination with Kenya-K5 and Kenya-K17 gRNAs. In some embodiments, a concatenated gRNA may comprise a 1450 gRNA in combination with a SD2 gRNA. In some embodiments, a concatenated gRNA may comprise at least one of a HPFH5-1, HPFH5-D, HPFH5-T5, HPFH5-T7, Kenya-K5, or Kenya-K1 gRNA in combination with at least one additional HPFH5-1, HPFH5-D, HPFH5-T5, HPFH5-T7, Kenya-K5, or Kenya-K1 gRNA. In some embodiments, a concatenated gRNA may comprise a HPFH5-1 gRNA in combination with a HPFH5-1, HPFH5-D, HPFH5-T5, HPFH5-T7, Kenya-K5, or Kenya-K1 gRNA. In some embodiments, a concatenated gRNA may comprise a HPFH5-D gRNA in combination with a HPFH5-1, HPFH5-D, HPFH5-T5, HPFH5-T7, Kenya-K5, or Kenya-K1 gRNA. In some embodiments, a concatenated gRNA may comprise a HPFH5-T5 gRNA in combination with a HPFH5-1, HPFH5-D, HPFH5-T5, HPFH5-T7, Kenya-K5, or Kenya-K1 gRNA. In some embodiments, a concatenated gRNA may comprise a HPFH5-T7 gRNA in combination with a HPFH5-1, HPFH5-D, HPFH5-T5, HPFH5-T7, Kenya-K5, or Kenya-K1 gRNA.

Two or More Concatenated gRNAs

Two or more concatenated gRNAs can be used simultaneously to introduce a deletion, inversion, or mutation within or near a human beta globin locus on chromosome 11 and within or near one or more of: a BCL11A gene on chromosome 2, and a DNA sequence that encodes a transcriptional control region of the BCL11A gene on chromosome 2. The first concatenated gRNA comprises a first gRNA and a second gRNA. The first gRNA of the first concatenated gRNA can comprise a gRNA specific for the human beta globin locus, as described in Examples 1-6 and disclosed in the Sequence Listing. The second gRNA of the first concatenated gRNA can comprise a gRNA specific for the BCL11A gene or a DNA sequence that encodes a transcriptional control region of the BCL11A gene, as described in Examples 14-19 or the Figures; and disclosed in the Sequence Listing. The second concatenated gRNA comprises a first gRNA and a second gRNA. The first gRNA of the second concatenated gRNA can comprise a gRNA specific for the human beta globin locus, as described in Examples 1-6 and disclosed in the Sequence Listing. The second gRNA of the second concatenated gRNA can comprise a gRNA specific for the BCL11A gene or a DNA sequence that encodes a transcriptional control region of the BCL11A gene, as described in Examples 14-19 of the Figures; and disclosed in the Sequence Listing.

Two or more concatenated gRNAs can be used to introduce a deletion, inversion, or mutation within or near a human beta globin locus on chromosome 11 and within or near one or more of: a BCL11A gene on chromosome 2, and a DNA sequence that encodes a transcriptional control region of the BCL11A gene on chromosome 2. The first concatenated gRNA comprises a first gRNA and a second gRNA. The first gRNA of the first concatenated gRNA can comprise a gRNA specific for the human beta globin locus, as described in Examples 1-6 and disclosed in the Sequence Listing. The second gRNA of the first concatenated gRNA can comprise a gRNA specific for the human beta globin locus, as described in Examples 1-6 and disclosed in the Sequence Listing. The second concatenated gRNA comprises a first gRNA and a second gRNA. The first gRNA of the second concatenated gRNA can comprise a gRNA specific for the BCL11A gene or a DNA sequence that encodes a transcriptional control region of the BCL11A gene, as described in Examples 14-19 or the Figures; and disclosed in the Sequence Listing. The second gRNA of the second concatenated gRNA can comprise a gRNA specific for the BCL11A gene or a DNA sequence that encodes a transcriptional control region of the BCL11A gene, as described in Examples 14-19 of the Figures; and disclosed in the Sequence Listing.

Spacer Extension Sequence

Examples of genome-targeting nucleic acids, a spacer extension sequence can modify activity, provide stability and/or provide a location for modifications of a genome-targeting nucleic acid. A spacer extension sequence can modify on- or off-target activity or specificity. In some examples, a spacer extension sequence can be provided. The spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. The spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. The spacer extension sequence can comprise less than 10 nucleotides in length. The spacer extension sequence can comprise between 10-30 nucleotides in length. The spacer extension sequence can comprise between 30-70 nucleotides in length.

The spacer extension sequence can comprise another moiety (e.g., a stability control sequence, an endoribonuclease binding sequence, a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells.

Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

Spacer Sequence

The spacer sequence hybridizes to a sequence in a target nucleic acid of interest. The spacer of a genome-targeting nucleic acid can interact with a target nucleic acid in a sequence-specific manner via hybridization (i.e., base pairing). The nucleotide sequence of the spacer can vary depending on the sequence of the target nucleic acid of interest.

In a CRISPR/Cas system herein, the spacer sequence can be designed to hybridize to a target nucleic acid that is located 5' of a PAM of the Cas9 enzyme used in the system. The spacer can perfectly match the target sequence or can have mismatches. Each Cas9 enzyme has a particular PAM sequence that it recognizes in a target DNA. For example, *S. pyogenes* recognizes in a target nucleic acid a PAM that comprises the sequence 5'-NRG-3', where R comprises either A or G, where N is any nucleotide and N is immediately 3' of the target nucleic acid sequence targeted by the spacer sequence.

The target nucleic acid sequence can comprise 20 nucleotides. The target nucleic acid can comprise less than 20 nucleotides. The target nucleic acid can comprise more than 20 nucleotides. The target nucleic acid can comprise at least: 5, 10, 15, 16, 17, 18, 19, 20, 21, 22, 23, 24, 25, 30 or more nucleotides. The target nucleic acid can comprise at most: 5, 10, 15, 16, 17, 18, 19, 20, 21, 22, 23, 24, 25, 30 or more nucleotides. The target nucleic acid sequence can comprise 20 bases immediately 5' of the first nucleotide of the PAM. For example, in a sequence comprising 5'-NNNNNNNNNNNNNNNNNNNNNRG-3' (SEQ ID NO 228,301), the target nucleic acid can comprise the sequence that corresponds to the Ns, wherein N is any nucleotide, and the underlined NRG sequence is the *S. pyogenes* PAM.

The spacer sequence that hybridizes to the target nucleic acid can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. In some examples, the spacer can comprise 19 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which may be thought of as a bulge or bulges.

The spacer sequence can be designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

A minimum CRISPR repeat sequence can be a sequence with at least: about 30%, about 40%, about 50%, about 60%, about 65%, about 70%, about 75%, about 80%, about 85%, about 90%, about 95%, or 100% sequence identity to a reference CRISPR repeat sequence (e.g., crRNA from *S. pyogenes*).

A minimum CRISPR repeat sequence can comprise nucleotides that can hybridize to a minimum tracrRNA sequence in a cell. The minimum CRISPR repeat sequence and a minimum tracrRNA sequence can form a duplex, i.e. a base-paired double-stranded structure. Together, the minimum CRISPR repeat sequence and the minimum tracrRNA sequence can bind to the site-directed polypeptide. At least a part of the minimum CRISPR repeat sequence can hybridize to the minimum tracrRNA sequence. At least a part of the minimum CRISPR repeat sequence can comprise at least: about 30%, about 40%, about 50%, about 60%, about 65%, about 70%, about 75%, about 80%, about 85%, about 90%, about 95%, or 100% complementary to the minimum tracrRNA sequence. At least a part of the minimum CRISPR repeat sequence can comprise at most: about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from about 7 nucleotides to about 100 nucleotides. For example, the length of the minimum CRISPR repeat sequence is from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some examples, the minimum CRISPR repeat sequence can be approximately 9 nucleotides in length. The minimum CRISPR repeat sequence can be approximately 12 nucleotides in length.

The minimum CRISPR repeat sequence can be at least about 60% identical to a reference minimum CRISPR repeat sequence (e.g., wild-type crRNA from *S. pyogenes*) over a stretch of at least 6, 7, or 8 contiguous nucleotides. For example, the minimum CRISPR repeat sequence can be at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

A minimum tracrRNA sequence can be a sequence with at least: about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from *S. pyogenes*).

A minimum tracrRNA sequence can comprise nucleotides that hybridize to a minimum CRISPR repeat sequence in a cell. A minimum tracrRNA sequence and a minimum CRISPR repeat sequence form a duplex, i.e. a base-paired double-stranded structure. Together, the minimum tracrRNA sequence and the minimum CRISPR repeat can bind to a site-directed polypeptide. At least a part of the minimum tracrRNA sequence can hybridize to the minimum CRISPR repeat sequence. The minimum tracrRNA sequence can be at least: about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA 23-48 nt described in Jinek et al., supra.

The minimum tracrRNA sequence can be at least about 60% identical to a reference minimum tracrRNA (e.g., wild type, tracrRNA from *S. pyogenes*) sequence over a stretch of at least: 6, 7, or 8 contiguous nucleotides. For example, the minimum tracrRNA sequence can be at least: about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least: 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about: 1, 2, 3, 4, 5, 6, 7, 8, 9, or 10 or more nucleotides. The duplex between the minimum CRISPR RNA and the minimum tracrRNA can comprise at most about: 1, 2, 3, 4, 5, 6, 7, 8, 9, or 10 or more nucleotides.

The duplex can comprise a mismatch (i.e., the two strands of the duplex are not 100% complementary). The duplex can comprise at least about: 1, 2, 3, 4, or 5 or mismatches. The duplex can comprise at most about: 1, 2, 3, 4, or 5 or mismatches. The duplex can comprise no more than 2 mismatches.

Bulges

In some cases, there can be a "bulge" in the duplex between the minimum CRISPR RNA and the minimum tracrRNA. A bulge is an unpaired region of nucleotides within the duplex. A bulge can contribute to the binding of the duplex to the site-directed polypeptide. The bulge can comprise, on one side of the duplex, an unpaired 5'-XXXY-3' where X is any purine and Y comprises a nucleotide that can form a wobble pair with a nucleotide on the opposite strand, and an unpaired nucleotide region on the other side of the duplex. The number of unpaired nucleotides on the two sides of the duplex can be different.

In one example, the bulge can comprise an unpaired purine (e.g., adenine) on the minimum CRISPR repeat strand of the bulge. In some examples, the bulge can comprise an unpaired 5'-AAGY-3' of the minimum tracrRNA sequence strand of the bulge, where Y comprises a nucleotide that can form a wobble pairing with a nucleotide on the minimum CRISPR repeat strand.

A bulge on the minimum CRISPR repeat side of the duplex can comprise at least: 1, 2, 3, 4, or 5 or more unpaired nucleotides. A bulge on the minimum CRISPR repeat side of the duplex can comprise at most: 1, 2, 3, 4, or 5 or more unpaired nucleotides. A bulge on the minimum CRISPR repeat side of the duplex can comprise 1 unpaired nucleotide.

A bulge on the minimum tracrRNA sequence side of the duplex can comprise at least: 1, 2, 3, 4, 5, 6, 7, 8, 9, or 10 or more unpaired nucleotides. A bulge on the minimum tracrRNA sequence side of the duplex can comprise at most: 1, 2, 3, 4, 5, 6, 7, 8, 9, or 10 or more unpaired nucleotides. A bulge on a second side of the duplex (e.g., the minimum tracrRNA sequence side of the duplex) can comprise 4 unpaired nucleotides.

A bulge can comprise at least one wobble pairing. A bulge can comprise at most one wobble pairing. A bulge can comprise at least one purine nucleotide. A bulge can comprise at least 3 purine nucleotides. A bulge sequence can comprise at least 5 purine nucleotides. A bulge sequence can comprise at least one guanine nucleotide. A bulge sequence can comprise at least one adenine nucleotide.

Hairpins

In various examples, one or more hairpins can be located 3' to the minimum tracrRNA in the 3' tracrRNA sequence.

The hairpin can start at least about: 1, 2, 3, 4, 5, 6, 7, 8, 9, 10, 15, or 20 or more nucleotides 3' from the last paired nucleotide in the minimum CRISPR repeat and minimum tracrRNA sequence duplex. The hairpin can start at most about: 1, 2, 3, 4, 5, 6, 7, 8, 9 or 10 or more nucleotides 3' of the last paired nucleotide in the minimum CRISPR repeat and minimum tracrRNA sequence duplex.

The hairpin can comprise at least about: 1, 2, 3, 4, 5, 6, 7, 8, 9, 10, 15, or 20 or more consecutive nucleotides. The hairpin can comprise at most about: 1, 2, 3, 4, 5, 6, 7, 8, 9, 10, 15, or more consecutive nucleotides.

The hairpin can comprise a CC dinucleotide (i.e., two consecutive cytosine nucleotides).

The hairpin can comprise duplexed nucleotides (e.g., nucleotides in a hairpin, hybridized together). For example, a hairpin can comprise a CC dinucleotide that is hybridized to a GG dinucleotide in a hairpin duplex of the 3' tracrRNA sequence.

One or more of the hairpins can interact with guide RNA-interacting regions of a site-directed polypeptide.

In some examples, there are two or more hairpins, and in other examples there are three or more hairpins.

3' tracrRNA Sequence

A 3' tracrRNA sequence can comprise a sequence with at least: about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

The 3' tracrRNA sequence can have a length from about 6 nucleotides to about 100 nucleotides. For example, the 3' tracrRNA sequence can have a length of from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. The 3' tracrRNA sequence can have a length of approximately 14 nucleotides.

The 3' tracrRNA sequence can be at least about 60% identical to a reference 3' tracrRNA sequence (e.g., wild type 3' tracrRNA sequence from *S. pyogenes*) over a stretch of at least: 6, 7, or 8 contiguous nucleotides. For example, the 3' tracrRNA sequence can be at least: about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from *S. pyogenes*) over a stretch of at least 6, 7, or 8 contiguous nucleotides.

The 3' tracrRNA sequence can comprise more than one duplexed region (e.g., hairpin, hybridized region). The 3' tracrRNA sequence can comprise two duplexed regions.

The 3' tracrRNA sequence can comprise a stem loop structure. The stem loop structure in the 3' tracrRNA can comprise at least: 1, 2, 3, 4, 5, 6, 7, 8, 9, 10, 15 or 20 or more nucleotides. The stem loop structure in the 3' tracrRNA can comprise at most: 1, 2, 3, 4, 5, 6, 7, 8, 9 or 10 or more nucleotides. The stem loop structure can comprise a functional moiety. For example, the stem loop structure can comprise an aptamer, a ribozyme, a protein-interacting hairpin, a CRISPR array, an intron, or an exon. The stem loop structure can comprise at least about: 1, 2, 3, 4, or 5 or more functional moieties. The stem loop structure can comprise at most about: 1, 2, 3, 4, or 5 or more functional moieties.

The hairpin in the 3' tracrRNA sequence can comprise a P-domain. In some examples, the P-domain can comprise a double-stranded region in the hairpin.

tracrRNA Extension Sequence

A tracrRNA extension sequence may be provided whether the tracrRNA is in the context of single-molecule guides or double-molecule guides. The tracrRNA extension sequence can have a length from about 1 nucleotide to about 400 nucleotides. The tracrRNA extension sequence can have a length of more than: 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. The tracrRNA extension sequence can have a length from about 20 to about 5000 or more nucleotides. The tracrRNA extension sequence can have a length of more than 1000 nucleotides. The tracrRNA extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. The tracrRNA extension sequence can have a length of less than 1000 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). In some aspects, a functional moiety comprises a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt. The functional moiety can function in a eukaryotic cell. The functional moiety can function in a prokaryotic cell. The functional moiety can function in both eukaryotic and prokaryotic cells.

Non-limiting examples of suitable tracrRNA extension functional moieties include: a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like). The tracrRNA extension sequence can comprise a primer binding site or a molecular index (e.g., barcode sequence). The tracrRNA extension sequence can comprise one or more affinity tags.

Single-Molecule Guide Linker Sequence

The linker sequence of a single-molecule guide nucleic acid can have a length from about 3 nucleotides to about 100 nucleotides. In Jinek et al., supra, for example, a simple 4 nucleotide "tetraloop" (-GAAA-) was used, Science, 337 (6096): 816-821 (2012). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about: 100, 500, 1000, 1500, 2000, 2500, 3000, 3500, 4000, 4500, 5000, 5500, 6000, 6500, or 7000 or more nucleotides. The linker can be at most about: 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples, the linker will not comprise sequences that have extensive regions of homology with other portions of the guide RNA, which might cause intra-molecular binding that could interfere with other functional regions of the guide. In Jinek et al., supra, a simple 4 nucleotide sequence -GAAA- was used, Science, 337 (6096): 816-821 (2012), but numerous other sequences, including longer sequences can likewise be used.

The linker sequence can comprise a functional moiety. For example, the linker sequence can comprise one or more features, including an aptamer, a ribozyme, a protein-inter-acting hairpin, a protein binding site, a CRISPR array, an intron, or an exon. The linker sequence can comprise at least about: 1, 2, 3, 4, or 5 or more functional moieties. In some examples, the linker sequence can comprise at most about: 1, 2, 3, 4, or 5 or more functional moieties.

Complexes of a Nucleic Acid-Targeting Nucleic Acid and a Site-Directed Polypeptide A nucleic acid-targeting nucleic acid interacts with a site-directed polypeptide (e.g., a nucleic acid-guided nucle-ase such as Cas9), thereby forming a complex. The nucleic acid-targeting nucleic acid guides the site-directed polypep-tide to a target nucleic acid.

Target Sequence Selection

Shifts in the location of the 5' boundary and/or the 3' boundary relative to particular reference loci can be used to facilitate or enhance particular applications of gene editing, which depend in part on the endonuclease system selected for the editing, as further described and illustrated herein.

In a first nonlimiting example of such target sequence selection, many endonuclease systems have rules or criteria that can guide the initial selection of potential target sites for cleavage, such as the requirement of a PAM sequence motif in a particular position adjacent to the DNA cleavage sites in the case of CRISPR Type II or Type V endonucleases.

In another nonlimiting example of target sequence selec-tion or optimization, the frequency of off-target activity for a particular combination of target sequence and gene editing endonuclease (i.e. the frequency of DSBs occurring at sites other than the selected target sequence) can be assessed relative to the frequency of on-target activity. In some cases, cells that have been correctly edited at the desired locus can have a selective advantage relative to other cells. Illustrative, but nonlimiting, examples of a selective advantage include the acquisition of attributes such as enhanced rates of replication, persistence, resistance to certain conditions, enhanced rates of successful engraftment or persistence in vivo following introduction into a patient, and other attri-butes associated with the maintenance or increased numbers or viability of such cells. In other cases, cells that have been correctly edited at the desired locus can be positively selected for by one or more screening methods used to identify, sort or otherwise select for cells that have been correctly edited. Both selective advantage and directed selection methods can take advantage of the phenotype associated with the correction. In some cases, cells can be edited two or more times in order to create a second modification that creates a new phenotype that is used to select or purify the intended population of cells. Such a second modification could be created by adding a second gRNA for a selectable or screenable marker. In some cases, cells can be correctly edited at the desired locus using a DNA fragment that contains the cDNA and also a selectable marker.

Whether any selective advantage is applicable or any directed selection is to be applied in a particular case, target sequence selection can also be guided by consideration of off-target frequencies in order to enhance the effectiveness of the application and/or reduce the potential for undesired alterations at sites other than the desired target. As described further and illustrated herein and in the art, the occurrence of off-target activity can be influenced by a number of factors including similarities and dissimilarities between the target site and various off-target sites, as well as the par-ticular endonuclease used. Bioinformatics tools are available that assist in the prediction of off-target activity, and fre-quently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein, and others are known in the art.

Another aspect of target sequence selection relates to homologous recombination events. Sequences sharing regions of homology can serve as focal points for homolo-gous recombination events that result in deletion of inter-vening sequences. Such recombination events occur during the normal course of replication of chromosomes and other DNA sequences, and also at other times when DNA sequences are being synthesized, such as in the case of repairs of double-strand breaks (DSBs), which occur on a regular basis during the normal cell replication cycle but can also be enhanced by the occurrence of various events (such as UV light and other inducers of DNA breakage) or the presence of certain agents (such as various chemical induc-ers). Many such inducers cause DSBs to occur indiscrimi-nately in the genome, and DSBs can be regularly induced and repaired in normal cells. During repair, the original sequence can be reconstructed with complete fidelity, how-ever, in some cases, small insertions or deletions (referred to as "indels") are introduced at the DSB site.

DSBs can also be specifically induced at particular loca-tions, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems, such as CRISPR, in which homology directed repair is used to insert a sequence of interest, provided through use of a "donor" polynucleotide, into a desired chromosomal location.

Regions of homology between particular sequences, which can be small regions of "microhomology" that can comprise as few as ten basepairs or less, can also be used to bring about desired deletions. For example, a single DSB can be introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process.

In some circumstances, however, selecting target sequences within regions of homology can also give rise to much larger deletions, including gene fusions (when the deletions are in coding regions), which may or may not be desired given the particular circumstances.

Nucleic Acid Modifications

In some cases, polynucleotides introduced into cells can comprise one or more modifications that can be used individually or in combination, for example, to enhance activity, stability or specificity, alter delivery, reduce innate immune responses in host cells, or for other enhancements, as further described herein and known in the art.

In certain examples, modified polynucleotides can be used in the CRISPR/Cas9/Cpf1 system, in which case the guide RNAs (either single-molecule guides or double-molecule guides) and/or a DNA or an RNA encoding a Cas or Cpf1 endonuclease introduced into a cell can be modified, as described and illustrated below. Such modified polynucleotides can be used in the CRISPR/Cas9/Cpf1 system to edit any one or more genomic loci.

Using the CRISPR/Cas9/Cpf1 system for purposes of nonlimiting illustrations of such uses, modifications of guide RNAs can be used to enhance the formation or stability of the CRISPR/Cas9/Cpf1 genome editing complex comprising guide RNAs, which can be single-molecule guides or double-molecule, and a Cas or Cpf1 endonuclease. Modifications of guide RNAs can also or alternatively be used to enhance the initiation, stability or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in aspects in which a Cas or Cpf1 endonuclease is introduced into the cell to be edited via an RNA that needs to be translated in order to generate endonuclease, because increasing the half-life of guide RNAs introduced at the same time as the RNA encoding the endonuclease can be used to increase the time that the guide RNAs and the encoded Cas or Cpf1 endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNAses present in the cell), modifications that enhance translation of the resulting product (i.e. the endonuclease), and/or modifications that decrease the likelihood or degree to which the RNAs introduced into cells elicit innate immune responses.

Combinations of modifications, such as the foregoing and others, can likewise be used. In the case of CRISPR/Cas9/Cpf1, for example, one or more types of modifications can be made to guide RNAs (including those exemplified above), and/or one or more types of modifications can be made to RNAs encoding Cas endonuclease (including those exemplified above).

By way of illustration, guide RNAs used in the CRISPR/Cas9/Cpf1 system, or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach that can be used for generating chemically-modified RNAs of greater length is to produce two or more molecules that are ligated together. Much longer RNAs, such as those encoding a Cas9 endonuclease, are more readily generated enzymatically. While fewer types of modifications are available for use in enzymatically produced RNAs, there are still modifications that can be used to, e.g., enhance stability, reduce the likelihood or degree of innate immune response, and/or enhance other attributes, as described further below and in the art; and new types of modifications are regularly being developed.

By way of illustration of various types of modifications, especially those used frequently with smaller chemically synthesized RNAs, modifications can comprise one or more nucleotides modified at the 2' position of the sugar, in some aspects a 2'-O-alkyl, 2'-O-alkyl-O-alkyl, or 2'-fluoro-modified nucleotide. In some examples, RNA modifications can comprise 2'-fluoro, 2'-amino or 2' O-methyl modifications on the ribose of pyrimidines, abasic residues, or an inverted base at the 3' end of the RNA. Such modifications can be routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly CH2-NH—O—CH2, CH, ~N(CH3)~O~CH2 (known as a methylene(methylimino) or MMI backbone), CH2-O—N(CH3)-CH2, CH2-N(CH3)-N(CH3)-CH2 and O—N(CH3)-CH2-CH2 backbones, wherein the native phosphodiester backbone is represented as O—P—O—CH); amide backbones [see De Mesmaeker et al., Ace. Chem. Res., 28:366-374 (1995)]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, Biochemistry, 41 (14): 4503-4510 (2002); Genesis, Volume 30, Issue 3, (2001); Heasman, Dev. Biol., 243:209-214 (2002); Nasevicius et al., Nat. Genet., 26:216-220 (2000); Lacerra et al., Proc. Natl. Acad. Sci., 97:9591-9596 (2000); and U.S. Pat. No. 5,034,506, issued Jul. 23, 1991.

Cyclohexenyl nucleic acid oligonucleotide mimetics are described in Wang et al., J. Am. Chem. Soc., 122:8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and CH2 component parts; see U.S. Pat. Nos. 5,034,506; 5,166,315; 5,185, 444; 5,214,134; 5,216,141; 5,235,033; 5,264,562; 5,264, 564; 5,405,938; 5,434,257; 5,466,677; 5,470,967; 5,489, 677; 5,541,307; 5,561,225; 5,596,086; 5,602,240; 5,610, 289; 5,602,240; 5,608,046; 5,610,289; 5,618,704; 5,623, 070; 5,663,312; 5,633,360; 5,677,437; and 5,677,439.

One or more substituted sugar moieties can also be included, e.g., one of the following at the 2' position: OH, SH, $SCH_3$, F, OCN, OCH3 OCH3, OCH3 O(CH2)n CH3, O(CH2)n NH2, or O(CH2)n CH3, where n is from 1 to about 10; C1 to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some aspects, a modification includes 2'-methoxyethoxy (2'-0-CH2CH2OCH3, also known as 2'-O-(2-methoxyethyl)) (Martin et al, Helv. Chim. Acta, 1995, 78, 486). Other modifications include 2'-methoxy (2'-0-CH3), 2'-propoxy (2'-OCH2 CH2CH3) and 2'-fluoro (2'-F). Similar modifications can also be made at other positions on the oligonucleotide, particularly the 3' position of the sugar on the 3' terminal nucleotide and the 5' position of 5' terminal nucleotide. Oligonucleotides can also have sugar mimetics, such as cyclobutyls in place of the pentofuranosyl group.

In some examples, both a sugar and an internucleoside linkage, i.e., the backbone, of the nucleotide units can be replaced with novel groups. The base units can be maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide can be replaced with an amide containing backbone, for example, an aminoethylglycine backbone. The nucleobases can be retained and bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719, 262. Further teaching of PNA compounds can be found in Nielsen et al, Science, 254:1497-1500 (1991).

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino) adenine, 2-(imidazolylalkyl) adenine, 2-(aminoalklyamino) adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl) adenine, and 2,6-diaminopurine. Kornberg, A., DNA Replication, W. H. Freeman & Co., San Francisco, pp 75-77 (1980); Gebeyehu et al., Nucl. Acids Res. 15:4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine, and 3-deazaguanine and 3-deazaadenine.

Further, nucleobases can comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are aspects of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and U.S. Patent Application Publication 2003/0158403.

Thus, the term "modified" refers to a non-natural sugar, phosphate, or base that is incorporated into a guide RNA, an endonuclease, or both a guide RNA and an endonuclease. It is not necessary for all positions in a given oligonucleotide to be uniformly modified, and in fact more than one of the aforementioned modifications can be incorporated in a single oligonucleotide, or even in a single nucleoside within an oligonucleotide.

The guide RNAs and/or mRNA (or DNA) encoding an endonuclease can be chemically linked to one or more moieties or conjugates that enhance the activity, cellular distribution, or cellular uptake of the oligonucleotide. Such moieties comprise, but are not limited to, lipid moieties such as a cholesterol moiety [Letsinger et al., Proc. Natl. Acad. Sci. USA, 86:6553-6556 (1989)]; cholic acid [Manoharan et al., Bioorg. Med. Chem. Let., 4:1053-1060 (1994)]; a thioether, e.g., hexyl-S-tritylthiol [Manoharan et al, Ann. N. Y. Acad. Sci., 660:306-309 (1992) and Manoharan et al., Bioorg. Med. Chem. Let., 3:2765-2770 (1993)]; a thiocholesterol [Oberhauser et al., Nucl. Acids Res., 20:533-538 (1992)]; an aliphatic chain, e.g., dodecandiol or undecyl residues [Kabanov et al., FEBS Lett., 259:327-330 (1990) and Svinarchuk et al., Biochimie, 75:49-54 (1993)]; a phospholipid, e.g., di-hexadecyl-rac-glycerol or triethylammonium 1,2-di-O-hexadecyl-rac-glycero-3-H-phosphonate [Manoharan et al., Tetrahedron Lett., 36:3651-3654 (1995) and Shea et al., Nucl. Acids Res., 18:3777-3783 (1990)]; a polyamine or a polyethylene glycol chain [Mancharan et al., Nucleosides & Nucleotides, 14:969-973 (1995)]; adamantane acetic acid [Manoharan et al., Tetrahedron Lett., 36:3651-3654 (1995)]; a palmityl moiety [(Mishra et al., Biochim. Biophys. Acta, 1264:229-237 (1995)]; or an octadecylamine or hexylamino-carbonyl-t oxycholesterol moiety [Crooke et al., J. Pharmacol. Exp. Ther., 277:923-937 (1996)]. See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); see, e.g., Hu, et al., Protein Pept Lett. 21 (10): 1025-30 (2014). Other systems known in the art and regularly developed can be used to target biomolecules of use in the present case and/or complexes thereof to particular target cells of interest.

These targeting moieties or conjugates can include conjugate groups covalently bound to functional groups, such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs can be further developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics, such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation, as illustrated in publications by Kormann et al. and Warren et al. referred to below.

It has been shown that chemically modified mRNA delivered in vivo can be used to achieve improved therapeutic effects; see, e.g., Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found that substituting just one quarter of the uridine and cytidine residues with 2-Thio-U and 5-Methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al., supra.

It has also been shown that repeated administration of synthetic messenger RNAs incorporating modifications designed to bypass innate anti-viral responses can reprogram differentiated human cells to pluripotency. See, e.g., Warren, et al., Cell Stem Cell, 7 (5): 618-30 (2010). Such modified mRNAs that act as primary reprogramming proteins can be an efficient means of reprogramming multiple human cell types. Such cells are referred to as induced pluripotency stem cells (iPSCs), and it was found that enzymatically synthesized RNA incorporating 5-Methyl-CTP, Pseudo-UTP and an Anti Reverse Cap Analog (ARCA) could be used to effectively evade the cell's antiviral response; see, e.g., Warren et al., supra.

Other modifications of polynucleotides described in the art include, for example, the use of polyA tails, the addition of 5' cap analogs (such as m7G(5')ppp(5')G (mCAP)), modifications of 5' or 3' untranslated regions (UTRs), or treatment with phosphatase to remove 5' terminal phosphates—and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules; see, e.g., the reviews by Angart et al., Pharmaceuticals (Basel) 6 (4): 440-468 (2013); Kanasty et al., Molecular Therapy 20 (3): 513-524 (2012); Burnett et al., Biotechnol J. 6 (9): 1130-46 (2011); Judge and MacLachlan, Hum Gene Ther 19 (2): 111-24 (2008); and references cited therein.

A large variety of modifications have been developed and applied to enhance RNA stability, reduce innate immune responses, and/or achieve other benefits that can be useful in connection with the introduction of polynucleotides into human cells, as described herein; see, e.g., the reviews by Whitehead K A et al., Annual Review of Chemical and Biomolecular Engineering, 2:77-96 (2011); Gaglione and Messere, Mini Rev Med Chem, 10 (7): 578-95 (2010); Chernolovskaya et al, Curr Opin Mol Ther., 12 (2): 158-67 (2010); Deleavey et al., Curr Protoc Nucleic Acid Chem Chapter 16: Unit 16.3 (2009); Behlke, Oligonucleotides 18 (4): 305-19 (2008); Fucini et al., Nucleic Acid Ther 22 (3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) have been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g., Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g., Kariko, K. et al., Immunity 23:165-175 (2005).

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers and aptamers; see, e.g., the review by Winkler, Ther. Deliv. 4:791-809 (2013), and references cited therein.

Codon-Optimization

A polynucleotide encoding a site-directed polypeptide can be codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

Complexes of a Genome-Targeting Nucleic Acid and a Site-Directed Polypeptide

A genome-targeting nucleic acid interacts with a site-directed polypeptide (e.g., a nucleic acid-guided nuclease such as Cas9), thereby forming a complex. The genome-targeting nucleic acid guides the site-directed polypeptide to a target nucleic acid.

RNPs

The site-directed polypeptide and genome-targeting nucleic acid can each be administered separately to a cell or a patient. On the other hand, the site-directed polypeptide can be pre-complexed with one or more genome-targeting nucleic acids (guide RNAs, sgRNA, or crRNA together with a tracrRNA). The pre-complexed material can then be administered to a cell or a patient. Such pre-complexed material is known as a ribonucleoprotein particle (RNP). The site-directed polypeptide in the RNP can be, for example, a Cas9 endonuclease or a Cpf1 endonuclease. The site-directed polypeptide can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS. The weight ratio of genome-targeting nucleic acid to site-directed polypeptide in the RNP can be 1:1. For example, the weight ratio of sgRNA to Cas9 endonuclease in the RNP can be 1:1.

Nucleic Acids Encoding System Components

The present disclosure provides a nucleic acid comprising a nucleotide sequence encoding a genome-targeting nucleic acid of the disclosure, a site-directed polypeptide of the disclosure, and/or any nucleic acid or proteinaceous molecule necessary to carry out the aspects of the methods of the disclosure.

The nucleic acid encoding a genome-targeting nucleic acid of the disclosure, a site-directed polypeptide of the disclosure, and/or any nucleic acid or proteinaceous molecule necessary to carry out the aspects of the methods of the disclosure can comprise a vector (e.g., a recombinant expression vector).

The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, CA (1990). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Figure 7A:
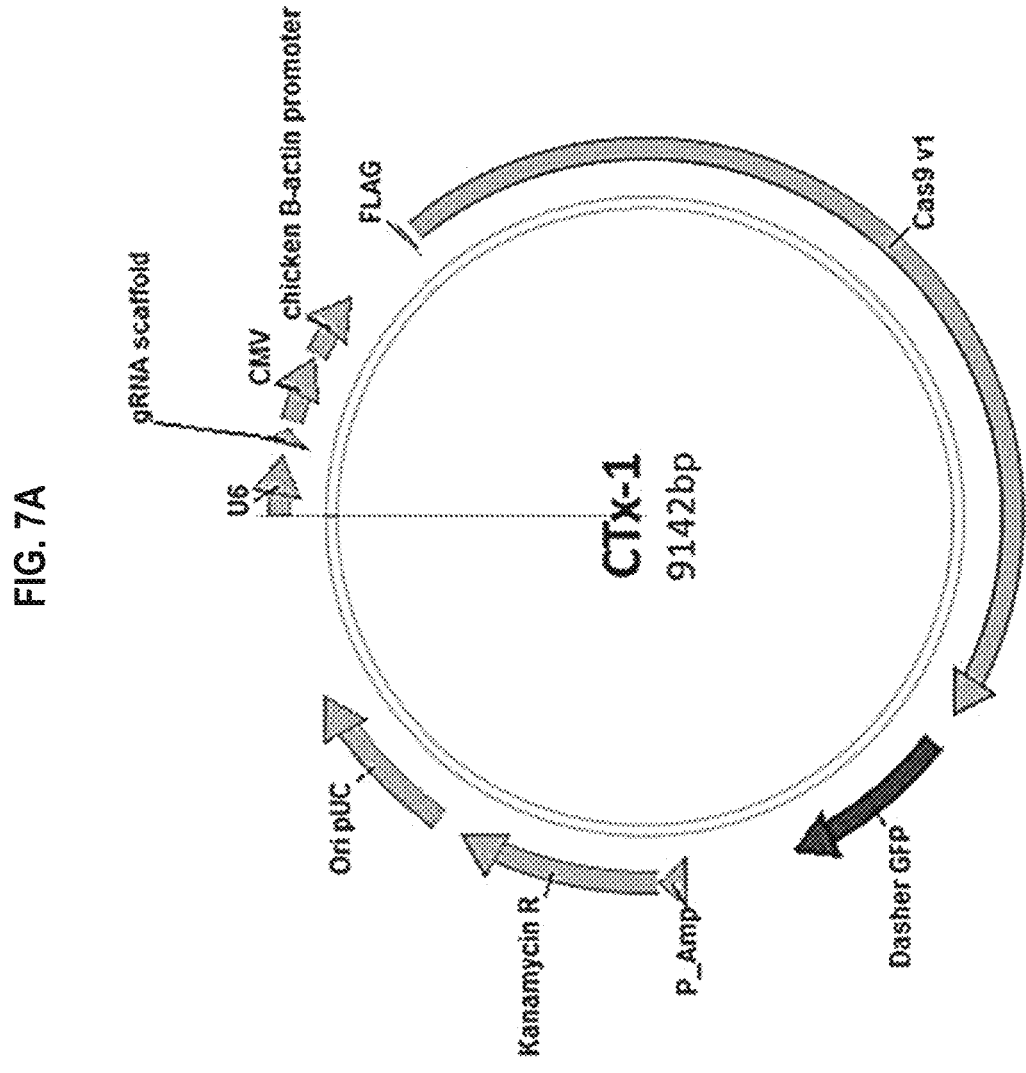
FIGS. 7A-7C show plasmids (CTx-1, CTx-2, CTx-3) comprising a codon optimized gene for *S. pyogenes* Cas9 endonuclease.
Figure 7B:
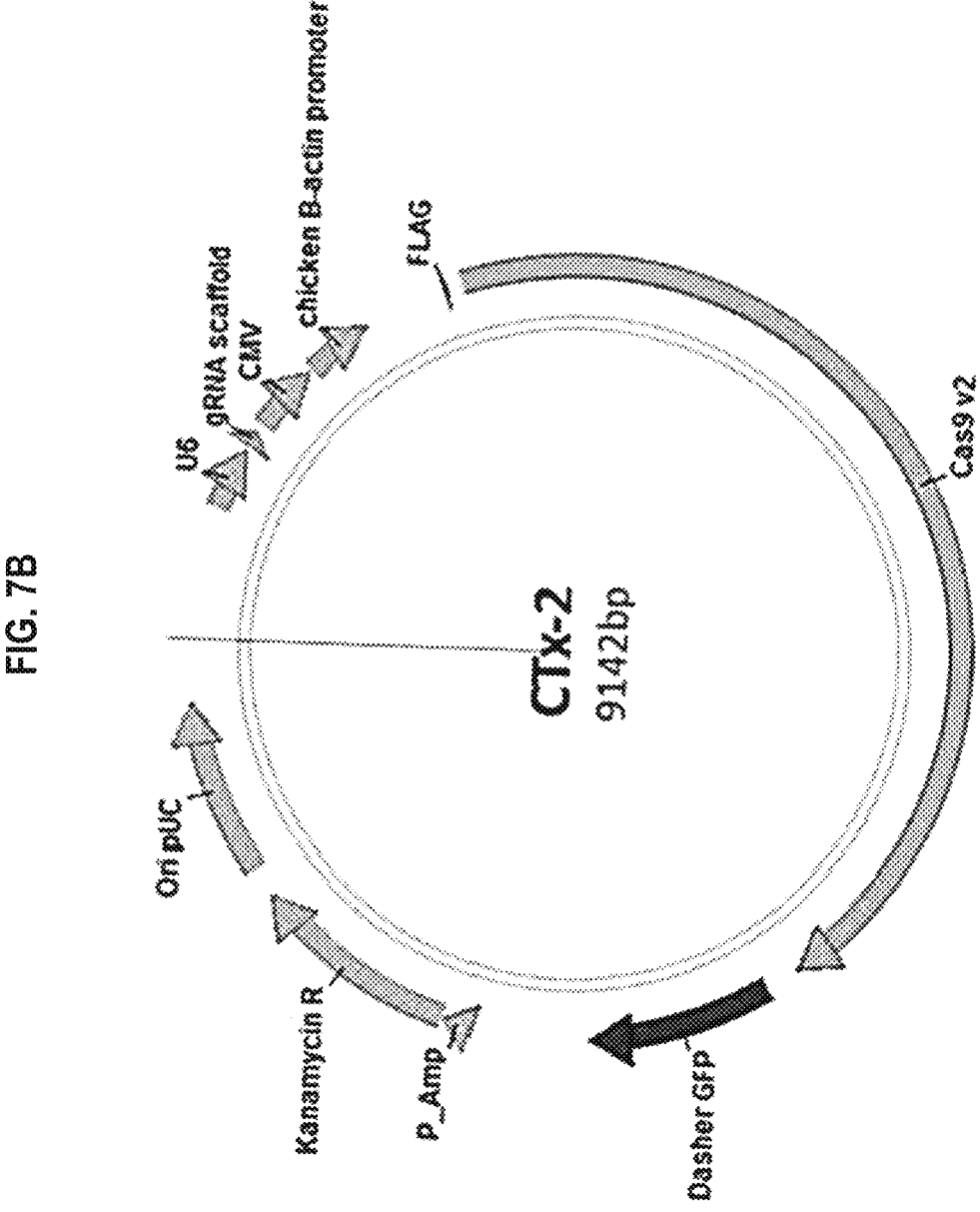
Figure 7C:
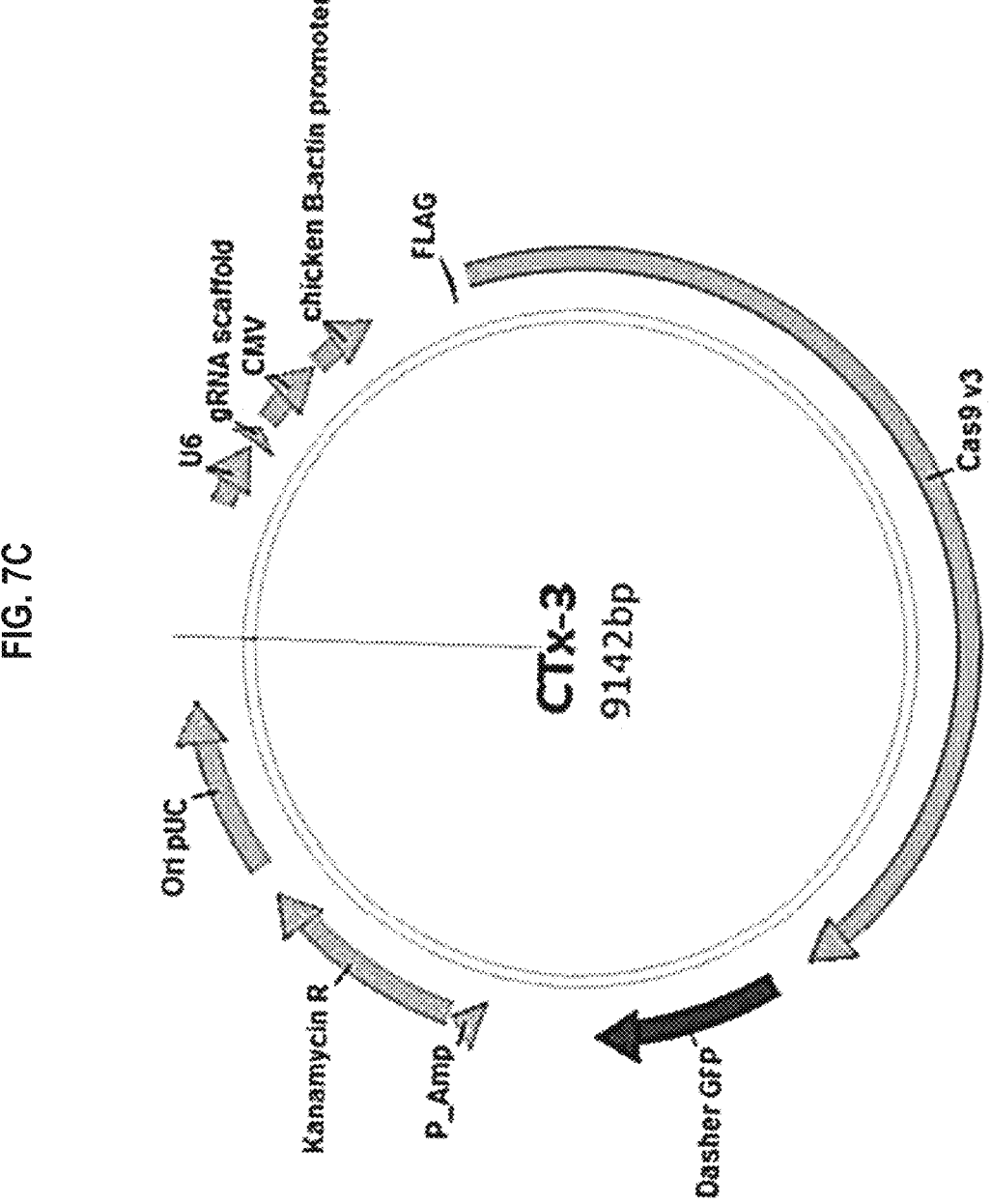
Figure 8A:
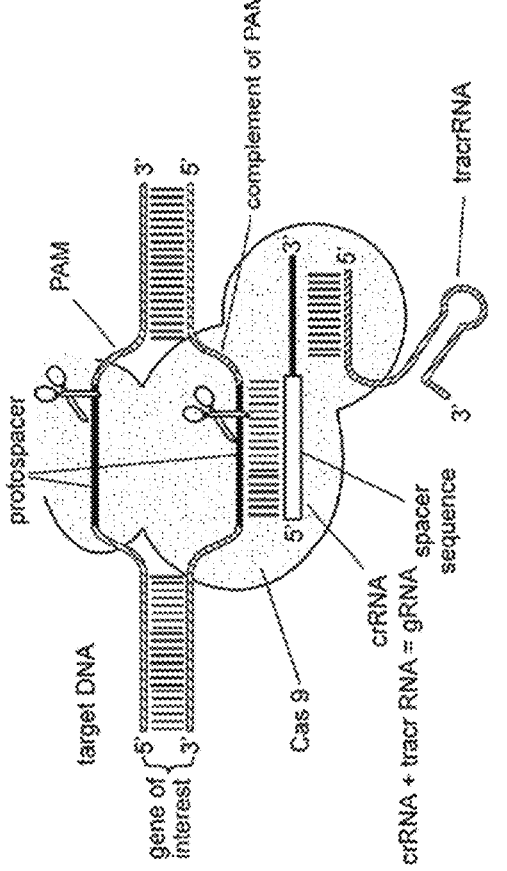
FIGS. 8A-8B depict the type II CRISPR/Cas system.
Figure 8B:
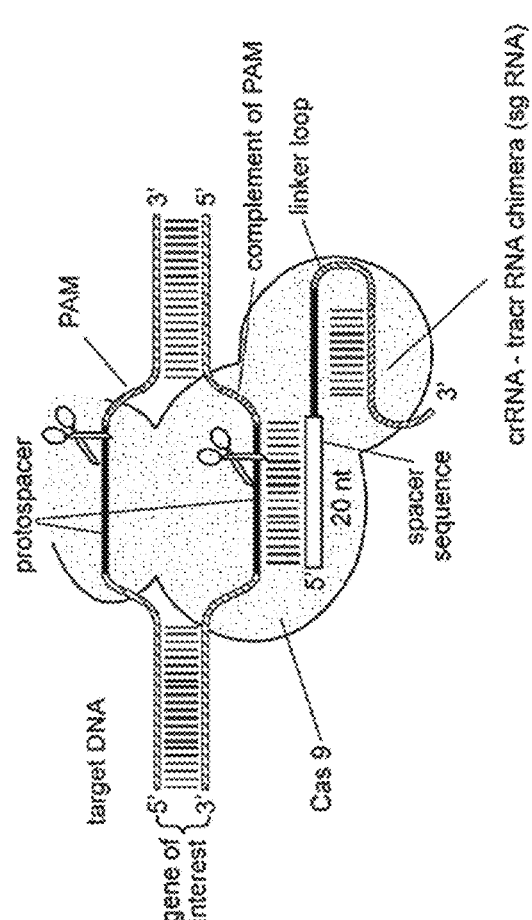

Expression vectors contemplated include, but are not limited to, viral vectors based on vaccinia virus, poliovirus, adenovirus, adeno-associated virus, SV40, herpes simplex virus, human immunodeficiency virus, a retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Additional vectors contemplated for eukaryotic target cells include, but are not limited to, the vectors pCTx-1, pCTx-2, and pCTx-3, which are described in FIGS. 7A to 7C. Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art and additional information and approaches are regularly being described; see, e.g., Ma, H. et al., *Molecular Therapy—Nucleic Acids* 3, e161 (2014) doi: 10.1038/mtna.2014.12.

The expression vector can also contain a ribosome binding site for translation initiation and a transcription terminator. The expression vector can also comprise appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

The nucleic acid encoding a genome-targeting nucleic acid of the disclosure and/or a site-directed polypeptide can be packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Delivery

Guide RNA polynucleotides (RNA or DNA) and/or endonuclease polynucleotide(s) (RNA or DNA) can be delivered by viral or non-viral delivery vehicles known in the art, such as electroporation, mechanical force, cell deformation (SQZ Biotech), and cell penetrating peptides. Alternatively, endonuclease polypeptide(s) can be delivered by viral or non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Electroporation is a delivery technique in which an electrical field is applied to one or more cells in order to increase the permeability of the cell membrane, which allows substances such as drugs, nucleic acids (genome-targeting nucleic acids), proteins (site-directed polypeptides), or RNPs, to be introduced into the cell. In general, electroporation works by passing thousands of volts across a distance of one to two millimeters of suspended cells in an electroporation cuvette (1.0-1.5 kV, 250-750V/cm). As used herein, the term "zap" or "zapping" may be used to describe an electroporation event.

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18:1127-1133 (2011) (which focuses on non-viral delivery vehicles for siRNA that are also useful for delivery of other polynucleotides).

Polynucleotides, such as guide RNA, sgRNA, and mRNA encoding an endonuclease, can be delivered to a cell or a patient by a lipid nanoparticle (LNP).

A LNP refers to any particle having a diameter of less than 1000 nm, 500 nm, 250 nm, 200 nm, 150 nm, 100 nm, 75 nm, 50 nm, or 25 nm. Alternatively, a nanoparticle can range in size from 1-1000 nm, 1-500 nm, 1-250 nm, 25-200 nm, 25-100 nm, 35-75 nm, or 25-60 nm.

LNPs can be made from cationic, anionic, or neutral lipids. Neutral lipids, such as the fusogenic phospholipid DOPE or the membrane component cholesterol, can be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs can also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce a LNP. In addition, the polynucleotide(s) can be combined with lipid(s) in a wide range of molar ratios to produce a LNP.

As stated previously, the site-directed polypeptide and genome-targeting nucleic acid can each be administered separately to a cell or a patient. On the other hand, the site-directed polypeptide can be pre-complexed with one or more guide RNAs, or one or more crRNA together with a tracrRNA. The pre-complexed material can then be administered to a cell or a patient. Such pre-complexed material is known as a ribonucleoprotein particle (RNP).

RNA is capable of forming specific interactions with RNA or DNA. While this property is exploited in many biological processes, it also comes with the risk of promiscuous interactions in a nucleic acid-rich cellular environment. One solution to this problem is the formation of ribonucleoprotein particles (RNPs), in which the RNA is pre-complexed with an endonuclease. Another benefit of the RNP is protection of the RNA from degradation.

The endonuclease in the RNP can be modified or unmodified. Likewise, the gRNA, crRNA, tracrRNA, or sgRNA can be modified or unmodified. Numerous modifications are known in the art and can be used.

The endonuclease and sgRNA can be generally combined in a 1:1 molar ratio. Alternatively, the endonuclease, crRNA and tracrRNA can be generally combined in a 1:1:1 molar ratio. However, a wide range of molar ratios can be used to produce a RNP.

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived, and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, international patent application publication number WO 01/83692. See Table 3.

TABLE 3

| AAV Serotype | Genbank Accession No. |
|---|---|
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

A method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); Mclaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995)

Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others. See Table 4.

TABLE 4

| Tissue/Cell Type | Serotype |
|---|---|
| Liver | AAV8, AAV3, AAV5, AAV9 |
| Skeletal muscle | AAV1, AAV7, AAV6, AAV8, AAV9 |
| Central nervous system | AAV5, AAV1, AAV4 |
| RPE | AAV5, AAV4 |
| Photoreceptor cells | AAV5 |
| Lung | AAV9 |
| Heart | AAV8 |
| Pancreas | AAV8 |
| Kidney | AAV2, AA8 |

In addition to adeno-associated viral vectors, other viral vectors can be used. Such viral vectors include, but are not limited to, lentivirus, alphavirus, enterovirus, pestivirus, baculovirus, herpesvirus, Epstein Barr virus, papovaviruses, poxvirus, vaccinia virus, and herpes simplex virus.

In some cases, Cas9 mRNA, sgRNA targeting one or two loci within or near a human beta globin locus on chromosome 11 and within or near one or more of: a BCL11A gene on chromosome 2, and a DNA sequence that encodes a transcriptional control region of the BCL11A gene on chromosome 2 can each be separately formulated into lipid nanoparticles, or are all co-formulated into one lipid nanoparticle.

In some cases, Cas9 mRNA can be formulated in a lipid nanoparticle, while sgRNA can be delivered in an AAV vector.

Options are available to deliver the Cas9 nuclease as a DNA plasmid, as mRNA or as a protein. The guide RNA can be expressed from the same DNA, or can also be delivered as an RNA. The RNA can be chemically modified to alter or improve its half-life, or decrease the likelihood or degree of immune response. The endonuclease protein can be complexed with the gRNA prior to delivery. Viral vectors allow efficient delivery; split versions of Cas9 and smaller orthologs of Cas9 can be packaged in AAV. A range of non-viral delivery methods also exist that can deliver each of these components, or non-viral and viral methods can be employed in tandem. For example, nano-particles can be used to deliver the protein and guide RNA, while AAV can be used to deliver a donor DNA.

Guide RNA Formulation

Guide RNAs of the invention can be formulated with pharmaceutically acceptable excipients such as carriers, solvents, stabilizers, adjuvants, diluents, etc., depending upon the particular mode of administration and dosage form. Guide RNA compositions can be generally formulated to achieve a physiologically compatible pH, and range from a pH of about 3 to a pH of about 11, about pH 3 to about pH 7, depending on the formulation and route of administration. In alternative aspects, the pH can be adjusted to a range from about pH 5.0 to about pH 8. In some aspects, the compositions can comprise a therapeutically effective amount of at least one compound as described herein, together with one or more pharmaceutically acceptable excipients. Optionally, the compositions can comprise a combination of the compounds described herein, or may include a second active ingredient useful in the treatment or prevention of bacterial growth (for example and without limitation, anti-bacterial or anti-microbial agents), or may include a combination of reagents of the invention.

Suitable excipients can include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol) wetting or emulsifying agents, pH buffering substances, and the like.

Genetically Modified Cells

The term "genetically modified cell" refers to a cell that comprises at least one genetic modification introduced by genome editing (e.g., using the CRISPR/Cas9/Cpf1 system). In some ex-vivo examples herein, the genetically modified cell can be a genetically modified progenitor cell. In some in vivo examples herein, the genetically modified cell can be a genetically modified hematopoietic progenitor cell. A genetically modified cell comprising an exogenous genome-targeting nucleic acid and/or an exogenous nucleic acid encoding a genome-targeting nucleic acid is contemplated herein.

In connection with de-repressing γ-globin expression, the phrase "increasing γ-globin levels in a cell" or "increased γ-globin expression in a cell" indicates that γ-globin in a cell or population of cells is at least 2% higher in the cell or population of cells subject to genome editing than in a comparable, control population, in which there has been no genome editing. In some aspects, the increase in γ-globin expression is at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 100-fold or more than a comparable control treated population. The term "control treated population" describes a population of cells that has been treated with identical media, viral induction, nucleic acid sequences, temperature, confluency, flask size, pH, etc., with the exception of the addition of the genome editing components. Any method known in the art can be used to measure an increase in γ-globin expression, for example, Western Blot analysis of γ-globin or quantifying γ-globin mRNA.

The term "isolated cell" refers to a cell that has been removed from an organism in which it was originally found, or a descendant of such a cell. Optionally, the cell can be cultured in vitro, e.g., under defined conditions or in the presence of other cells. Optionally, the cell can be later introduced into a second organism or re-introduced into the organism from which it (or the cell from which it is descended) was isolated.

The term "isolated population" with respect to an isolated population of cells refers to a population of cells that has been removed and separated from a mixed or heterogeneous population of cells. In some cases, the isolated population can be a substantially pure population of cells, as compared to the heterogeneous population from which the cells were isolated or enriched. In some cases, the isolated population can be an isolated population of human hematopoietic progenitor cells, e.g., a substantially pure population of human hematopoietic progenitor cells as compared to a heterogeneous population of cells comprising human hematopoietic progenitor cells and cells from which the human hematopoietic progenitor cells were derived.

The term "substantially enhanced," with respect to a particular cell population, refers to a population of cells in which the occurrence of a particular type of cell is increased relative to pre-existing or reference levels, by at least 2-fold, at least 3-, at least 4-, at least 5-, at least 6-, at least 7-, at least 8-, at least 9, at least 10-, at least 20-, at least 50-, at least 100-, at least 400-, at least 1000-, at least 5000-, at least 20000-, at least 100000- or more fold depending, e.g., on the desired levels of such cells for ameliorating a hemoglobinopathy.

The term "substantially enriched" with respect to a particular cell population, refers to a population of cells that is at least: about 10%, about 20%, about 30%, about 40%, about 50%, about 60%, about 70% or more with respect to the cells making up a total cell population.

The term "substantially pure" with respect to a particular cell population, refers to a population of cells that is at least about 75%, at least about 85%, at least about 90%, or at least about 95% pure, with respect to the cells making up a total cell population. That is, the terms "substantially pure" or "essentially purified," with regard to a population of hematopoietic progenitor cells, refers to a population of cells that contain fewer than: about 20%, about 15%, about 10%, about 9%, about 8%, about 7%, about 6%, about 5%, about 4%, about 3%, about 2%, about 1%, or less than 1%, of cells that are not hematopoietic progenitor cells as defined by the terms herein.

Human Cells

For ameliorating hemoglobinopathies, as described and illustrated herein, the principal targets for gene editing are human cells. For example, in the ex-vivo methods, the human cells can be somatic cells, which after being modified using the techniques as described, can give rise to red blood cells (RBCs) or progenitor cells with increased levels of HbF in a patient suffering from a hemoglobinopathy such as β-thalassemia or sickle cell disease.

As described herein and in the art, even relatively modest and incremental increases in levels of HbF in a patient suffering from a hemoglobinopathy such as β-thalassemia or sickle cell disease can be beneficial for improvement of symptoms and/or survival. In some aspects, the levels of HbF achieved can tend toward those observed in patients with HPFH, which vary among patients and type of HPFH but in a substantial number of cases result in HbF comprising in the range of 10-30% of total hemoglobin (versus 1-2% in typical adults). However, studies have shown that lower levels of HbF can nevertheless have effects that are significant enough to be regarded as decreasing overall mortality expectations among groups of patients with SCD; see, e.g., Platt et al., *N Engl J Med.* 330 (23): 1639-1644 (1994). And even modest improvements of symptoms can have beneficial effects for patients. For example, a reduction in the need for transfusions, a lessening of the incidence or severity of one or more symptoms of a hemoglobinopathy, or a reduction of side effects as a result of reduced levels or frequency of treatments or procedures can all be meaningful and beneficial for patients. Accordingly, in some aspects, the increase in HbF can be in the range of about 80%, 60%, 40% or 20% of the levels of HbF observed in patients with HPFH. Further considerations regarding levels of HbF that can be achieved are provided herein, including the detailed description and examples, as supplemented by references cited herein and/or published in the art.

By performing gene editing as described herein in progenitor cells such as erythroid progenitor cells, such as autologous progenitor cells that are derived from and therefore already completely matched with the patient in need, it can be possible to generate cells that can be safely reintroduced into the patient and effectively give rise to a population of circulating RBCs that can be effective in ameliorating one or more clinical conditions associated with the patient's disease.

While the presence of significant numbers of RBCs having elevated levels of HbF is beneficial, in some aspects more than one quarter of circulating red blood cells (RBCs) can have significantly elevated levels of HbF, in some aspects at least half of circulating RBCs can have significantly elevated levels of HbF, and in some aspects at least 80% of circulating RBCs can have significantly elevated levels of HbF in order to effectively prevent clinical erythrocyte sickling.

Progenitor cells (also referred to as stem cells herein), such as erythroid or hematopoietic progenitor cells, are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell can derive from a multipotent cell that itself is derived from a multipotent cell, and so on. While each of these multipotent cells can be considered stem cells, the range of cell types that each can give rise to may vary considerably. Some differentiated cells also have the capacity to give rise to cells of greater developmental potential. Such capacity can be natural or can be induced artificially upon treatment with various factors. In many biological instances, stem cells can also be "multipotent" because they can produce progeny of more than one distinct cell type, but this is not required for "stem-ness."

Self-renewal can be another important aspect of the stem cell. In theory, self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated," or "differentiating" is a relative term. A "differentiated cell" is a cell that has progressed further down the developmental pathway than the cell to which it is being compared. Thus, stem cells can differentiate into lineage-restricted precursor cells (such as a hematopoietic progenitor cell), which in turn can differentiate into other types of precursor cells further down the pathway (such as an erythrocyte precursor), and then to an end-stage differentiated cell, such as an erythrocyte, which plays a characteristic role in a certain tissue type, and may or may not retain the capacity to proliferate further.

The term "hematopoietic progenitor cell" refers to cells of a stem cell lineage that give rise to all the blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells).

A "cell of the erythroid lineage" indicates that the cell being contacted is a cell that undergoes erythropoiesis such that upon final differentiation it forms an erythrocyte or red blood cell. Such cells originate from bone marrow hematopoietic progenitor cells. Upon exposure to specific growth factors and other components of the hematopoietic microenvironment, hematopoietic progenitor cells can mature through a series of intermediate differentiation cellular types, all intermediates of the erythroid lineage, into RBCs. Thus, cells of the "erythroid lineage" comprise hematopoietic progenitor cells, rubriblasts, prorubricytes, erythroblasts, metarubricytes, reticulocytes, and erythrocytes.

The hematopoietic progenitor cell can express at least one of the following cell surface markers characteristic of hematopoietic progenitor cells: CD34+, CD59+, Thy1/CD90+, CD3810/−, and C-kit/CDI 17+. In some examples provided herein, the hematopoietic progenitors can be CD34+.

The hematopoietic progenitor cell can be a peripheral blood stem cell obtained from the patient after the patient has been treated with one or more factors such as granulocyte colony stimulating factor (optionally in combination with Plerixaflor). In illustrative aspects, CD34+ cells are enriched using CliniMACS® Cell Selection System (Miltenyi Biotec). CD34+ cells can be stimulated in serum-free medium (e.g., CellGrow SCGM media, CellGenix) with cytokines (e.g., SCF, rhTPO, rhFLT3) before genome editing. Addition of SR1 and dmPGE2 and/or other factors is contemplated to improve long-term engraftment.

The hematopoietic progenitor cells of the erythroid lineage can have a cell surface marker characteristic of the erythroid lineage: such as CD71 and Terl 19.

Hematopoietic stem cells (HSCs) can be an important target for gene therapy as they provide a prolonged source of the corrected cells. HSCs give rise to both the myeloid and lymphoid lineages of blood cells. Mature blood cells have a finite life-span and must be continuously replaced throughout life. Blood cells are continually produced by the proliferation and differentiation of a population of pluripotent HSCs that can be replenished by self-renewal. Bone marrow (BM) is the major site of hematopoiesis in humans and a good source for hematopoietic stem and progenitor cells (HSPCs). HSPCs can be found in small numbers in the peripheral blood (PB). In some indications or treatments their numbers increase. The progeny of HSCs mature through stages, generating multi-potential and lineage-committed progenitor cells. Treated cells, such as CD34+ cells, would be returned to the patient. The level of engraftment can be important, as is the ability of the cells' multilineage engraftment of gene-edited cells following CD34+ infusion in vivo.

Induced Pluripotent Stem Cells

The genetically engineered human cells described herein can be induced pluripotent stem cells (iPSCs). An advantage of using iPSCs is that the cells can be derived from the same subject to which the progenitor cells are to be administered. That is, a somatic cell can be obtained from a subject, reprogrammed to an induced pluripotent stem cell, and then re-differentiated into a hematopoietic progenitor cell to be administered to the subject (e.g., autologous cells). Because the progenitors are essentially derived from an autologous source, the risk of engraftment rejection or allergic response can be reduced compared to the use of cells from another subject or group of subjects. In some aspects, the hematopoietic progenitors are derived from non-autologous sources. In addition, the use of iPSCs negates the need for cells obtained from an embryonic source. Thus, in one aspect, the stem cells used in the disclosed methods are not embryonic stem cells.

Although differentiation is generally irreversible under physiological contexts, several methods have been recently developed to reprogram somatic cells to iPSCs. Exemplary methods are known to those of skill in the art and are described briefly herein below.

The term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. Reprogramming can encompass complete reversion of the differentiation state of a differentiated cell (e.g., a somatic cell) to a pluripotent state or a multipotent state. Reprogramming can encompass complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain examples described herein, reprogramming of a differentiated cell (e.g., a somatic cell) can cause the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods described herein can also be of use for such purposes, in some examples.

Many methods are known in the art that can be used to generate pluripotent stem cells from somatic cells. Any such method that reprograms a somatic cell to the pluripotent phenotype would be appropriate for use in the methods described herein.

Reprogramming methodologies for generating pluripotent cells using defined combinations of transcription factors have been described. Mouse somatic cells can be converted to ES cell-like cells with expanded developmental potential by the direct transduction of Oct4, Sox2, Klf4, and c-Myc; see, e.g., Takahashi and Yamanaka, *Cell* 126 (4): 663-76 (2006). iPSCs resemble ES cells as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission [see, e.g., Maherali and Hochedlinger, *Cell Stem Cell*. 3 (6): 595-605 (2008)], and tetraploid complementation.

Human iPSCs can be obtained using similar transduction methods, and the transcription factor trio, OCT4, SOX2, and NANOG, has been established as the core set of transcription factors that govern pluripotency; see, e.g., Budniatzky and Gepstein, *Stem Cells Transl Med*. 3 (4): 448-57 (2014); Barrett et al., *Stem Cells Trans Med* 3:1-6 sctm.2014-0121 (2014); Focosi et al., *Blood Cancer Journal* 4: e211 (2014); and references cited therein. The production of iPSCs can be achieved by the introduction of nucleic acid sequences encoding stem cell-associated genes into an adult, somatic cell, historically using viral vectors.

iPSCs can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., *Cell Stem Cell,* 7 (5): 618-30 (2010). Reprogramming can be achieved by introducing a combination of nucleic acids encoding stem cell-associated genes including, for example Oct-4 (also known as Oct-3/4 or Pouf51), SoxI, Sox2, Sox3, Sox 15, Sox 18, NANOG, KlfI, Klf2, Klf4, Klf5, NR5A2, c-Myc, 1-Myc, n-Myc, Rem2, Tert, and LIN28. Reprogramming using the methods and compositions described herein can further comprise introducing one or more of Oct-3/4, a member of the Sox family, a member of the Klf family, and a member of the Myc family to a somatic cell. The methods and compositions described herein can further comprise introducing one or more of each of Oct-4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one aspect the reprogramming is not affected by a method that alters the genome. Thus, in such examples, reprogramming can be achieved, e.g., without the use of viral or plasmid vectors.

The efficiency of reprogramming (i.e., the number of reprogrammed cells) derived from a population of starting cells can be enhanced by the addition of various agents, e.g., small molecules, as shown by Shi et al., *Cell—Stem Cell* 2:525-528 (2008); Huangfu et al., *Nature Biotechnology* 26 (7): 795-797 (2008) and Marson et al., *Cell—Stem Cell* 3:132-135 (2008). Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-IH,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Titan Pharmaceuticals, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecatl, Esgl, Eras, Gdf3, Fgf4, Cripto, Daxl, Zpf296, Slc2a3, Rexl, Utfl, and Natl. In one case, for example, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. Detection can involve not only RT-PCR, but can also include detection of protein markers. Intracellular markers may be best identified via RT-PCR, or protein detection methods such as immunocytochemistry, while cell surface markers are readily identified, e.g., by immunocytochemistry.

The pluripotent stem cell character of isolated cells can be confirmed by tests evaluating the ability of the iPSCs to differentiate into cells of each of the three germ layers. As one example, teratoma formation in nude mice can be used to evaluate the pluripotent character of the isolated clones. The cells can be introduced to nude mice and histology and/or immunohistochemistry can be performed on a tumor arising from the cells. The growth of a tumor comprising cells from all three germ layers, for example, further indicates that the cells are pluripotent stem cells.

Creating Patient Specific iPSCs

One step of the ex vivo methods of the present disclosure can involve creating a patient specific iPS cell, patient specific iPS cells, or a patient specific iPS cell line. There are many established methods in the art for creating patient specific iPS cells, as described in Takahashi and Yamanaka 2006; Takahashi, Tanabe et al. 2007. For example, the creating step can comprise: a) isolating a somatic cell, such as a skin cell or fibroblast, from the patient; and b) introducing a set of pluripotency-associated genes into the somatic cell in order to induce the cell to become a pluripotent stem cell. The set of pluripotency-associated genes can be one or more of the genes selected from the group consisting of OCT4, SOX2, KLF4, Lin28, NANOG, and cMYC.

Performing a Biopsy or Aspirate of the Patient's Bone Marrow

A biopsy or aspirate is a sample of tissue or fluid taken from the body. There are many different kinds of biopsies or aspirates. Nearly all of them involve using a sharp tool to remove a small amount of tissue. If the biopsy will be on the skin or other sensitive area, numbing medicine can be applied first. A biopsy or aspirate can be performed according to any of the known methods in the art. For example, in a bone marrow aspirate, a large needle is used to enter the pelvis bone to collect bone marrow.

Isolating a Mesenchymal Stem Cell

Mesenchymal stem cells can be isolated according to any method known in the art, such as from a patient's bone marrow or peripheral blood. For example, marrow aspirate can be collected into a syringe with heparin. Cells can be washed and centrifuged on a Percoll™ density gradient. Percoll™ is composed of colloidal silica coated with polyvinylpyrrolidone (PVP). The silica particles are 15 to 30 nm in diameter and are coated with non-dialyzable polyvinylpyrrolidone (PVP). Cells, such as blood cells, liver cells, interstitial cells, macrophages, mast cells, and thymocytes, can be separated using Percoll™. The cells can be cultured in Dulbecco's modified Eagle's medium (DMEM) (low glucose) containing 10% fetal bovine serum (FBS) (Pittinger M F, Mackay A M, Beck S C et al., Science 1999; 284:143-147).

Treating a Patient with GCSF

A patient can optionally be treated with granulocyte colony stimulating factor (GCSF) in accordance with any method known in the art. The GCSF can be administered in combination with Plerixaflor (also known as Mozobil®).

Plerixaflor is an immunostimulant used to mobilize hematopoietic stem cells into the blood stream.

Isolating a Hematopoietic Progenitor Cell from a Patient

A hematopoietic progenitor cell can be isolated from a patient by any method known in the art. CD34+ cells can be enriched, e.g., using CliniMACS® Cell Selection System (Miltenyi Biotec). CD34+ cells can be weakly stimulated in serum-free medium (e.g., CellGrow SCGM media, CellGenix) with cytokines (e.g., SCF, rhTPO, rhFLT3) before genome editing.

Differentiation of Genome-Edited iPSCs into Hematopoietic Progenitor Cells

Another step of the ex vivo methods of the present disclosure can comprise differentiating the genome-edited iPSCs into hematopoietic progenitor cells. The differentiating step can be performed according to any method known in the art.

Differentiation of Genome-Edited Mesenchymal Stem Cells into Hematopoietic Progenitor Cells Another step of the ex vivo methods of the present disclosure can comprise differentiating the genome-edited mesenchymal stem cells into hematopoietic progenitor cells. The differentiating step can be performed according to any method known in the art.

Implanting Cells into Patients

Another step of the ex vivo methods of the present disclosure can comprise implanting the cells into patients. This implanting step can be accomplished using any method of implantation known in the art. For example, the genetically modified cells can be injected directly in the patient's blood or otherwise administered to the patient. The genetically modified cells may be purified ex vivo using a selected marker.

One advantage of an ex vivo cell therapy approach is the ability to conduct a comprehensive analysis of the therapeutic prior to administration. Nuclease-based therapeutics can have some level of off-target effects. Performing gene correction ex vivo allows one to characterize the corrected cell population prior to implantation. The present disclosure includes sequencing the entire genome of the corrected cells to ensure that the off-target effects, if any, can be in genomic locations associated with minimal risk to the patient. Furthermore, populations of specific cells, including clonal populations, can be isolated prior to implantation.

Another advantage of ex vivo cell therapy relates to genetic correction in iPSCs compared to other primary cell sources. iPSCs are prolific, making it easy to obtain the large number of cells that will be required for a cell-based therapy. Furthermore, iPSCs are an ideal cell type for performing clonal isolations. This allows screening for the correct genomic correction, without risking a decrease in viability. In contrast, other primary cells are viable for only a few passages and difficult to clonally expand. Thus, manipulation of iPSCs for the treatment of hemoglobinopathies can be much easier, and can shorten the amount of time needed to make the desired genetic correction.

For ex vivo therapy, transplantation requires clearance of bone-marrow niches or the donor HSCs to engraft. Current methods rely on radiation and/or chemotherapy. Due to the limitations these impose, safer conditioning regiments have been and are being developed, such as immunodepletion of bone marrow cells by antibodies or antibody toxin conjugates directed against hematopoietic cell surface markers, for example CD117, c-kit and others. Success of HSC transplantation depends upon efficient homing to bone marrow, subsequent engraftment, and bone marrow repopulation. The level of gene-edited cells engrafted is important, as is the ability of the cells' multilineage engraftment.

Hematopoietic stem cells (HSCs) are an important target for ex vivo gene therapy as they provide a prolonged source of the corrected cells. Treated CD34+ cells would be returned to the patient.

Methods can also include an in vivo based therapy. Chromosomal DNA of the cells in the patient is edited using the materials and methods described herein. The cells can be bone marrow cells, hematopoietic progenitor cells, or CD34+ cells.

Although blood cells present an attractive target for ex vivo treatment and therapy, increased efficacy in delivery may permit direct in vivo delivery to the hematopoietic stem cells (HSCs) and/or other B and T cell progenitors, such as CD34+ cells. Ideally the targeting and editing would be directed to the relevant cells. Cleavage in other cells can also be prevented by the use of promoters only active in certain cells and or developmental stages. Additional promoters are inducible, and therefore can be temporally controlled if the nuclease is delivered as a plasmid. The amount of time that delivered RNA and protein remain in the cell can also be adjusted using treatments or domains added to change the half-life. In vivo treatment would eliminate a number of treatment steps, but a lower rate of delivery can require higher rates of editing. In vivo treatment can eliminate problems and losses from ex vivo treatment and engraftment.

An advantage of in vivo gene therapy can be the ease of therapeutic production and administration. The same therapeutic approach and therapy will have the potential to be used to treat more than one patient, for example a number of patients who share the same or similar genotype or allele. In contrast, ex vivo cell therapy typically requires using a patient's own cells, which are isolated, manipulated and returned to the same patient.

Pharmaceutically Acceptable Carriers

The ex vivo methods of administering progenitor cells to a subject contemplated herein can involve the use of therapeutic compositions comprising progenitor cells.

Therapeutic compositions can contain a physiologically tolerable carrier together with the cell composition, and optionally at least one additional bioactive agent as described herein, dissolved or dispersed therein as an active ingredient. In some cases, the therapeutic composition is not substantially immunogenic when administered to a mammal or human patient for therapeutic purposes, unless so desired.

In general, the progenitor cells described herein can be administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethyl-amino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerine, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

Administration and Efficacy

The terms "administering", "introducing" and "transplanting" are used interchangeably in the context of the placement of cells, e.g., progenitor cells, into a subject, by a method or route that results in at least partial localization of the introduced cells at a desired site, such as a site of injury or repair, such that a desired effect(s) is produced. The cells e.g., progenitor cells, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the lifetime of the patient, i.e., long-term engraftment. For example, in some aspects described herein, an effective amount of hematopoietic progenitor cells is administered via a systemic route of administration, such as an intraperitoneal or intravenous route.

The terms "individual", "subject," "host" and "patient" are used interchangeably herein and refer to any subject for whom diagnosis, treatment or therapy is desired. In some aspects, the subject is a mammal. In some aspects, the subject is a human being.

When provided prophylactically, progenitor cells described herein can be administered to a subject in advance of any symptom of a hemoglobinopathy, e.g., prior to initiation of the switch from fetal γ-globin to predominantly β-globin and/or prior to the development of significant anemia or other symptom associated with the hemoglobinopathy. Accordingly, the prophylactic administration of a hematopoietic progenitor cell population serves to prevent a hemoglobinopathy, as disclosed herein.

When provided therapeutically, hematopoietic progenitor cells are provided at (or after) the onset of a symptom or indication of a hemoglobinopathy, e.g., upon the onset of disease.

The hematopoietic progenitor cell population being administered according to the methods described herein can comprise allogeneic hematopoietic progenitor cells obtained from one or more donors. "Allogeneic" refers to a hematopoietic progenitor cell or biological samples comprising hematopoietic progenitor cells obtained from one or more different donors of the same species, where the genes at one or more loci are not identical. For example, a hematopoietic progenitor cell population being administered to a subject can be derived from umbilical cord blood obtained from one more unrelated donor subjects, or from one or more non-identical siblings. In some cases, syngeneic hematopoietic progenitor cell populations can be used, such as those obtained from genetically identical animals, or from identical twins. The hematopoietic progenitor cells can be autologous cells; that is, the hematopoietic progenitor cells can be obtained or isolated from a subject and administered to the same subject, i.e., the donor and recipient are the same.

The term "effective amount" refers to the amount of a population of progenitor cells or their progeny needed to prevent or alleviate at least one or more sign or symptom of a hemoglobinopathy, and relates to a sufficient amount of a composition to provide the desired effect, e.g., to treat a subject having a hemoglobinopathy. The term "therapeutically effective amount" therefore refers to an amount of progenitor cells or a composition comprising progenitor cells that is sufficient to promote a particular effect when administered to a typical subject, such as one who has or is at risk for a hemoglobinopathy. An effective amount, as used herein, would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

For use in the various aspects described herein, an effective amount of progenitor cells, comprises at least $10^2$ progenitor cells, at least $5 \times 10^2$ progenitor cells, at least $10^3$ progenitor cells, at least $5 \times 10^3$ progenitor cells, at least $10^4$ progenitor cells, at least $5 \times 10^4$ progenitor cells, at least $10^5$ progenitor cells, at least $2 \times 10^5$ progenitor cells, at least $3 \times 10^5$ progenitor cells, at least $4 \times 10^5$ progenitor cells, at least $5 \times 10^5$ progenitor cells, at least $6 \times 10^5$ progenitor cells, at least $7 \times 10^5$ progenitor cells, at least $8 \times 10^5$ progenitor cells, at least $9 \times 10^5$ progenitor cells, at least $1 \times 10^6$ progenitor cells, at least $2 \times 10^6$ progenitor cells, at least $3 \times 10^6$ progenitor cells, at least $4 \times 10^6$ progenitor cells, at least $5 \times 10^6$ progenitor cells, at least $6 \times 10^6$ progenitor cells, at least $7 \times 10^6$ progenitor cells, at least $8 \times 10^6$ progenitor cells, at least $9 \times 10^6$ progenitor cells, or multiples thereof. The progenitor cells can be derived from one or more donors, or are can be obtained from an autologous source. In some examples described herein, the progenitor cells can be expanded in culture prior to administration to a subject in need thereof.

Modest and incremental increases in the levels of HbF expressed in cells of patients having a hemoglobinopathy can be beneficial for ameliorating one or more symptoms of the disease, for increasing long-term survival, and/or for reducing side effects associated with other treatments. In some embodiments, upon administration of such cells to human patients, the presence of RBCs that are producing increased levels of HbF is beneficial. In some aspects, effective treatment of a subject gives rise to at least about 9% HbF relative to total Hb in the treated subject. In some aspects, HbF will be at least about 14% of total Hb. In some aspects HbF will be at least about 20% to 30% of total Hb. Similarly, the introduction of even relatively limited sub-populations of cells having significantly elevated levels of HbF (referred to as "F-cells") can be beneficial in various patients since in some situations normalized cells will have a selective advantage relative to diseased cells. However, even modest levels of circulating RBCs with elevated levels of HbF can be beneficial for ameliorating one or more aspects of hemoglobinopathy in patients. In some aspects, about 10%, about 20%, about 30%, about 40%, about 50%, about 60%, about 70%, about 80%, about 90% or more of the RBCs in patients to whom such cells are administered are producing increased levels of HbF as described herein.

"Administered" refers to the delivery of a progenitor cell composition into a subject by a method or route that results in at least partial localization of the cell composition at a desired site. A cell composition can be administered by any appropriate route that results in effective treatment in the subject, i.e. administration results in delivery to a desired location in the subject where at least a portion of the composition delivered, i.e. at least $1 \times 10^4$ cells are delivered to the desired site for a period of time. Modes of administration include injection, infusion, instillation, or ingestion. "Injection" includes, without limitation, intravenous, intra-muscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some examples, the route is intravenous. For the delivery of cells, administration by injection or infusion can be made.

The cells can be administered systemically. The phrases "systemic administration," "administered systemically", "peripheral administration" and "administered peripherally" refer to the administration of a population of progenitor cells other than directly into a target site, tissue, or organ, such that it enters, instead, the subject's circulatory system and, thus, is subject to metabolism and other like processes.

The efficacy of a treatment comprising a composition for the treatment of a hemoglobinopathy can be determined by the skilled clinician. However, a treatment is considered "effective treatment," if any one or all of the signs or symptoms of, as but one example, levels of functional fetal hemoglobin, γ-globin expression, and functional BCL11A are altered in a beneficial manner (e.g., increased by at least 10% for HbF, increased by at least 30% for γ-globin expression, and/or decreased by at least 10% for BCL11A), or other clinically accepted symptoms or markers of disease are improved or ameliorated. Efficacy can also be measured by failure of an individual to worsen as assessed by hospitalization or need for medical interventions (e.g., reduced transfusion dependence, or progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the pro-gression of symptoms; or (2) relieving the disease, e.g., causing regression of symptoms; and (3) preventing or reducing the likelihood of the development of symptoms.

In some embodiments, the treatment according to the present invention ameliorates one or more symptoms asso-ciated with a β-hemoglobinopathy by increasing the amount of fetal hemoglobin in the individual. Symptoms and signs typically associated with a hemoglobinopathy, include for example, anemia, tissue hypoxia, organ dysfunction, abnor-mal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemoly-sis, jaundice, anemic pain crises, acute chest syndrome, splenic sequestration, priapism, stroke, hand-foot syndrome, and pain such as angina pectoris.

Kits

The present disclosure provides kits for carrying out the methods described herein. A kit can include one or more of: a genome-targeting nucleic acid, a polynucleotide encoding a genome-targeting nucleic acid, a site-directed polypeptide, a polynucleotide encoding a site-directed polypeptide, and/ or any nucleic acid or proteinaceous molecule necessary to carry out the aspects of the methods described herein, or any combination thereof.

A kit can comprise: (1) a vector comprising a nucleotide sequence encoding a genome-targeting nucleic acid, (2) the site-directed polypeptide or a vector comprising a nucleotide sequence encoding the site-directed polypeptide, and (3) a reagent for reconstitution and/or dilution of the vector(s) and or polypeptide.

A kit can comprise: (1) a vector comprising (i) a nucleo-tide sequence encoding a genome-targeting nucleic acid, and (ii) a nucleotide sequence encoding the site-directed poly-peptide; and (2) a reagent for reconstitution and/or dilution of the vector.

In any of the above kits, the kit can comprise a single-molecule guide genome-targeting nucleic acid. In any of the above kits, the kit can comprise a double-molecule genome-targeting nucleic acid. In any of the above kits, the kit can comprise two or more double-molecule guides or single-molecule guides. The kits can comprise a vector that encodes the nucleic acid targeting nucleic acid.

In any of the above kits, the kit can further comprise a polynucleotide to be inserted to effect the desired genetic modification.

Components of a kit can be in separate containers, or combined in a single container.

Any kit described above can further comprise one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. A kit can also comprise one or more components that can be used to facilitate or enhance the on-target binding or the cleavage of DNA by the endonu-clease, or improve the specificity of targeting.

In addition to the above-mentioned components, a kit can further comprise instructions for using the components of the kit to practice the methods. The instructions for prac-ticing the methods can be recorded on a suitable recording medium. For example, the instructions can be printed on a substrate, such as paper or plastic, etc. The instructions can be present in the kits as a package insert, in the labeling of the container of the kit or components thereof (i.e., associ-ated with the packaging or subpackaging), etc. The instruc-tions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this case is a kit that comprises a web address where the instructions can be viewed and/or from which the instructions can be downloaded. As with the instructions, this means for obtaining the instructions can be recorded on a suitable substrate.

Electroporation

The process of electroporation generally involves the formation of pores in a cell membrane, or in a vesicle, by the application of electric field pulses across a liquid cell suspension containing cells or vesicles. During the poration process, cells are often suspended in a liquid media and then subjected to an electric field pulse. The medium can be electrolyte, non-electrolyte, or a mixture of electrolytes and non-electrolytes. The strength of the electric field applied to the suspension and the length of the pulse (the time that the electric field is applied to a cell suspension) varies according to the cell type. To create a pore in a cell's outer membrane, the electric field must be applied for such a length of time and at such a voltage as to create a set potential across the cell membrane for a period of time long enough to create a pore.

Applying a voltage across a plasma membrane that exceeds a certain threshold level forms a pore in the membrane. If the strength of the applied electrical field and/or duration of exposure to it are properly chosen, the pores formed by the electrical pulse reseal after a short period of time, during which extracellular compounds have a chance to enter into the cell. However, excessive exposure of live cells to electrical fields can cause apoptosis and/or necrosis-processes that result in cell death.

Generally, the process of electroporation is often used for the transformation of bacteria, yeast, plant protoplasts, cultured cells and other cells or vesicles as a way of introducing some substance into a cell or a vesicle, such as loading it with a molecular probe, a drug that can change the cell's function, or pieces of DNA or forms of RNA, such as mRNA, siRNA, guide RNA (gRNA) or microRNA. This procedure is also highly efficient for the introduction of chemical or biological agents that specifically intervene in molecular pathways in tissue culture cells or primary cells, especially mammalian cells. For example, electroporation is used in the process of producing knockout mice, as well as in tumor treatment, gene therapy, and cell-based therapy.

Successive Gene Editing

In some embodiments, the present disclosure utilizes multiple, successive gene editing steps. In some embodiments, successive gene editing steps involve the use of multiple, successive electroporations to introduce gene editing compositions, e.g., gRNA(s) and CRISPR endonucleases (e.g., Cas9 or Cpf1).

In some embodiments, each successive gene editing step (e.g., each electroporation step) involves use the same compositions, e.g., use the same gRNA(s) and same CRISPR endonuclease(s). In other embodiments, successive gene editing steps (e.g., successive electroporation steps) involve different compositions, e.g., use of different gRNA(s) and/or different CRISPR endonuclease(s). In some embodiments, each successive gene editing step (e.g., each electroporation step) targets the same chromosomal locus. In other embodiments, successive gene editing steps (e.g., successive electroporation steps) target different chromosomal loci. In some embodiments, successive gene editing steps (e.g., successive electroporation steps) involve targeting of a human beta globin locus on chromosome 11 and/or one or more BCL11A-related loci on chromosome 2.

In some embodiments, successive gene editing steps (e.g., successive electroporation steps) may comprise the use of a HPFH5 gRNA, e.g., HPFH5-1, HPFH5-D, HPFH5-T5, or HPFH5-T7, a Kenya gRNA, e.g., Kenya-K5, Kenya-K17, a 1450 gRNA, a SPY101 gRNA, and/or a SD2 gRNA. In some embodiments, successive gene editing steps (e.g., successive electroporation steps) may comprise the use of one or more gRNAs provided in Table 2. In some embodiments, successive gene editing steps may comprise the use of at least one SPY101 gRNA in combination with at least one HPFH5 gRNA (e.g., one editing step with SPY101 gRNA and another editing step with at least one HPFH5 gRNA). In some embodiments, successive gene editing steps may comprise the use of a SPY101 gRNA in combination with a HPFH5-1 gRNA (e.g., one editing step with SPY101 gRNA and another editing step with HPFH5-1 gRNA). In some embodiments, successive gene editing steps may comprise the use of a SPY101 gRNA in combination with a HPFH5-D gRNA (e.g., one editing step with SPY101 gRNA and another editing step with HPFH5-D gRNA). In some embodiments, successive gene editing steps may comprise the use of a SPY101 gRNA in combination with a HPFH5-T5 gRNA (e.g., one editing step with SPY101 gRNA and another editing step with HPFH5-T5 gRNA). In some embodiments, successive gene editing steps may comprise the use of a SPY101 gRNA in combination with a HPFH5-T7 gRNA (e.g., one editing step with SPY101 gRNA and another editing step with HPFH5-T7 gRNA). In some embodiments, successive gene editing steps may comprise the use of at least one SPY101 gRNA in combination with at least one Kenya gRNA (e.g., one editing step with SPY101 gRNA and another editing step with at least one Kenya gRNA). In some embodiments, successive gene editing steps may comprise the use of a SPY101 gRNA in combination with a Kenya-K5 gRNA (e.g., one editing step with SPY101 gRNA and another editing step with Kenya-K5 gRNA). In some embodiments, successive gene editing steps may comprise the use of a SPY101 gRNA in combination with a Kenya-K17 gRNA (e.g., one editing step with SPY101 gRNA and another editing step with Kenya-K17 gRNA). In some embodiments, successive gene editing steps may comprise the use of a SPY101 gRNA in combination with HPFH5-1 and HPFH5-D gRNAs (e.g., one editing step with SPY101 gRNA and another one or two editing steps with HPFH5-1 and HPFH5-D gRNAs). In some embodiments, successive gene editing steps may comprise the use of a SPY101 gRNA in combination with HPFH5-T7 and HPFH5-D gRNAs (e.g., one editing step with SPY101 gRNA and another one or two editing steps with HPFH5-T7 and HPFH5-D gRNAs). In some embodiments, successive gene editing steps may comprise the use of a SPY101 gRNA in combination with HPFH5-T5 and HPFH5-1 gRNAs (e.g., one editing step with SPY101 gRNA and another one or two editing steps with HPFH5-T5 and HPFH5-1 gRNAs). In some embodiments, successive gene editing steps may comprise the use of a SPY101 gRNA in combination with Kenya-K5 and Kenya-K17 gRNAs (e.g., one editing step with SPY101 gRNA and another one or two editing steps with Kenya-K5 and Kenya-K17 gRNAs). In some embodiments, successive gene editing steps may comprise the use of a SPY101 gRNA in combination with a SD2 gRNA (e.g., one editing step with SPY101 gRNA and another editing step with SD2 gRNA). In some embodiments, successive gene editing steps may comprise the use of at least one 1450 gRNA in combination with at least one HPFH5 gRNA (e.g., one editing step with 1450 gRNA and another editing step with at least one HPFH5 gRNA). In some embodiments, successive gene editing steps may comprise the use of a 1450 gRNA in combination with a HPFH5-1 gRNA (e.g., one editing step with 1450 gRNA and another editing step with HPFH5-1 gRNA). In some embodiments, successive gene editing steps may comprise the use of a 1450 gRNA in combination with a HPFH5-D gRNA (e.g., one editing step with 1450 gRNA and another editing step with HPFH5-D gRNA). In some embodiments, successive gene editing steps may comprise the use of a 1450 gRNA in combination with a HPFH5-T5 gRNA (e.g., one editing step with 1450 gRNA and another editing step with HPFH5-T5 gRNA). In some embodiments, successive gene editing steps may comprise the use of a 1450 gRNA in combination with a HPFH5-T7 gRNA (e.g., one editing step with 1450 gRNA and another editing step with HPFH5-T7 gRNA). In some embodiments, successive gene editing steps may comprise the use of at least one 1450 gRNA in combination with at least one Kenya gRNA (e.g., one editing step with 1450 gRNA and another editing step with at least one Kenya gRNA). In some embodiments, successive gene editing steps may comprise the use of a 1450 gRNA in combination with a Kenya-K5 gRNA (e.g., one editing step with 1450 gRNA and another editing step with Kenya-K5 gRNA). In some embodiments, successive gene editing steps may comprise the use of a 1450 gRNA in combination with a Kenya-K17 gRNA (e.g., one editing step with 1450 gRNA and another editing step with Kenya-K17 gRNA). In some embodiments, successive gene editing steps may comprise the use of a 1450 gRNA in combination with HPFH5-1 and HPFH5-D gRNAs (e.g., one editing step with 1450 gRNA and another one or two editing steps with HPFH5-1 and HPFH5-D gRNAs). In some embodiments, successive gene editing steps may comprise the use of a 1450 gRNA in combination with HPFH5-T7 and HPFH5-D gRNAs (e.g., one editing step with 1450 gRNA and another one or two editing steps with HPFH5-T7 and HPFH5-D gRNAs). In some embodiments, successive gene editing steps may comprise the use of a 1450 gRNA in combination with HPFH5-T5 and HPFH5-1 gRNAs (e.g., one editing step with 1450 gRNA and another one or two editing steps with HPFH5-T5 and HPFH5-1 gRNAs). In some embodiments, successive gene editing steps may comprise the use of a 1450 gRNA in combination with Kenya-K5 and Kenya-K17 gRNAs (e.g., one editing step with 1450 gRNA and another one or two editing steps with Kenya-K5 and Kenya-K17 gRNAs). In some embodiments, successive gene editing steps may comprise the use of a 1450 gRNA in combination with a SD2 gRNA (e.g., one editing step with 1450 gRNA and another editing step with SD2 gRNA). In some embodiments, successive gene editing steps may comprise the use of at least one of a HPFH5-1, HPFH5-D, HPFH5-T5, HPFH5-T7, Kenya-K5, or Kenya-K1 gRNA in combination with at least one additional HPFH5-1, HPFH5-D, HPFH5-T5, HPFH5-T7, Kenya-K5, or Kenya-K1 gRNA. In some embodiments, successive gene editing steps may comprise the use of a HPFH5-1 gRNA in combination with a HPFH5-1, HPFH5-D, HPFH5-T5, HPFH5-T7, Kenya-K5, or Kenya-K1 gRNA. In some embodiments, successive gene editing steps may comprise the use of a HPFH5-D gRNA in combination with a HPFH5-1, HPFH5-D, HPFH5-T5, HPFH5-T7, Kenya-K5, or Kenya-K1 gRNA. In some embodiments, successive gene editing steps may comprise the use of a HPFH5-T5 gRNA in combination with a HPFH5-1, HPFH5-D, HPFH5-T5, HPFH5-T7, Kenya-K5, or Kenya-K1 gRNA. In some embodiments, successive gene editing steps may comprise the use of a HPFH5-T7 gRNA in combination with a HPFH5-1, HPFH5-D, HPFH5-T5, HPFH5-T7, Kenya-K5, or Kenya-K1 gRNA.

In some embodiments, successive gene editing (e.g., successive electroporation) may involve 2, 3, 4, 5, 6, or more gene editing steps. In some embodiments, successive gene editing may involve 2 gene editing steps. In some embodiments, successive gene editing may involve 3 gene editing steps.

In some embodiments, successive gene editing steps may involve the use of a concatenated gRNA.

In some embodiments, successive gene editing steps (e.g., successive electroporation steps) provide improved persistence of gene editing, higher levels of gene editing, improved biological outcomes, e.g., increased levels of HbF, fewer off-target effects, and/or fewer translocations, compared to single gene editing events. In some embodiments, successive gene editing steps (e.g., successive electroporation steps) provide fewer translocations compared to single gene editing events (e.g., a single electroporation step).

In some embodiments, successive gene editing steps (e.g., successive electroporation steps) may occur 12, 18, 24, 36, 48, 72, or more hours apart from one another, e.g., a second electroporation may occur 48 hours after a first electroporation. In some embodiments, successive gene editing steps (e.g., successive electroporation steps) occur 12-72, 12-48, or 36-72 hours apart from one another. In some embodiments, successive gene editing steps (e.g., successive electroporation steps) occur 36 hours apart. In some embodiments, successive gene editing steps (e.g., successive electroporation steps) occur 48 hours apart.

In some embodiments, a first gene editing step (e.g., a first successive electroporation step) may occur within 12, 36, 48, or 72 of thawing a population of cells or obtaining a population of cells from a biological source, e.g., a human subject or human patient.

In some embodiments, a population of edited cells may be purified, e.g., using FACS, between two successive gene editing steps, e.g., between a first and second electroporation, or after completing a series of successive gene editing steps (e.g., a series of successive electroporation steps). In some embodiments, a population of cells may be allowed to differentiate and/or enucleate between two successive gene editing steps (e.g., successive electroporation steps) or after completing a series of successive gene editing steps (e.g., successive electroporation steps).

In some embodiments, successive gene editing steps (e.g., successive electroporation steps) may be performed on any cell type described herein, e.g., HSPC, mPB CD34+. In some embodiments, successive gene editing steps (e.g., successive electroporation steps) may be performed on myeloid progenitor cells.

Definitions

The term "comprising" or "comprises" is used in reference to compositions, methods, and respective component(s) thereof, that are essential to the invention, yet open to the inclusion of unspecified elements, whether essential or not.

The term "consisting essentially of" refers to those elements required for a given aspect. The term permits the presence of additional elements that do not materially affect the basic and novel or functional characteristic(s) of that aspect of the invention.

The term "consisting of" refers to compositions, methods, and respective components thereof as described herein, which are exclusive of any element not recited in that description of the aspect.

The singular forms "a," "an," and "the" include plural references unless the context clearly dictates otherwise.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112 (a) and Article 123 (2) EPC. Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

EXAMPLES

The invention will be more fully understood by reference to the following examples, which provide illustrative non-limiting aspects of the invention.

The examples describe the use of the CRISPR/Cas system as an illustrative genome editing technique to create defined therapeutic genomic deletions or single base substitutions, collectively termed "genomic modifications" herein, in the human beta globin gene locus on chromosome 11 and BCL11A gene on chromosome 2 or a DNA sequence that encodes a transcriptional control region of the BCL11A gene on chromosome 2, that lead to an upregulation of expression of HbF. Exemplary therapeutic modifications are genetically and/or functionally similar or identical to those observed in hematopoietic cells of individuals with hemoglobinopathy such as sickle cell or β-thalassemia in which the modifications de-repress, or lead to the re-expression of, γ-globin and thus fetal hemoglobin. Introduction of the defined therapeutic modifications represents a novel therapeutic strategy for the potential amelioration of hemoglobinopathies, as described and illustrated herein.

Example 1—CRISPR/SpCas9 Target Sites for the Human Beta Globin Locus

Regions of the human beta globin locus were scanned for target sites. Each area was scanned for a protospacer adjacent motif (PAM) having the sequence NRG. gRNA 20 bp spacer sequences corresponding to the PAM were identified, as shown in SEQ ID NOs: 1-56,961 of the Sequence Listing.

Example 2—CRISPR/SaCas9 Target Sites for the Human Beta Globin Locus

Regions of the human beta globin locus were scanned for target sites. Each area was scanned for a protospacer adjacent motif (PAM) having the sequence NNGRRT. gRNA 20 bp spacer sequences corresponding to the PAM were identified, as shown in SEQ ID NOs: 56,962-64,104 of the Sequence Listing.

Example 3—CRISPR/NmCas9 Target Sites for the Human Beta Globin Locus

Regions of the human beta globin locus were scanned for target sites. Each area was scanned for a protospacer adjacent motif (PAM) having the sequence NNNNGATT. gRNA 24 bp spacer sequences corresponding to the PAM were identified, as shown in SEQ ID NOs: 64,105-66,258 of the Sequence Listing.

Example 4—CRISPR/StCas9 Target Sites for the Human Beta Globin Locus

Regions of the human beta globin locus were scanned for target sites. Each area was scanned for a protospacer adjacent motif (PAM) having the sequence NNAGAAW. gRNA 24 bp spacer sequences corresponding to the PAM were identified, as shown in SEQ ID NOs: 66,259-69,152 of the Sequence Listing.

Example 5—CRISPR/TdCas9 Target Sites for the Human Beta Globin Locus

Regions of the human beta globin locus were scanned for target sites. Each area was scanned for a protospacer adjacent motif (PAM) having the sequence NAAAAC. gRNA 24 bp spacer sequences corresponding to the PAM were identified, as shown in SEQ ID NOs: 69,153-70,300 of the Sequence Listing.

Example 6—CRISPR/Cpf1 Target Sites for the Human Beta Globin Locus

Regions of the human beta globin locus were scanned for target sites. Each area was scanned for a protospacer adjacent motif (PAM) having the sequence TTN. gRNA 20-24 bp spacer sequences corresponding to the PAM were identified, as shown in SEQ ID NOs: 70,301-156,352 of the Sequence Listing.

Example 7—Creation of Deletions Proximal to Chr11:5224779-5237723

In this example, we illustrate use of the methods described herein to generate certain deletions that are proximal to the region Chr11:5224779-5237723. Deletions in this region have been observed in human patients designated as HPFH-5 (or "HPFH Sicilian") described in Camaschella et al., *Haematologica*, 75 (Suppl 5): 26-30 (1990). The 13 kb deletion variant in the human β-globin locus observed in the human patients was associated with the clinical phenotype of hereditary persistence of fetal hemoglobin (HPFH), in which the presence of fetal hemoglobin can complement the defect in adult hemoglobin synthesis or function, and ameliorate disease, in sickle cell anemia or β-thalassemia.

In this example, we illustrate that the CRISPR/Cas system can be used to create deletions functionally resembling those associated with natural HPFH alleles such as HPFH-5. Guide RNAs were designed to eliminate the pathogenic sickle cell allele by deleting the δ and β globin genes as well as substantial portion of the Y globin gene 3' region. FIG. 1A shows the human beta globin locus with hollow boxes highlighting the HPFH-5 5' and 3' target sites. The 13 kb deletion starts 3 kb 5' to the δβ1 gene and ends 1.7 kb 3' to the end of the β gene (690 bp downstream from the β gene polyA signal). See FIG. 1B. In addition, guide RNAs were designed to target sites throughout the 13 kb region in order to determine the therapeutic potential of smaller deletions within this locus.

Experimental Methods

Selection of Target Sites

Regions of the β-globin gene cluster were scanned for target sites, including the 5' and 3' regions associated with hereditary persistence of fetal hemoglobin-5 (HPFH-5). Each area was scanned for protospacer adjacent motifs (PAMs) having the sequence NGG and/or NRG. Guide strands corresponding to the PAMs were identified.

For this illustrative example, candidate guides were screened and selected in a multi-step process that involved both theoretical binding and experimentally assessed activity. By way of illustration, candidate guides having sequences that match a particular on-target site with adjacent PAM can be assessed for their potential to cleave at off-target sites having similar sequences, using one or more of a variety of bioinformatics tools available for assessing off-target binding, as described and illustrated in more detail below, in order to assess the likelihood of effects at chromosomal positions other than those intended. Candidates predicted to have relatively lower potential for off-target activity can then be assessed experimentally to measure their on-target activity, and then off-target activities at various sites. Preferred guides have sufficiently high on-target activity to achieve desired levels of gene editing at the selected locus, and relatively lower off-target activity, to reduce the likelihood of alterations at other chromosomal loci. The ratio of on-target to off-target activity is often referred to as the "specificity" of a guide.

For initial screening of predicted off-target activities, there are a number of bioinformatics tools known and publicly available that can be used to predict the most likely off-target sites; and since binding to target sites in the CRISPR Cas9 nuclease system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called COSMID (CRISPR Off-target Sites with Mismatches, Insertions and Deletions) (available on the web at crispr dot bme dot gatech dot edu) compiles such similarities.

CRISPR Cloning

Plasmids expressing the Cas9 protein and guide strand RNA were assembled using a vector that expressed humanized Cas9 from *S. pyogenes* and the single-molecule guide RNA. Complementary oligonucleotides corresponding to the guide strand were obtained (Operon or IDT), kinased, annealed and cloned into the vector. Guide RNAs were tested in cells:

The first three spacer sequences target the 5' boundary of the region to be deleted, and the last three target the 3' boundary of the region to be deleted.

Cell Transfection

K-562 cells were cultured in RPMI media supplemented with 10% FBS and 2 mM fresh L-glutamine and passaged as they approached a confluency of $1 \times 10^5$/ml. An Amaxa Nucleofector 4D was used to transfect 200,000 K-562 cells with 1 μg vector expressing HPFH5 targeting sgRNAs, and 1000 ng of plasmid expressing Cas9 following manufacturer's instructions. The genomic DNA was harvested after 3 days using QuickExtract DNA extraction solution (Epicentre, Madison, WI), as described.

Hek293T cells were seeded 24 hours prior to transfection in 24-well plates at a density of 80,000 cells per well and cultured in DMEM media supplemented with 10% FBS and 2 mM fresh L-glutamine. Cells were transfected with 1000 ng of plasmid expressing Cas9 and gRNA using 2 μl of Lipofectamine 2000 (Life technologies), according to manufacturer's instructions. Genomic DNA was harvested at 72 hours after transfection using QuickExtract DNA Extraction Solution (Epicenter).

On- and Off-Target Mutation Detection by Sequencing

To sequence the on-target sites and putative off-target sites, the appropriate amplification primers were identified and reactions were set up with these primers using the genomic DNA harvested using QuickExtract DNA extraction solution (Epicentre) from treated cells three days post-transfection. The amplification primers contain the gene specific portion flanked by adapters. The forward primer's 5' end includes a modified forward (read1) primer-binding site. The reverse primer's 5' end contains a combined modified reverse (read2) and barcode primer-binding site, in opposite orientation. The individual PCR reactions were validated by separating on agarose gels, then purified and re-amplified. The second round forward primers contain the Illumina P5 sequence, followed by a proportion of the modified forward (read1) primer binding site. The second round reverse primers contain the Illumina P7 sequence (at the 5' end), followed by the 6-base barcode and the combined modified reverse (read2) and barcode primer binding site. The second round amplifications were also checked on agarose gels, then purified, and quantitated using a NanoDrop spectrophotometer. The amplification products were pooled to match concentration and then submitted to the Emory Integrated Genomic core for library prepping and sequencing on an Illumina Miseq machine.

The sequencing reads were sorted by barcode and then aligned to the reference sequences supplied by bioinformatics for each product. Insertion and deletion rates in the aligned sequencing reads were detected in the region of the putative cut sites using software previously described; see, e.g., Lin et al., *Nucleic Acids Res.*, 42:7473-7485 (2014). The levels of insertions and deletions detected in this window were then compared to the level seen in the same location in genomic DNA isolated from in mock transfected cells to minimize the effects of sequencing artifacts.

Mutation Detection Assays

The on- and off-target cleavage activities of Cas9 and guide RNA combinations were measured using the mutation rates resulting from the imperfect repair of double-strand breaks by NHEJ.

On-target loci were amplified using AccuPrime Taq DNA Polymerase High Fidelity (Life Technologies, Carlsbad, CA) following manufacturer's instructions for 40 cycles (94° C., 30 s; 52-60° C., 30 s; 68° C., 60 s) in 50 μl reactions containing 1 μl of the cell lysate, and 1 μl of each 10 UM amplification primer. T7EI mutation detection assays were performed, as per manufacturers protocol [Reyon et al., *Nat. Biotechnol.*, 30:460-465 (2012)], with the digestions separated on 2% agarose gels and quantified using ImageJ [Guschin et al., *Methods Mol. Biol.*, 649:247-256 (2010)]. The assays determine the percentage of insertions/deletions ("indels") in the bulk population of cells.

Detecting Inversions and Deletions by End-Point PCR

All end-point PCR reactions were performed using AccuPrime Taq DNA Polymerase High Fidelity (Life Technologies) following manufacturer's instructions for 40 cycles (94° C., 30 s; 60° C., 30 s; 68° C., 45 s) in a 50 μl reaction containing 1 μl of the cell lysate, and 1 μl of each 10 μM target region amplification primer.

Deletion Quantification Using Drop Digital PCR (ddPCR)

The level of joined chromosomal ends, indicating the intended chromosomal deletions, was quantitated using the BioRad (Hercules, CA) drop digital PCR machine (ddPCR) QX200. The machines allow absolute quantification by breaking individual PCR reactions into ~20,000 droplets that are individually tested by end-point PCR using a Cyber green-like reagent and a reader that can effectively differentiate between PCR-positive and PCR-negative droplets. Genomic DNA for ddPCR was extracted from K-562 cells using the QiaAMP DNA mini kit (Qiagen, Valencia, CA). PCR reactions contained 2×ddPCR EvaGreen supermix, 200 ng of genomic DNA, primers, and HindIII (1 U/reaction). Reactions were run for 40 cycles (94° C., 30 s; 55-65° C., 30 s; 72° C., 90 s).

Example 8—Creation of Deletions Proximal to Chr11:5233055-5240389

Figure 3:
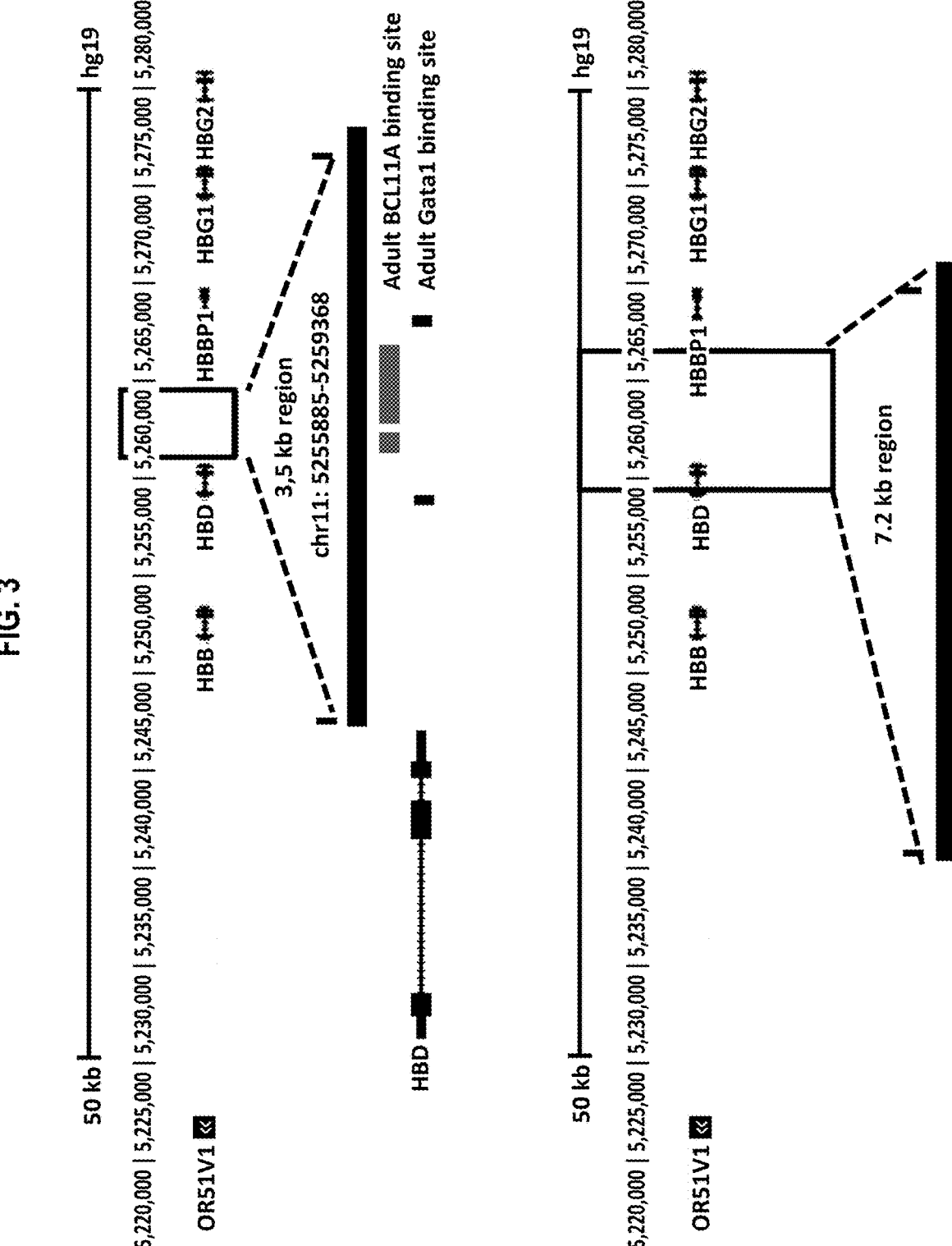
FIG. 3 shows a schematic of the genomic location of HPFH Corfu 3.5 kb and 7.2 kb deletions.

In this example, we illustrate use of the methods described herein to generate certain deletions that are proximal to the region Chr11:5233055-5240389. Deletions in this region have been observed in human patients with a 7.2 kb deletion in the human β-globin locus on chromosome 11 that is referred to herein as the "Corfu long" deletion. In the homozygous state, such a deletion is associated with a complete absence of hemoglobin A and A2 and a high level of fetal hemoglobin and HPFH [Wainscoat et al, *Ann. NY Acad Sci* 445:20 (1985) and Kulozik et al, *Blood* 71:457 (1988)]. This deletion is depicted in FIG. 3. We further determined that known binding sites for key regulators of γ-globin-BCL11a and Gata1—are located within a 3.5 kb subregion within the 7.2 kb region (FIG. 3). It is contemplated that deletion of this smaller region alone (deletion in chromosome 11 within region Chr11:5233055-5240389) might be sufficient to confer an HPFH phenotype comparable to that seen with the larger deletion and, moreover, may be achievable at a higher efficiently of genome editing than for the larger deletion. CRISPR guide RNAs were designed to effect cleavage at each end of the 7.2 kb and 3.5 kb regions and their ability to effect deletion of the intervening fragment was validated.

Individual guide RNAs directed towards the boundaries of each of the Corfu deletions were tested for their efficiency of gene editing. Vectors encoding the guide RNAs were generated and introduced into cells as described in Example 7.

Example 9—Creation of Deletions Proximal to Chr11:5226631-5249422

Figure 4:
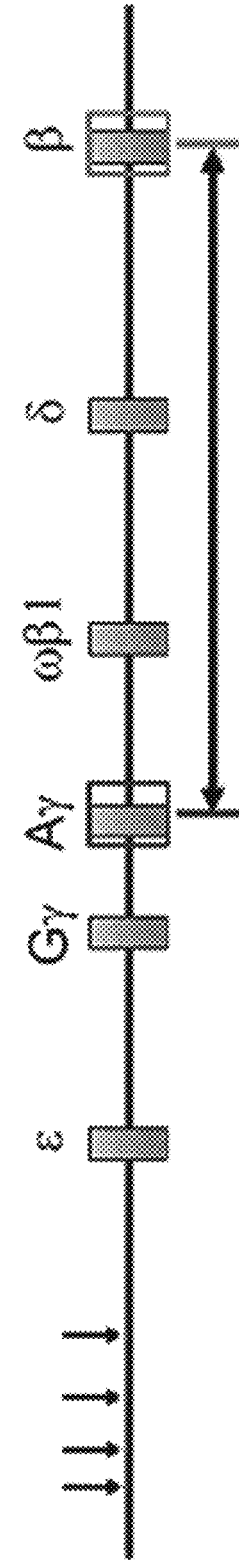
FIG. 4 is a schematic of the β-globin locus showing the location of the Kenya deletion, 5' (left box) and 3' (right box)

In this example, we illustrate use of the methods described herein to generate certain deletions that are proximal to the region Chr11:5226631-5249422. Deletions in this region have been observed in human patients with a large deletion in the human β-globin locus on chromosome 11 that is referred to herein as the HPFH Kenya-like variant [Huisman et al, *Arch. Biochem. Biophys.* 152:850 (1972) and Ojwang et al, *Hemoglobin* 7:115 (1983)]. The naturally-occurring variant appears to have resulted from non-homologous crossing over between amino acids 80-87 of the $^A\gamma$ and β-globin genes and deletion of the intervening ~23 kb of sequence in chromosome 11 within region Chr11:5226631-5249422. The Kenya fusion protein contains amino acid residues 1-80 of the $^A\gamma$ chain and 87-146 of the β chain. CRISPR guide RNAs used to effect cleavage at each boundary of the ~23 kb region (FIG. 4) were designed and validated. Vectors encoding the guide RNAs were generated and introduced into cells as described in Example 7.

Example 10—Creation of Deletions Proximal to Chr11:5249959-5249971

Figure 5A:
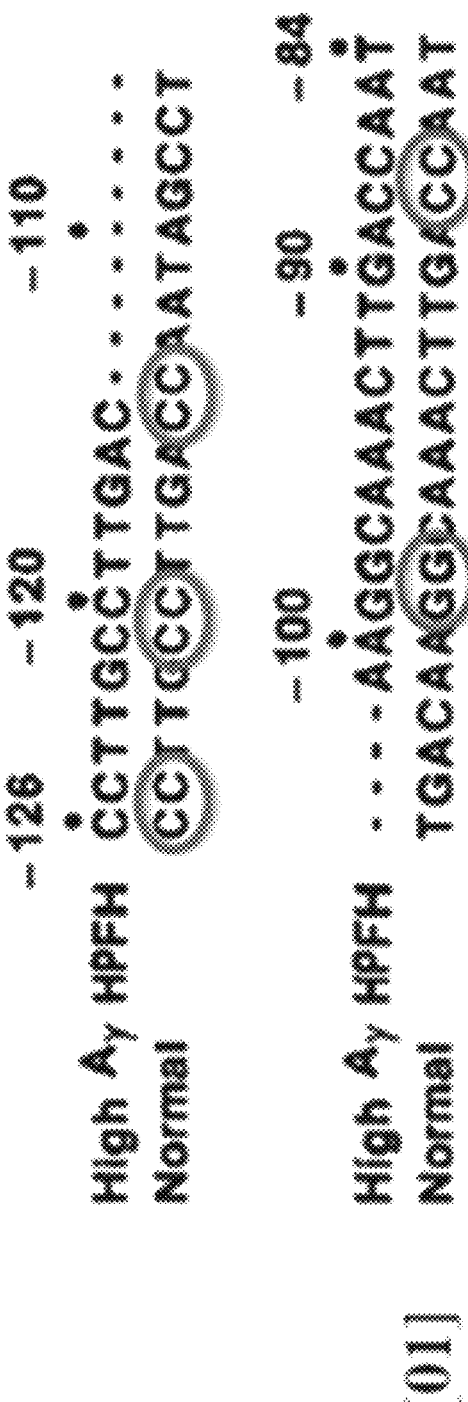
Figure 5B:
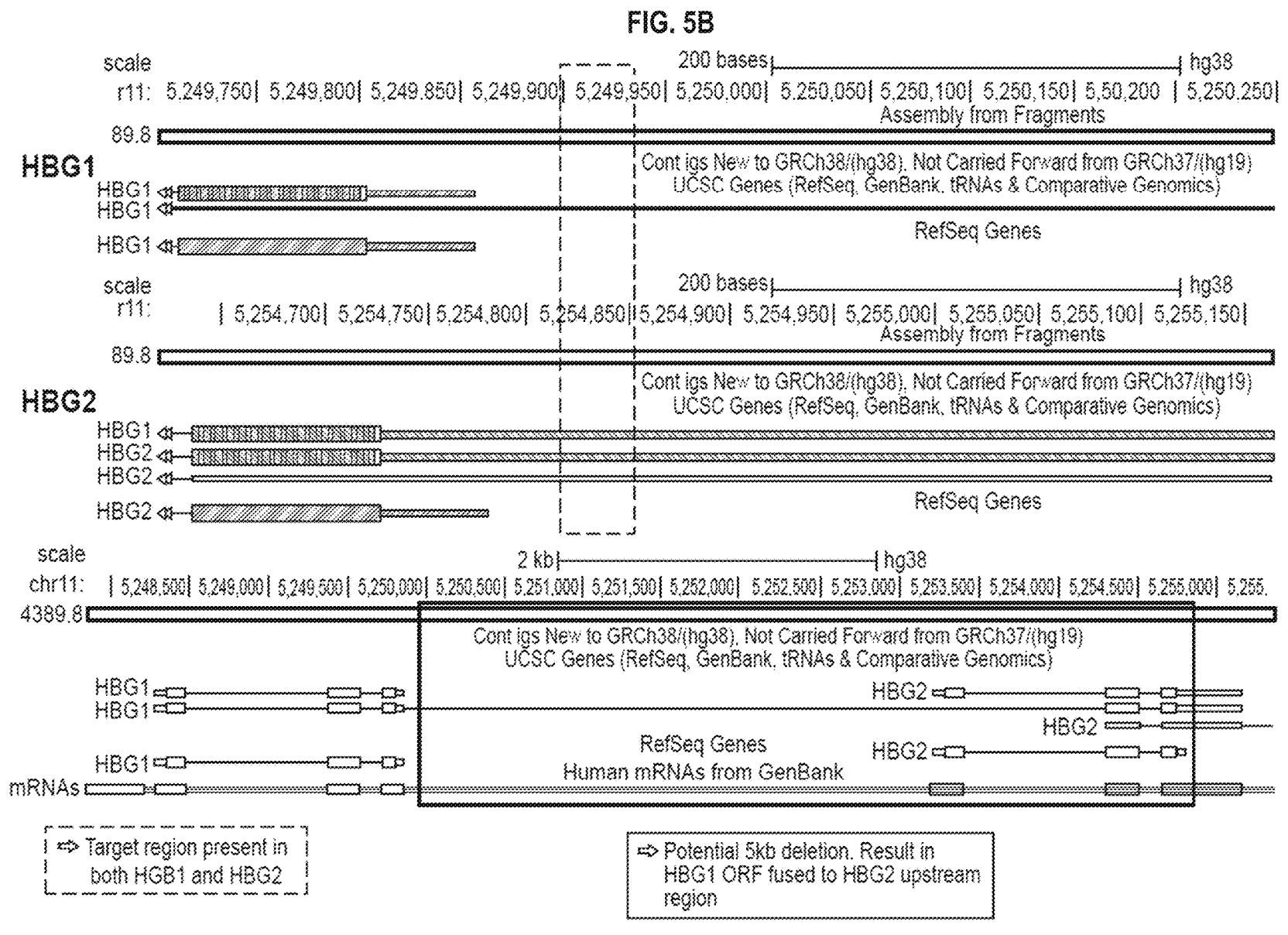

In this example, we illustrate use of the methods described herein to generate certain deletions that are proximal to the region Chr11:5249959-5249971. Deletions in this region have been observed in human patients with a small deletion variant of the β-globin locus in chromosome 11 within region Chr11:5249959-5249971 that was identified and shown to be associated with HPFH [Gilman et al, *Nucleic acids Research* 16 (22): 10635 (1988)]. This deletion spans −102 to −114 of the γ-globin gene and encompasses the distal CCAAT box believed important for regulation of the γ-gene promoter (FIG. 5A). Potential PAM sites for CRISPR are circled (FIG. 5A).

One approach is to cleave this locus within the 13 bp region and allow NHEJ to mis-repair the lesion with the expectation that in some instances the exact 13 bp deletion might be recapitulated. However, the repair outcome by NHEJ alone cannot be assured and it is unlikely that the precise 13 bp deletion will occur at a clinically significant frequency-rather than additional deletions or insertions, which may themselves have the desired therapeutic consequence. Alternatively, the DSB could be repaired by HDR in the presence of a co-delivered repair template donor that specifies the precise 13 bp deletion.

A third approach to creating the 13 bp deletion could be taken that makes use of microhomology at the intended mutation site and the repair pathway of MMEJ. In the present example analysis of the sequence encompassing and adjacent to the 13 bp deletion site revealed the presence of two 8 bp repeat sequences which we predicted would likely recombine during MMEJ-mediated repair to produce the 13 bp deletion in the presence of a single double-strand break. Vectors encoding the guide RNAs were generated and introduced into cells as described in Example 7.

Example 11—Creation of Deletions Proximal to Chr11:5196709-5239223

In this example, we illustrate use of the methods described herein to generate certain deletions that are proximal to the region Chr11:5196709-5239223. Deletions in this region have been observed in human patients with a large deletion in the human β-globin locus on chromosome 11 that is referred to as the HPFH-4 (or "HPFH Italian") allele [Camaschella et al, *Haematologia* 75 (5): 26 (1990)] and is characterized by a 40 kb deletion (FIG. 6A) in chromosome 11 within region Chr11:5196709-5239223 that fully encompasses the shorter (13 kb) HPFH-5 allele. It is contemplated that genome editing technologies such as CRISPR can be used to create a targeted deletion of the corresponding or similar genomic region, or subset thereof, in hematopoietic cells of individuals with hemoglobinopathy such as sickle cell or β-thalassemia to de-repress, or lead to the re-expression of, γ-globin and thus fetal hemoglobin.

Example 12—Creation of Deletions Proximal to Chr11:5225700-5236750

In this example, we illustrate use of the methods described herein to generate certain deletions that are proximal to the region Chr11:5225700-5236750. Deletions in this region have been observed in human patients with the HPFH Black allele [Anagnou et al., *Blood* 65:1245 (1985)], which is characterized by a large deletion (FIG. 6B) in chromosome 11 within region Chr11:5225700-5236750 that overlaps completely with theHPFH-4 and HPFH-5 deletions. It is contemplated that genome editing technologies such as CRISPR can be used to create a targeted deletion of the corresponding or similar genomic region, or subset thereof, in hematopoietic cells of individuals with hemoglobinopathy such as sickle cell or β-thalassemia to de-repress, or lead to the re-expression of, γ-globin and thus fetal hemoglobin.

Example 13—Creation of HPFH-Associated Non-Deletion Mutations

The −175 (T to C) point mutation in the $^G\gamma$ or $^A\gamma$ gene of β-globin locus is associated with a phenotype of pancellular HPFH, i.e. across many cells with fairly uniform distribution; see, e.g., Ottolenghi et al., *Blood* 71:815 (1988) and Surrey et al., *Blood* 71:807 (1988). The HPFH phenotype is believed to be due to disruption of one or more cis-elements to which regulatory factors normally bind and repress γ-globin expression, or to enhancement of binding of regulatory factors that upregulate γ-globin expression. It is contemplated that genome editing technologies such as CRISPR can be used to create the point mutation, or other modification resulting in changes in regulatory factor binding, in hematopoietic cells of individuals with hemoglobinopathy such as sickle cell or β-thalassemia to de-repress, or lead to the re-expression of, γ-globin and thus fetal hemoglobin.

Figures 6A, 6B, 6C:
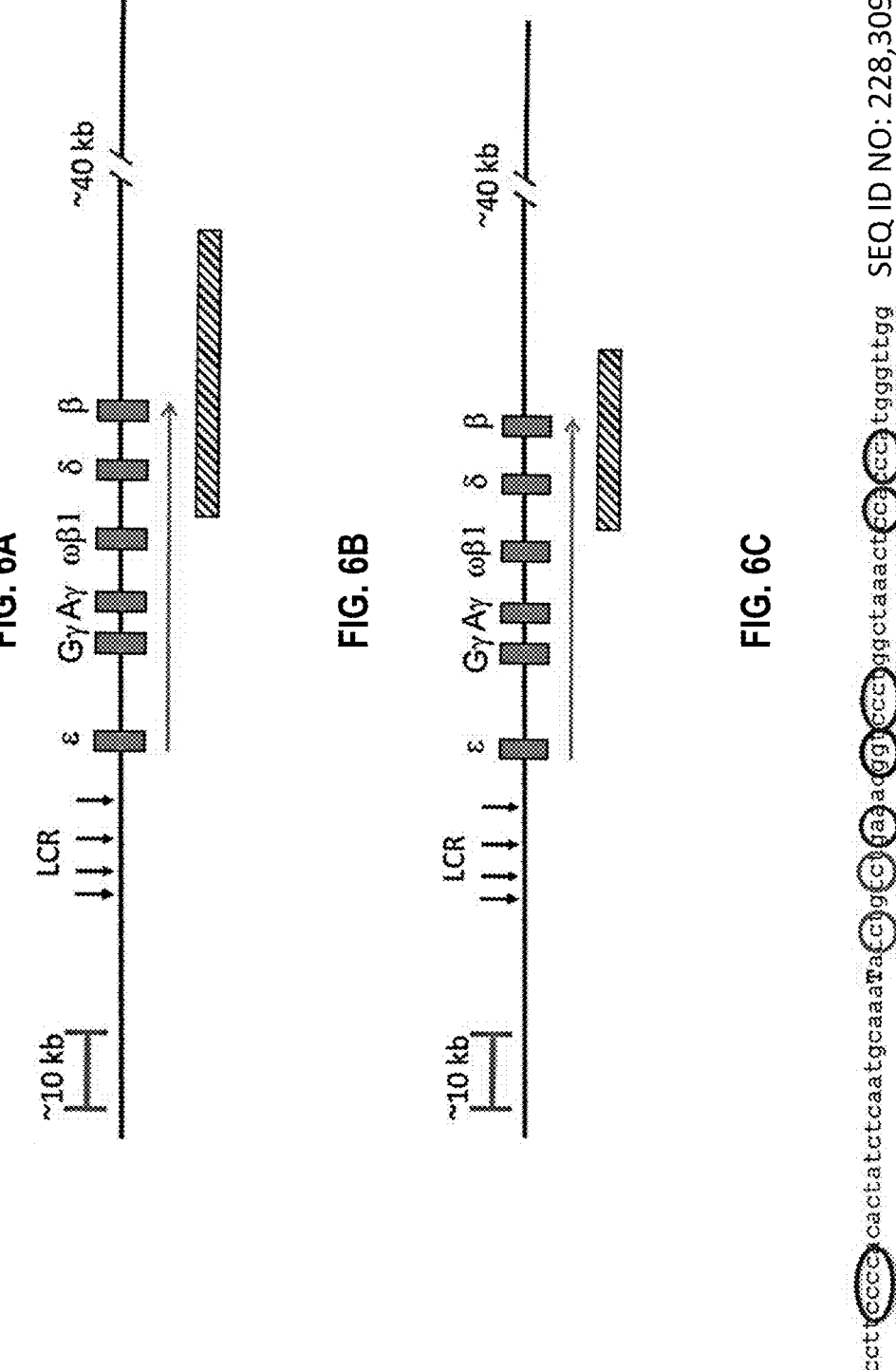
FIGS. 6A-6C show other deletion and non-deletion modifications of the β-globin locus associated with HPFH.

Multiple putative PAM sequences for *S. pyogenes* Cas9 are located adjacent to this target site (FIG. 6C). Potential PAM sites for *S. pyogenes* Cas9 are circled. Nucleotide T175 is shown in bold (FIG. 6C).

Example 14—CRISPR/SpCas9 Target Sites for the Transcriptional Control Sequence of the BCL11A Gene Regions of the 12.4 kb transcriptional control sequence of the BCL11A gene were scanned for target sites. Each area was scanned for a protospacer adjacent motif (PAM) having the sequence NRG. gRNA 20 bp spacer sequences corresponding to the PAM were identified, as shown in SEQ ID NOs: 156,353-185,834 of the Sequence Listing.

Example 15—CRISPR/SaCas9 Target Sites for the Transcriptional Control Sequence of the BCL11A Gene Regions of the 12.4 kb transcriptional control sequence of the BCL11A gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 185,835-188,739 of the Sequence Listing.

Example 16—CRISPR/StCas9 Target Sites for the Transcriptional Control Sequence of the BCL11A Gene Regions of the 12.4 kb transcriptional control sequence of the BCL11A gene were scanned for target sites. Each area was scanned for a protospacer adjacent motif (PAM) having the sequence NNAGAAW. gRNA 24 bp spacer sequences corresponding to the PAM were identified, as shown in SEQ ID NOS: 188,740-189,772 of the Sequence Listing.

Example 17—CRISPR/TdCas9 Target Sites for the Transcriptional Control Sequence of the BCL11A Gene Regions of the 12.4 kb transcriptional control sequence of the BCL11A gene were scanned for target sites. Each area was scanned for a protospacer adjacent motif (PAM) having the sequence NAAAAC. gRNA 24 bp spacer sequences corresponding to the PAM were identified, as shown in SEQ ID NOS: 189,773-190,203 of the Sequence Listing.

Example 18—CRISPR/NmCas9 Target Sites for the Transcriptional Control Sequence of the BCL11A Gene Regions of the 12.4 kb transcriptional control sequence of the BCL11A gene were scanned for target sites. Each area was scanned for a protospacer adjacent motif (PAM) having the sequence NNNNGATT. gRNA 24 bp spacer sequences corresponding to the PAM were identified, as shown in SEQ ID NOS: 190,204-193,083 of the Sequence Listing.

Example 19—CRISPR/Cpf1 Target Sites for the Transcriptional Control Sequence of the BCL11A Gene Regions of the 12.4 kb transcriptional control sequence of the BCL11A gene were scanned for target sites. Each area was scanned for a protospacer adjacent motif (PAM) having the sequence TTN. gRNA 20-24 bp spacer sequences corresponding to the PAM were identified, as shown in SEQ ID NOs: 193,084-228,299 of the Sequence Listing.

Example 20—Bioinformatics Analysis of the Guide Strands

Candidate guides from Examples 14-19 will be screened and selected in a multi-step process that involves both theoretical binding and experimentally assessed activity, as previously described in Example 7. By way of illustration, candidate guides having sequences that match a particular on-target site, such as a site within the transcriptional control sequence of the BCL11A gene, with adjacent PAM can be assessed for their potential to cleave at off-target sites having similar sequences, using one or more of a variety of bioinformatics tools available for assessing off-target binding, as described and illustrated in more detail below, in order to assess the likelihood of effects at chromosomal positions other than those intended. Candidates predicted to have relatively lower potential for off-target activity can then be assessed experimentally to measure their on-target activity, and then off-target activities at various sites. Preferred guides have sufficiently high on-target activity to achieve desired levels of gene editing at the selected locus, and relatively lower off-target activity to reduce the likelihood of alterations at other chromosomal loci. The ratio of on-target to off-target activity is often referred to as the "specificity" of a guide.

For initial screening of predicted off-target activities, there are a number of bioinformatics tools known and publicly available that can be used to predict the most likely off-target sites; and since binding to target sites in the CRISPR/Cas9 or CRISPR/Cpf1 nuclease system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called COSMID (CRISPR Off-target Sites with Mismatches, Insertions and Deletions) (available on the web at crispr.b-me.gatech.edu) compiles such similarities. Other bioinformatics tools include, but are not limited to autoCOSMID and CCTop.

Bioinformatics were used to minimize off-target cleavage in order to reduce the detrimental effects of mutations and chromosomal rearrangements. Studies on CRISPR/Cas9 systems suggested the possibility of off-target activity due to non-specific hybridization of the guide strand to DNA sequences with base pair mismatches and/or bulges, particularly at positions distal from the PAM region. Therefore, it is important to have a bioinformatics tool that can identify potential off-target sites that have insertions and/or deletions between the RNA guide strand and genomic sequences, in addition to base-pair mismatches. Bioinformatics tools based upon the off-target prediction algorithm CCTop were used to search genomes for potential CRISPR off-target sites (CCTop is available on the web at crispr.cos.uni-heidelberg.de/). The output ranked lists of the potential off-target sites based on the number and location of mismatches, allowing more informed choice of target sites, and avoiding the use of sites with more likely off-target cleavage.

Additional bioinformatics pipelines were employed that weigh the estimated on- and/or off-target activity of gRNA targeting sites in a region. Other features that may be used to predict activity include information about the cell type in question, DNA accessibility, chromatin state, transcription factor binding sites, transcription factor binding data, and other CHIP-seq data. Additional factors are weighed that predict editing efficiency, such as relative positions and directions of pairs of gRNAs, local sequence features and micro-homologies.

Example 21—Testing of Preferred Guides in Cells for On-Target Activity

Figure 9:
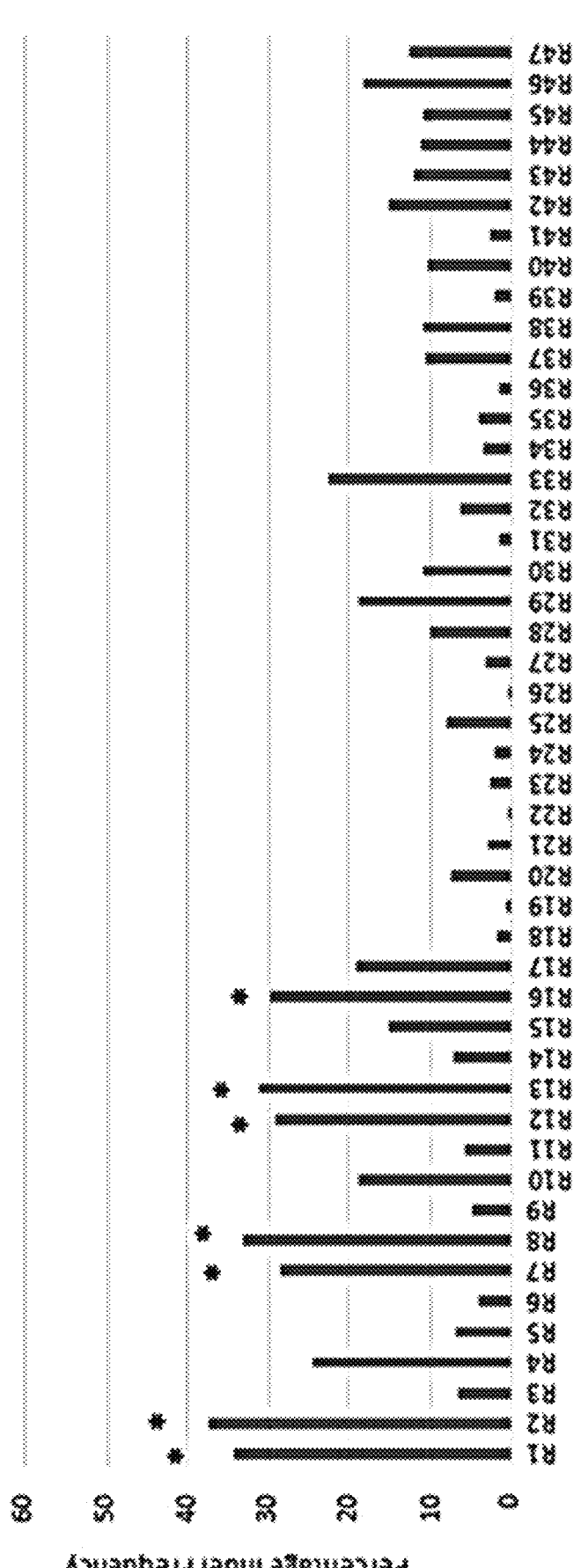
FIG. 9 is a table showing indel frequencies for various gRNAs that are specific for the +58 DNA hypersensitive site (DHS) of the BCL11A gene.
Figure 9:
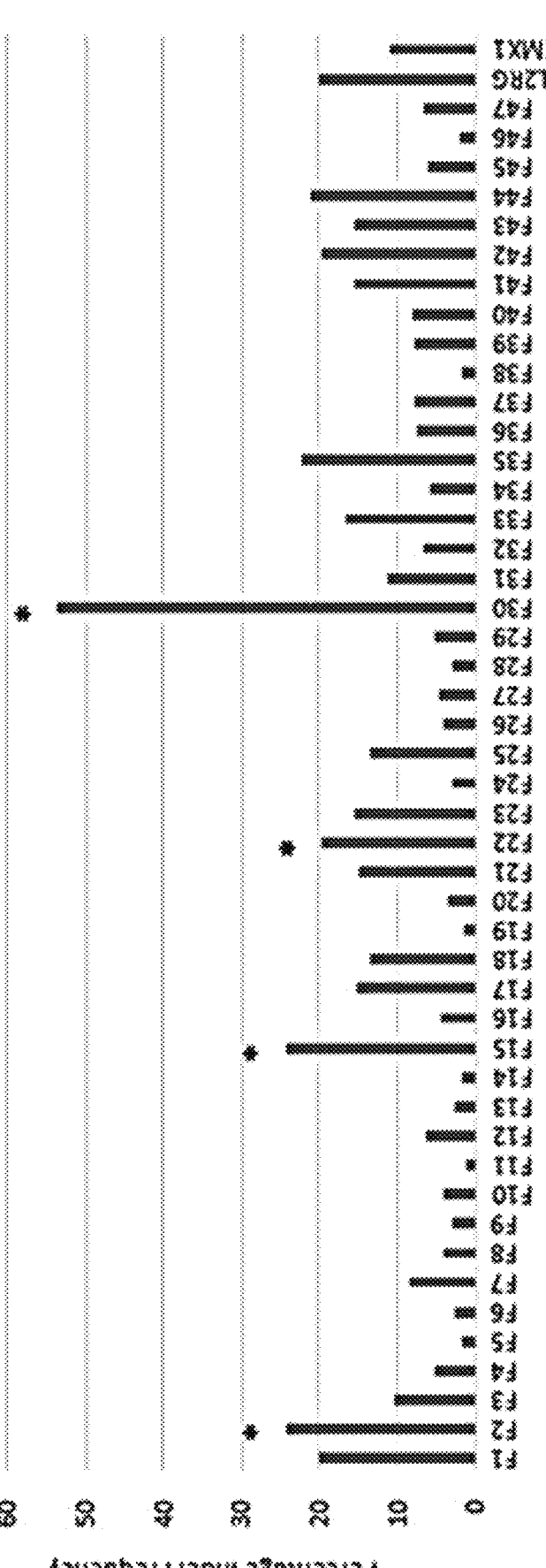

The gRNAs from Examples 14-19 predicted to have the lowest off-target activity were then tested for on-target activity in K562 cells, and evaluated for indel frequency using TIDE as demonstrated in FIG. 9. The gRNA sequences shown in FIG. 9 are included in FIGS. 11A, 11B, and 11C.

TIDE is a web tool to rapidly assess genome editing by CRISPR-Cas9 of a target locus determined by a guide RNA (gRNA or sgRNA). Based on quantitative sequence trace data from two standard capillary sequencing reactions, the TIDE software quantifies the editing efficacy and identifies the predominant types of insertions and deletions (indels) in the DNA of a targeted cell pool. See Brinkman et al, Nucl.

Acids Res. (2014) for a detailed explanation and examples. An alternative method is Next-generation sequencing (NGS), also known as high-throughput sequencing, which is the catch-all term used to describe a number of different modern sequencing technologies including: Illumina (Solexa) sequencing, Roche 454 sequencing, Ion torrent: Proton/PGM sequencing, and SOLID sequencing. These recent technologies allow one to sequence DNA and RNA much more quickly and cheaply than the previously used Sanger sequencing, and as such have revolutionised the study of genomics and molecular biology.

Transfection of tissue culture cells, allows screening of different constructs and a robust means of testing activity and specificity. Tissue culture cell lines, such as K562 or HEK293T are easily transfected and result in high activity. These or other cell lines will be evaluated to determine the cell lines that match with CD34+ and provide the best surrogate. These cells will then be used for many early stage tests. For example, individual gRNAs for *S. pyogenes* Cas9 can be transfected into the cells using plasmids, such as, for example, CTx-1, CTx-2, or CTx-3 described in FIG. 7A-7C, which are suitable for expression in human cells. Alternatively, commercially available vectors may also be used. For the Indel Freq assessment of the BCL11A gRNAs described herein, a commercially available Cas9 expression plasmid (GeneArt, Thermo Fisher) was employed. Several days later (48 hrs for this experiment), the genomic DNA was harvested and the target site amplified by PCR. The cutting activity was measured by the rate of insertions, deletions and mutations introduced by NHEJ repair of the free DNA ends. Although this method cannot differentiate correctly repaired sequences from uncleaved DNA, the level of cutting can be gauged by the amount of mis-repair. Off-target activity can be observed by amplifying identified putative off-target sites and using similar methods to detect cleavage. Translocation can also be assayed using primers flanking cut sites, to determine if specific cutting and translocations happen. Un-guided assays have been developed allowing complementary testing of off-target cleavage including guide-seq. The gRNA or pairs of gRNA with significant activity can then be followed up in cultured cells to measure the modulation or inactivation of the +58 DNA hypersensitive site (DHS) within the transcriptional control sequence of the BCL11A gene. Off-target events can be followed again. Similarly CD34+ cells can be transfected and the level of modulation or inactivation of the +58 DNA hypersensitive site (DHS) within the transcriptional control sequence of the BCL11A gene and possible off-target events measured. These experiments allow optimization of nuclease and donor design and delivery.

Example 22—Testing of Preferred BCL11A gRNAs in Cells for Off-Target Activity The BCL11A gRNAs from Examples 14-19 having the best on-target activity from the TIDE and next generation sequencing studies in the above example will then be tested for off-target activity using whole genome sequencing. Candidate gRNAs will be more completely evaluated in CD34+ cells or iPSCs.

Example 23—Testing of Preferred BCL11A gRNA Combinations in Cells

The BCL11A gRNAs from Examples 14-19 having the best on-target activity from the TIDE and next generation sequencing studies and lowest off-target activity will be tested in combinations to evaluate the size of the deletion resulting from the use of each gRNA combination. Potential gRNA combinations will be evaluated in primary human CD34 cells.

Figure 10A:
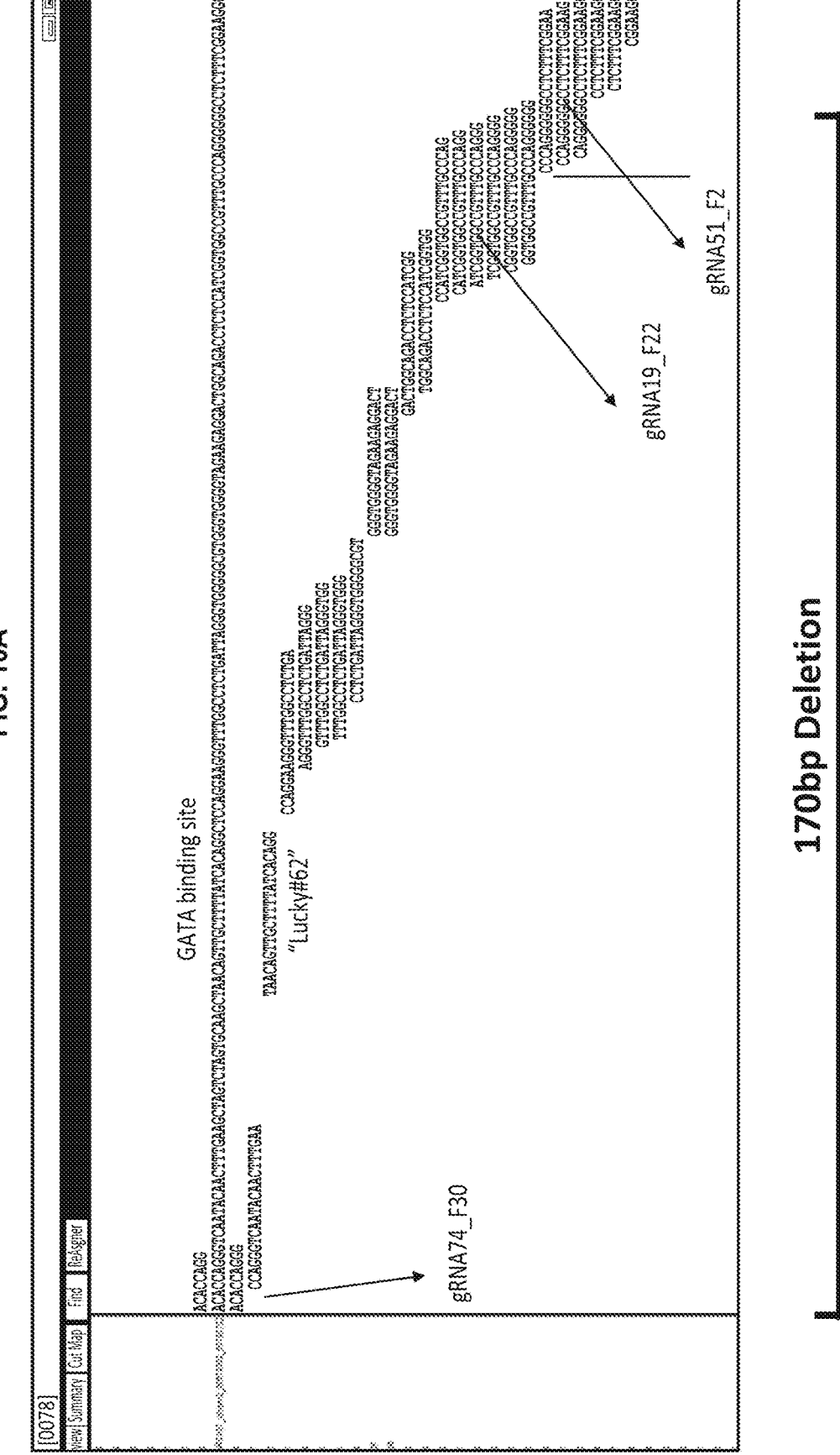

For example, gRNA combinations will be tested for efficiency of deleting all or a portion of the transcriptional control sequence of the BCL11A gene. The gRNA combinations will also be tested for efficiency of deleting all or a portion of the +58 DNA hypersensitive site (DHS) of the BCL11A gene as depicted in FIG. 10A and as demonstrated in FIG. 10B.

Example 24—Editing Cells Using gRNAs that Target the Human Beta Globin Locus and gRNAs that Target the BCL11A Gene Mobilized human peripheral blood CD34+ cells were cultured in serum free STEMSPAN media with erythroid expansion (100×) cytokine cocktail for two days. 100,000 cells were washed and electroporated using Cas9 mRNA with one or more gRNA specific for the human beta globin locus (gRNAs described in Examples 1-6 and disclosed in the Sequence Listing) and one or more gRNA specific for the BCL11A gene or a DNA sequence that encodes a transcriptional control region of the BCL11A gene (gRNAs described in Examples 14-19 or the Figures; and disclosed in the Sequence Listing). Cells were allowed to recover for one day before being switched to an erythroid differentiation medium (IMDM+Glutamax supplemented with 5% human serum, 10 ug/ml insulin, 20 ug/ml SCF, 5 ug/ml IL-3, 3 U/ml EPO, 1 uM dexamethasone, 1 uM β-estradiol, 330 ug/ml holo-transferrin and 2 U/ml heraprin). Single erythroid progenitors were generated using flow cytometry one day later and cultured in the erythroid differentiation medium. Half of the colonies were collected 12 days post sorting for DNA and RNA analysis. The rest were collected 16 days post sorting for the analysis of hemoglobin proteins. Globin expression (HBG/HBA or HBG/(HBB+HBG)) was determined by real-time PCR and compared for each of the edited erythroid clones.

Example 25—Editing Cells with a Concatenated gRNA

Mobilized human peripheral blood CD34+ cells were cultured in serum free STEMSPAN media with erythroid expansion (100×) cytokine cocktail for two days. 100,000 cells were washed and electroporated using Cas9 mRNA with a concatenated gRNA comprising a first gRNA and second gRNA. The first gRNA can comprise a gRNA specific for the human beta globin locus, as described in Examples 1-6 and disclosed in the Sequence Listing. The second gRNA can comprise a gRNA specific for the BCL11A gene or a DNA sequence that encodes a transcriptional control region of the BCL11A gene, as described in Examples 14-19 or the Figures; and disclosed in the Sequence Listing. Cells were allowed to recover for one day before being switched to an erythroid differentiation medium (IMDM+Glutamax supplemented with 5% human serum, 10 ug/ml insulin, 20 ug/ml SCF, 5 ug/ml IL-3, 3 U/ml EPO, 1 uM dexamethasone, 1 uM β-estradiol, 330 ug/ml holo-transferrin and 2 U/ml heraprin). Single erythroid progenitors were generated using flow cytometry one day later and cultured in the erythroid differentiation medium. Half of the colonies were collected 12 days post sorting for DNA and RNA analysis. The rest were collected 16 days post sorting for the analysis of hemoglobin proteins. Globin expression (HBG/HBA or HBG/(HBB+HBG)) was determined by real-time PCR and compared for each of the edited erythroid clones.

Example 26—Editing Cells with a Concatenated gRNA

Mobilized human peripheral blood CD34+ cells were cultured in serum free STEMSPAN media with erythroid expansion (100×) cytokine cocktail for two days. 100,000 cells were washed and electroporated using Cas9 mRNA with a concatenated gRNA comprising a first gRNA, a second gRNA, and a third gRNA. The first gRNA can comprise a gRNA specific for the human beta globin locus, as described in Examples 1-6 and disclosed in the Sequence Listing. The second gRNA can comprise a gRNA specific for the human beta globin locus, as described in Examples 1-6 and disclosed in the Sequence Listing. The third gRNA can comprise a gRNA specific for the BCL11A gene or a DNA sequence that encodes a transcriptional control region of the BCL11A gene, as described in Examples 14-19 or the Figures; and disclosed in the Sequence Listing. Cells were allowed to recover for one day before being switched to an erythroid differentiation medium (IMDM+Glutamax supplemented with 5% human serum, 10 ug/ml insulin, 20 ug/ml SCF, 5 ug/ml IL-3, 3 U/ml EPO, 1 uM dexamethasone, 1 uM β-estradiol, 330 ug/ml holo-transferrin and 2 U/ml heraprin). Single erythroid progenitors were generated using flow cytometry one day later and cultured in the erythroid differentiation medium. Half of the colonies were collected 12 days post sorting for DNA and RNA analysis. The rest were collected 16 days post sorting for the analysis of hemoglobin proteins. Globin expression (HBG/HBA or HBG/(HBB+HBG)) was determined by real-time PCR and compared for each of the edited erythroid clones.

Example 27—Editing Cells with a Concatenated gRNA

Mobilized human peripheral blood CD34+ cells were cultured in serum free STEMSPAN media with erythroid expansion (100×) cytokine cocktail for two days. 100,000 cells were washed and electroporated using Cas9 mRNA with a concatenated gRNA comprising a first gRNA, a second gRNA, and a third gRNA. The first gRNA can comprise a gRNA specific for the human beta globin locus, as described in Examples 1-6 and disclosed in the Sequence Listing. The second gRNA can comprise a gRNA specific for the BCL11A gene or a DNA sequence that encodes a transcriptional control region of the BCL11A gene, as described in Examples 14-19 or the Figures; and disclosed in the Sequence Listing. The third gRNA can comprise a gRNA specific for the BCL11A gene or a DNA sequence that encodes a transcriptional control region of the BCL11A gene, as described in Examples 14-19 or the Figures; and disclosed in the Sequence Listing. Cells were allowed to recover for one day before being switched to an erythroid differentiation medium (IMDM+Glutamax supplemented with 5% human serum, 10 ug/ml insulin, 20 ug/ml SCF, 5 ug/ml IL-3, 3 U/ml EPO, 1 uM dexamethasone, 1 uM β-estradiol, 330 ug/ml holo-transferrin and 2 U/ml heraprin). Single erythroid progenitors were generated using flow cytometry one day later and cultured in the erythroid differentiation medium. Half of the colonies were collected 12 days post sorting for DNA and RNA analysis. The rest were collected 16 days post sorting for the analysis of hemoglobin proteins. Globin expression (HBG/HBA or HBG/(HBB+

HBG)) was determined by real-time PCR and compared for each of the edited erythroid clones.

Example 28—Editing Cells with Two Concatenated gRNAs

Mobilized human peripheral blood CD34+ cells were cultured in serum free STEMSPAN media with erythroid expansion (100x) cytokine cocktail for two days. 100,000 cells were washed and electroporated using Cas9 mRNA with two concatenated gRNAs. The first concatenated gRNA comprises a first gRNA and a second gRNA. The first gRNA of the first concatenated gRNA can comprise a gRNA specific for the human beta globin locus, as described in Examples 1-6 and disclosed in the Sequence Listing. The second gRNA of the first concatenated gRNA can comprise a gRNA specific for the BCL11A gene or a DNA sequence that encodes a transcriptional control region of the BCL11A gene, as described in Examples 14-19 or the Figures; and disclosed in the Sequence Listing. The second concatenated gRNA comprises a first gRNA and a second gRNA. The first gRNA of the second concatenated gRNA can comprise a gRNA specific for the human beta globin locus, as described in Examples 1-6 and disclosed in the Sequence Listing. The second gRNA of the second concatenated gRNA can comprise a gRNA specific for the BCL11A gene or a DNA sequence that encodes a transcriptional control region of the BCL11A gene, as described in Examples 14-19 or the Figures; and disclosed in the Sequence Listing. Cells were allowed to recover for one day before being switched to an erythroid differentiation medium (IMDM+Glutamax supplemented with 5% human serum, 10 ug/ml insulin, 20 ug/ml SCF, 5 ug/ml IL-3, 3 U/ml EPO, 1 uM dexamethasone, 1 uM β-estradiol, 330 ug/ml holo-transferrin and 2 U/ml heraprin). Single erythroid progenitors were generated using flow cytometry one day later and cultured in the erythroid differentiation medium. Half of the colonies were collected 12 days post sorting for DNA and RNA analysis. The rest were collected 16 days post sorting for the analysis of hemoglobin proteins. Globin expression (HBG/HBA or HBG/(HBB+HBG)) was determined by real-time PCR and compared for each of the edited erythroid clones.

Example 29—Editing Cells with Two Concatenated gRNAs

Mobilized human peripheral blood CD34+ cells were cultured in serum free STEMSPAN media with erythroid expansion (100x) cytokine cocktail for two days. 100,000 cells were washed and electroporated using Cas9 mRNA with two concatenated gRNAs. The first concatenated gRNA comprises a first gRNA and a second gRNA. The first gRNA of the first concatenated gRNA can comprise a gRNA specific for the human beta globin locus, as described in Examples 1-6 and disclosed in the Sequence Listing. The second gRNA of the first concatenated gRNA can comprise a gRNA specific for the human beta globin locus, as described in Examples 1-6 and disclosed in the Sequence Listing. The second concatenated gRNA comprises a first gRNA and a second gRNA. The first gRNA of the second concatenated gRNA can comprise a gRNA specific for the BCL11A gene or a DNA sequence that encodes a transcriptional control region of the BCL11A gene, as described in Examples 14-19 or the Figures; and disclosed in the Sequence Listing. The second gRNA of the second concatenated gRNA can comprise a gRNA specific for the BCL11A gene or a DNA sequence that encodes a transcriptional control region of the BCL11A gene, as described in Examples 14-19 or the Figures; and disclosed in the Sequence Listing. Cells were allowed to recover for one day before being switched to an erythroid differentiation medium (IMDM+Glutamax supplemented with 5% human serum, 10 ug/ml insulin, 20 ug/ml SCF, 5 ug/ml IL-3, 3 U/ml EPO, 1 uM dexamethasone, 1 uM β-estradiol, 330 ug/ml holo-transferrin and 2 U/ml heraprin). Single erythroid progenitors were generated using flow cytometry one day later and cultured in the erythroid differentiation medium. Half of the colonies were collected 12 days post sorting for DNA and RNA analysis. The rest were collected 16 days post sorting for the analysis of hemoglobin proteins. Globin expression (HBG/HBA or HBG/(HBB+HBG)) was determined by real-time PCR and compared for each of the edited erythroid clones.

Example 30—Clinical Studies and Pharmacology

It is well established that an increase in HbF levels reduces HbS polymerization and thereby ameliorates the phenotype of SCA, reducing clinical complications.

In the context of the CRISPR/Cas9 technology, or by using other endonucleases for gene editing as described herein, the main objectives of primary pharmacodynamic studies in human subjects/patients will be to demonstrate successful de-repression of γ-globin and concomitant increases and beneficial effects of HbF, and to determine the safety and efficacy of such genetic modifications for the treatment of hemoglobinopathies.

Cell-based studies can include both wild-type cells, such as normal CD34+ hHSCs, which do not normally express high levels of HbF, but are edited as described herein to increase their levels of HbF; as well as cells such as CD34+ cells that are derived from patients having a hemoglobinopathy such as β-thalassemia or SCD.

Total red cell HbF will be measured by cationic HPLC and the distribution of HbF in red cells will be quantified in F-cells (cells with detectable HbF levels) using FACS. Although even small incremental increases in HbF have been shown to have beneficial effects in the context of SCD, as discussed above, in some aspects at least about 9% of total Hb in a subject will be HbF, which is associated with decreased mortality in SCD; see, e.g., Platt et al., *N Engl J Med.* 330 (23): 1639-1644 (1994). In some aspects, HbF will be at least about 14%, which is associated with additional clinical benefits, and in some aspects HbF will be at least about 20% to 30%, which is associated with substantial normalization of phenotype in the context of SCD. Similarly, the introduction of even relatively limited subpopulations of cells having significantly elevated levels of HbF (referred to as "F-cells") can be beneficial in various patients since in some situations normalized cells will have a selective advantage relative to diseased cells. Even modest levels of circulating RBCs with elevated levels of HbF can be beneficial for ameliorating one or more aspects of hemoglobinopathy in patients. However, it is generally contemplated that at least one tenth of circulating red blood cells (RBCs) will have elevated levels of HbF, more than one quarter of circulating RBCs will have elevated levels of HbF, or at least one third of circulating RBCs will have elevated levels of HbF. In some aspects, at least about one half, and in some aspects at least about three quarters or more, of circulating RBCs will have elevated levels of HbF.

Example 31—Biodistribution

A preliminary feasibility study (non-GLP) will be performed to demonstrate engraftment of CD34+ hHSCs in NOD/SCID IL2Rγ mice. A GLP biodistribution and persistence study will be performed in immune-compromised NOD/SCID IL2Rγ mice. CRISPR/Cas9-modified human CD34+ HSCs will be administered by i.v. injection (or other routes, e.g. intraosseous) to NOD/SCID IL2Rγ mice. Non-modified CD34+ hHSCs will be used as a control.

Example 32—In Vivo Pharmacology Study

In an illustrative example of in vivo pharmacology, gene-edited HSCs are introduced into immunodeficient mice, and results such as HSC engraftment are assessed. For example, "NSG" or NOD scid gamma (NOD.Cg-Prkdcscid Il2rgtm1Wjl/SzJ), is a strain of inbred laboratory mice, among the most immunodeficient described to date; see, e.g., Shultz et al., *Nat. Rev. Immunol.* 7 (2): 118-130 (2007). Another immune-compromised mouse model applicable for investigating hematopoietic stem cell transplantation is the NOD/MrkBomTac-Prkdc$^{scid}$ mouse (www dot Taconic dot com/NODSC).

One illustrative approach employing an immune-compromised mouse model is to inject CRISPR/Cas9-modified CD34+ human HSCs into immune-compromised NOD/SCID/IL2rγ mice to demonstrate homing and engraftment capabilities.

It is also possible to consider studies in model animals, provided such models are reasonably predictive of one or more aspects of conditions in human patients. Development of animal models providing information relevant to certain aspects of various diseases continues to be the subject of regular improvements in the art, and the use of CRISPR/Cas-9 gene editing is greatly facilitating the more rapid creation of such disease-relevant animal models.

Example 33—Use of Edited Cells for the Amelioration of β-Thalassemia

Using the methods described and illustrated herein, human cells expressing increased levels of HbF can be produced. Such cells can include, for example, human hematopoietic stem cells (human HSCs) that are capable of giving rise to cells of the erythroid lineage such as red blood cells (RBCs). Such HSCs can therefore be used to ameliorate one or more symptoms associated with β-thalassemia.

For example, when the genome editing procedure is applied to increase the levels of HbF in cells of a patient suffering from a β-thalassemia, one or more symptoms or complications of the β-thalassemia can be ameliorated, as a result of the combination of two beneficial effects. First, HbF provides a functional form of hemoglobin that can play a significant role in ameliorating the anemia and associated clinical conditions of β-thalassemia (i.e. in β-thalassemia major and β-thalassemia intermedia), in which the adult β-globin chains that would normally be expressed from the HBB gene are absent or reduced. Second, the level of unpaired α-globin chains, which is a cause of a number of other problems associated clinically β-thalassemia, are reduced because the α-globin chains can be paired with β-globin chains encoded by the γ-globin genes, expression of which is increased as described herein.

As also noted herein, β-thalassemia RBCs have selective disadvantages compared to normal RBCs in terms of survival and other factors; and treatment of cells as described herein overcomes certain disadvantages by, e.g., increasing the levels of HbF, and concomitantly decreasing the levels of unpaired α-globin chains.

In addition, other techniques can be applied to enhance the delivery, expansion and/or persistence of cells modified by genome editing as described herein. These include ablation techniques in which some resident cells are eliminated prior to the introduction of cells. Such techniques are routinely used, for example, in the context of bone marrow transplantation and other procedures in which normal or corrected cells are introduced into patients. Numerous such procedures are known in the art and routinely practiced in connection with the treatment of human patients.

One illustrative and nonlimiting example of the use of such techniques for the amelioration of β-thalassemia is as follows.

In an autologous procedure, genome editing is performed on cells derived from a patient with β-thalassemia. Since the patient's own cells are already matched, they do not therefore raise the potential issues associated with use of allogeneic cells. Correction of such cells ex vivo followed by their reintroduction into the patient presents a means of ameliorating the disease.

As one illustrative example of cells that can be used, peripheral blood stem cells (PBSCs) from a patient with β-thalassemia can be derived from the bloodstream. A process called apheresis or leukapheresis can be used to obtain the PBSCs. For 4 or 5 days before apheresis, the patient may be given a medication to increase the number of stem cells released into the bloodstream. In apheresis, blood is removed through a large vein in the arm or a central venous catheter (a flexible tube that is placed in a large vein in the neck, chest, or groin area). The blood goes through a machine that removes stem cells.

As another illustrative example of cells that can be used, hematopoietic stem cells (HSCs) can be harvested from the patient's bone marrow using well known techniques. CD34 is an antigen associated with hematopoietic stem cells, and isolation of CD34+ HSCs can likewise be accomplished by well-known and clinically-validated methods. For example, a magnetic bead separation process that has been FDA-approved for use in various transplantation contexts and that is available commercially from Miltenyi Biotec, along with preparations for the handling and maintenance of such cells, can be used.

For treating a human patient with β-thalassemia as described herein, a population of CD34+ HSCs adjusted to reflect the patient's weight can be used, e.g. a population comprising about ten million CD34+ HSCs per kilogram of weight. This population of cells is then modified using the genome editing methods described herein. By way of illustration, if Cas9 is the genome editing endonuclease, the protein can be introduced into the CD34+ HSCs by transfection of mRNA using various known techniques; along with the introduction, potentially simultaneously in the transfection, of guide RNAs (which can be single-molecule guides or double-molecule guides) that target loci as described herein. Depending on the procedure used, a portion of the cells (e.g., half the original cells) may then be used for reintroduction into the patient. If ablation is to be used to enhance engraftment of the newly-introduced cells, the patient may be subject to, e.g., mild bone marrow conditioning prior to introduction of the genome edited HSCs. Following any conditioning, the population of genome edited HSCs can be reintroduced into the patient, e.g., by transfusion. Over time, the HSCs give rise to cells of the erythroid lineage, including red blood cells (RBCs).

In the resulting RBCs, genome editing in the case of β-thalassemia results in an increase in the level of HbF, and a concomitant decrease in unpaired-globin chains; as a result of which one or more symptoms or complications associated with the β-thalassemia are ameliorated.

Example 34—Use of Edited Cells for the Amelioration of Sickle Cell Anemia

Using the methods described and illustrated herein, human cells expressing increased levels of HbF can be produced. Such cells can include, for example, human hematopoietic stem cells (human HSCs) that are capable of giving rise to cells of the erythroid lineage such as red blood cells (RBCs). Such HSCs can therefore be used to ameliorate one or more symptoms associated with Sickle Cell Disease, such as Sickle Cell Anemia.

For example, when the genome editing procedure is applied to increase the levels of HbF in cells of a patient suffering from a Sickle Cell Anemia (SCA), one or more symptoms or complications of SCA can be ameliorated. In certain aspects, at least one copy of the mutant β-globin gene is knocked down or eliminated, resulting in combination of two beneficial effects. First, HbF provides a functional form of hemoglobin that can play a significant role in ameliorating the anemia and associated clinical conditions of SCA. Second, the level of sickle cell hemoglobin (HbS) expressed from the mutant β-globin is reduced or eliminated. The presence of HbS causes a number of the problems associated clinically with SCA, and even modest reductions in the presence of HbS can be used to reduce or essentially prevent sickling, as described herein and in the art.

As also noted herein, sickle cell RBCs have selective disadvantages compared to normal RBCs in terms of survival and other factors; and treatment of cells as described herein overcomes certain disadvantages by, e.g., increasing the levels of HbF, and, in aspects in which the mutant β-globin gene is knocked down or eliminated, concomitantly decreasing the levels of HbS.

In addition, other techniques can be applied to enhance the delivery, expansion and/or persistence of cells modified by genome editing as described herein. These include ablation techniques in which some resident cells are eliminated prior to the introduction of cells. Such techniques are routinely used, for example, in the context of bone marrow transplantation and other procedures in which normal or corrected cells are introduced into patients. Numerous such procedures are known in the art and routinely practiced in connection with the treatment of human patients.

One illustrative and nonlimiting example of the use of such techniques for the amelioration of SCA is as follows.

In an autologous procedure, genome editing is performed on cells derived from a patient with SCA. Since the patient's own cells are already matched, they do not therefore raise the potential issues associated with use of allogeneic cells. Correction of such cells ex vivo followed by their reintroduction into the patient presents a means of ameliorating the disease.

As one illustrative example of cells that can be used, PBSCs from a patient with SCA can be derived from the bloodstream, or HSCs can be harvested from the patient's bone marrow, each as described above in the preceding example using well-known techniques. CD34+ cells can then be derived, using procedures as described in the preceding example and well-known techniques.

For treating a human patient with SCA as described herein, a population of CD34+ HSCs adjusted to reflect the patient's weight can be used, e.g. a population comprising about ten million CD34+ HSCs per kilogram of weight. This population of cells is then modified using the genome editing methods described herein. By way of illustration, if Cas9 is the genome editing endonuclease, the protein can be introduced into the CD34+ HSCs by transfection of mRNA using various known techniques; along with the introduction, potentially simultaneously in the transfection, of guide RNAs (which can be single-molecule guides or double-molecule guides) that target loci as described herein. Depending on the procedure used, a portion of the cells (e.g., half the original cells) may then be used for reintroduction into the patient. If ablation is to be used to enhance engraftment of the newly-introduced cells, the patient may be subject to, e.g., mild bone marrow conditioning prior to introduction of the genome edited HSCs. Following any conditioning, the population of genome edited HSCs can be reintroduced into the patient, e.g., by transfusion. Over time, the HSCs give rise to cells of the erythroid lineage, including red blood cells (RBCs).

In the resulting RBCs, genome editing in the case of SCA results in an increase in the level of HbF, and in aspects in which the mutant β-globin gene is knocked down or eliminated, concomitantly decreasing the levels of HbS; as a result of which one or more symptoms or complications associated with the β-thalassemia are ameliorated.

Example 35—Successive Electroporations Using Dual Guide RNAs (SPY101 and SD2)

Successive electroporation is a method of electroporating cells 36-48 hours after thawing, followed by a second electroporation 36-48 hours later.

Figure 12:
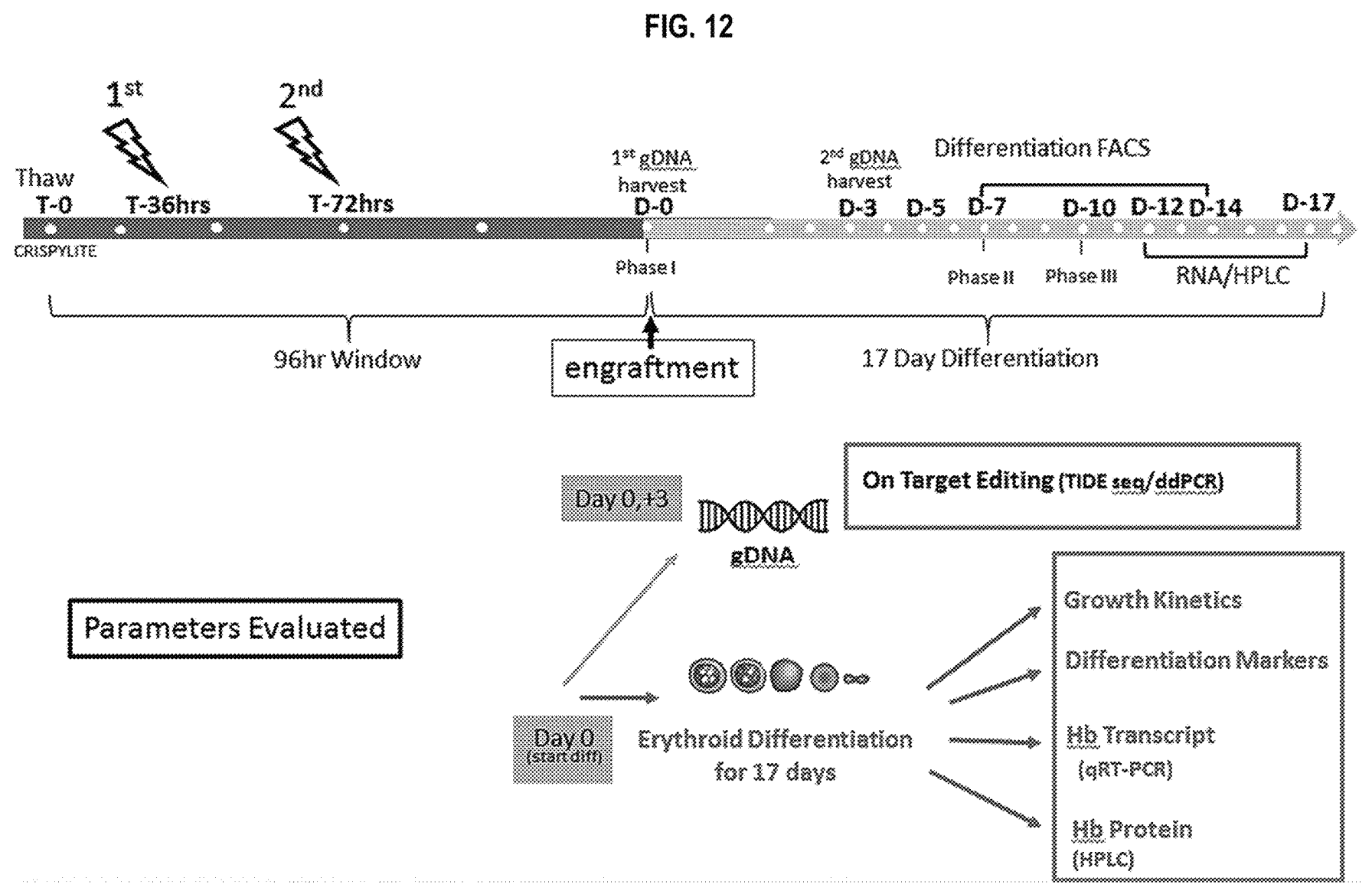

Successive electroporations using dual guide RNAs were performed using the experimental design shown in FIG. 12. Human mobilized peripheral blood (mPB) CD34+ cells were obtained from Fred Hutch Donor 304 and Donor LKP06B and either: successively electroporated with 1.5 μg SPY101 and then 1.5 μg SD2 (SPY/SD); successively electroporated with 1.5 μg SD2 and then 1.5 μg SPY101 (SD/SPY); simultaneously electroporated with 1.5 μg SPY101 and 1.5 μg SD2 (SPY&SD); individually electroporated with 3 μg SPY101 (SPY); individually electroporated with 3 μg SD2 (SD); simultaneously electroporated with 1.5 μg of a guide RNA that targets Exon 2 and 1.5 μg of a second guide RNA that targets Exon 2 (EX2); electroporated with Cas9 RNP (mock); or not electroporated (untreated).

Successive electroporations using SPY101 and then SD2 (or SD2 and then SPY101) were compared to single guide RNA electroporations (both individually using SPY101 or SD2; and simultaneously using SPY101 and SD2 at the same time) to determine the impact of successive electroporations using SPY101 and then SD2 (or SD2 and then SPY101) on the cell's health, editing rates, ability to differentiate, globin mRNA levels, and HbF protein levels.

Figures 13A, 13B:
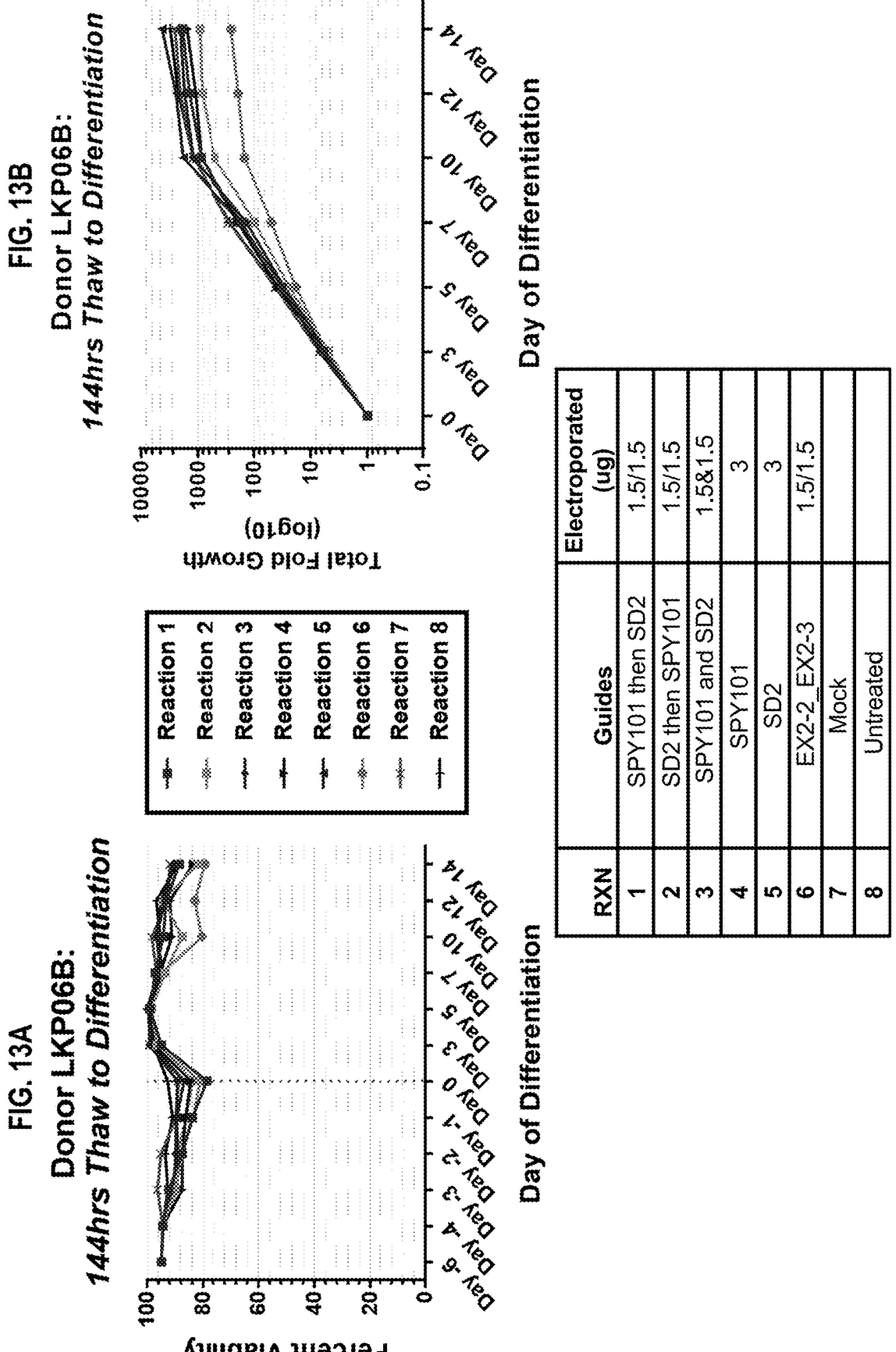
FIGS. 13A-13B show the viability and growth kinetics of human mobilized peripheral blood (mPB) CD34+ cells from Donor LKP06B successively electroporated with dual guide RNAs compared to human mPB CD34+ cells from Donor LKP06B electroporated with a single guide RNA.

Cell health of each of the electroporated mPBs described herein was accessed by measuring the viability and growth kinetics of the electroporated mPBs at various time points (Day−6, Day−4, Day−3, Day−2, Day−1, Day0, Day 3, Day 5, Day 7, Day 10, Day 12, and Day 14). Day−6 cells were thawed mPB cells that were not yet electroporated. Day−4 cells were mPBs that were thawed 48-hours earlier and electroporated for the first time at this time point. Day−3 cells were mPBs that were thawed 72-hours earlier and electroporated 24 hours earlier. Day−2 cells were mPBs that were thawed 96-hours earlier and electroporated for the second time at this time point for those mPBs that received successive electroporations. Day−1 cells were mPBs that were thawed 120-hours earlier and electroporated for the second time 24-hours earlier for those mPBs that received successive electroporations. DO cells were mPBs that were thawed 144-hours earlier and electroporated for the second time 48-hours earlier for those mPBs that received successive electroporations. Each time point after DO refers to a stage of mPB differentiation to erythrocytes, such D3, D5, D7, D10, D12, and D14. As demonstrated in FIGS. 13A-B, cell viability and cell growth kinetics are similar between mPB CD34+ cells from Donor LKP06B successively electroporated with SPY101 and then SD2 (or SD2 and then SPY101) and mPB CD34+ cells from Donor LKP06B electroporated with a single guide RNA (regardless of whether the single guide electroporation used SPY101 or SD2; or simultaneously used SPY101 and SD2).

Figures 14A, 14B:
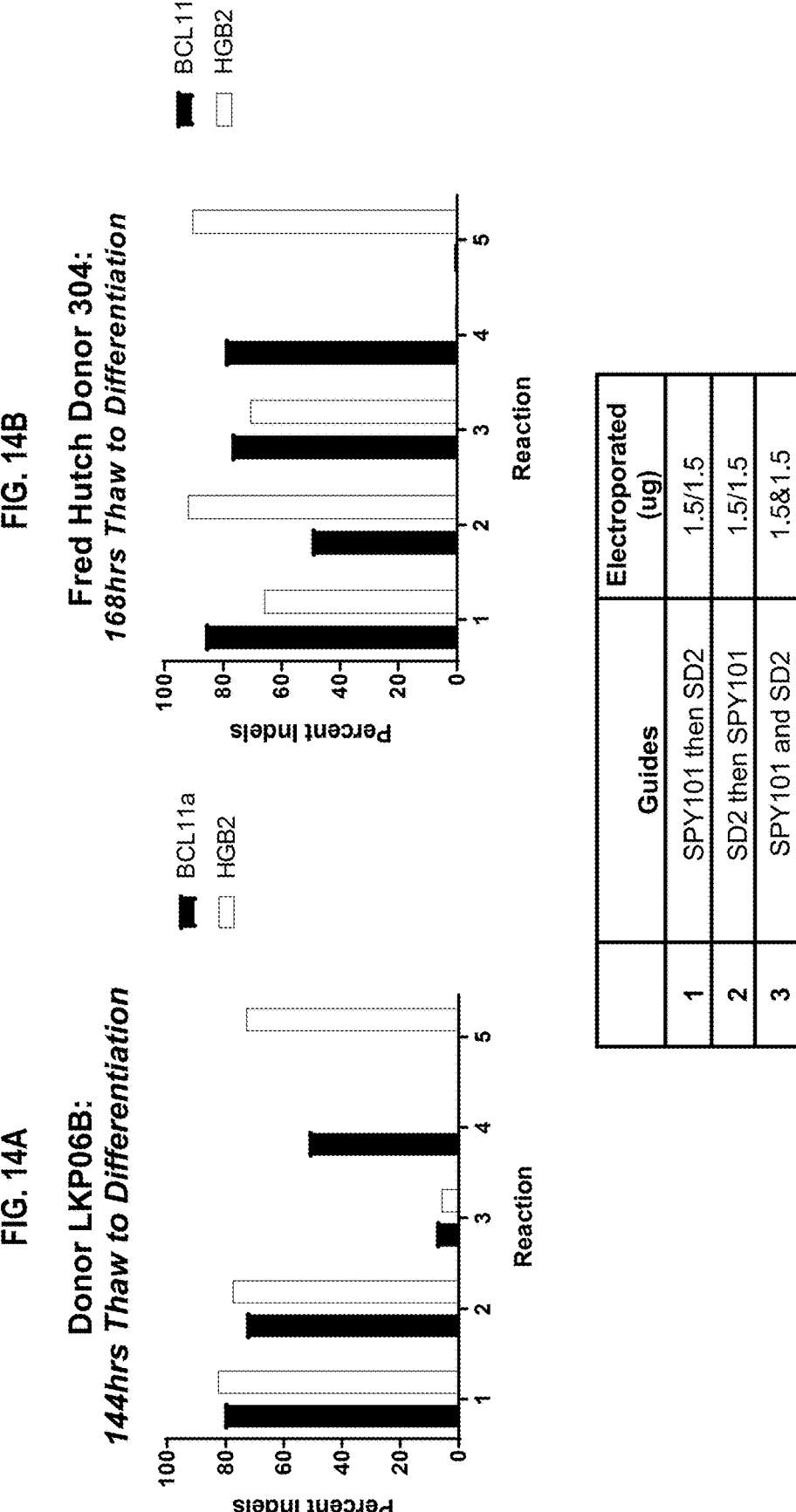
FIGS. 14A-14B show the rate of DNA editing (% indels) at the BCL11a locus and HBG2 locus in human mPB CD34+ cells successively electroporated with dual guide RNAs compared to human mPB CD34+ cells electroporated with a single guide RNA.

Editing rates of each of the electroporated samples described herein were accessed by measuring the cutting efficiencies (percent Indels) of cells from each of the electroporated mPBs. Genomic DNA was isolated at Day 3 and cutting efficiency was evaluated using TIDE analysis. As demonstrated in FIGS. 14A-B, editing rates are similar between mPB CD34+ cells from Fred Hutch Donor 304 and Donor LKP06B successively electroporated with SPY101 and then SD2 (or SD2 and then SPY101) and mPB CD34+ cells from Fred Hutch Donor 304 and Donor LKP06B electroporated with a single guide RNA (regardless of whether the single guide electroporation used SPY101 or SD2; or simultaneously used SPY101 and SD2).

Figures 15A, 15B:
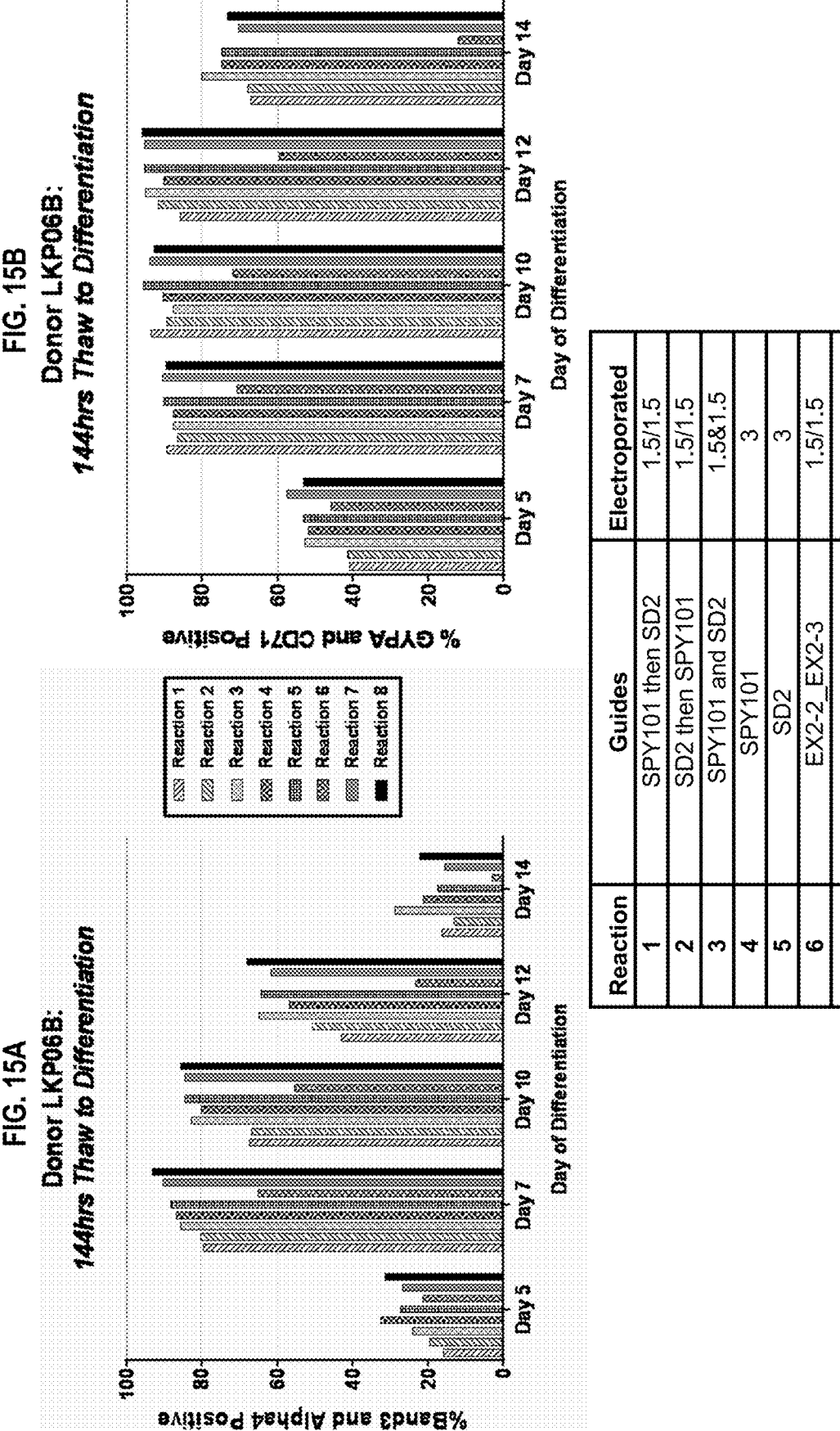
FIGS. 15A-15B show the differentiation of human mPB CD34+ cells from Donor LKP06B successively electroporated with dual guide RNAs compared to human mPB CD34+ cells from Donor LKP06B electroporated with a single guide RNA. Differentiation was determined by measuring the percentage of Band3, Alpha4, GYPA, and CD71.

Differentiation of mPBs to erythrocytes for each of the electroporated mPBs described herein was accessed by measuring the expression of Band3, Alpha4, GYPA, and CD71 for each of the electroporated mPBs at various time points (Day 5, Day 7, Day 10, Day 12, and Day 14) via FACs. As demonstrated in FIGS. 15A-B, there were minimal differences in differentiation between mPB CD34+ cells from Donor LKP06B successively electroporated with SPY101 and then SD2 (or SD2 and then SPY101) and mPB CD34+ cells from Donor LKP06B electroporated with a single guide RNA (regardless of whether the single guide electroporation used SPY101 or SD2; or simultaneously used SPY101 and SD2).

Differentiation of mPBs to erythrocytes for each of the electroporated mPBs described herein was also accessed by measuring the percentage of enucleation for each of the electroporated mPBs at various time points (Day 5, Day 7, Day 10, Day 12, and Day 14). As demonstrated in FIG. 16, there were minimal differences in enucleation between mPB CD34+ cells from Donor LKP06B successively electroporated with SPY101 and then SD2 (or SD2 and then SPY101) and mPB34+ cells from Donor LKP06B electroporated with a single guide RNA (regardless of whether the single guide electroporation used SPY101 or SD2; or simultaneously used SPY101 and SD2).

Figures 17A, 17B:
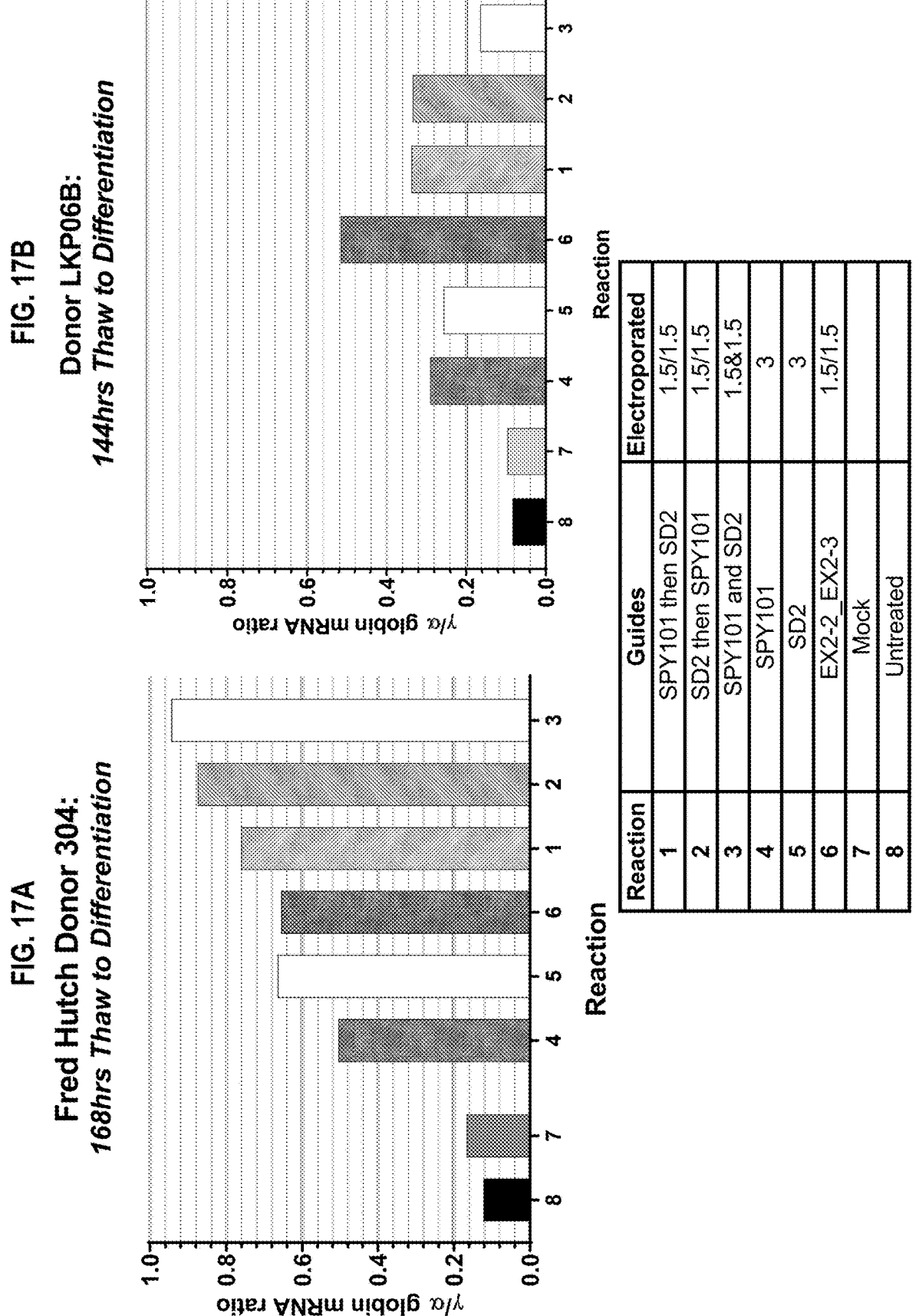
FIGS. 17A-17B show the γ/α globin mRNA ratio in human mPB CD34+ cells successively electroporated with dual guide RNAs compared to human mPB CD34+ cells electroporated with a single guide RNA.

Globin expression ($\gamma/\alpha$ globin mRNA) was measured for each of the electroporated mPBs described herein that differentiated into erythrocytes (Day 12 differentiated cells) using quantitative real-time PCR (qRT-PCR). As demonstrated in FIGS. 17A-B, $\gamma/\alpha$ globin mRNA expression increased from 15-70% for mPB CD34+ cells successively electroporated with SPY101 and then SD2 (or SD2 and then SPY101) compared to mPB CD34+ cells electroporated with a single guide RNA (regardless of whether the single guide electroporation used SPY101 or SD2; or simultaneously used SPY101 and SD2).

Figures 18A, 18B:
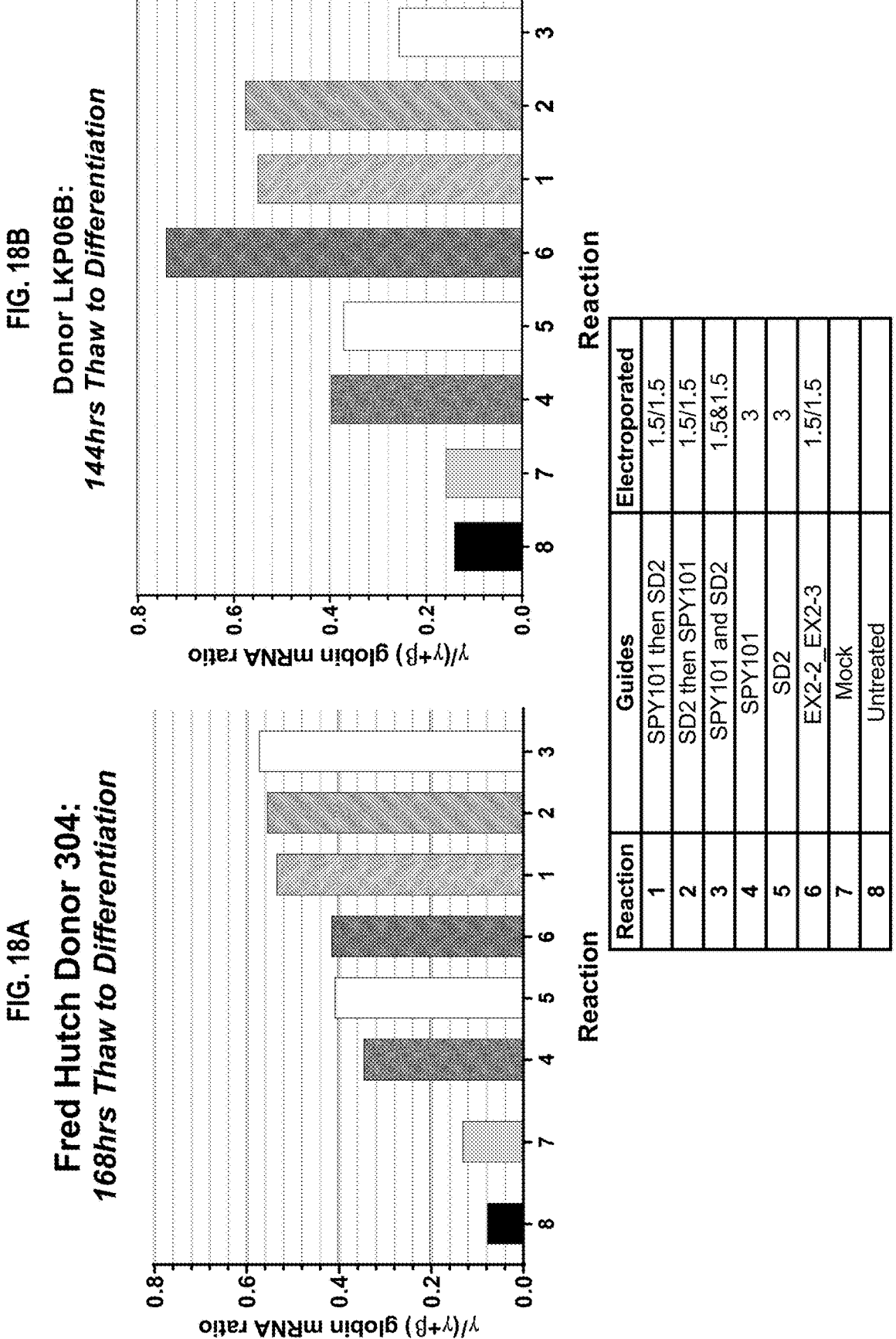
FIGS. 18A-18B show the globin mRNA ratio in human mPB CD34+ cells successively electroporated with dual guide RNAs compared to human mPB CD34+ cells electroporated with a single guide RNA.

Globin expression ($\gamma(\gamma+\beta)$ globin mRNA) was measured for each of the electroporated mPBs described herein that differentiated into erythrocytes (Day 12 differentiated cells) using qRT-PCR. As demonstrated in FIGS. 18A-B, $\gamma(\gamma+\beta)$ globin mRNA expression increased from 30-60% for mPB CD34+ cells successively electroporated with SPY101 and then SD2 (or SD2 and then SPY101) compared to mPB CD34+ cells electroporated with a single guide RNA (regardless of whether the single guide electroporation used SPY101 or SD2; or simultaneously used SPY101 and SD2).

Figures 19A, 19B:
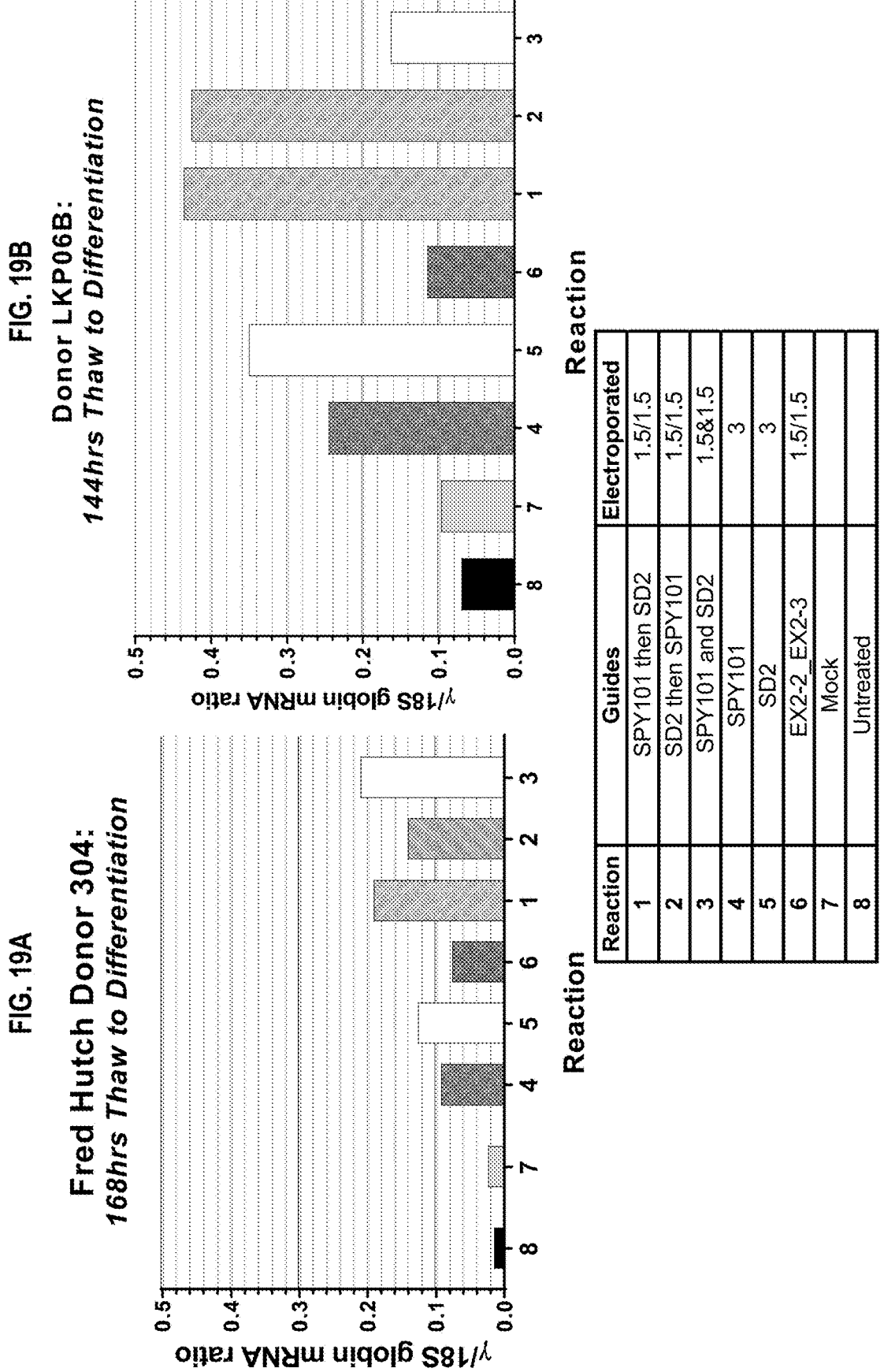
FIGS. 19A-19B show the γ/18S globin mRNA ratio in human mPB CD34+ cells successively electroporated with dual guide RNAs compared to human mPB CD34+ cells electroporated with a single guide RNA.
Figure 21A:
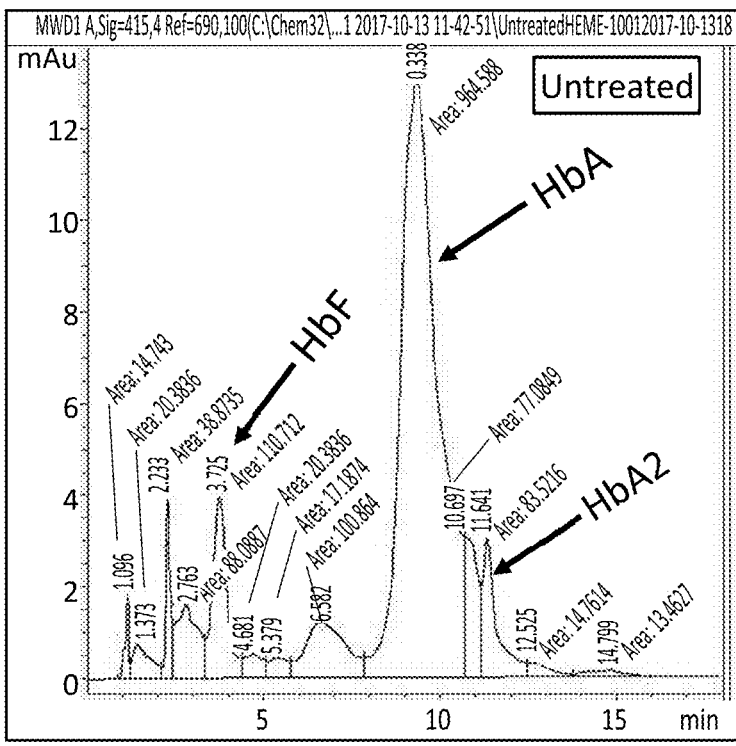
FIGS. 21A-21E show HbF expression in human mPB CD34+ cells successively electroporated with dual guide RNAs, human mPB CD34+ cells electroporated with a single guide RNA, and untreated human mPB CD34+ cells.
Figure 21B:
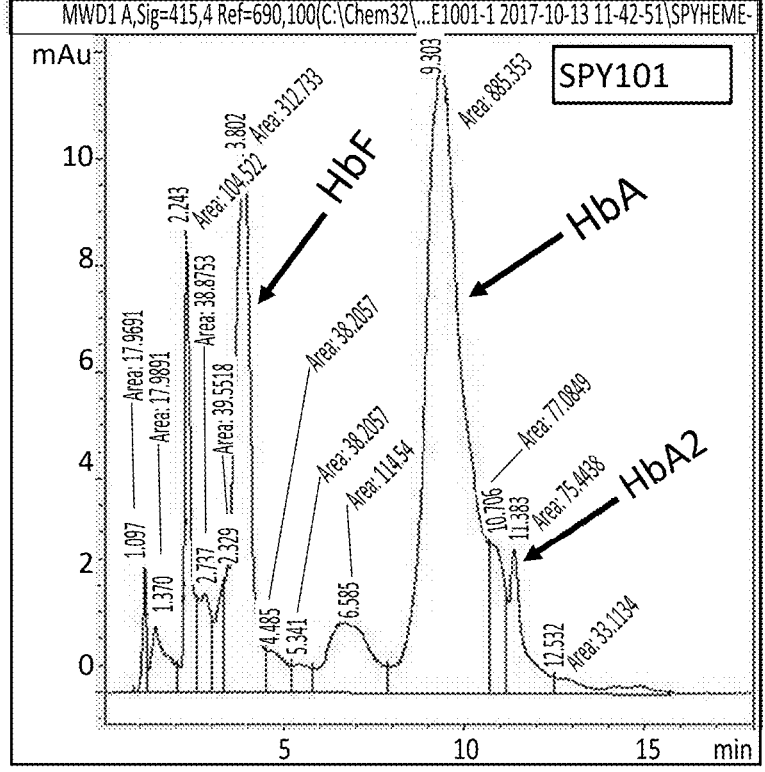
Figure 21C:
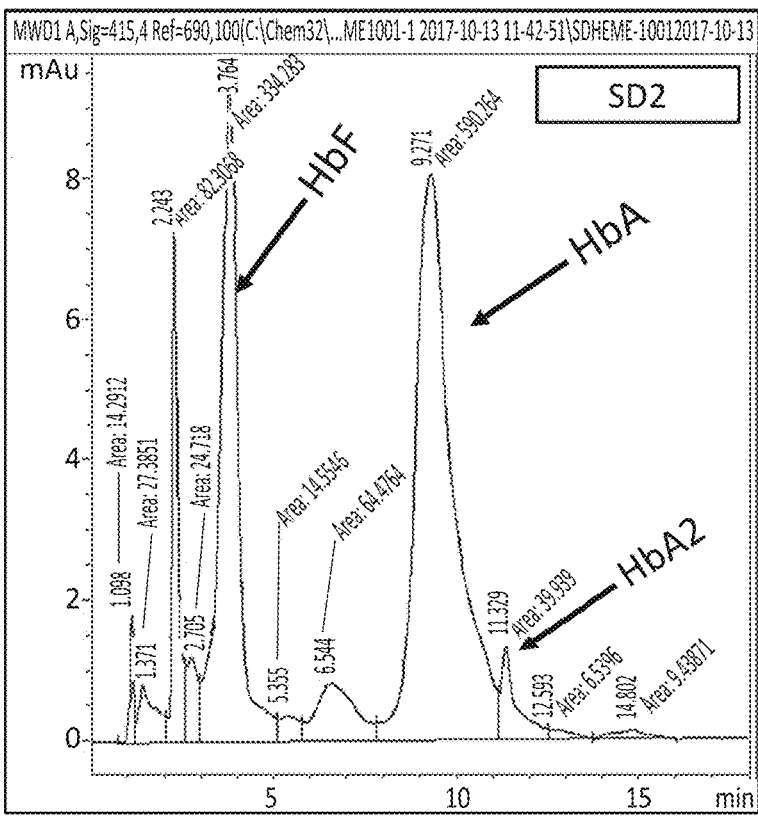
Figure 21D:
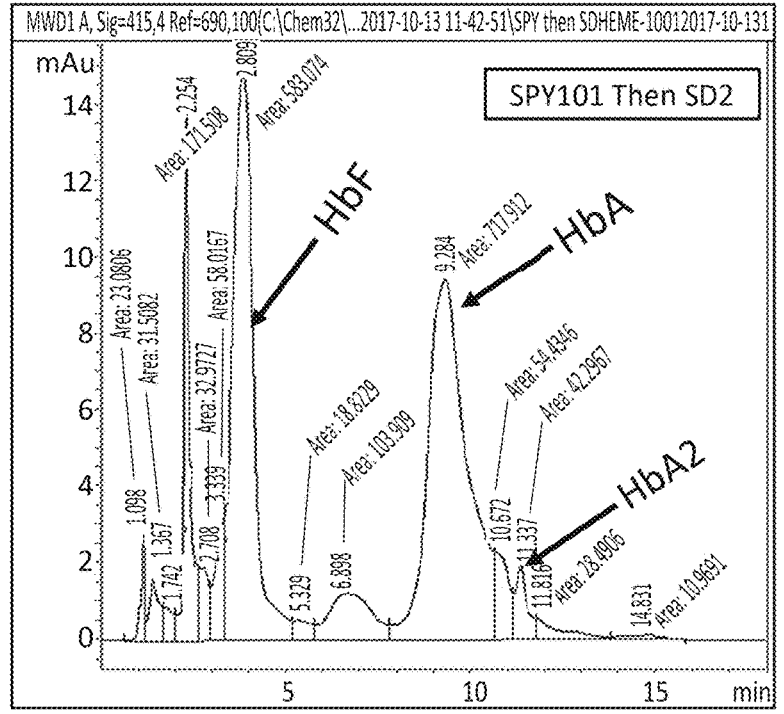
Figure 21E:
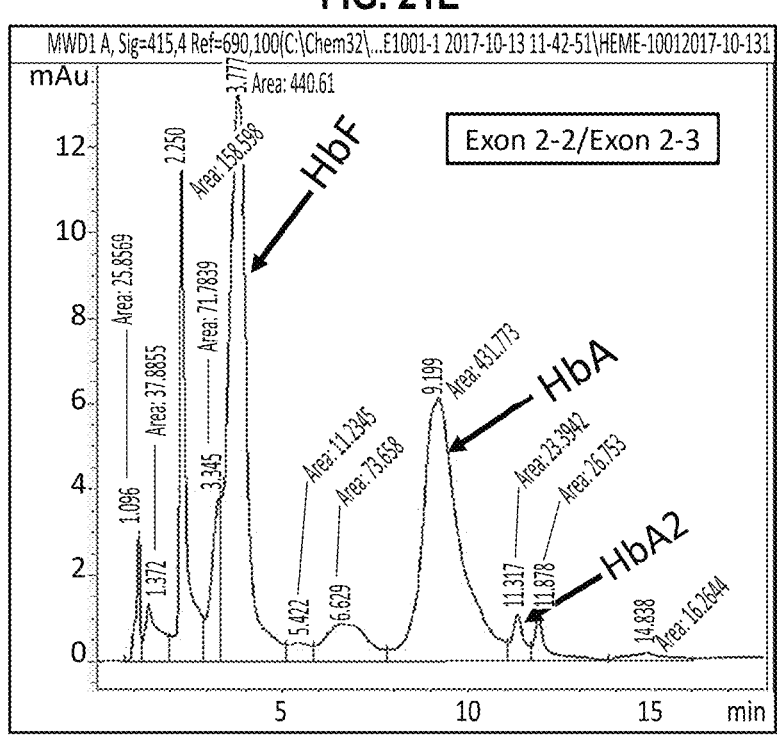

Globin expression ($\gamma/18S$ globin mRNA) was measured for each of the electroporated mPBs described herein that differentiated into erythrocytes (Day 12 differentiated cells) using qRT-PCR. As demonstrated in FIGS. 19A-B, $\gamma/18S$ globin mRNA expression increased for mPB CD34+ cells successively electroporated with SPY101 and then SD2 (or SD2 and then SPY101) compared to mPB CD34+ cells electroporated with a single guide RNA (regardless of whether the single guide electroporation used SPY101 or SD2; or simultaneously used SPY101 and SD2).

HbF expression was measured for each of the electroporated mPBs described herein that differentiated into erythrocytes (Day 17 differentiated cells) using HPLC. As demonstrated in FIGS. 20 and 21A-E, HbF expression increased for mPB CD34+ cells successively electroporated with SPY101 and then SD2 (or SD2 and then SPY101) compared to mPB CD34+ cells electroporated with a single guide RNA (regardless of whether the single guide electroporation used SPY101 or SD2; or simultaneously used SPY101 and SD2).

Figure 22:
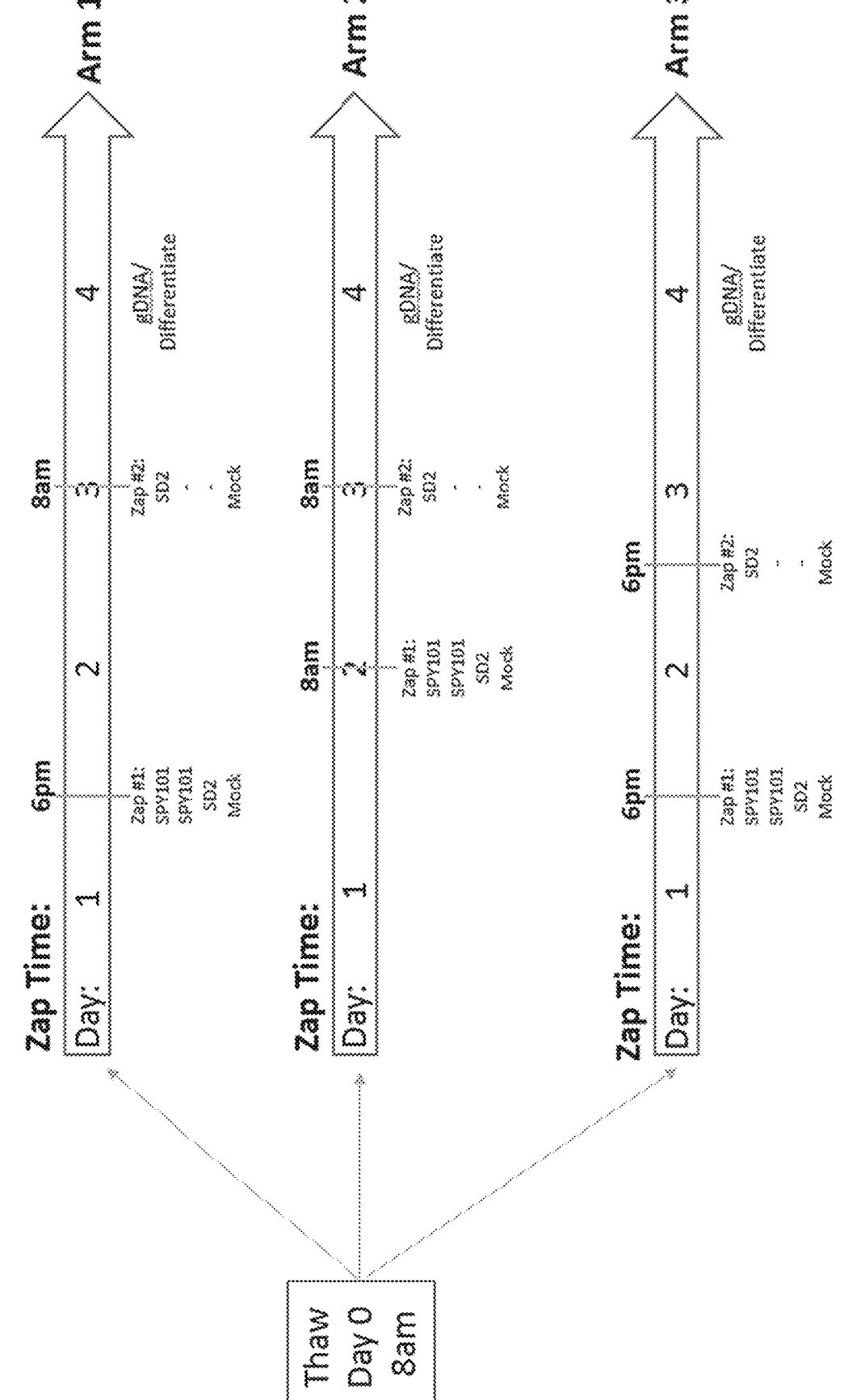
FIG. 22 shows three different experimental designs (Arms 1-3) that include successive electroporations using dual guide RNAs. Each experimental design tests different timing options for the successive electroporations.

Three different experimental designs (Arm conditions 1-3), depicted in FIG. 22, were tested to determine the optimal time points for a first electroporation and a second electroporation within a 96-hour time frame prior to differentiation and the optimal time period between the first and second electroporations. Arm 1 conditions include a first electroporation of mPB CD34+ cells at 34 hours after thawing, a second electroporation at 72-hours after thawing, and 38 hours between the first and second electroporations. Arm 2 conditions include a first electroporation of mPB CD34+ cells at 48 hours after thawing, a second electroporation at 72-hours after thawing, and 24 hours between the first and second electroporations. Arm 3 conditions include a first electroporation of mPB CD34+ cells at 34 hours after thawing, a second electroporation at 58-hours after thawing, and 24 hours between the first and second electroporations.

Successive electroporations using dual guide RNAs under Arm conditions 1-3 were performed using the experimental design shown in FIGS. 12 and 22. Human mPB CD34+ cells were obtained from Donor LKP06B and either: successively electroporated with 1.5 µg SPY101 and then 1.5 µg SD2 (SPY/SD); individually electroporated with 3 µg SPY101 (SPY); individually electroporated with 3 µg SD2 (SD); electroporated with Cas9 RNP (mock); or not electroporated (untreated).

Figures 24A, 24B:
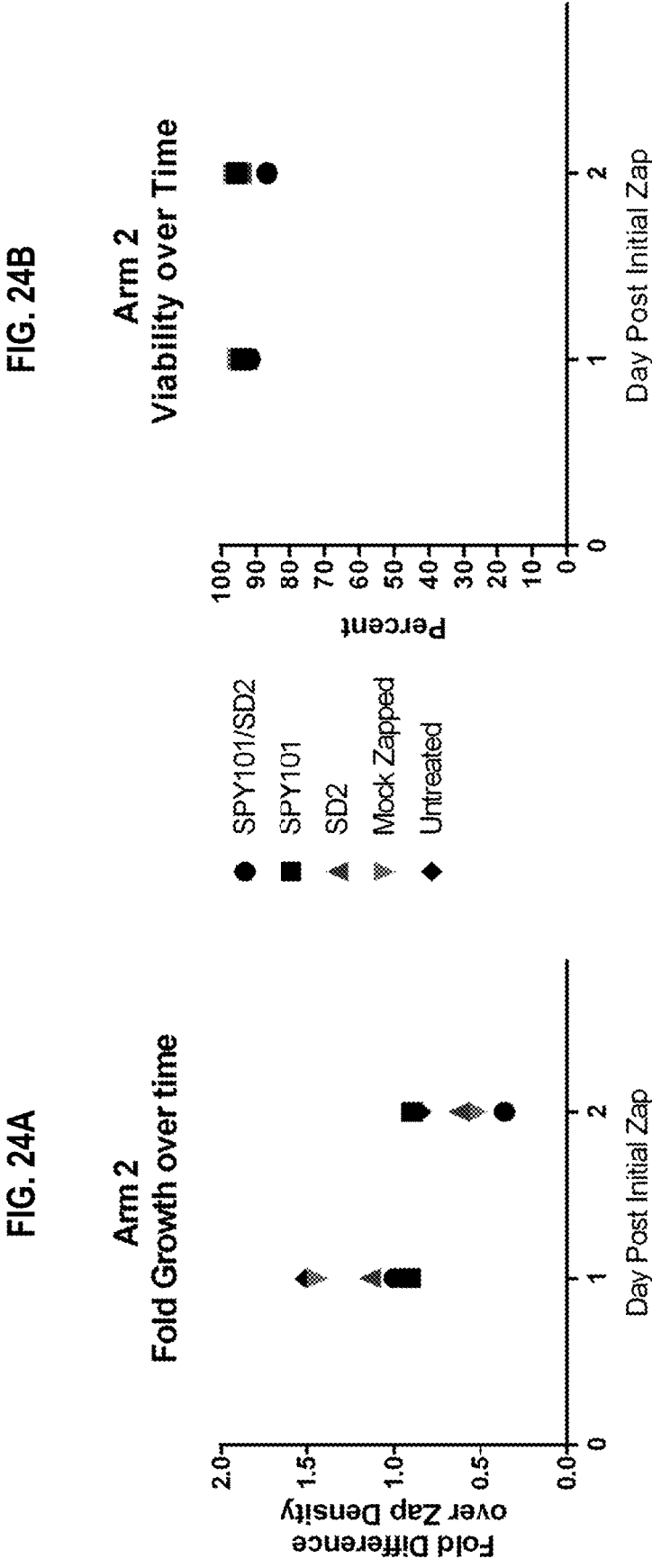
FIGS. 24A-24B show the growth kinetics and viability of human mPB CD34+ cells successively electroporated with dual guide RNAs under Arm 2 conditions compared to human mPB CD34+ cells electroporated with a single guide RNA under Arm 2 conditions.
Figures 26A, 26B:
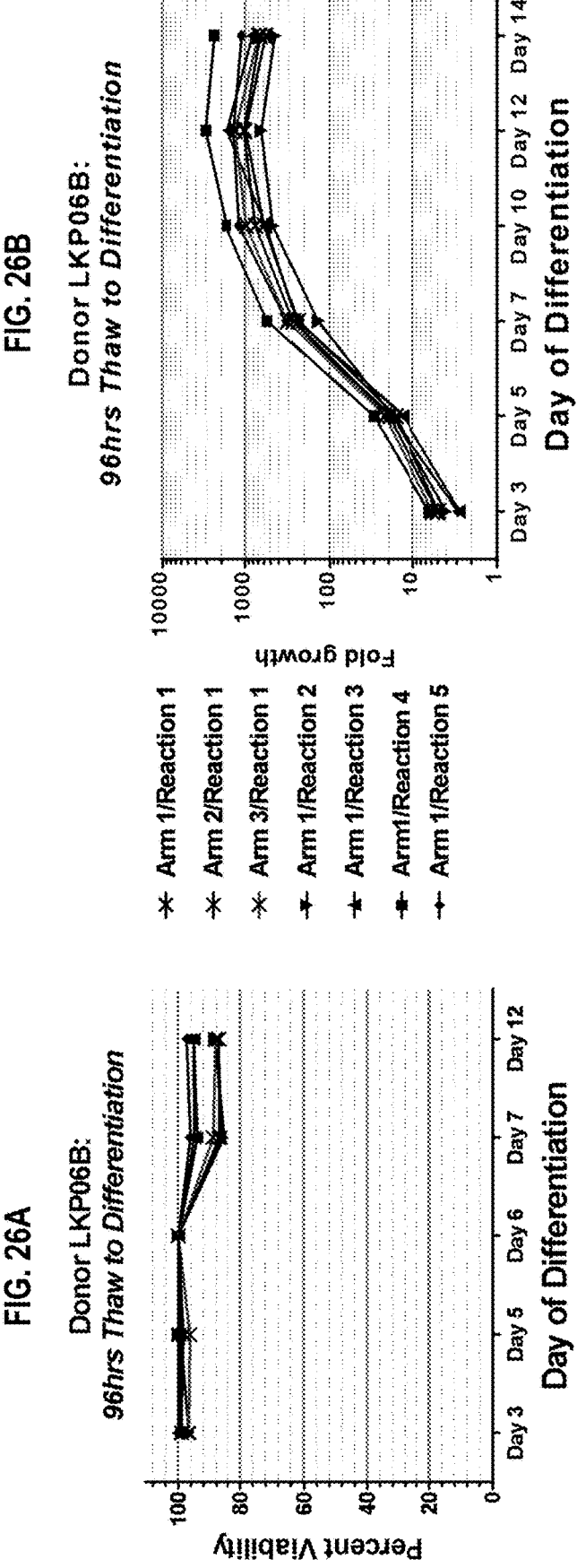
FIGS. 26A-26B shows the viability and growth kinetics of human mPB CD34+ cells successively electroporated with dual guide RNAs under Arm conditions 1-3 compared to human mPB CD34+ cells electroporated with a single guide RNA under Arm conditions 1-3.

Cell health of each of the electroporated mPBs described herein under Arm conditions 1-3 was accessed by measuring the viability and growth kinetics of the electroporated mPBs at various time points post the initial or first electroporation (Day 1, Day 2, Day 3). As demonstrated in FIGS. 23A-B, under Arm 1 conditions, there was slowed growth 1-day after the first electroporation, but the viability remained consistent. As demonstrated in FIGS. 24A-B, under the Arm 2 conditions, there was a loss of cells within 24 hours between the two electroporations, but viability remained consistent. As demonstrated in FIGS. 25A-B, under the Arm 3 conditions, there was slowed growth between the thawing of the cells and the first electroporation. There was also slowed growth between the first electroporation and second electroporation. As demonstrated in FIGS. 26A-B, there was no difference in cell viability and growth kinetics between edited mPBs and unedited mPBs throughout differentiation.

Editing rates of each of the electroporated mPBs described herein under Arm conditions 1-3 were accessed by measuring the cutting efficiencies (percent Indels) of cells from each of the electroporated mPBs. Genomic DNA was isolated at Day 3 and cutting efficiency was evaluated using TIDE analysis. As demonstrated in FIG. 27, editing rates are similar between mPB CD34+ cells from Donor LKP06B successively electroporated with SPY101 and then SD2 and mPB CD34+ cells from Donor LKP06B electroporated with a single guide RNA (a single guide electroporation used SPY101 or SD2). These results demonstrate that the timing between thaw and electroporations or in between electroporations does not impact editing rates.

Figure 28A:
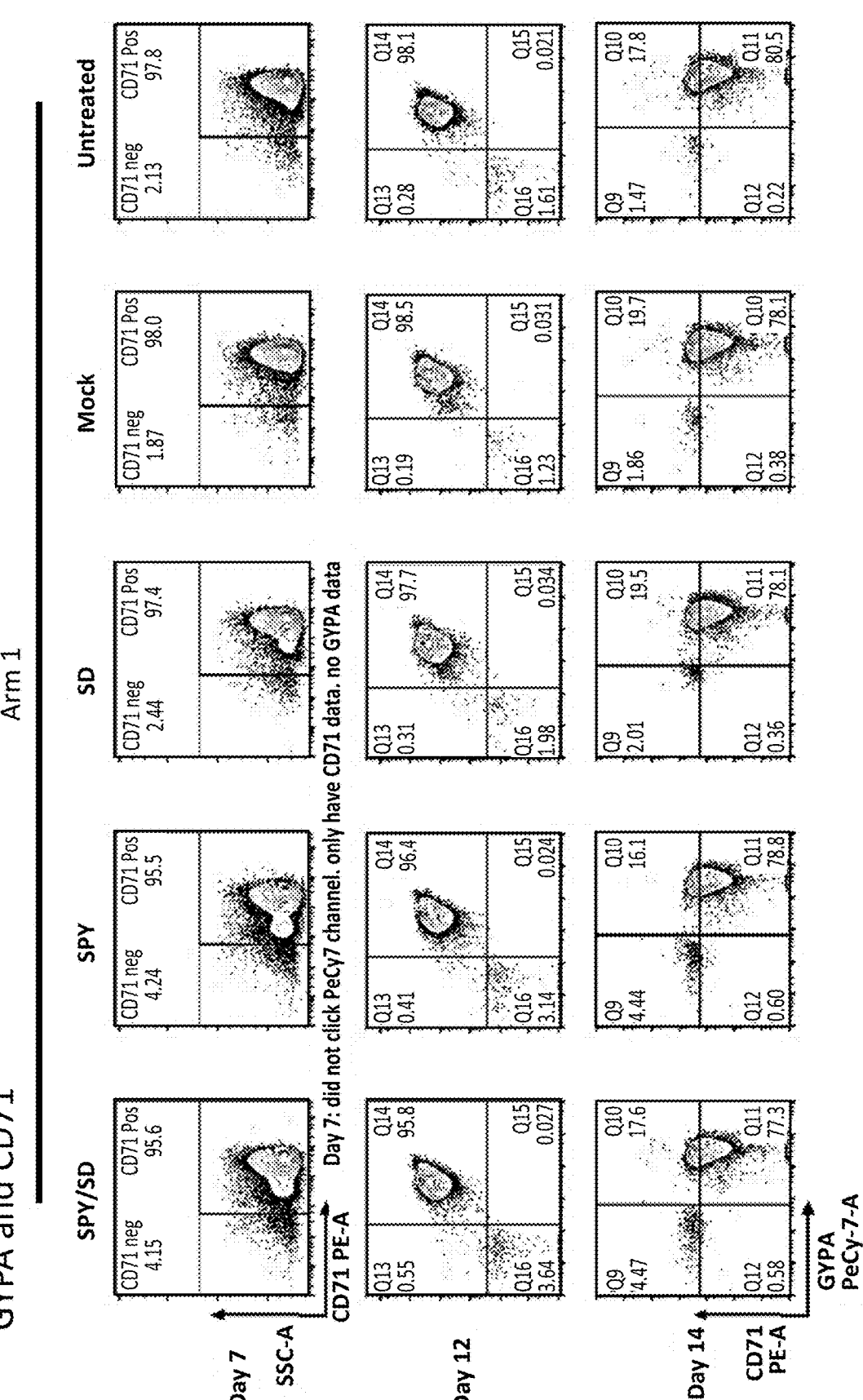
FIGS. 28A-28B show the differentiation of human mPB CD34+ cells successively electroporated with dual guide RNAs under Arm conditions 1-3 compared to human mPB CD34+ cells electroporated with a single guide RNA under Arm conditions 1-3. Differentiation was determined by measuring the percentage of Band3, Alpha4, GYPA, and CD71.
Figure 28A:
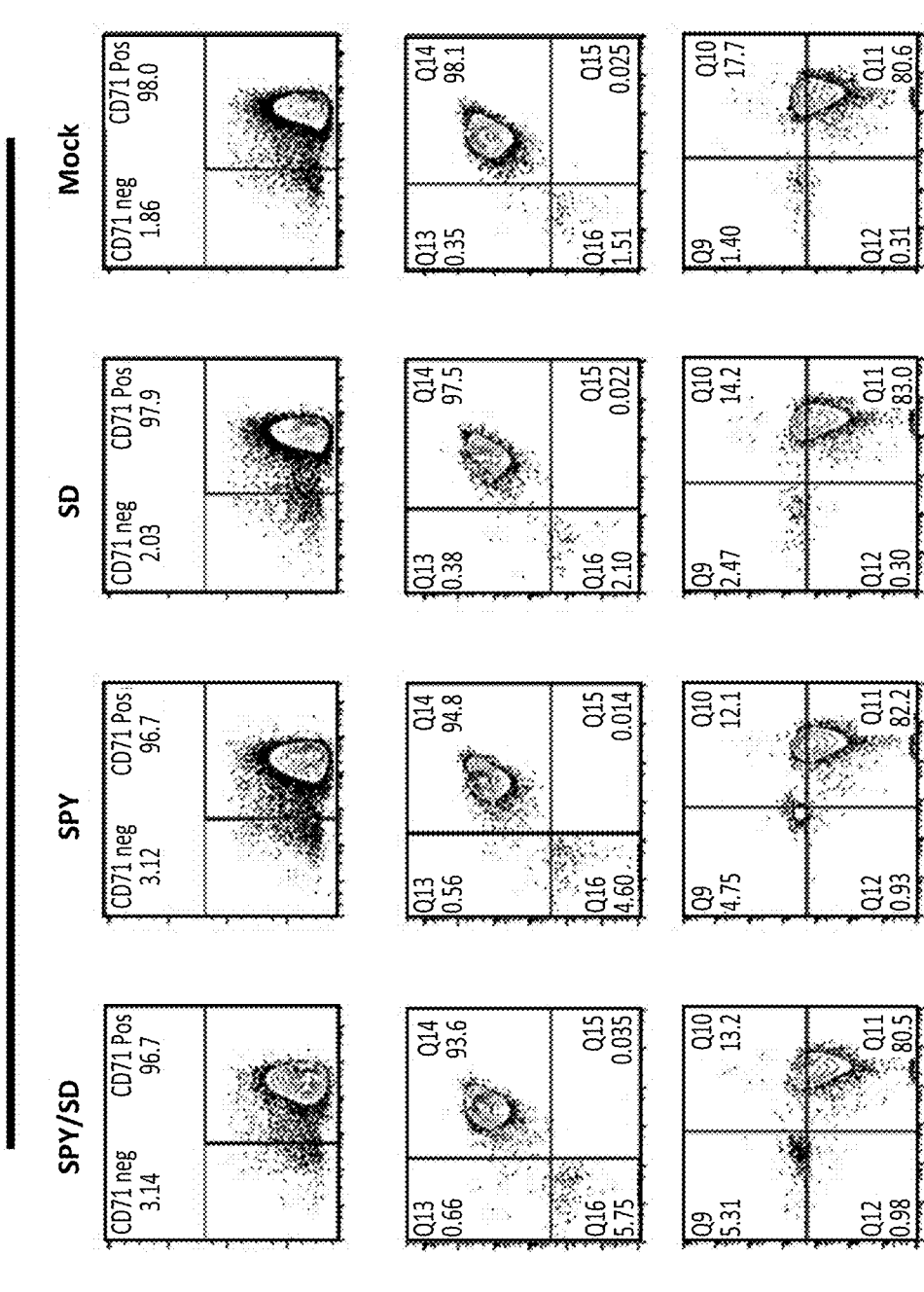
Figure 28A:
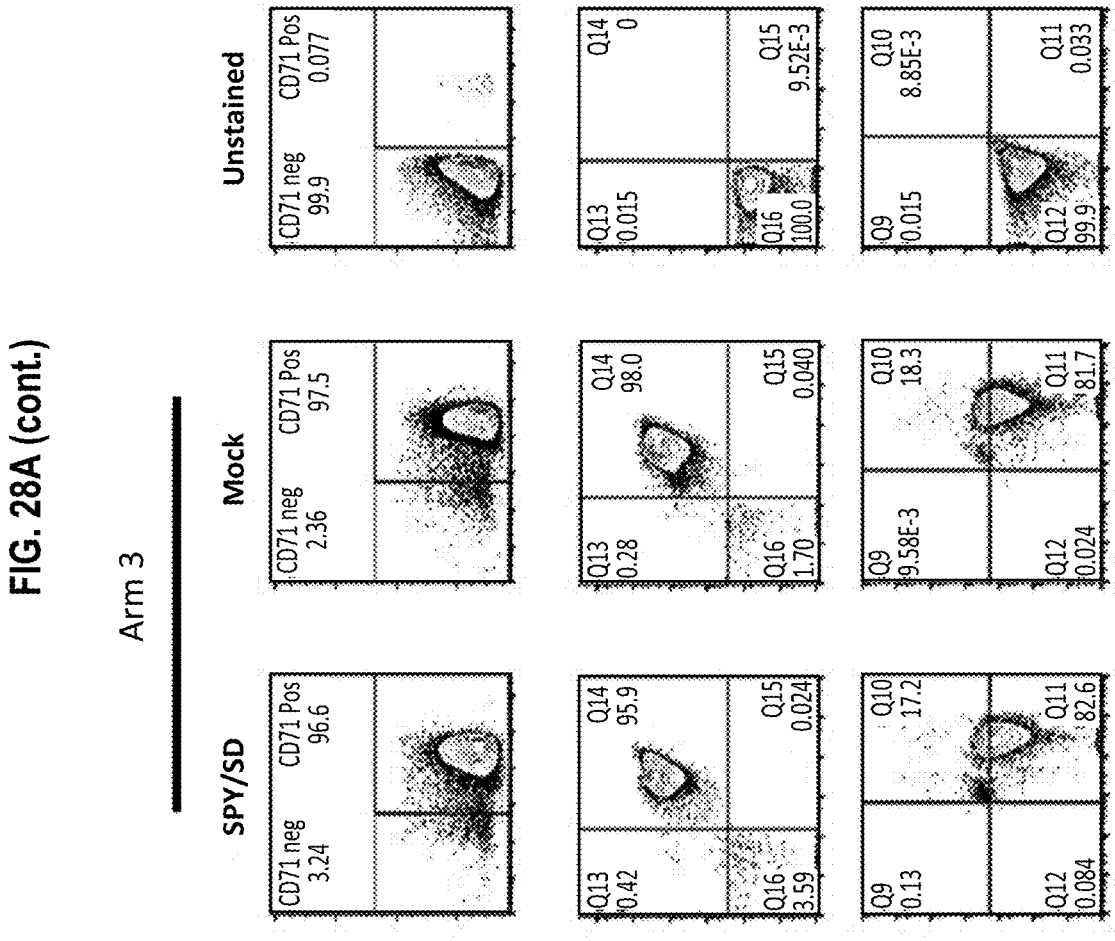
Figure 28B:
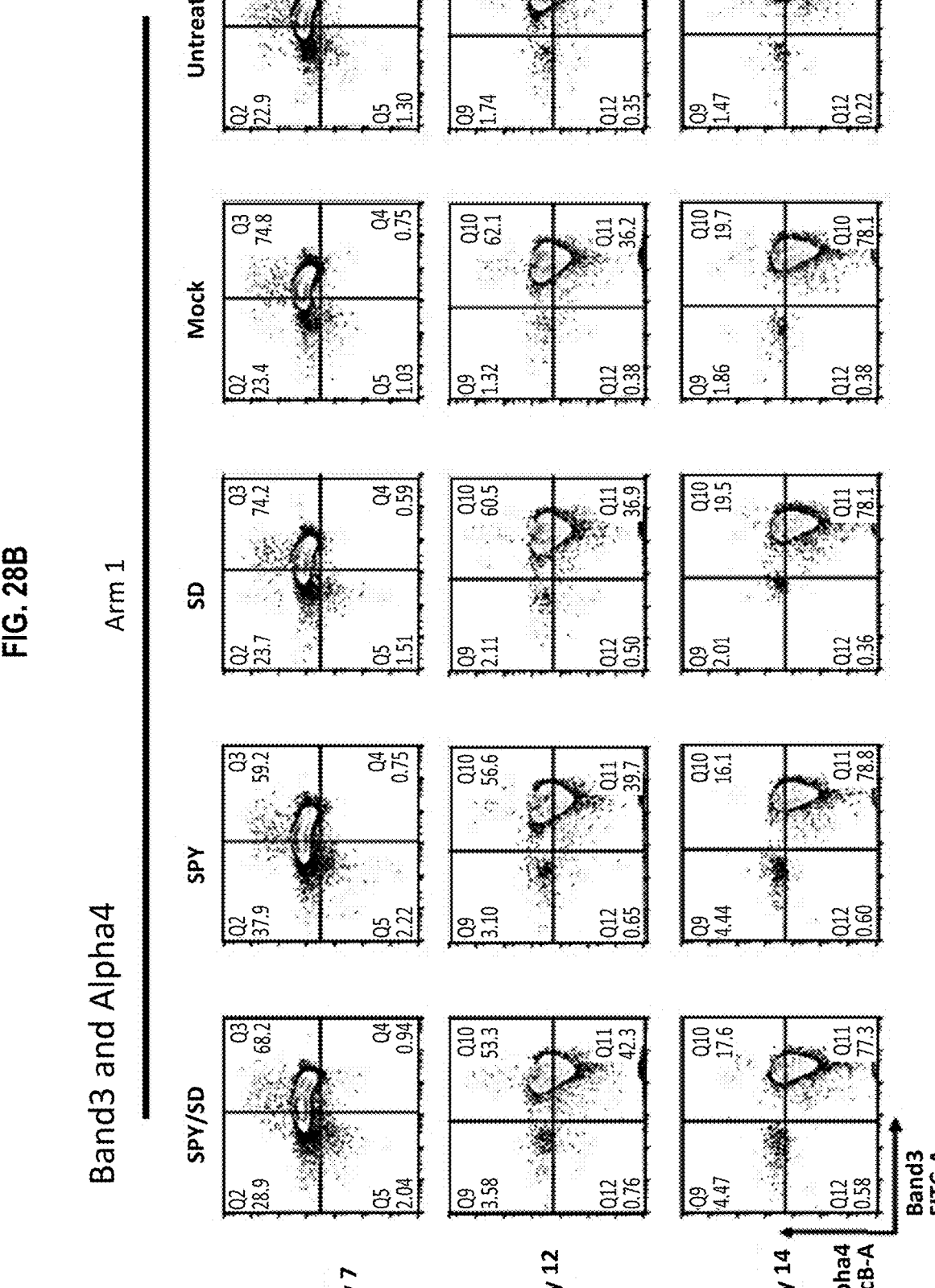
Figure 28B:
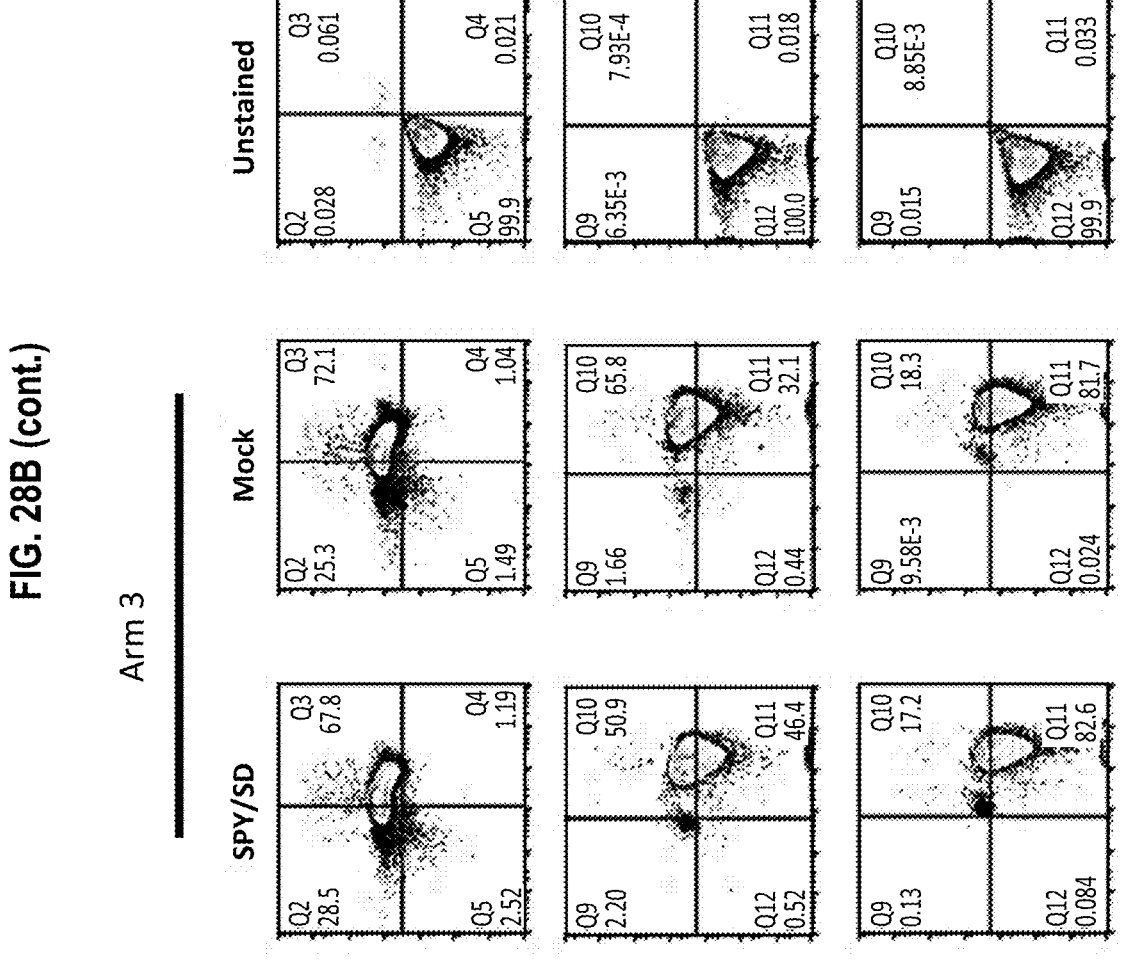

Differentiation of mPBs to erythrocytes for each of the electroporated mPBs described herein under Arm conditions 1-3 was accessed by measuring the expression of Band3, Alpha4, GYPA, and CD71 for each of the electroporated mPBs at various time points (Day 7, Day 12, and Day 14) via FACs. As demonstrated in FIGS. 28A-B, there were no differences in differentiation between mPB CD34+ cells from Donor LKP06B successively electroporated with SPY101 and then SD2 under Arm conditions 1-3 and mPB CD34+ cells from Donor LKP06B electroporated with a single guide RNA (an electroporation using SPY101 or SD2) under Arm conditions 1-3.

Figure 29:
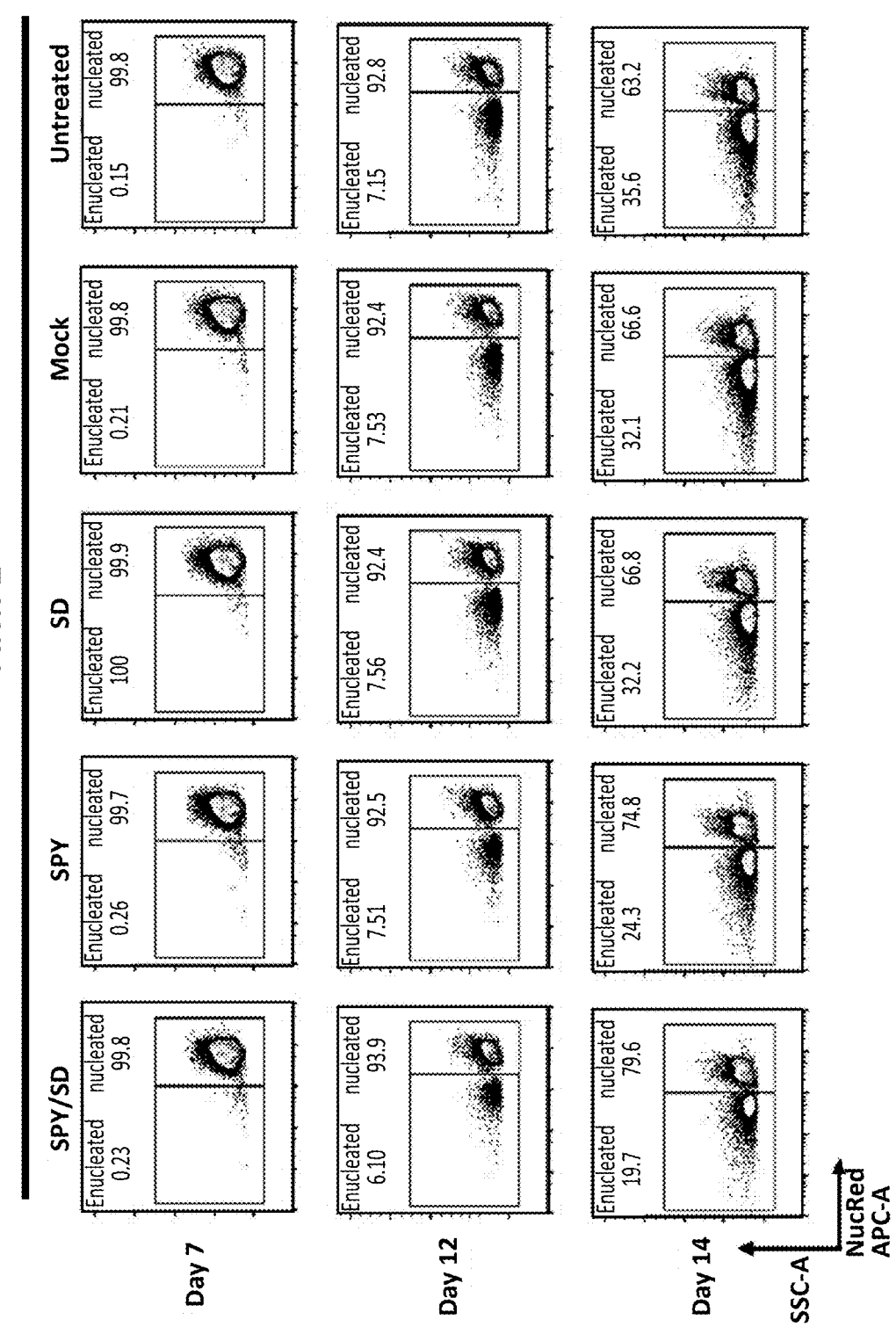
FIG. 29 shows the enucleation of human mPB CD34+ cells successively electroporated with dual guide RNAs under Arm conditions 1-3 compared to human mPB CD34+ cells electroporated with a single guide RNA under Arm conditions 1-3.
Figure 29:
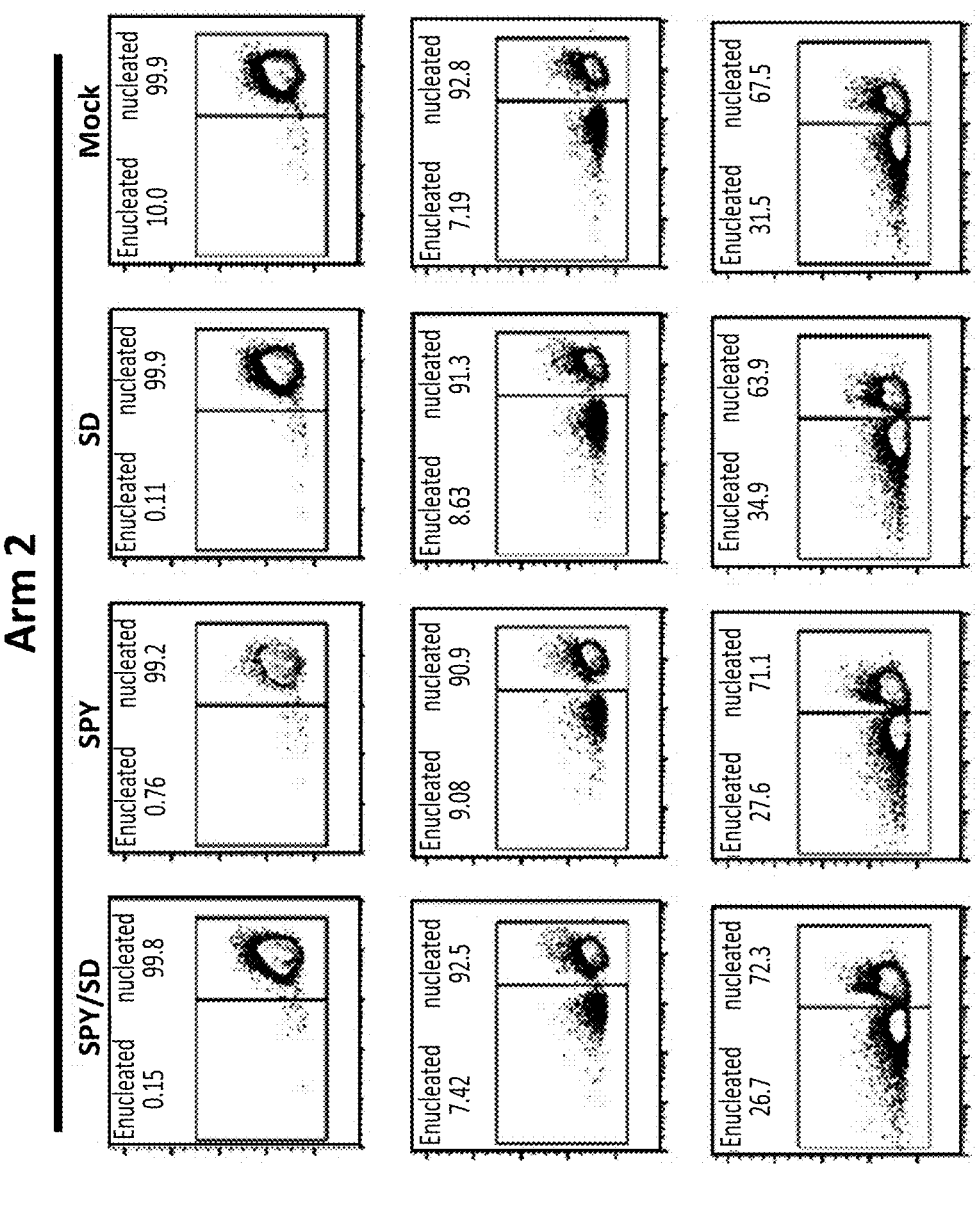
Figure 29:
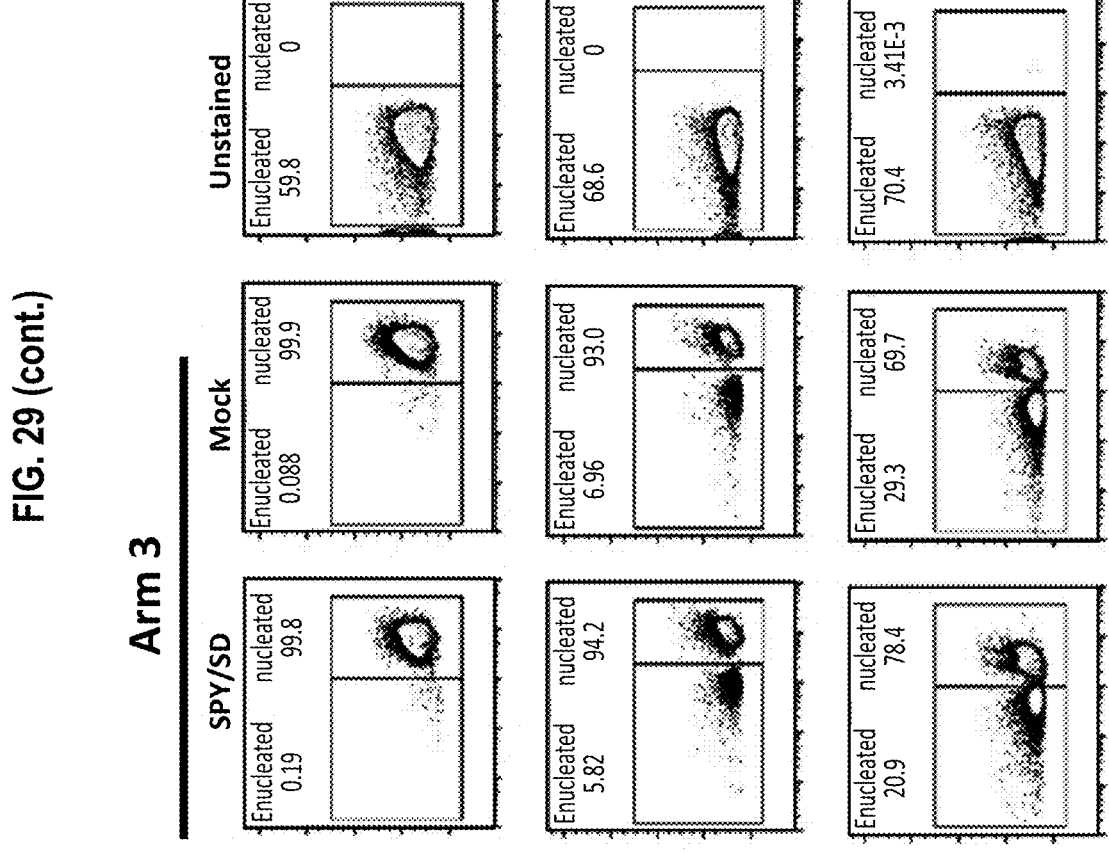

Differentiation of mPBs to erythrocytes for each of the electroporated mPBs described herein under Arm conditions 1-3 was also accessed by measuring the level of enucleation for each of the electroporated mPBs at various time points (Day 7, Day 12, and Day 14). As demonstrated in FIG. 29, there were no differences in differentiation between mPB CD34+ cells from Donor LKP06B successively electroporated with SPY101 and then SD2 under Arm conditions 1-3 and mPB CD34+ cells from Donor LKP06B electroporated with a single guide RNA (an electroporation using SPY101 or SD2) under Arm conditions 1-3.

Figure 30:
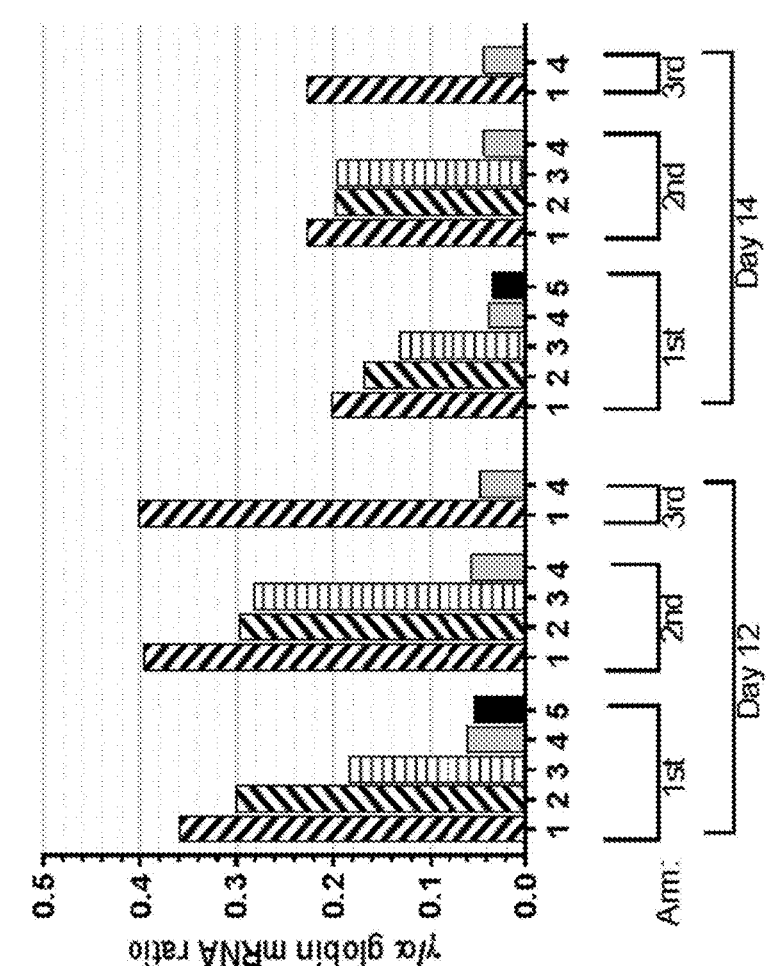
FIG. 30 shows the γ/α globin mRNA ratio in human mPB CD34+ cells from Donor LKP06B successively electroporated with dual guide RNAs under Arm conditions 1-3 compared to human mPB CD34+ cells from Donor LKP06B electroporated with a single guide RNA under Arm conditions 1-3.

Globin expression (γ/α globin mRNA) was measured using qRT-PCR for each of the electroporated mPBs described herein that differentiated into erythrocytes (Day 12 differentiated cells). Each of the electroporated mPBs was electroporated under Arm conditions 1-3. As demonstrated in FIG. 30, the timing between the thaw and first electroporation and timing between the first and second electroporations does not impact the γ/α globin mRNA percent increase between mPB CD34+ cells successively electroporated with SPY101 and then SD2 and mPB CD34+ cells electroporated with a single guide RNA (a single guide electroporation using SPY101 or SD2).

Globin expression (γ/(γ+β) globin mRNA) was measured using qRT-PCR for each of the electroporated mPBs described herein that differentiated into erythrocytes (Day 12 differentiated cells). Each of the electroporated mPBs was electroporated under Arm conditions 1-3. As demonstrated in FIG. 31, the timing between the thaw and first electroporation and timing between the first and second electroporations does not impact the γ/(γ+β) globin mRNA percent increase between mPB CD34+ cells successively electroporated with SPY101 and then SD2 and mPB CD34+ cells electroporated with a single guide RNA (a single guide electroporation using SPY101 or SD2).

Globin expression (γ/18S globin mRNA) was measured using qRT-PCR for each of the electroporated mPBs described herein that differentiated into erythrocytes (Day 12 differentiated cells). Each of the electroporated mPBs was electroporated under Arm conditions 1-3. As demonstrated in FIG. 32, the timing between the thaw and first electroporation and timing between the first and second electroporations does not impact the γ/18S globin mRNA percent increase between mPB CD34+ cells successively electroporated with SPY101 and then SD2 and mPB CD34+ cells electroporated with a single guide RNA (a single guide electroporation using SPY101 or SD2).

Example 36—Successive Electroporations Using Dual Guide RNAs (SPY101 and SD2) in a NSG Mouse Model System Human CD34+ cells that had been edited with Cas9/gRNAs using successive electroporation were introduced into NSG mice (immunodeficient mice) in order to evaluate on-target gene editing, translocations, and human chimerism in mouse blood and bone marrow samples.

Two different experimental designs, as shown in FIGS. 33A-33B, were utilized. The first design involved a first electroporation 36 hours after thawing CD34+ cells followed by a second electroporation 72 hours after thawing (36 hours between electroporations). The second design involved a first electroporation 48 hours after thawing CD34+ cells followed by a second electroporation 96 hours after thawing (48 hours between electroporations). In both experimental designs, cells were intravenously dosed into NSG mice 96 hours after thawing of cells and following successive electroporation. The gRNAs (or mock doses) used during the first and second electroporations are provided in FIG. 33B.

Samples of peripheral blood were taken from all mice at weeks 8 and 12; mice were sacrificed at week 16. Peripheral blood samples were subsequently tested for human chimerism, as shown in FIG. 34. Mice transplanted with cells edited using a successive electroporation method (e.g., 48/48/6 group with guides, e.g., first electroporation at hour 48, second electroporation at hour 96, transplantation at hour 102) show a reduction in % chimerism relative to the Mock EP group.

Bone marrow was extracted from the mice after death at week 16 and similarly tested for human chimerism, as shown in FIG. 35. Mice transplanted with cells edited using a successive electroporation method (e.g., 48/48/6 group with guides, e.g., first electroporation at hour 48, second electroporation at hour 96, transplantation at hour 102) show a reduction in % chimerism relative to the Mock EP group. Genomic DNA of bone marrow samples were also tested for percent indels resulting from the gene editing prior to cellular administration. As shown in FIG. 36, mice in the 48/48/6 group with guides, e.g., first electroporation at hour 48, second electroporation at hour 96, showed high % indels. These data demonstrate that successive electroporation strategies provide surprisingly effective persistence of genetic editing, e.g., in bone marrow tissues.

Example 37—Successive Electroporations Using Dual Guide RNAs in Human mPB CD34+ Cells from Donor LP06a and Donor LKP12

Human mPB CD34+ cells from Donor LP06a and Donor LKP12 were successively electroporated with Cas9 endonuclease and two gRNAs to edit the human beta globin locus on chromosome 11 (HPFH5 gRNAs, e.g., HPFH5-1, HPFH5-D, HPFH5-T5, and HPFH5-T7; Kenya gRNAs, e.g., Kenya-K5, Kenya-K17) and a BCL11A locus on chromosome 2 (1450 gRNA, SPY101 gRNA).

As shown in FIG. 37, cells were subjected to a first electroporation with gRNA(s) and Cas9 3.5 days before a first genomic DNA (gDNA) harvest and a second electroporation (in selected reaction conditions) with gRNAs and Cas9 2 days before the first genomic DNA harvest. gDNA was harvested on Day 0 and Day 3. Beginning at Day 7, cells were allowed to differentiate and enucleate.

Reaction conditions included successive electroporation experiments as well as single electroporation experiments.

As shown in FIG. 38, each reaction condition was assayed for average fold growth during the differentiation stage, editing at Chr2, editing (deletion) at Chr11, and percent HbF relative to (HbF+HbA). Reaction conditions with two successive electroporations with two gRNAs provided editing at Chr2 and Chr11 at comparable levels to corresponding single electroporation reaction conditions. Notably, reaction conditions with two successive electroporations with two gRNAs provided increased HbF expression (see, e.g., 64±2% HbF for 'SPY Then HPFH5-1&D' reaction condition) relative to single electroporation conditions (see, e.g., 38±7% HbF for 'SPY Alone').

As shown in FIG. 39, a ddPCR assay was performed on Days 4 and 14 of the experiment to test for deletion rates (%) in Chr11. Most reaction conditions provided similar levels of deletion, with deletion % between about 30-40%. However, notably, successive electroporation to introduce two different gRNA sets that targeted Chr11 (see, 'HPFH5-T7&D Then HPFH5-1&T5') provided deletion % of about 60% at Day 4 and about 55% at Day 14.

Cells of the experiment were subjected to an enucleation gating strategy using FACS (FIG. 40). Reaction conditions using successive electroporation with two gRNAs had levels and rates of enucleation that were comparable with single electroporation reaction conditions (FIG. 41).

At Day 18 of the experiment, after differentiation was complete, cells were again tested for percent HbF relative to (HbF+HbA). As shown in FIG. 42, reaction conditions using successive electroporation with two gRNAs had higher relative levels of HbF. Note that percent HbF was determined using HPLC. Protein globin levels may routinely be measured using HPLC.

Example 38—Successive Electroporations Using Varying Amounts of Cas9 Endonuclease Human mPB CD34+ cells from Donor LP06a and Donor LKP12 were successively electroporated with two gRNAs and varying levels of Cas9 endonuclease to edit the human beta globin locus on chromosome 11 and a BCL11A locus on chromosome 2.

As shown in FIG. 43, cells were subjected to a first electroporation with 1450 gRNA and varying amounts of Cas9 endonuclease 3.5 days before a first genomic DNA (gDNA) harvest and a second electroporation with HPFH5 gRNAs and varying amounts of Cas9 endonuclease 2 days before the first genomic DNA harvest. gDNA was harvested on Day 0 and Day 3. Beginning at Day 7, cells were allowed to differentiate and enucleate.

As shown in FIGS. 44-46, each reaction condition was assayed for editing at Chr2, editing (deletion) at Chr11, mRNA transcript ratios for (γ globin)/(α globin), mRNA transcript ratios for (γ globin)/(γ globin+β globin), and percent HbF relative to (HbF+HbA). Notably, levels of gene editing and percent HbF were consistent for experiments using 0.375, 0.75, 1.5, and 3 µg Cas9 endonuclease, particularly in the first electroporation step. These data suggest that relatively small amounts of endonuclease can provide useful and efficient gene editing in a successive electroporation context.

Example 38—Comparison of Differing Electroporation Strategies in Human mPB CD34+ Cells on Gene Editing and Translocations An experimental design, as shown in FIG. 47, to compare single electroporation with one guide RNA, single electroporation with two guide RNAs, and successive electroporations with two guide RNAs to edit a BCL11A locus on Chr2 (SPY101 gRNA) and a human beta globin locus on Chr11 (SD2 gRNA) in human mPB CD34+ cells from Fred Hutch Donor 304 was performed.

Cells were subjected to a first electroporation with gRNA (s) and Cas9 4 days before a second genomic DNA (gDNA) harvest and a second electroporation (in selected reaction conditions) with gRNA(s) and Cas9 2 days before the second genomic DNA harvest. gDNA was harvested on Day−2 and Day 0. Beginning at Day 5, cells were allowed to differentiate.

Reaction conditions included single electroporation experiments with one guide RNA (SPY101 or SD2) and Cas9, single electroporation experiments with both SPY101 and SD2 (i.e., simultaneous electroporation), and successive electroporations with both SPY101 and SD2.

Genomic DNA was tested for % indels, as shown in FIG. 48. Cells that were successively electroporated with two guide RNAs (SPY101/SD2; SD2/SPY101) had comparable levels of percent indels relative to single electroporation experiments with one or two gRNAs.

There are three potential translocation events when using these two gRNAs (SPY101 and SD2), as shown in FIG. 49. The three points of fusion (translocation event) occur at the sites cut by Cas9 when directed by the aforementioned gRNAs. The third of these fusions occurs as a result of an inversion of Chr11 induced by SD2.

In order to assess relative amounts of translocations across reaction conditions of this experimental design, genomic DNA was amplified using PCR. PCR primers specific for each of the three possible translocations were used to amplify each gDNA sample from edited cells. Notably, as shown in agarose gels of FIG. 50, it was found that successive electroporation conditions (e.g., SPY101 Then SD2) produced fewer translocation events than simultaneous electroporation conditions (e.g., SPY101 And SD2). These data suggest that successive electroporation produce fewer undesirable and/or off-target gene edits than simultaneous electroporation.

Example 39—Comparison of Differing Electroporation Strategies in Human mPB CD34+ Cells on Gene Editing and Translocations An experimental design, as shown in FIG. 51, to compare single electroporation with one guide RNA, single electroporation with two guide RNAs, and successive electroporations with two guide RNAs to edit a BCL11A locus on Chr2 (SPY101 gRNA) and a human beta globin locus on Chr11 (SD2 gRNA) in human mPB CD34+ cells from Fred Hutch Donor 304 was performed. This experimental design further tested the effect of altering the time between the first and second electroporations in successive electroporation conditions.

Cells were subjected to a first electroporation with gRNA/Cas9 on either Day 3 or Day 3.5 after thawing cells. In successive electroporation reaction conditions, a second electroporation with gRNA/Cas9 was performed on Day 5. Genomic DNA (gDNA) was harvested from Days 6-10.

Reaction conditions included single electroporation experiments with one guide RNA (SPY101 or SD2) and Cas9, single electroporation experiments with both SPY101 and SD2 (i.e., simultaneous electroporation), and successive electroporations with both SPY101 and SD2.

Genomic DNA was tested for % indels, as shown in FIG. 52. Cells that were successively electroporated with a 48-hour period between electroporations had slightly higher levels of percent indels relative to cells that were successively electroporated with a 36-hour period between electroporations. Cells edited with simultaneous electroporation strategies had significantly lower percent indels than all successive electroporation conditions.

As described in Example 38 and shown in FIG. 49, there are three potential translocation events when using these two gRNAs (SPY101 and SD2). In order to assess relative amounts of translocations across reaction conditions of this experimental design, genomic DNA was amplified using PCR. PCR primers specific for each of the three possible translocations were used to amplify each gDNA sample from edited cells. Notably, as shown in agarose gels of FIGS. 53A-53C, it was found that successive electroporation conditions (e.g., SPY101 Then SD2) produced fewer translocation events than simultaneous electroporation conditions (e.g., SPY101 And SD2). Further, successive electroporation conditions with a 48-hour period between electroporations had fewer translocation events than conditions with a 36-hour period.

A ddPCR assay for secondary determination of chromosomal translocations following gene editing with SD2 and SPY101 gRNAs was then designed, as shown in FIG. 54. The 'A:E' translocation event is assayed by the use of one primer that binds the 'A' region; and a second primer that binds the 'E' region (amplicon size of around 600 bp). The 'D:C' translocation event is assayed by the use of one primer that binds 'D' region; and a second primer that binds the 'C' region (amplicon size of around 2000 bp). The 'A:D' translocation event is assayed by the use of one primer that binds 'A' region; and a second primer that binds the 'D' region (amplicon size of around 600 bp). The 'C:E' translocation event is assayed by the use of one primer that binds 'C' region; and a second primer that binds the 'E' region (amplicon size of around 2000 bp).

This ddPCR assay provided secondary confirmation, as shown in FIG. 55, that simultaneous electroporation with two gRNAs (SPY101 And SD2) leads to increased translocation events compared to successive electroporation with two gRNAs (e.g., SPY101 Then SD2). Further, this assay provides secondary confirmation that successive electroporation conditions with a 48-hour period between electroporations had fewer translocation events than conditions with a 36-hour period.

Note Regarding Illustrative Examples

While the present disclosure provides descriptions of various specific aspects for the purpose of illustrating various aspects of the present invention and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

---

SEQUENCE LISTING

The patent contains a lengthy sequence listing. A copy of the sequence listing is available in electronic form from the USPTO web site (https://seqdata.uspto.gov/docdetail?docId=US12644137B2). An electronic copy of the sequence listing will also be available from the USPTO upon request and payment of the fee set forth in 37 CFR 1.19(b)(3).

---

What is claimed is:

1. An ex vivo or in vitro method of genome editing in a human cell comprising: introducing into the human cell one or more deoxyribonucleic acid (DNA) endonuclease and two or more guide ribonucleic acids (gRNAs) to effect (i) a first single-strand break (SSB) or double-strand break (DSB) within a human beta globin locus on chromosome 11; and (ii) a second SSB or DSB within a BCL11A gene on chromosome 2 or a DNA sequence that encodes a transcriptional control region of the BCL11A gene on chromosome 2;

wherein the first SSB or DSB results in a permanent deletion or inversion within the human beta globin locus on chromosome 11 or a mutation within the human beta globin locus on chromosome 11;

wherein the second SSB or DSB results in a permanent deletion or inversion within the BCL11A gene on chromosome 2, a mutation within the BCL11A gene on chromosome 2, a permanent deletion or inversion within the DNA sequence that encodes a transcriptional control region of the BCL11A gene on chromosome 2, or a mutation within the DNA sequence that encodes a transcriptional control region of the BCL11A gene on chromosome 2; and wherein the two or more gRNAs comprise at least two of the nucleic acid sequences of SEQ ID NOs: 228,428-228,436.

2. The method of claim 1, wherein the permanent deletion within the human beta globin locus on chromosome 11 is a hereditary persistence of fetal hemoglobin (HPFH) deletion selected from the group consisting of a HPFH-4 deletion, a HPFH-5 deletion, a HPFH-Kenya deletion, a HPFH-Black deletion, a large Corfu deletion, a small Corfu deletion, a small deletion, and combinations thereof.

3. The method of claim 1, wherein the one or more DNA endonuclease is Cas9 (also known as Csn1 and Csx12) or a homolog thereof.

4. The method of claim 1, wherein the two or more gRNAs comprises:
    (i) a concatenated gRNA comprising a first gRNA and a second gRNA, wherein the first gRNA and the second gRNA are attached via a linker, optionally wherein the linker is a chemical linker or one or more nucleotides; or
    (ii) one or more single-molecule guide RNA (sgRNA).

5. The method of claim 1 wherein the two or more gRNAs are delivered to the cell by successive electroporation.

6. The method of claim 5 comprising:
    introducing a first guide RNA into the human cell using a first electroporation wherein the first guide RNA targets a human beta globin locus on chromosome 11; and
    introducing a second guide RNA into the human cell using a second electroporation wherein the second guide RNA targets a BCL11A gene on chromosome 2 or a DNA sequence that encodes a transcriptional control region of the BCL11A gene on chromosome 2.

7. The method of claim 5 comprising:
    introducing a first guide RNA into the human cell using a first electroporation wherein the first guide RNA targets a human beta globin locus on chromosome 11; and
    introducing a second guide RNA into the human cell using a second electroporation wherein the second guide RNA targets the human beta globin locus on chromosome 11.

8. The method of claim 5 comprising:
    introducing a first guide RNA into the human cell using a first electroporation wherein the first guide RNA targets a BCL11A gene on chromosome 2 or a DNA sequence that encodes a transcriptional control region of the BCL11A gene on chromosome 2; and
    introducing a second guide RNA into the human cell using a second electroporation wherein the second guide RNA targets a BCL11A gene on chromosome 2 or a DNA sequence that encodes a transcriptional control region of the BCL11A gene on chromosome 2.

9. The method of claim 5, wherein each electroporation step occurs 12-72, 12-48, or 36-72 hours apart from one another.

10. The method of claim 1, wherein the two or more gRNAs comprise:
    (a) the nucleic acid sequence of SEQ ID NO: 228,429; and
    (b) the nucleic acid sequence of any one of the nucleic acid sequences of SEQ ID NOs: 228,431-228,436.

11. The method of claim 1, wherein the two or more gRNAs comprise:
    (a) the nucleic acid sequence of SEQ ID NO: 228,430; and (b) the nucleic acid sequence of any one of the nucleic acid sequences of SEQ ID NOs: 228,431-228,436.

12. The method of claim 1, wherein the two or more gRNAs comprise:
    (a) the nucleic acid sequence of SEQ ID NO: 228,429; and
    (b) the nucleic acid sequence of SEQ ID NO: 228,428.

13. The method of claim 1, wherein the two or more gRNAs comprise:
    (a) the nucleic acid sequence of SEQ ID NO: 228,430; and
    (b) the nucleic acid sequence of SEQ ID NO: 228,428.

14. The method of claim 1, wherein the two or more gRNAs comprise at least two of the nucleic acid sequence of any one of the nucleic acid sequences of SEQ ID NOs: 228,431-228,436.

15. An ex vivo method for treating a patient with a hemoglobinopathy, the method comprising:
    isolating a hematopoietic progenitor cell from the patient;
    genome editing the hematopoietic progenitor cell by the method of claim 1; and
    implanting the genome-edited hematopoietic progenitor cell into the patient, wherein the genome-edited hematopoietic progenitor cell has reduced expression of human beta-globin and/or BCL11A.

16. A method of treating a patient with a hemoglobinopathy by administering an edited autologous cell to the patient, wherein the edited cell has
    (i) a permanent deletion or inversion within the human beta globin locus on chromosome 11 or a mutation within the human beta globin locus on chromosome 11, and
    (ii) a permanent deletion or inversion within the BCL11A gene on chromosome 2,
    a mutation within the BCL11A gene on chromosome 2, a permanent deletion or inversion within the DNA sequence that encodes a transcriptional control region of the BCL11A gene on chromosome 2, or a mutation within the DNA sequence that encodes a transcriptional control region of the BCL11A gene on chromosome 2,
    wherein the deletions, inversions or mutations are made by two or more gRNAs, wherein the two or more gRNAs comprise at least two of the nucleic acid sequences of SEQ ID NOs: 228,428-228,436, wherein the deletions, inversions or mutations result in reduced expression of human beta globin and/or BCL11A in the edited cell.

17. The method of claim 16, wherein the two or more gRNAs comprise:
    (a) the nucleic acid sequence of SEQ ID NO: 228,429; and
    (b) the nucleic acid sequence of any one of the nucleic acid sequences of SEQ ID NOs: 228,428 and 228,431-228,436.

18. The method of claim 16, wherein the two or more gRNAs comprise:
    (a) the nucleic acid sequence of SEQ ID NO: 228,430; and
    (b) the nucleic acid sequence of any one of the nucleic acid sequences of SEQ ID NOs: 228,428 and 228,431-228,436.

* * * * *